United States Patent [19]

Ligon et al.

[11] Patent Number: 5,662,898

[45] Date of Patent: Sep. 2, 1997

[54] GENES FOR THE SYNTHESIS OF ANTIPATHOGENIC SUBSTANCES

[75] Inventors: James M. Ligon, Basel; Thomas Schupp, Möhlin, both of Switzerland; James Joseph Beck; Dwight Steven Hill, both of Cary, N.C.; John Andrew Ryals, Durham, N.C.; Thomas Deane Gaffney, Chapel Hill, N.C.; Stephen Ting Lam, Raleigh, N.C.; Philip E. Hammer, Cary, N.C.; Scott Joseph Uknes, Apex, N.C.

[73] Assignee: Ciba-Geigy Corporation, Tarrytown, N.Y.

[21] Appl. No.: 457,342

[22] Filed: Jun. 1, 1995

Related U.S. Application Data

[63] Continuation-in-part of Ser. No. 937,648, Aug. 31, 1992, abandoned, and a division of Ser. No. 258,261, Jun. 8, 1994, which is a continuation-in-part of Ser. No. 87,636, Jul. 1, 1993, abandoned, which is a continuation-in-part of Ser. No. 908,284, Jul. 2, 1992, abandoned, which is a continuation-in-part of Ser. No. 570,184, Aug. 20, 1990, abandoned, and a continuation-in-part of PCT/US93/07954, filed Aug. 24, 1993, which is a continuation-in-part of Ser. No. 937,648, Aug. 31, 1992, abandoned.

[51] Int. Cl.$^6$ .............................. A01N 63/00; C12N 1/20
[52] U.S. Cl. ................................... 424/93.2; 435/252.3
[58] Field of Search ........................ 424/93.2; 435/252.3

[56] References Cited

U.S. PATENT DOCUMENTS

| | | | |
|---|---|---|---|
| 4,306,027 | 12/1981 | Alexander et al. | 435/253 |
| 4,456,684 | 6/1984 | Weller et al. | 435/34 |
| 4,695,455 | 9/1987 | Barnes et al. | 424/93 |
| 4,729,951 | 3/1988 | Ferenczy et al. | 435/80 |
| 4,798,723 | 1/1989 | Dart et al. | 424/93 |
| 4,812,312 | 3/1989 | Lopez Berestein | 424/417 |
| 4,880,745 | 11/1989 | Kijima et al. | 435/252.3 |
| 4,940,840 | 7/1990 | Suslow et al. | 800/205 |
| 4,948,413 | 8/1990 | Maekawa et al. | 71/65 |
| 4,952,496 | 8/1990 | Studier et al. | 435/91 |
| 4,970,147 | 11/1990 | Huala et al. | 435/69.1 |
| 4,975,277 | 12/1990 | Janisiewicz et al. | 424/93 |
| 4,994,495 | 2/1991 | Clough et al. | 514/574 |
| 4,999,381 | 3/1991 | Crowley et al. | 514/618 |
| 5,008,276 | 4/1991 | Clough et al. | 514/335 |
| 5,041,290 | 8/1991 | Gindrat et al. | 424/93 |
| 5,049,379 | 9/1991 | Handelsman et al. | 424/115 |
| 5,059,605 | 10/1991 | Clough et al. | 514/269 |
| 5,068,105 | 11/1991 | Lewis et al. | 424/93 |
| 5,279,951 | 1/1994 | Terasawa et al. | 435/172.3 |

FOREIGN PATENT DOCUMENTS

| | | |
|---|---|---|
| 0357119A2 | 9/1989 | European Pat. Off. . |
| 0414404 | 2/1991 | European Pat. Off. . |
| 0468220A2 | 6/1991 | European Pat. Off. . |
| 0471564 | 2/1992 | European Pat. Off. . |
| 0543195A2 | 10/1992 | European Pat. Off. . |
| 89-09264 | 10/1989 | WIPO . |
| WO/9105475 | 5/1991 | WIPO . |
| 9208355 | 5/1992 | WIPO . |

OTHER PUBLICATIONS

European Serach Report dated Sep. 28, 1995.

Chen, C.W., et al., "Cloning and Expression of a DNA Sequence Conferring Cephamycin C Production", *Biotechnology*, 6(10):1222–1224 (1988).

Gaffney, T.D., et al., "Global Regulation of Expression of Antifungal Factors by *Pseudomonas fluorescens* Biological Control Strain", *Molecular Plant–Microbe Interactions*, 7(4):455–463 (1994).

Hain, R., et al., "Disease resistance results from foreign phytoalexin expression in a novel plant", *Nature*, 361:153–156 (1993).

Hoffmann–LaRoche & Co., "Phenazine Derivatives and a Process for the Manufacture Thereof", *GB–A–1 285 010 Patent Specification*, 1–8 (1972).

Lam, S.T., et al., "Genetic regulation of biocontrol factors in *Pseudomonas fluorescens*", *Third International Workshop on Plant–Promoting Rhizobacteria*, Australia 97–99 (1994).

Maruzen Oil Abstract, 27 (1979).

"Nikkomycin–Antibiotic for Plants", *NTIS Tech Notes*, 5:374 (1990).

Toohey, J.I., et al., "Toxicity of Phenazine Carboxylic Acids to Some Bacteria, Algae, Higher Plants, and Animals", *Canadian Journal of Botany*, 43:1151–1155 (1965).

Chen et al. (1988) Biotechnology 6(10): 1222–1224.

Hill et al. (1994) Appl. Environ. Microbiol. 60(1):78–85.

Pfender et al. (1994) Phytopathology 83: 1223–1228.

Albright et al., "Prokaryotic Signal Transduction Mediated by Sensor and Regulator Protein Pairs", *Annu. Rev. Genet.*, 23:311–336 (1989).

Baker et al., "Biological Control of Plant Pathogens", *American Phytopathological Society*, St. Paul, Minn., 61–106 (1982).

Bourret et al., "Signal Transuction Pathways Involving Protein Phosphorylation in Prokaryotes", *Annu. Rev. Biochem.*, 60:401–441 (1991).

Brisbane, et al., *Antimicrobiol. Agents and Chemotherapy*, 31(12):1967–1971 (1987).

Brisbane, et al., *Soil. Biol. Biochem.*, 21(8):1019–1026 (1989).

Clarke et al., *Journal of Bacteriology*, 154:508–512 (1983).

Cook et al., *Soil. Biol. Biochem.*, 8:269–273 (1976).

(List continued on next page.)

Primary Examiner—Robert A. Wax
Assistant Examiner—Lisa J. Hobbs
Attorney, Agent, or Firm—J. Timothy Meigs

[57] ABSTRACT

The present invention is directed to the production of an antipathogenic substance (APS) in a host via recombinant expression of the polypeptides needed to biologically synthesize the APS. Genes encoding polypeptides necessary to produce particular antipathogenic substances are provided, along with methods for identifying and isolating genes needed to recombinantly biosynthesize any desired APS. The cloned genes may be transformed and expressed in a desired host organisms to produce the APS according to the invention for a variety of purposes, including protecting the host from a pathogen, developing the host as a biocontrol agent, and producing large, uniform amounts of the APS.

5 Claims, 9 Drawing Sheets

OTHER PUBLICATIONS

Ding et al., "Orientation and expression of the cloned hemolysin gene of Pseudomonas aeruginosa", Gene, 33(3):313–321 (1985).

Ditta et al., PNAS:USA, 77:7347–7351 (1980).

Gambello et al., "Cloning and Characterization of the Pseudomonas aeruginosa lasR Gene, a Transcriptional Activator of Elastase Expression", Journal of Bacteriology, 173(9):3000–3009 (1991).

Gurusiddaiah, et al., Antimicrobiol. Agents and Chemotherapy, 79(3):488–495 (1986).

Gutterson, et al., Journal of Bacteriology, 165(3):696–703 (1986).

Hamdan et al., Applied and Environ. Microbiology, 57:3270–3277 (1991).

Horn et al., "Autogenous Regulation and Kinetics of Induction of Pseudomonas aeruginosa recA Transcription as Analyzed with Operon Fusions", Journal of Bacteriology, 170(10):4699–4705 (1988).

Howell et al., Phytopathology, 69:480–482 (1979).

Howell et al., Phytopathology, 69(5):480–482 (1979).

Howell et al., Phytopathology, 70:712–715 (1980).

Howell et al., Can. J. Microbiology, 29:321–324 (1983).

Howie et al., "Directed Enhancement of Biocontrol in Psuedomonas by Constitutive Antibiotic Biosynthesis", Phytopathology, 79(10):1160 Abstract 291, Annual Meeting, 8th American Phytopathological Society (1989).

Inouye et al., "Molecular Cloning of Regulatory Gene xylR and Operator–Promoter Regions of the xylABC and xylDEGF Operons of TOL Plasmid", Journal of Bacteriology, 155(3):1192–1199 (1983).

James, et al., "Applied and Environmental Microbiology", 52(5):1183–1189 (1986).

Jeenes et al., Mol. Gen. Genet., 203:421–429 (1986).

Kaphammer et al., "Cloning and Characterization of tfdS, the Repressor–Activator Gene of tfdB, from the 2,4–Dichlorophenoxyacetic Acid Catabolic Plasmid pJP4", Journal of Bacteriology, 172(10):5856–5862 (1990).

Keel et al., Symbiosis, 9(1–3):327–341 (1990).

Klee et al., The Plant Cell, 3:1187–1193 (1991).

Kloepper et al., Phytopathology, 71:1020–1024 (1981).

Kraus et al., "TN5 Insertion Mutants of Psuedomonas Fluorescens PF5 Altered in Production of the Antibiotics Pyrrolnitrin and Pyoluteorin", Phytopathology, 79(10):1160, Abstract for Annual Meeting, Por–Sr Division, The American Phytopathological Society (1989).

Kroos et al., PNAS USA, 81:5816–5820 (1984).

Laville et al., "Global control in Pseudomonas fluorescens mediating antibiotic synthesis and suppression of black root rot of tobacco", PNAS USA, 89:1562–1566 (1992).

Lievens et al., Pesticide Science, 27(2):141–154 (1989).

Loper, Phytopathology, 78:166–171 (1988).

Mekalanos, J.J., "Environmental Signals Controlling Expression of Virulence Determinants in Bacteria", Journal of Bacteriology, 174:1–7 (1992).

Mermod et al., "Vector for Regulated Expression of Cloned Genes in a Wide Range of Gram–Negative Bacteria", Journal of Bacteriology, 167(2):447–454 (1986).

Mohr et al., "Expression patters of genes encoding elastase and controlling mucoidy: coordinate regulation of two virulence factors in Pseudomonas aeruginosa isolates from cystic fibrosis", Molecular Microbiology, 4(12):2103–2110 (1990).

Moolenaar et al., "Regulation of the Escherichia coli excision repair gene uvrC. Overlap between the uvrC structural gene and the region coding for a 24 kD protein", Nucleic Acids Research, 15(10):4273–4289 (1989).

Orlik–Eisel et al., "The cytotoxin of Pseudomonas aeruginosa: Cytotoxicity requires proteolytic activation", Microbiology, 153(6):561–568 (1990).

Ramos et al., "Redesigning Metabolic Routes: Manipulation of TOL Plasmid Pathway for Catabolism of Alkylbenzoates", Science, 235(4788):593–596 (1987).

Rothmel et al., "Functional Analysis of the Pseudomonas putida Regulatory Protein CatR: Transcriptional Studies and Determination of the CatR DNA–Binding Site by Hydroxyl–Radical Footprinting", Journal of Bacteriology, 173(15):4717–4724 (1991).

Schell, M.A., "Transcriptional control of the nah and sal hydrocarbon–degradation operons by the nahR gene product", Gene, 36(3):301–309 (1985).

Scher et al., Phytopathology, 70:412–417 (1980).

Schroth et al., Science, 216:1376–1381 (1982).

Spena et al., Mol. Gen. Genet., 227:205–212 (1991).

Starnbach et al., "The fliA (rpoF) gene of Pseudomonas aeruginosa encodes an alternative sigma factor required for flagellin synthesis", Molecular Microbiology, 6(4):459–469 (1992).

Stock et al., "Protein Phosphorylation and Regulation of Adaptive Responses in Bacteria", Microbiological Reviews, 53(4):450–490 (1989).

Tanaka et al., "Cloning and Characterization of Bacillus Substilis iep. Which Has Positive and Negative Effects on Production of Extracellular Proteases", Journal of Bacteriology, 170(8):3593–3600 (1988).

Thomashow et al., Journal of Bacteriology, 170:3499–3508 (1988).

Toder et al., "Pseudomonas aeruginosa LasA: a second elastase under the transcriptional control of lasR", Molecular Microbiology, 5(8):2003–2010 (1991).

Weller et al., Phytopathology, 73:463–469 (1983).

Weller et al., "Biochemical and Ecological Aspects of Competition in Biological Control", Journal of Cellular Biochemistry, Supplemental 13A:134, Abstract CB 104 (1989).

GENES FOR THE SYNTHESIS OF ANTIPATHOGENIC SUBSTANCES

This is a divisional application of Ser. No. 08/258,261, filed Jun. 8, 1994, which is a Continuation-in-Part of U.S. Ser. No. 08/087,636, filed 1 Jul. 1993 now abandoned, which is itself a Continuation-in-Part of U.S. Ser. No. 07/908,284, filed 2 Jul. 1992 (now abandoned) which is itself a Continuation-in-Part of U.S. Ser. No. 07/570,184, filed 20 Aug. 1990 (now abandoned). This application is a Continuation-in-Part of international PCT application Ser. No. US93/07954 filed on 24 Aug. 1993 (WO 94/05793), which is itself a Continuation-in-Part of U.S. Ser. No. 07/937,648, filed 31 Aug. 1992 (now abandoned).

FIELD OF THE INVENTION

The present invention relates generally to the protection of host organisms against pathogens, and more particularly to the protection of plants against phytopathogens. In one aspect it provides transgenic plants which have enhanced resistance to phytopathogens and biocontrol organisms with enhanced biocontrol properties. It further provides methods for protecting plants against phytopathogens and methods for the production of antipathogenic substances.

BACKGROUND OF THE INVENTION

Plants routinely become infected by fungi and bacteria, and many microbial species have evolved to utilize the different niches provided by the growing plant. Some phytopathogens have evolved to infect foliar surfaces and are spread through the air, from plant-to-plant contact or by various vectors, whereas other phytopathogens are soil-borne and preferentially infect roots and newly germinated seedlings. In addition to infection by fungi and bacteria, many plant diseases are caused by nematodes which are soil-borne and infect roots, typically causing serious damage when the same crop species is cultivated for successive years on the same area of ground.

Plant diseases cause considerable crop loss from year to year resulting both in economic hardship to farmers and nutritional deprivation for local populations in many parts of the world. The widespread use of fungicides has provided considerable security against phytopathogen attack, but despite $1 billion worth of expenditure on fungicides, worldwide crop losses amounted to approximately 10% of crop value in 1981 (James, Seed Sci. & Technol. 9:679–685 (1981). The severity of the destructive process of disease depends on the aggressiveness of the phytopathogen and the response of the host, and one aim of most plant breeding programs is to increase the resistance of host plants to disease. Novel gene sources and combinations developed for resistance to disease have typically only had a limited period of successful use in many crop-pathogen systems due to the rapid evolution of phytopathogens to overcome resistance genes. In addition, there are several documented cases of the evolution of fungal strains which are resistant to particular fungicides. As early as 1981, Fletcher and Wolfe (Proc. 1981 Brit. Crop Prot. Conf. (1981)) contended that 24% of the powdery mildew populations from spring barley, and 53% from winter barley showed considerable variation in response to the fungicide triadimenol and that the distribution of these populations varied between barley varieties with the most susceptible variety also giving the highest incidence of less susceptible fungal types. Similar variation in the sensitivity of fungi to fungicides has been documented for wheat mildew (also to triadimenol), Botrytis (to benomyl), Pyrenophora (to organomercury), Pseudocercosporella (to MBC-type fungicides) and *Mycosphaerella fijiensis* to triazoles to mention just a few (Jones and Clifford; Cereal Diseases, John Wiley, 1983). Diseases caused by nematodes have also been controlled successfully by pesticide application. Whereas most fungicides are relatively harmless to mammals and the problems with their use lie in the development of resistance in target fungi, the major problem associated with the use of nematicides is their relatively high toxicity to mammals. Most nematicides used to control soil nematodes are of the carbamate, organochlorine or organophosphorous groups and must be applied to the soil with particular care.

In some crop species, the use of biocontrol organisms has been developed as a further alternative to protect crops. Biocontrol organisms have the advantage of being able to colonize and protect parts of the plant inaccessible to conventional fungicides. This practice developed from the recognition that crops grown in some soils are naturally resistant to certain fungal phytopathogens and that the suppressive nature of these soils is lost by autoclaving. Furthermore, it was recognized that soils which are conducive to the development of certain diseases could be rendered suppressive by the addition of small quantities of soil from a suppressive field (Scher et al. Phytopathology 70:412–417 (1980). Subsequent research demonstrated that root colonizing bacteria were responsible for this phenomenon, now known as biological disease control (Baker et al. Biological Control of Plant Pathogens, Freeman Press, San Francisco, 1974). In many cases, the most efficient strains of biological disease controlling bacteria are of the species *Pseudomonas fluorescens* (Weller et al. Phytopathology 73:463–469 (1983); Kloepper et al. Phytopathology 71:1020–1024 (1981)). Important plant pathogens that have been effectively controlled by seed inoculation with these bacteria include *Gaemannomyces graminis*, the causative agent of take-all in wheat (Cook et al. Soil Biol. Biochem 8:269–273 (1976)) and the Pythium and Rhizoctonia phytopathogens involved in damping off of cotton (Howell et al. Phytopathology 69:480–482 (1979)). Several biological disease controlling Pseudomonas strains produce antibiotics which inhibit the growth of fungal phytopathogens (Howell et al. Phytopathology 69:480–482 (1979); Howell et al. Phytopathology 70:712–715 (1980)) and these have been implicated in the control of fungal phytopathogens in the rhizosphere. Although biocontrol was initially believed to have considerable promise as a method of widespread application for disease control, it has found application mainly in the environment of glasshouse crops where its utility in controlling soil-borne phytopathogens is best suited for success. Large scale field application of naturally occurring microorganisms has not proven possible due to constraints of microorganism production (they are often slow growing), distribution (they are often short lived) and cost (the result of both these problems). In addition, the success of biocontrol approaches is also largely limited by the identification of naturally occurring strains which may have a limited spectrum of efficacy. Some initial approaches have also been taken to control nematode phytopathogens using biocontrol organisms. Although these approaches are still exploratory, some Streptomyces species have been reported to control the root knot nematode (Meliodogyne spp.) (WO 93/18135 to Research Corporation Technology), and toxins from some *Bacillus thuringiensis* strains (such as *israeliensis*) have been shown to have broad anti-nematode activity and spore or bacillus preparations may thus provide suitable biocontrol opportunities (EP 0 352 052 to Mycogen, WO 93/19604 to Research Corporation Technologies).

The traditional methods of protecting crops against disease, including plant breeding for disease resistance, the continued development of fungicides, and more recently, the identification of biocontrol organisms, have all met with success. It is apparent, however, that scientists must constantly be in search of new methods with which to protect crops against disease. This invention provides novel methods for the protection of plants against phytopathogens.

SUMMARY OF THE INVENTION

The present invention reveals the genetic basis for substances produced by particular microorganisms via a multigene biosynthetic pathway which have a deleterious effect on the multiplication or growth of plant pathogens. These substances include carbohydrate containing antibiotics such as aminoglycosides, peptide antibiotics, nucleoside derivatives and other heterocyclic antibiotics containing nitrogen and/or oxygen, polyketides, macrocyclic lactones, and quinones.

The invention provides the entire set of genes required for recombinant production of particular antipathogenic substances in a host organism. It further provides methods for the manipulation of APS gene sequences for their expression in transgenic plants. The transgenic plants thus modified have enhanced resistance to attack by phytopathogens. The invention provides methods for the cellular targeting of APS gene products so as to ensure that the gene products have appropriate spatial localization for the availability of the required substrate/s. Further provided are methods for the enhancement of throughput through the APS metabolic pathway by overexpression and overproduction of genes encoding substrate precursors.

The invention further provides a novel method for the identification and isolation of the genes involved in the biosynthesis of any particular APS in a host organism.

The invention also describes improved biocontrol strains which produce heterologous APSs and which are efficacious in controlling soil-borne and seedling phytopathogens outside the usual range of the host.

Thus, the invention provides methods for disease control. These methods involve the use of transgenic plants expressing APS biosynthetic genes and the use of biocontrol agents expressing APS genes.

The invention further provides methods for the production of APSs in quantities large enough to enable their isolation and use in agricultural formulations. A specific advantage of these production methods is the chirality of the molecules produced; production in transgenic organisms avoids the generation of populations of racemic mixtures, within which some enantiomers may have reduced activity.

DEFINITIONS

As used in the present application, the following terms have the meanings set out below. Antipathogenic Substance: A substance which requires one or more nonendogenous enzymatic activities foreign to a plant to be produced in a host where it does not naturally occur, which substance has a deleterious effect on the multiplication or growth of a pathogen (i.e. pathogen). By "nonendogenous enzymatic activities" is meant enzymatic activities that do not naturally occur in the host where the antipathogenic substance does not naturally occur. A pathogen may be a fungus, bacteria, nematode, virus, viroid, insect or combination thereof, and may be the direct or indirect causal agent of disease in the host organism. An antipathogenic substance can prevent the multiplication or growth of a phytopathogen or can kill a phytopathogen. An antipathogenic substance may be synthesized from a substrate which naturally occurs in the host. Alternatively, an antipathogenic substance may be synthesized from a substrate that is provided to the host along with the necessary nonendogenous enzymatic activities. An antipathogenic substance may be a carbohydrate containing antibiotic, a peptide antibiotic, a heterocyclic antibiotic containing nitrogen, a heterocyclic antibiotic containing oxygen, a heterocyclic antibiotic containing nitrogen and oxygen, a polyketide, a macrocyclic lactone, and a quinone. Antipathogenic substance is abbreviated as "APS" throughout the text of this application.

Anti-phytopathogenic substance: An antipathogenic substance as herein defined which has a deleterious effect on the multiplication or growth of a plant pathogen (i.e. phytopathogen).

Biocontrol agent: An organism which is capable of affecting the growth of a pathogen such that the ability of the pathogen to cause a disease is reduced. Biocontrol agents for plants include microorganisms which are capable of colonizing plants or the rhizosphere. Such biocontrol agents include gram-negative microorganisms such as Pseudomonas, Enterobacter and Serratia, the gram-positive microorganism Bacillus and the fungi Trichoderma and Gliocladium. Organisms may act as biocontrol agents in their native state or when they are genetically engineered according to the invention.

Pathogen: Any organism which causes a deleterious effect on a selected host under appropriate conditions. Within the scope of this invention the term pathogen is intended to include fungi, bacteria, nematodes, viruses, viroids and insects.

Promoter or Regulatory DNA Sequence: An untranslated DNA sequence which assists in, enhances, or otherwise affects the transcription, translation or expression of an associated structural DNA sequence which codes for a protein or other DNA product. The promoter DNA sequence is usually located at the 5' end of a translated DNA sequence, typically between 20 and 100 nucleotides from the 5' end of the translation start site.

Coding DNA Sequence: A DNA sequence that is translated in an organism to produce a protein.

Operably Linked to/Associated With: Two DNA sequences which are "associated" or "operably linked" are related physically or functionally. For example, a promoter or regulatory DNA sequence is said to be "associated with" a DNA sequence that codes for an RNA or a protein if the two sequences are operably linked, or situated such that the regulator DNA sequence will affect the expression level of the coding or structural DNA sequence.

Chimeric Construction/Fusion DNA Sequence: A recombinant DNA sequence in which a promoter or regulatory DNA sequence is operably linked to, or associated with, a DNA sequence that codes for an mRNA or which is expressed as a protein, such that the regulator DNA sequence is able to regulate transcription or expression of the associated DNA sequence. The regulator DNA sequence of the chimeric construction is not normally operably linked to the associated DNA sequence as found in nature. The terms "heterologous" or "non-cognate" are used to indicate a recombinant DNA sequence in which the promoter or regulator DNA sequence and the associated DNA sequence are isolated from organisms of different species or genera.

BRIEF DESCRIPTION OF THE SEQUENCES IN THE SEQUENCE LISTING

Figure 1:
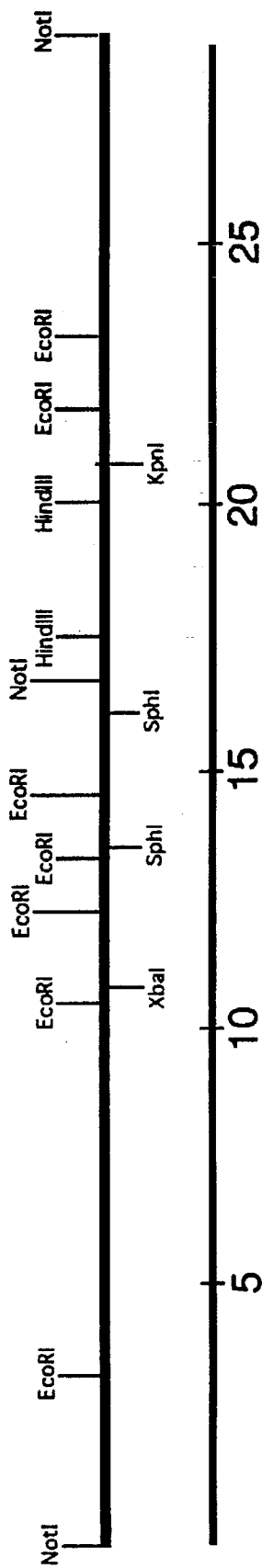
FIG. 1: Restriction map of the cosmid clone pCIB169 from *Pseudomonas fluorescens* carrying the pyrrolnitrin biosynthetic gene region.

SEQ ID NO:1:—Sequence of the Pyrrolnitrin Gene Cluster
SEQ ID NO:2:—protein sequence for ORF1 of pyrrolnitrin gene cluster
SEQ ID NO:3:—protein sequence for ORF2 of pyrrolnitrin gene cluster
SEQ ID NO:4:—protein sequence for ORF3 of pyrrolnitrin gene cluster
SEQ ID NO:5:—protein sequence for ORF4 of pyrrolnitrin gene cluster
SEQ ID NO:6:—Sequence of the Soraphen Gene Cluster
SEQ ID NO:7:—Sequence of a Plant Consensus Translation Initiator (Clontech)
SEQ ID NO:8:—Sequence of a Plant Consensus Translation Initiator (Joshi)
SEQ ID NO:9:—Sequence of an Oligonucleotide for Use in a Molecular Adaptor
SEQ ID NO:10:—Sequence of an Oligonucleotide for Use in a Molecular Adaptor
SEQ ID NO:11:—Sequence of an Oligonucleotide for Use in a Molecular Adaptor
SEQ ID NO:12:—Sequence of an Oligonucleotide for Use in a Molecular Adaptor
SEQ ID NO:13:—Sequence of an Oligonucleotide for Use in a Molecular Adaptor
SEQ ID NO:14:—Sequence of an Oligonucleotide for Use in a Molecular Adaptor
SEQ ID NO:15:—oligonucleotide used to change restriction site
SEQ ID NO:16:—oligonucleotide used to change restriction site
SEQ ID NO:17:—Sequence of the Phenazine Gene Cluster
SEQ ID NO:18:—protein sequence for phz1 from the phenazine gene cluster
SEQ ID NO:19:—protein sequence for phz2 from the phenazine gene cluster
SEQ ID NO:20:—protein sequence for phz3 from the phenazine gene cluster
SEQ ID NO:21:—DNA sequence for phz4 of Phenazine gene cluster
SEQ ID NO:22:—protein sequence for phz4 from the phenazine gene cluster

DETAILED DESCRIPTION OF THE INVENTION

Production of Antipathogenic Substances by Microorganisms

Many organisms produce secondary metabolites and some of these inhibit the growth of other organisms. Since the discovery of penicillin, a large number of compounds with antibiotic activity have been identified, and the number continues to increase with ongoing screening efforts. Antibiotically active metabolites comprise a broad range of chemical structures. The most important include: aminoglycosides (e.g. streptomycin) and other carbohydrate containing antibiotics, peptide antibiotics (e.g. β-lactAPS, rhizocticin (see Rapp, C. et al., *Liebigs Ann. Chem.*: 655–661 (1988)), nucleoside derivatives (e.g. blasticidin S) and other heterocyclic antibiotics containing nitrogen (e.g. phenazine and pyrrolnitrin) and/or oxygen, polyketides (e.g. soraphen), macrocyclic lactones (e.g. erythromycin) and quinones (e.g. tetracycline).

Aminoglycosides and Other Carbohydrate Containing Antibiotics

The aminoglycosides are oligosaccharides consisting of an aminocyclohexanol moiety glycosidically linked to other amino sugars. Streptomycin, one of the best studied of the group, is produced by *Streptomyces griseus*. The biochemistry and biosynthesis of this compound is complex (for review see Mansouri et al. in: Genetics and Molecular Biology of Industrial Microorganisms (ed.: Hershberger et al.), American Society for Microbiology, Washington, D.C. pp 61–67 (1989)) and involves 25 to 30 genes, 19 of which have been analyzed so far (Retzlaff et al. in: Industrial Microorganisms: Basic and Applied Molecular Genetics (ed.: Baltz et al.), American Society for Microbiology, Washington, D.C. pp 183–194 (1993)). Streptomycin, and many other aminoglycosides, inhibits protein synthesis in the target organisms.

Peptide Antibiotics

Peptide antibiotics are classifiable into two groups: (1) those which are synthesized by enzyme systems without the participation of the ribosomal apparatus, and (2) those which require the ribosomally-mediated translation of an mRNA to provide the precursor of the antibiotic.

Non-Ribosomal Peptide Antibiotics are assembled by large, multifunctional enzymes which activate, modify, polymerize and in some cases cyclize the subunit amino acids, forming polypeptide chains. Other acids, such as aminoadipic acid, diaminobutyric acid, diaminopropionic acid, dihydroxyamino acid, isoserine, dihydroxybenzoic acid, hydroxyisovaleric acid, (4R)-4-[(E)-2-butenyl]-4,N-dimethyl-L-threonine, and ornithine are also incorporated (Katz & Demain, Bacteriological Review 41:449–474 (1977); Kleinkauf & von Dohren, Annual Review of Microbiology 41:259–289 (1987)). The products are not encoded by any mRNA, and ribosomes do not directly participate in their synthesis. Peptide antibiotics synthesized non-ribosomally can in turn be grouped according to their general structures into linear, cyclic, lactone, branched cyclopeptide, and depsipeptide categories (Kleinkauf & von Dohren, European Journal of Biochemistry 192:1–15 (1990)). These different groups of antibiotics are produced by the action of modifying and cyclizing enzymes; the basic scheme of polymerization is common to them all. Non-ribosomally synthesized peptide antibiotics are produced by both bacteria and fungi, and include edeine, linear gramicidin, tyrocidine and gramicidin S from *Bacillus brevis*, mycobacillin from *Bacillus subtilis*, polymyxin from *Bacillus polymyxa*, etamycin from *Streptomyces griseus*, echinomycin from *Streptomyces echinatus*, actinomycin from *Streptomyces clavuligerus*, enterochelin from *Escherichia coli*, gamma-(alpha-L-aminoadipyl)-L-cysteinyl-D-valine (ACV) from , *Aspergillus nidulans*, alamethicine from *Trichoderma viride*, destruxin from *Metarhizium anisolpliae*, enniatin from *Fusarium oxysporum*, and beauvericin from *Beauveria bassiana*. Extensive functional and structural similarity exists between the prokaryotic and eukaryotic systems, suggesting a common origin for both. The activities of peptide antibiotics are similarly broad, toxic effects of different peptide antibiotics in animals, plants, bacteria, and fungi are known (Hansen, Annual Review of Microbiology 47:535–564 (1993); Katz & Demain, Bacteriological Reviews 41:449–474 (1977); Kleinkauf & von Dohren, Annual Review of Microbiology 41:259–289 (1987); Kleinkauf & von Dohren, European Journal of Biochemistry 192:1–15 (1990); Kolter & Moreno, Annual Review of Microbiology 46:141–163 (1992)).

Ribosomally-Synthesized Peptide Antibiotics are characterized by the existence of a structural gene for the antibiotic itself, which encodes a precursor that is modified by specific enzymes to create the mature molecule. The use of the general protein synthesis apparatus for peptide antibiotic synthesis opens up the possibility for much longer polymers to be made, although these peptide antibiotics are not necessarily very large. In addition to a structural gene, further genes are required for extracellular secretion and immunity, and these genes are believed to be located close to the structural gene, in most cases probably on the same operon. Two major groups of peptide antibiotics made on ribosomes exist: those which contain the unusual amino acid lanthionine, and those which do not. Lanthionine-containing antibiotics (lantibiotics) are produced by gram-positive bacteria, including species of Lactococcus, Staphylococcus, Streptococcus, Bacillus, and Streptomyces. Linear lantibiotics (for example, nisin, subtilin, epidermin, and gallidermin), and circular lantibiotics (for example, duramycin and cinnamycin), are known (Hansen, Annual Review of Microbiology 47:535–564 (1993); Kolter & Moreno, Annual Review of Microbiology 46:141–163 (1992)). Lantibiotics often contain other characteristic modified residues such as dehydroatanine (DHA) and dehydrobutyrine (DHB), which are derived from the dehydration of serine and threonine, respectively. The reaction of a thiol from cysteine with DHA yields lanthionine, and with DHB yields β-methyllanthionine. Peptide antibiotics which do not contain lanthionine may contain other modifications, or they may consist only of the ordinary amino acids used in protein synthesis. Non-lanthionine-containing peptide antibiotics are produced by both gram-positive and gram-negative bacteria, including Lactobacillus, Lactococcus, Pediococcus, Enterococcus, and Escherichia. Antibiotics in this category include lactacins, lactocins, sakacin A, pediocins, diplococcin, lactococcins, and microcins (Hansen, supra; Kolter & Moreno, supra).

Nucleoside Derivatives and Other Heterocyclic Antibiotics Containing Nitrogen and/or Oxygen These compounds all contain heterocyclic rings but are otherwise structurally diverse and, as illustrated in the following examples, have very different biological activities.

Polyoxins and Nikkomycins are nucleoside derivatives and structurally resemble UDP-N-acetylglucosamine, the substrate of chitin synthase. They have been identified as competitive inhibitors of chitin synthase (Gooday, in: Biochemistry of Cell Walls and Membranes in Fungi (ed.: Kuhn et al.), Springer-Verlag, Berlin p. 61 (1990)). The polyoxins are produced by *Streptomyces cacaoi* and the Nikkomycins are produced by *S. tendae*.

Phenazines are nitrogen-containing heterocyclic compounds with a common planar aromatic tricyclic structure. Over 50 naturally occurring phenazines have been identified, each differing in the substituent groups on the basic ring structure. This group of compounds are found produced in nature exclusively by bacteria, in particular Streptomyces, Sorangium, and Pseudomonas (for review see Turner & Messenger, Advances in Microbiol Physiology 27:211–275 (1986)). Recently, the phenazine biosynthetic genes of a *P. aureofaciens* strain has been isolated (Pierson & Thomashow MPMI 5:330–339 (1992)). Because of their planar aromatic structure, it has been proposed that phenazines may form intercalative complexes with DNA (Hollstein & van Gemert, Biochemistry 10:497 (1971)), and thereby interfere with DNA metabolism. The phenazine myxin was shown to intercalate DNA (Hollstein & Butler, Biochemistry 11:1345 (1972)) and the phenazine lomofungin was shown to inhibit RNA synthesis in yeast (Cannon & Jiminez, Biochemical Journal 142:457 (1974); Ruet et al., Biochemistry 14:4651 (1975)).

Pyrrolnitrin is a phenylpyrrole derivative with strong antibiotic activity and has been shown to inhibit a broad range of fungi (Homma et al., Soil Biol. Biochem. 21:723–728 (1989); Nishida et al., J. Antibiot., ser A, 18:211–219 (1965)). It was originally isolated from *Pseudomonas pyrrocinia* (Arima et al, J. Antibiot., ser. A, 18:201–204 (1965)), and has since been isolated from several other Pseudomonas species and Myxococcus species (Gerth et al. J. Antibiot. 35:1101–1103 (1982)). The compound has been reported to inhibit fungal respiratory electron transport (Tripathi & Gottlieb, J. Bacteriol. 100:310–318 (1969)) and uncouple oxidative phosphorylation (Lambowitz & Slayman, J. Bacteriol. 112:1020–1022 (1972)). It has also been proposed that pyrrolnitrin causes generalized lipoprotein membrane damage (Nose & Arima, J. Antibiot., ser A, 22:135–143 (1969); Carlone & Scannerini, Mycopahtologia et Mycologia Applicata 53:111–123 (1974)). Pyrrolnitrin is biosynthesized from tryptophan (Chang et al. J. Antibiot. 34:555–566) and the biosynthetic genes from *P. fluorescens* have now been cloned (see Section C of examples).

Polyketide Synthases

Many antibiotics, in spite of the apparent structural diversity, share a common pattern of biosynthesis. The molecules are built up from two carbon building blocks, the β-carbon of which always carries a keto group, thus the name polyketide. The tremendous structural diversity derives from the different lengths of the polyketide chain and the different side-chains introduced, either as part of the two carbon building blocks, or after the polyketide backbone is formed. The keto groups may also be reduced to hydroxyls or removed altogether. Each round of two carbon addition is carried out by a complex of enzymes called the polyketide synthases (PKS) in a manner similar to fatty acid biosynthesis. The biosynthetic genes for an increasing number of polyketide antibiotics have been isolated and sequenced. It is quite apparent that the PKS genes are structurally conserved. The encoded proteins generally fall into two types: type I proteins are polyfunctional, with several catalytic domains carrying out different enzymatic steps covalently linked together (e.g. PKS for erythromycin, soraphen, and avermectin (Joaua et al. Plasmid 28:157–165 (1992); MacNeil et al. in: Industrial Microorganisms: Basic and Applied Molecular Genetics, (ed.: Baltz et al.), American Society for Microbiology, Washington D.C. pp. 245–256 (1993)); whereas type II proteins are monofunctional (Hutchinson et al. in: Industrial Microorganisms: Basic and Applied Molecular Genetics, (ed.: Baltz et al.), American Society for Microbiology, Washington D.C. pp. 203–216 (1993)). For the simpler polyketide antibiotics such as actinorhodin (produced by *Streptomyces coelicolor*), the several rounds of two carbon additions are carried out iteratively on PKS enzymes encoded by one set of PKS genes. In contrast, synthesis of the more complicated compounds such as erythromycin and soraphen (see Section E of examples) involves sets of PKS genes organized into modules, with each module carrying out one round of two carbon addition (for review see Hopwood et al. in: Industrial Microorganisms: Basic and Applied Molecular Genetics, (ed.: Baltz et al.), American Society for Microbiology, Washington D.C. pp. 267–275 (1993)).

Macrocyclic Lactones

This group of compounds shares the presence of a large lactone ring with various ring substituents. They can be further classified into subgroups, depending on the ring size and other characteristics. The macrolides, for example, contain 12-, 14-, 16-, or 17-membered lactone rings glycosidically linked to one or more aminosugars and/or deoxysugars. They are inhibitors of protein synthesis, and are particularly effective against gram-positive bacteria. Erythromycin A, a well-studied macrolide produced by *Saccharopolyspora erythraea*, consists of a 14-membered lactone ring linked to two deoxy sugars. Many of the biosynthetic genes have been cloned; all have been located within a 60 kb segment of the *S. erythraea* chromosome. At least 22 closely linked open reading frames have been identified to be likely involved in erythromycin biosynthesis (Donadio et al., in: Industrial Microorganisms: Basic and Applied Molecular Genetics, (ed.: Baltz et al.), American Society for Microbiology, Washington D.C. pp 257–265 (1993)).

Quinones

Quinones are aromatic compounds with two carbonyl groups on a fully unsaturated ring. The compounds can be broadly classified into subgroups according to the number of aromatic rings present, i.e., benzoquinones, napthoquinones, etc. A well studied group is the tetracyclines, which contain a napthacene ring with different substituents. Tetracyclines are protein synthesis inhibitors and are effective against both gram-positive and gram-negative bacteria, as well as rickettsias, mycoplasma, and spirochetes. The aromatic rings in the tetracyclines are derived from polyketide molecules. Genes involved in the biosynthesis of oxytetracycline (produced by *Streptomyces rimosus*) have been cloned and expressed in *Streptomyces lividans* (Binnie et al. J. Bacteriol. 171:887–895 (1989)). The PKS genes share homology with those for actinorhodin and therefore encode type II (monofunctional) PKS proteins (Hopewood & Sherman, Ann. Rev. Genet. 24:37–66 (1990)).

Other Types of APS

Several other types of APSs have been identified. One of these is the antibiotic 2-hexyl-5-propyl-resorcinol which is produced by certain strains of Pseudomonas. It was first isolated from the Pseudomonas strain B-9004 (Kanda et al. J. Antibiot. 28:935–942 (1975)) and is a dialkyl-substituted derivative of 1,3-dihydroxybenzene. It has been shown to have antipathogenic activity against Gram-positive bacteria (in particular Clavibacter sp.), mycobacteria, and fungi. Another type of APS are the methoxyacrylates, such as strobilurin B. Strobilurin B is produced by Basidiomycetes and has a broad spectrum of fungicidal activity (Anke, T. et al., *Journal of Antibiotics* (Tokyo) 30:806–810 (1977). In particular, strobilurin B is produced by the fungus *Bolinia lutea*. Strobilurin B appears to have antifungal activity as a result of its ability to inhibit cytochrome b dependent electron transport thereby inhibiting respiration (Becker, W. et al., *FEBS Letters* 132:329–333 (1981).

Most antibiotics have been isolated from bacteria, actinomycetes, and fungi. Their role in the biology of the host organism is often unknown, but many have been used with great success, both in medicine and agriculture, for the control of microbial pathogens. Antibiotics which have been used in agriculture are: blasticidin S and kasugamycin for the control of rice blast (*Pyricularia oryzae*), validamycin for the control of Rhizoctonia solani, prumycin for the control of Botrytis and Sclerotinia species, and mildiomycin for the control of mildew.

To date, the use of antibiotics in plant protection has involved the production of the compounds through chemical synthesis or fermentation and application to seeds, plant parts, or soil. This invention describes the identification and isolation of the biosynthetic genes of a number of antiphytopathogenic substances and further describes the use of these genes to create transgenic plants with enhanced disease resistance characteristics and also the creation of improved biocontrol strains by expression of the isolated genes in organisms which colonize host plants or the rhizosphere. Furthermore, the availability of such genes provides methods for the production of APSs for isolation and application in antipathogenic formulations.

Methods for Cloning Genes for Antipathogenic Substances

Genes encoding antibiotic biosynthetic genes can be cloned using a variety of techniques according to the invention. The simplest procedure for the cloning of APS genes requires the cloning of genomic DNA from an organism identified as producing an APS, and the transfer of the cloned DNA on a suitable plasmid or vector to a host organism which does not produce the APS, followed by the identification of transformed host colonies to which the APS-producing ability has been conferred. Using a technique such as λ::Tn5 transposon mutagenesis (de Bruijn & Lupski, Gene 27:131–149 (1984)), the exact region of the transforming APS-conferring DNA can be more precisely defined. Alternatively or additionally, the transforming APS-conferring DNA can be cleaved into smaller fragments and the smallest which maintains the APS-conferring ability further characterized. Whereas the host organism lacking the ability to produce the APS may be a different species to the organism from which the APS derives, a variation of this technique involves the transformation of host DNA into the same host which has had its APS-producing ability disrupted by mutagenesis. In this method, an APS-producing organism is mutated and non-APS producing mutants isolated, and these are complemented by cloned genomic DNA from the APS producing parent strain. A further example of a standard technique used to clone genes required for APS biosynthesis is the use of transposon mutagenesis to generate mutants of an APS-producing organism which, after mutagenesis, fail to produce the APS. Thus, the region of the host genome responsible for APS production is tagged by the transposon and can be easily recovered and used as a probe to isolate the native genes from the parent strain. APS biosynthetic genes which are required for the synthesis of APSs and which are similar to known APS compounds may be clonable by virtue of their sequence homology to the biosynthetic genes of the known compounds. Techniques suitable for cloning by homology include standard library screening by DNA hybridization.

This invention also describes a novel technique for the isolation of APS biosynthetic genes which may be used to clone the genes for any APS, and is particularly useful for the cloning of APS biosynthetic genes which may be recalcitrant to cloning using any of the above techniques. One reason why such recalcitrance to cloning may exist is that the standard techniques described above (except for cloning by homology) may preferentially lead to the isolation of regulators of APS biosynthesis. Once such a regulator has been identified, however, it can be used using this novel method to isolate the biosynthetic genes under the control of the cloned regulator. In this method, a library of transposon insertion mutants is created in a strain of microorganism which lacks the regulator or has had the regulator gene disabled by conventional gene disruption techniques. The insertion transposon used carries a promoter-less reporter gene (e.g. lacZ).

Once the insertion library has been made, a functional copy of the regulator gene is transferred to the library of cells (e.g. by conjugation or electroporation) and the plated cells are selected for expression of the reporter gene. Cells are assayed before and after transfer of the regulator gene. Colonies which express the reporter gene only in the presence of the regulator gene are insertions adjacent to the promoter of genes regulated by the regulator. Assuming the regulator is specific in its regulation for APS-biosynthetic genes, then the genes tagged by this procedure will be APS-biosynthetic genes. In a preferred embodiment, the cloned regulator gene is the gafA gene described in PCT application WO 94/01561 which regulates the expression of the biosynthetic genes for pyrrolnitrin. Thus, this method is a preferred method for the cloning of the biosynthetic genes for pyrrolnitrin.

In order for the cloned APS genes to be of use in transgenic expression, it is important that all the genes required for synthesis from a particular metabolite be identified and cloned. Using combinations of, or all the techniques described above, this is possible for any known APS. As most APS biosynthetic genes are clustered together in microorganisms, usually encoded by a single operon, the identification of all the genes will be possible from the identification of a single locus in an APS-producing microorganism. In addition, as regulators of APS biosynthetic genes are believed to regulate the whole pathway, then the cloning of the biosynthetic genes via their regulators is a particularly attractive method of cloning these genes. In many cases the regulator will control transcription of the single entire operon, thus facilitating the cloning of genes using this strategy.

Using the methods described in this application, biosynthetic genes for any APS can be cloned from a microorganism, and using the methods of gene manipulation and transgenic plant production describe in this specification, the cloned APS biosynthetic genes can be modified and expressed in transgenic plants. Suitable APS biosynthetic genes include those described at the beginning of this section, viz. aminoglycosides and other carbohydrate containing antibiotics (e.g. streptomycin), peptide antibiotics (both non-ribosomally and ribosomally synthesized types), nucleoside derivatives and other heterocyclic antibiotics containing nitrogen and/or oxygen (e.g. polyoxins, nikkomycins, phenazines, and pyrrolnitrin), polyketides, macrocyclic lactones and quinones (e.g. soraphen, erythromycin and tetracycline). Expression in transgenic plants will be under the control of an appropriate promoter and involves appropriate cellular targeting considering the likely precursors required for the particular APS under consideration. Whereas the invention is intended to include the expression in transgenic plants of any APS gene isolatable by the procedures described in this specification, those which are particularly preferred include pyrrolnitrin, soraphen, phenazine, and the peptide antibiotics gramicidin and epidermin. The cloned biosynthetic genes can also be expressed in soil-borne or plant colonizing organisms for the purpose of conferring and enhancing biocontrol efficacy in these organisms. Particularly preferred APS genes for this purpose are those which encode pyrrolnitrin, soraphen, phenazine, and the peptide antibiotics.

Production of Antipathogenic Substances in Heterologous Microbial Hosts

Cloned APS genes can be expressed in heterologous bacterial or fungal hosts to enable the production of the APS with greater efficiency than might be possible from native hosts. Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as Bacillus are also known in the art and can be used in the context of this invention (Quax et al. In.: Industrial Microorganisms: Basic and Applied Molecular Genetics, Eds. Baltz et al., American Society for Microbiology, Washington (1993)). Alternate systems for overexpression rely on yeast vectors and include the use of Pichia, Saccharomyces and Kluyveromyces (Sreekrishna, In: Industrial microorganisms: basic and applied molecular genetics, Baltz, Hegeman, and Skatrud eds., American Society for Microbiology, Washington (1993); Dequin & Barre, Biotechnology 12:173–177 (1994); van den Berg et al., Biotechnology 8:135–139 (1990)).

Cloned APS genes can also be expressed in heterologous bacterial and fungal hosts with the aim of increasing the efficacy of biocontrol strains of such bacterial and fungal hosts. Microorganisms which are suitable for the heterologous overexpression of APS genes are all microorganisms which are capable of colonizing plants or the rhizosphere. As such they will be brought into contact with phytopathogenic fungi, bacteria and nematodes causing an inhibition of their growth. These include gram-negative microorganisms such as Pseudomonas, Enterobacter and Serratia, the gram-positive microorganism Bacillus and the fungi Trichoderma and Gliocladium. Particularly preferred heterologous hosts are *Pseudomonas fluorescens, Pseudomonas putida, Pseudomonas cepacia, Pseudomonas aureofaciens, Pseudomonas aurantiaca, Enterobacter cloacae, Serratia marscesens, Bacillus subtilis, Bacillus cereus, Trichoderma viride, Trichoderma harzianum* and *Gliocladium virens*. In preferred embodiments of the invention the biosynthetic genes for pyrrolnitrin, soraphen, phenazine, and peptide antibiotics are transferred to the particularly preferred heterologous hosts listed above. In a particularly preferred embodiment, the biosynthetic genes for phenazine and/or soraphen are transferred to and expressed in *Pseudomonas fluorescens* strain CGA267356 (described in the published application EU 0 472 494) which has biocontrol utility due to its production of pyrrolnitrin (but not phenazine). In another preferred embodiment, the biosynthetic genes for pyrrolnitrin and/or soraphen are transferred to *Pseudomonas aureofaciens* strain 30-84 which has biocontrol characteristics due to its production of phenazine. Expression in heterologous biocontrol strains requires the selection of vectors appropriate for replication in the chosen host and a suitable choice of promoter. Techniques are well known in the art for expression in gram-negative and gram-positive bacteria and fungi and are described elsewhere in this specification.

Expression of Genes for Anti-phytopathogenic Substances in Plants

The APS biosynthetic genes of this invention are expressed in transgenic plants thus causing the biosynthesis of the selected APS in the transgenic plants. In this way transgenic plants with enhanced resistance to phytopathogenic fungi, bacteria and nematodes are generated. For their expression in transgenic plants, the APS genes and adjacent sequences may require modification and optimization.

Although in many cases genes from microbial organisms can be expressed in plants at high levels without modification, low expression in transgenic plants may result from APS genes having codons which are not preferred in plants. It is known in the art that all organisms have specific preferences for codon usage, and the APS gene codons can be changed to conform with plant preferences, while maintaining the amino acids encoded. Furthermore, high expression in plants is best achieved from coding sequences which have at least 35% GC content, and preferably more than 45%. Microbial genes which have low GC contents may express poorly in plants due to the existence of ATTTA motifs which may destabilize messages, and AATAAA motifs which may cause inappropriate polyadenylation. In addition, potential APS biosynthetic genes can be screened for the existence of illegitimate splice sites which may cause message truncation. All changes required to be made within the APS coding sequence such as those described above can be made using well known techniques of site directed mutagenesis, PCR, and synthetic gene construction using the methods described in the published patent applications EP 0 385 962 (to Monsanto), EP 0 359 472 (to Lubrizol, and WO 93/07278 (to Ciba-Geigy). The preferred APS biosynthetic genes may be unmodified genes, should these be expressed at high levels in target transgenic plant species, or alternatively may be genes modified by the removal of destabilization and inappropriate polyadenylation motifs and illegitimate splice sites, and further modified by the incorporation of plant preferred codons, and further with a GC content preferred for expression in plants. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)).

For efficient initiation of translation, sequences adjacent to the initiating methionine may require modification. The sequences cognate to the selected APS genes may initiate translation efficiently in plants, or alternatively may do so inefficiently. In the case that they do so inefficiently, they can be modified by the inclusion of sequences known to be effective in plants. Joshi has suggested an appropriate consensus for plants (NAR 15:6643-6653 (1987); SEQ ID NO:8)) and Clontech suggests a further consensus translation initiator (1993/1994 catalog, page 210; SEQ ID NO:7).

These consensuses are suitable for use with the APS biosynthetic genes of this invention. The sequences are incorporated into the APS gene construction, up to and including the ATG (whilst leaving the second amino acid of the APS gene unmodified), or alternatively up to and including the GTC subsequent to the ATG (with the possibility of modifying the second amino acid of the transgene).

Expression of APS genes in transgenic plants is behind a promoter shown to be functional in plants. The choice of promoter will vary depending on the temporal and spatial requirements for expression, and also depending on the target species. For the protection of plants against foliar pathogens, expression in leaves is preferred; for the protection of plants against ear pathogens, expression in inflorescences (e.g. spikes, particles, cobs etc.) is preferred; for protection of plants against root pathogens, expression in roots is preferred; for protection of seedlings against soilborne pathogens, expression in roots and/or seedlings is preferred. In many cases, however, expression against more than one type of phytopathogen will be sought, and thus expression in multiple tissues will be desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the APS biosynthetic genes. In some cases, expression of APSs in plants may provide protection against insect pests. Transgenic expression of the biosynthetic genes for the APS beauvericin (isolated from Beauveria bassiana) may, for example provide protection against insect pests of crop plants.

Preferred promoters which are expressed constitutively include the CaMV 35S and 19S promoters, and promoters from genes encoding actin or ubiquitin. Further preferred constitutive promoters are those from the 12(4-28), CP21, CP24, CP38, and CP29 genes whose cDNAs are provided by this invention.

The APS genes of this invention can also be expressed under the regulation of promoters which are chemically regulated. This enables the APS to be synthesized only when the crop plants are treated with the inducing chemicals, and APS biosynthesis subsequently declines. Preferred technology for chemical induction of gene expression is detailed in the published application EP 0 332 104 (to Ciba-Geigy) and pending application 08/121,271 (incorporated herein by reference). A preferred promoter for chemical induction is the tobacco PR-1a promoter.

A preferred category of promoters is that which is wound inducible. Numerous promoters have been described which are expressed at wound sites and also at the sites of phytopathogen infection. These are suitable for the expression of APS genes because APS biosynthesis is turned on by phytopathogen infection and thus the APS only accumulates when infection occurs. Ideally, such a promoter should only be active locally at the sites of infection, and in this way APS only accumulates in cells which need to synthesize the APS to kill the invading phytopathogen. Preferred promoters of this kind include those described by Stanford et al. Mol. Gen. Genet. 215:200–208 (1989), Xu et al. Plant Molec. Biol. 22:573–588 (1993), Logemann et al. Plant Cell 1:151–158 (1989), Rohrmeier & Lehle, Plant Molec. Biol. 22:783–792 (1993), Firek et al. Plant Molec. Biol. 22:129–142 (1993), and Warner et al. Plant J. 3:191–201 (1993).

Preferred tissue specific expression patterns include green tissue specific, root specific, stem specific, and flower specific. Promoters suitable for expression in green tissue include many which regulate genes involved in photosynthesis and many of these have been cloned from both monocotyledons and dicotyledons. A preferred promoter is the maize PEPC promoter from the phosphoenol carboxylase gene (Hudspeth & Grula, Plant Molec. Biol. 12:579–589 (1989)). A preferred promoter for root specific expression is that described by de Framond (FEBS 290:103–106 (1991); EP 0 452 269 to Ciba-Geigy) and a further preferred root-specific promoter is that from the T-1 gene provided by this invention. A preferred stem specific promoter is that described in patent application WO 93/07278 (to Ciba-Geigy) and which drives expression of the maize trpA gene.

Preferred embodiments of the invention are transgenic plants expressing APS biosynthetic genes in a root-specific fashion. In an especially preferred embodiment of the invention the biosynthetic genes for pyrrolnitrin are expressed behind a root specific promoter to protect transgenic plants against the phytopathogen Rhizoctonia. In another especially preferred embodiment of the invention the biosynthetic genes for phenazine are expressed behind a root specific promoter to protect transgenic plants against the phytopathogen *Gaeumannomyces graminis*. Further preferred embodiments are transgenic plants expressing APS biosynthetic genes in a wound-inducible or pathogen infection-inducible manner. For example, a further especially preferred embodiment involves the expression of the biosynthetic genes for soraphen behind a wound-inducible or pathogen-inducible promoter for the control of foliar pathogens.

In addition to the selection of a suitable promoter, constructions for APS expression in plants require an appropriate transcription terminator to be attached downstream of the heterologous APS gene. Several such terminators are available and known in the art (e.g. tml from CaMV, E9 from rbcS). Any available terminator known to function in plants can be used in the context of this invention.

Numerous other sequences can be incorporated into expression cassettes for APS genes. These include sequences which have been shown to enhance expression such as intron sequences (e.g. from Adh1 and bronze 1) and viral leader sequences (e.g. from TMV, MCMV and AMV).

The overproduction of APSs in plants requires that the APS biosynthetic gene encoding the first step in the pathway will have access to the pathway substrate. For each individual APS and pathway involved, this substrate will likely differ, and so too may its cellular localization in the plant. In many cases the substrate may be localized in the cytosol, whereas in other cases it may be localized in some subcellular organelle. As much biosynthetic activity in the plant occurs in the chloroplast, often the substrate may be localized to the chloroplast and consequently the APS biosynthetic gene products for such a pathway are best targeted to the appropriate organelle (e.g. the chloroplast). Subcellular localization of transgene encoded enzymes can be undertaken using techniques well known in the art. Typically, the DNA encoding the target peptide from a known organelle-targeted gene product is manipulated and fused upstream of the required APS gene/s. Many such target sequence are known for the chloroplast and their functioning in heterologous constructions has been shown. In a preferred embodiment of this invention the genes for pyrrolnitrin biosynthesis are targeted to the chloroplast because the pathway substrate tryptophan is synthesized in the chloroplast.

In some situations, the overexpression of APS gene may deplete the cellular availability of the substrate for a particular pathway and this may have detrimental effects on the cell. In situations such as this it is desirable to increase the amount of substrate available by the overexpression of genes which encode the enzymes for the biosynthesis of the substrate. In the case of tryptophan (the substrate for pyrrolnitrin biosynthesis) this can be achieved by overexpressing the trpA and trpB genes as well as anthranilate synthase subunits. Similarly, overexpression of the enzymes for chorismate biosynthesis such as DAHP synthase will be effective in producing the precursor required for phenazine production. A further way of making more substrate available is by the turning off of known pathways which utilize specific substrates (provided this can be done without detrimental side effects). In this manner, the substrate synthesized is channeled towards the biosynthesis of the APS and not towards other compounds.

Vectors suitable for plant transformation are described elsewhere in this specification. For Agrobacterium-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4:1093–1096 (1986)). For both direct gene transfer and Agrobacterium-mediated transfer, transformation is usually (but not necessarily) undertaken with a selectable marker which may provide resistance to an antibiotic (kanamycin, hygromycin or methatrexate) or a herbicide (basta). The choice of selectable marker is not, however, critical to the invention.

Synthesis of an APS in a transgenic plant will frequently require the simultaneous overexpression of multiple genes encoding the APS biosynthetic enzymes. This can be achieved by transforming the individual APS biosynthetic genes into different plant lines individually, and then crossing the resultant lines. Selection and maintenance of lines carrying multiple genes is facilitated if each the various transformation constructions utilize different selectable markers. A line in which all the required APS biosynthetic genes have been pyramided will synthesize the APS, whereas other lines will not. This approach may be suitable for hybrid crops such as maize in which the final hybrid is necessarily a cross between two parents. The maintenance of different inbred lines with different APS genes may also be advantageous in situations where a particular APS pathway may lead to multiple APS products, each of which has a utility. By utilizing different lines carrying different alternative genes for later steps in the pathway to make a hybrid cross with lines carrying all the remaining required genes it is possible to generate different hybrids carrying different selected APSs which may have different utilities.

Alternate methods of producing plant lines carrying multiple genes include the retransformation of existing lines already transformed with an APS gene or APS genes (and selection with a different marker), and also the use of single transformation vectors which carry multiple APS genes, each under appropriate regulatory control (i.e. promoter, terminator etc.). Given the ease of DNA construction, the manipulation of cloning vectors to carry multiple APS genes is a preferred method.

Production of Antipathogenic Substances in Heterologous Hosts

The present invention also provides methods for obtaining APSs. These APSs may be effective in the inhibition of growth of microbes, particularly phytopathogenic microbes. The APSs can be produced from organisms in which the APS genes have been overexpressed, and suitable organisms for this include gram-negative and gram-positive bacteria and yeast, as well as plants. For the purposes of APS production, the significant criteria in the choice of host organism are its ease of manipulation, rapidity of growth (i.e. fermentation in the case of microorganisms), and its lack of susceptibility to the APS being overproduced. These methods of APS production have significant advantages over the chemical synthesis technology usually used in the preparation of APSs such as antibiotics. These advantages are the cheaper cost of production, and the ability to synthesize compounds of a preferred biological enantiomer, as opposed to the racemic mixtures inevitably generated by organic synthesis. The ability to produce stereochemically appropriate compounds is particularly important for molecules with many chirally active carbon atoms. APSs produced by heterologous hosts can be used in medical (i.e. control of pathogens and/or infectious disease) as well as agricultural applications.

Formulation of Antipathogenic Compositions

The present invention further embraces the preparation of antifungal compositions in which the active ingredient is the antibiotic substance produced by the recombinant biocontrol agent of the present invention or alternatively a suspension or concentrate of the microorganism. The active ingredient is homogeneously mixed with one or more compounds or groups of compounds described herein. The present invention also relates to methods of treating plants, which comprise application of the active ingredient, or antifungal compositions containing the active ingredient, to plants.

The active ingredients of the present invention are normally applied in the form of compositions and can be applied to the crop area or plant to be treated, simultaneously or in succession, with further compounds. These compounds can be both fertilizers or micronutrient donors or other preparations that influence plant growth. They can also be selective herbicides, insecticides, fungicides, bactericides, nematicides, mollusicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

A preferred method of applying active ingredients of the present invention or an agrochemical composition which contains at least one of the active ingredients is leaf application. The number of applications and the rate of application depend on the intensity of infestation by the corresponding phytopathogen (type of fungus). However, the active ingredients can also penetrate the plant through the roots via the soil (systemic action) by impregnating the locus of the plant with a liquid composition, or by applying the compounds in solid form to the soil, e.g. in granular form (soil application). The active ingredients may also be applied to seeds (coating) by impregnating the seeds either with a liquid formulation containing active ingredients, or coating them with a solid formulation. In special cases, further types of application are also possible, for example, selective treatment of the plant stems or buds.

The active ingredients are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations, for example, in polymer substances. Like the nature of the compositions, the methods of application, such as spraying, atomizing, dusting, scattering or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 500 g a.i./ha.

The formulations, compositions or preparations containing the active ingredients and, where appropriate, a solid or liquid adjuvant, are prepared in known manner, for example by homogeneously mixing and/or grinding the active ingredients with extenders, for example solvents, solid carriers and, where appropriate, surface-active compounds (surfactants).

Suitable solvents include aromatic hydrocarbons, preferably the fractions having 8 to 12 carbon atoms, for example, xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidized vegetable oils such as epoxidized coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverized plant residues.

Depending on the nature of the active ingredient to be used in the formulation, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids (chains of 10 to 22 carbon atoms), for example the sodium or potassium salts of oleic or stearic acid, or of natural fatty acid mixtures which can be obtained for example from coconut oil or tallow oil. The fatty acid methyltaurin salts may also be used.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and have a 8 to 22 carbon alkyl radical which also includes the alkyl moiety of alkyl radicals, for example, the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnapthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which have, as N-substituent, at least one C8–C22 alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described, for example, in "McCutcheon's Detergents and Emulsifiers Annual," MC Publishing Corp. Ringwood, N.J., 1979, and Sisely and Wood, "Encyclopedia of Surface Active Agents," Chemical Publishing Co., Inc. New York, 1980.

The agrochemical compositions usually contain from about 0.1 to about 99%, preferably about 0.1 to about 95%, and most preferably from about 3 to about 90% of the active ingredient, from about 1 to about 99.9%, preferably from about 1 to about 99%, and most preferably from about 5 to about 95% of a solid or liquid adjuvant, and from about 0 to about 25%, preferably about 0.1 to about 25%, and most preferably from about 0.1 to about 20% of a surfactant.

Whereas commercial products are preferably formulated as concentrates, the end user will normally employ dilute formulations.

EXAMPLES

The following examples serve as further description of the invention and methods for practicing the invention. They are not intended as being limiting, rather as providing guidelines on how the invention may be practiced.

A. Identification of Microorganisms which Produce Antipathogenic Substances

Microorganisms can be isolated from many sources and screened for their ability to inhibit fungal or bacterial growth in vitro. Typically the microorganisms are diluted and plated on medium onto or into which fungal spores or mycelial fragments, or bacteria have been or are to be introduced. Thus, zones of clearing around a newly isolated bacterial colony are indicative of antipathogenic activity.

Example 1

Isolation of Microorganisms with Anti-Rhizoctonia Properties from Soil

A gram of soil (containing approximately $10^6$–$10^8$ bacteria) is suspended in 10 ml sterile water. After vigorously mixing, the soil particles are allowed to settle. Appropriate dilutions are made and aliquots are plated on nutrient agar plates (or other growth medium as appropriate) to obtain 50–100 colonies per plate. Freshly cultured Rhizoctonia mycelia are fragmented by blending and suspensions of fungal fragments are sprayed on to the agar plates after the bacterial colonies have grown to be just visible. Bacterial isolates with antifungal activities can be identified by the fungus-free zones surrounding them upon further incubation of the plates.

The production of bioactive metabolites by such isolates is confirmed by the use of culture filtrates in place of live colonies in the plate assay described above. Such bioassays can also be used for monitoring the purification of the metabolites. Purification may start with an organic solvent extraction step and depending on whether the active principle is extracted into the organic phase or left in the aqueous phase, different chromatographic steps follow. These chromatographic steps are well known in the art. Ultimately, purity and chemical identity are determined using spectroscopic methods.

B. Cloning Antipathogenic Biosynthetic Genes from Microorganisms

Example 2

Shotgun Cloning Antipathogenic Biosynthetic Genes from their Native Source

Related biosynthetic genes are typically located in close proximity to each other in microorganisms and more than one open reading frame is often encoded by a single operon. Consequently, one approach to the cloning of genes which encode enzymes in a single biosynthetic pathway is the transfer of genome fragments from a microorganism containing said pathway to one which does not, with subsequent screening for a phenotype conferred by the pathway.

In the case of biosynthetic genes encoding enzymes leading to the production of an antipathogenic substance (APS), genomic DNA of the antipathogenic substance producing microorganism is isolated, digested with a restriction endonuclease such as Sau3A, size fractionated for the isolation of fragments of a selected size (the selected size depends on the vector being used), and fragments of the selected size are cloned into a vector (e.g. the BamHI site of a cosmid vector) for transfer to E. coli. The resulting E. coli clones are then screened for those which are producing the antipathogenic substance. Such screens may be based on the direct detection of the antipathogenic substance, such as a biochemical assay.

Alternatively, such screens may be based on the adverse effect associated with the antipathogenic substance upon a target pathogen. In these screens, the clones producing the antipathogenic substance are selected for their ability to kill or retard the growth of the target pathogen. Such an inhibitory activity forms the basis for standard screening assays well known in the art, such as screening for the ability to produce zones of clearing on a bacterial plate impregnated with the target pathogen (eg. spores where the target pathogen is a fungus, cells where the target pathogen is a bacterium). Clones selected for their antipathogenic activity can then be further analyzed to confirm the presence of the antipathogenic substance using the standard chemical and biochemical techniques appropriate for the particular antipathogenic substance.

Further characterization and identification of the genes encoding the biosynthetic enzymes for the antipathogenic substance is achieved as follows. DNA inserts from positively identified E. coli clones are isolated and further digested into smaller fragments. The smaller fragments are then recloned into vectors and reinserted into E. coli with subsequent reassaying for the antipathogenic phenotype. Alternatively, positively identified clones can be subjected to λ::Tn5 transposon mutagenesis using techniques well known in the art (e.g. de Bruijn & Lupski, Gene 27:131–149 (1984)). Using this method a number of disruptive transposon insertions are introduced into the DNA shown to confer APS production to enable a delineation of the precise region/s of the DNA which are responsible for APS production. Subsequently, determination of the sequence of the smallest insert found to confer antipathogenic substance production on E. coli will reveal the open reading frames required for APS production. These open reading frames can ultimately be disrupted (see below) to confirm their role in the biosynthesis of the antipathogenic substance.

Various host organisms such as Bacillus and yeast may be substituted for *E. coli* in the techniques described using suitable cloning vectors known in the art for such host. The choice of host organism has only one limitation; it should not be sensitive to the antipathogenic substance for which the biosynthetic genes are being cloned.

Example 3

Cloning Biosynthetic Genes for an Antipathogenic Substance using Transposon Mutagenesis In many microorganisms which are known to produce antipathogenic substances, transposon mutagenesis is a routine technique used for the generation of insertion mutants. This technique has been used successfully in Pseudomonas (e.g. Lam et al., *Plasmid* 13:200–204 (1985)), Bacillus (e.g. Youngman et al., *Proc. Natl. Acad. Sci. USA* 80:2305–2309 (1983)), Staphylococcus (e.g. Pattee, J. Bacteriol. 145:479–488 (1981)), and Streptomyces (e.g. Schauer et al., *J. Bacteriol.* 173:5060–5067 (1991)), among others. The main requirement for the technique is the ability to introduce a transposon containing plasmid into the microorganism enabling the transposon to insert itself at a random position in the genome. A large library of insertion mutants is created by introducing a transposon carrying plasmid into a large number of microorganisms. Introduction of the plasmid into the microorganism can be by any appropriate standard technique such as conjugation, direct gene transfer techniques such as electroporation.

Once a transposon library has been created in the manner described above, the transposon insertion mutants are assayed for production of the APS. Mutants which do not produce the APS would be expected to predominantly occur as the result of transposon insertion into gene sequences required for APS biosynthesis. These mutants are therefore selected for further analysis.

DNA from the selected mutants which is adjacent to the transposon insert is then cloned using standard techniques. For instance, the host DNA adjacent to the transposon insert may be cloned as part of a library of DNA made from the genomic DNA of the selected mutant. This adjacent host DNA is then identified from the library using the transposon as a DNA probe. Alternatively, if the transposon used contains a suitable gene for antibiotic resistance, then the insertion mutant DNA can be digested with a restriction endonuclease which will be predicted not to cleave within this gene sequence or between its sequence and the host insertion point, followed by cloning of the fragments thus generated into a microorganism such as *E. coli* which can then be subjected to selection using the chosen antibiotic.

Sequencing of the DNA beyond the inserted transposon reveals the adjacent host sequences. The adjacent sequences can in turn be used as a hybridization probe to reclone the undisrupted native host DNA using a non-mutant host library. The DNA thus isolated from the non-mutant is characterized and used to complement the APS deficient phenotype of the mutant. DNA which complements may contain either APS biosynthetic genes or genes which regulate all or part of the APS biosynthetic pathway. To be sure isolated sequences encode biosynthetic genes they can be transferred to a heterologous host which does not produce the APS and which is insensitive to the APS (such as *E. coli*). By transferring smaller and smaller pieces of the isolated DNA and the sequencing of the smallest effective piece, the APS genes can be identified. Alternatively, positively identified clones can be subjected to λ::Tn5 transposon mutagenesis using techniques well known in the art (e.g. de Bruijn & Lupski, Gene 27:131–149 (1984)). Using this method a number of disruptive transoposon insertions are introduced into the DNA shown to confer APS production to enable a delineation of the precise region/s of the DNA which are responsible for APS production. These latter steps are undertaken in a manner analagous to that described in example 1. In order to avoid the possibility of the cloned genes not being expressed in the heterologous host due to the non-functioning of their heterologous promoter, the cloned genes can be transferred to an expression vector where they will be fused to a promoter known to function in the heterologous host. In the case of *E. coli* an example of a suitable expression vector is pKK223 which utilizes the tac promoter. Similar suitable expression vectors also exist for other hosts such as yeast and are well known in the art. In general such fusions will be easy to undertake because of the operon-type organization of related genes in microorganisms and the likelihood that the biosynthetic enzymes required for APS biosynthesis will be encoded on a single transcript requiring only a single promoter fusion.

Example 4

Cloning Antipathogenic Biosynthetic Genes using Mutagenesis and Complementation

A similar method to that described above involves the use of non-insertion mutagenesis techniques (such as chemical mutagenesis and radiation mutagenesis) together with complementation. The APS producing microorganism is subjected to non-insertion mutagenesis and mutants which lose the ability to produce the APS are selected for further analysis. A gene library is prepared from the parent APS-producing strain. One suitable approach would be the ligation of fragments of 20–30 kb into a vector such as pVK100 (Knauf et al. Plasmid 8:45–54 (1982)) into *E. coli* harboring the tra+ plasmid pRK2013 which would enable the transfer by triparental conjugation back to the selected APS-minus mutant (Ditta et al. Proc. Natl. Acad. Sci. USA 77:7247–7351 (1980)). A further suitable approach would be the transfer back to the mutant of the genes library via electroporation. In each case subsequent selection is for APS production. Selected colonies are further characterized by the retransformation of APS-minus mutant with smaller fragments of the complementing DNA to identify the smallest successfully complementing fragment which is then subjected to sequence analysis. As with example 2, genes isolated by this procedure may be biosynthetic genes or genes which regulate the entire or part of the APS biosynthetic pathway. To be sure that the isolated sequences encode biosynthetic gene they can be transferred to a heterologous host which does not produce the APS and is insensitive to the APS (such as E. coli). These latter steps are undertaken in a manner analagous to that described in example 2.

Example 5

Cloning Antipathogenic Biosynthetic Genes by Exploiting Regulators which Control the Expression of the Biosynthetic Genes A further approach in the cloning of APS biosynthetic genes relies on the use of regulators which control the expression of these biosynthetic genes. A library of transposon insertion mutants is created in a strain of microorganism which lacks the regulator or has had the regulator gene disabled by conventional gene disruption techniques. The insertion transposon used carries a promoter-less reporter gene (e.g. lacZ). Once the insertion library has been made, a functional copy of the regulator gene is transferred to the library of cells (e.g. by conjugation or electroporation) and the plated cells are selected for expression of the reporter gene. Cells are assayed before and after transfer of the regulator gene. Colonies which express the reporter gene only in the presence of the regulator gene are insertions adjacent to the promoter of genes regulated by the regulator. Assuming the regulator is specific in its regulation for APS-biosynthetic genes, then the genes tagged by this procedure will be APS-biosynthetic genes. These genes can then be cloned and further characterized using the techniques described in example 2.

Example 6

Cloning Antipathogenic Biosynthetic Genes by Homology

Standard DNA techniques can be used for the cloning of novel antipathogenic biosynthetic genes by virtue of their homology to known genes. A DNA library of the microorganism of interest is made and then probed with radiolabelled DNA derived from the gene/s for APS biosynthesis from a different organism. The newly isolated genes are characterized and sequences and introduced into a heterologous microorganism or a mutant APS-minus strain of the native microorganisms to demonstrate their conferral of APS production.

C. Cloning of Pyrrolnitrin Biosynthetic Genes from Pseudomonas

Pyrrolnitrin is an phenylpyrole compound produced by various strains of Pseudomonas fluorescens. P. fluorescens strains which produce pyrrolnitrin are effective biocontrol strains against Rhizoctonia and Pythium fungal pathogens (WO 94/01561). The biosynthesis of pyrrolnitrin is postulated to start from tryptophan (Chang et al. J. Antibiotics 34:555–566 (1981)).

Example 7

Use of the gafA Regulator Gene for the Isolation of Pyrrolnitrin Biosynthetic Genes from Pseudomonas The gene cluster encoding pyrrolnitrin biosynthetic enzymes was isolated using the basic principle described in example 5 above. The regulator gene used in this isolation procedure was the gafA gene from Pseudomonas fluorescens and is known to be part of a two-component regulatory system controlling certain biocontrol genes in Pseudomonas. The gafA gene is described in detail in pending application 08/087,636 which is hereby incorporated by reference in its entirety and in the published application WO 94/01561. gafA is further described in Gaffney et al. (1994; MPMI 7(4):455–463; also hereby incorporated in its entirety by reference) where it is referred to as "ORF5". The gafA gene has been shown to regulate pyrrolnitrin biosynthesis, chitinase, gelatinase and cyanide production. Strains which lack the gafA gene or which express the gene at low levels (and in consequence gafA-regulated genes also at low levels) are suitable for use in this isolation technique.

Example 8

Isolation of Pyrrolnitrin Biosynthesis Genes in Pseudomonas

The transfer of the gafA gene from MOCG134 to closely related non-pyrrolnitrin producing wild-type strains of Pseudomonas fluorescens results in the ability of these strains to produce pyrrolnitrin. (Gaffney et al., MPMI (1994)); see also Hill et al. Applied And Environmental Microbiology 60 78–85 (1994)). This indicates that these closely related strains have the structural genes needed for pyrrolnitrin biosynthesis but are unable to produce the compound without activation from the gafA gene. One such closely related strain, MOCG133, was used for the identification of the pyrrolnitrin biosynthesis genes. The transposon TnCIB116 (Lam, New Directions in Biological Control: Alternatives for Suppressing Agricultural Pests and Diseases, pp 767–778, Alan R. Liss, Inc. (1990)) was used to mutagenize MOCG133. This transposon, a Tn5 derivative, encodes kanamycin resistance and contains a promotorless lacZ reporter gene near one end. The transposon was introduced into MOCG133 by conjugation, using the plasmid vector pCIB116 (Lam, New Directions in Biological Control: Alternatives for Suppressing Agricultural Pests and Diseases, pp 767–778, Alan R. Liss, Inc. (1990)) which can be mobilized into MOCG133, but cannot replicate in that organism. Most, if not all, of the kanamycin resistant transconjugants were therefore the result of transposition of TnCIB116 into different sites in the MOCG133 genome. When the transposon integrates into the bacterial chromosome behind an active promoter the lacZ reporter gene is activated. Such gene activation can be monitored visually by using the substrate X-gal, which releases an insoluble blue product upon cleavage by the lacZ gene product. Kanamycin resistant transconjugants were collected and arrayed on master plates which were then replica plated onto lawns of E coli strain S17-1 (Simon et al., Bio/techonology 1:784–791 (1983)) transformed with a plasmid carrying the wide host range RK2 origin of replication, a gene for tetracycline selection and the gafA gene. E coli strain S17-1 contains chromosomally integrated tra genes for conjugal transfer of plasmids. Thus, replica plating of insertion transposon mutants onto a lawn of the S17-1/gafA E. coli results in the transfer to the insertion transposon mutants of the gafA-carrying plasmid and enables the activity of the lacZ gene to be assayed in the presence of the gafA regulator (expression of the host gafA is insufficient to cause lacZ expression, and introduction of gafA on a multicopy plasmid is more effective). Insertion mutants which had a "blue" phenotype (i.e. lacZ activity) only in the presence of gafA were identified. In these mutants, the transposon had integrated within genes whose expression were regulated by gafA. These mutants (with introduced gafA) were assayed for their ability to produce cyanide, chitinase, and pyrrolnitrin (as described in Gaffney et al., 1994 MPMI,)—activities known to be regulated by gafA (Gaffney et al., 1994 MPMI,). One mutant did not produce pyrrolnitrin but did produce cyanide and chitinase, indicating that the transposon had inserted in a genetic region involved only in pyrrolnitrin biosynthesis. DNA sequences flanking one end of the transposon were cloned by digesting chromosomal DNA isolated from the selected insertion mutant with XhoI, ligating the fragments derived from this digestion into the XhoI site of pSP72 (Promega, cat. #P2191) and selecting the E. coli transformed with the products of this ligation on kanamycin. The unique XhoI site within the transposon cleaves beyond the gene for kanamycin resistance and enabled the flanking region derived from the parent MOCG133 strain to be concurrently isolated on the same XhoI fragment.

In fact the XhoI site of the flanking sequence was found to be located approximately 1 kb away from the end on the transposon. A subfragment of the cloned XhoI fragment derived exclusively from the ~1 kb flanking sequence was then used to isolate the native (i.e. non-disrupted) gene region from a cosmid library of strain MOCG134. The cosmid library was made from partially Sau3A digested MOCG134 DNA, size selected for fragments of between 30 and 40 kb and cloned into the unique BamHI site of the cosmid vector pCIB119 which is a derivative of c2XB (Bates & Swift, Gene 26:137–146 (1983)) and pRK290 (Ditta et al. Proc. Natl. Acad. Sci. USA 77:7247–7351 (1980)). pCIB119 is a double-cos site cosmid vector which has the wide host range RK2 origin of replication and can therefore replicate in Pseudomonas as well as E. coli. Several clones were isolated from the MOCG134 cosmid clone library using the ~1 kb flanking sequence as a hybridization probe. Of these one clone was found to restore pyrrolnitrin production to the transposon insertion mutant which had lost its ability to produce pyrrolnitrin. This clone had an insertion of ~32 kb and was designated pCIB169. E. coli DH5α containing pCIB169 was deposited at the Agricultural Research Culture Collection (NRRL), 1815 N. University Street, Peoria, Ill. 61604 on May 20, 1994, and assigned accession number NRRL B-21256.

Example 9

Mapping and Tn5 Mutagenesis of pCIB169

Figure 2:
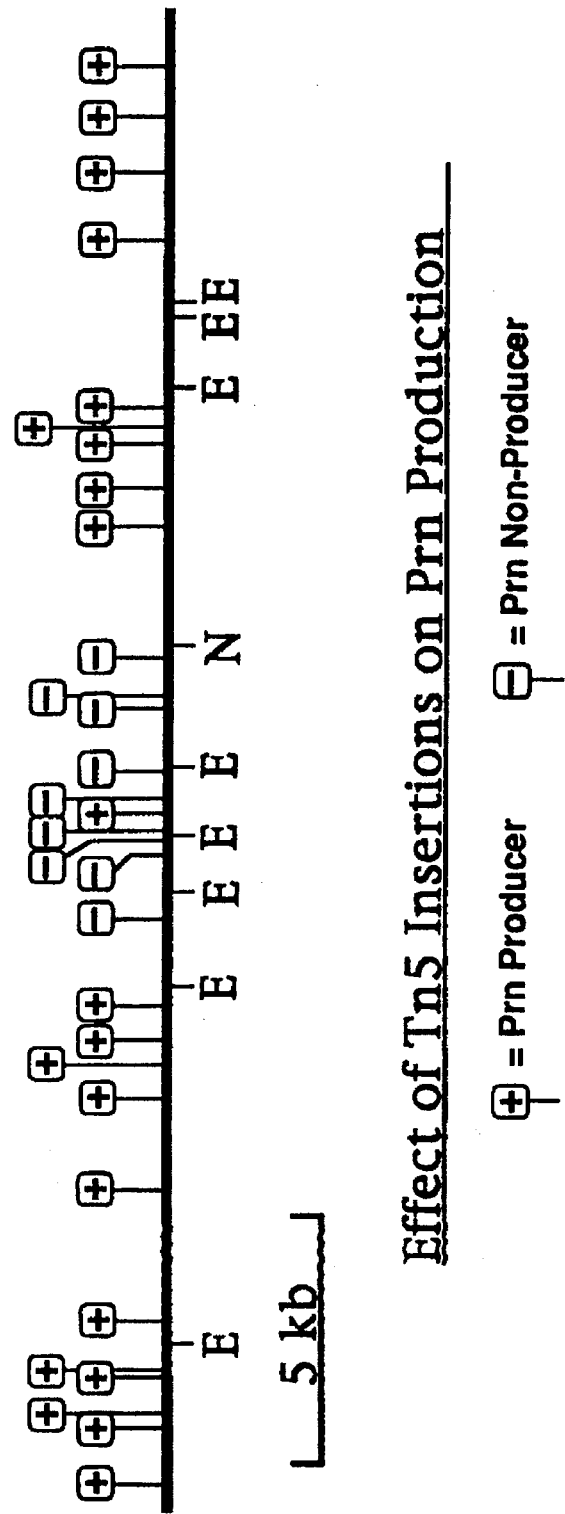
FIG. 2: Insertion points of 30 independent Tn5 insertions along the length of pCIB169 for the identification of the genes for pyrrolnitrin biosynthesis.
Figure 3:
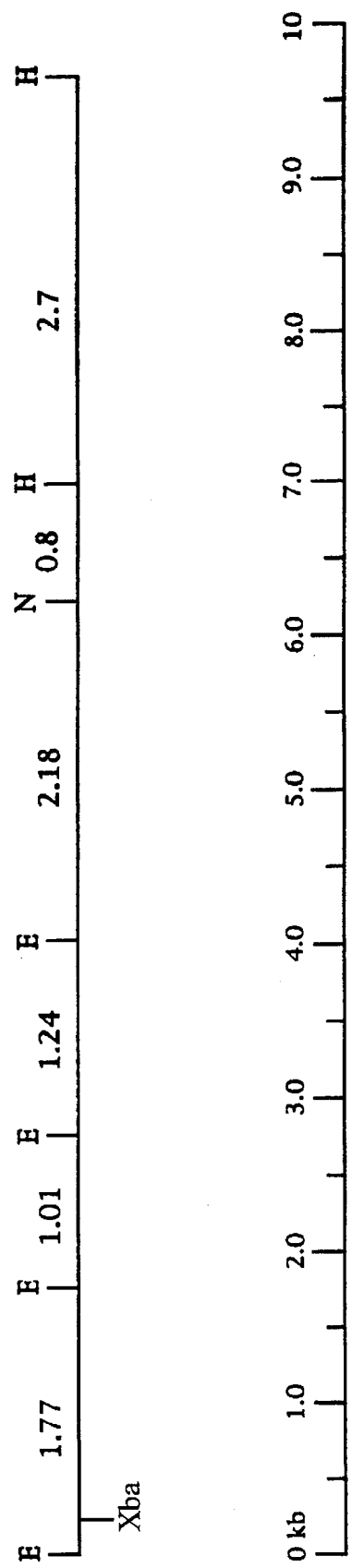
FIG. 3: Restriction map of a 9.7 kb fragment of pCIB169 involved in pyrrolnitrin biosynthesis.

The 32 kb insert of clone pCIB169 was subcloned into pCIB189 in E coli HB101, a derivative of pBR322 which contains a unique NotI cloning site. A convenient NotI site within the 32 kb insert as well as the presence of NotI sites flanking the BamHI cloning site of the parent cosmid vector pCIB119 allowed the subcloning of fragments of 14 and 18 kb into pCIB189. These clones were both mapped by restriction digestion and FIG. 1 shows the result of this. λTn5 transposon mutagenesis was carried out on both the 14 and 18 kb subclones using techniques well known in the art (e.g. de Bruijn & Lupski, Gene 27:131–149 (1984). λTn5 phage conferring kanamycin resistance was used to transfect both the 14 and the 18 kb subclones described above. λTn5 transfections were done at a multiplicity of infection of 0.1 with subsequent selection on kanamycin. Following mutagenesis plasmid DNA was prepared and retransformed into E coli HB101 with kanamycin selection to enable the isolation of plasmid clones carrying Tn5 insertions. A total of 30 independent Tn5 insertions were mapped along the length of the 32 kb insert (see FIG. 2). Each of these insertions was crossed into MOCG134 via double homologous recombination and verified by Southern hybridization using the Tn5 sequence and the pCIB189 vector as hybridization probes to demonstrate the occurrence of double homologous recombination i.e. the replacement of the wild-type MOCG134 gene with the Tn5-insertion gene. Pyrrolnitrin assays were performed on each of the insertions that were crossed into MOCG134 and a genetic region of approximately 6 kb was identified to be involved in pyrrolnitrin production (see FIGS. 3 and 5). This region was found to be centrally located in pCIB169 and was easily subcloned as an XbaI/NotI fragment into pBluescript II KS (Promega). The XbaI/NotI subclone was designated pPRN5.9X/N (see FIG. 4).

Example 10

Identification of Open Reading Frames in the Cloned Genetic Region

Figure 4:
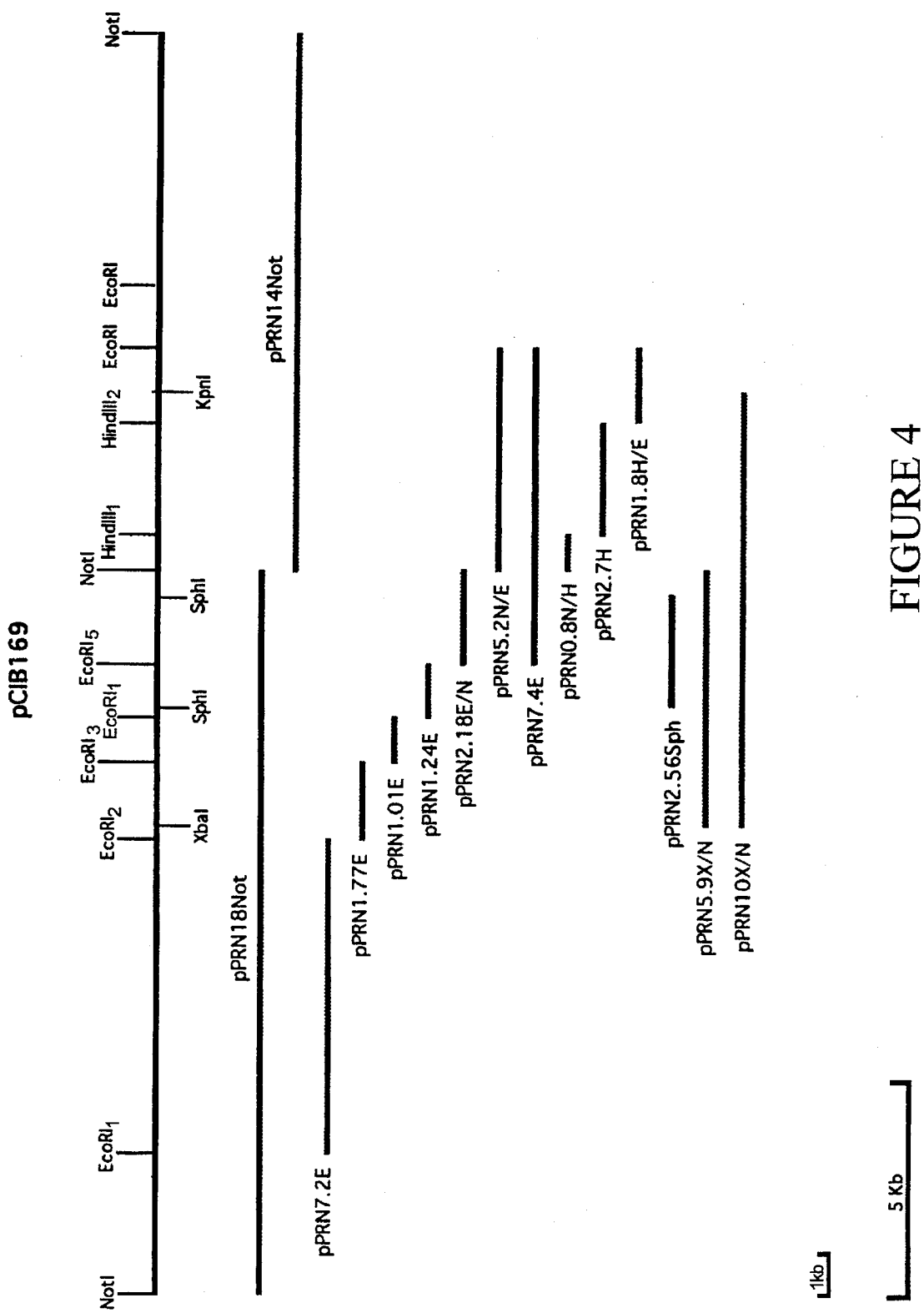
FIG. 4: Location of various subclones derived from pCIB169 isolated for sequence determination purposes.

The genetic region involved in pyrrolnitrin production was subcloned into six fragments for sequencing in the vector pBluescript II KS (see FIG. 4). These fragments spanned the ~6 kb XbaI/NotI fragment described above and extended from the EcoRI site on the left side of FIG. 4 to the rightmost HindIII site (see FIG. 4). The sequence of the inserts of clones pPRN1.77E, pPRN1.01E, pPRN1.24E, pPRN2.18E, pPRN0.8H/N, and pPRN2.7H was determined using the Taq DyeDeoxy Terminator Cycle Sequencing Kit supplied by Applied Biosystems, Inc., Foster City, Calif. following the protocol supplied by the manufacturer. Sequencing reactions were run on a Applied Biosystems 373A Automated DNA Sequencer and the raw DNA sequence was assembled and edited using the "INHERIT" software package also from Applied Biosystems, Inc. A contiguous DNA sequence of 9.7 kb was obtained corresponding to the EcoRI/HindIII fragment of FIG. 3 and bounded by EcoRI site #2 and HindIII site #2 depicted in FIG. 4.

Figure 5:
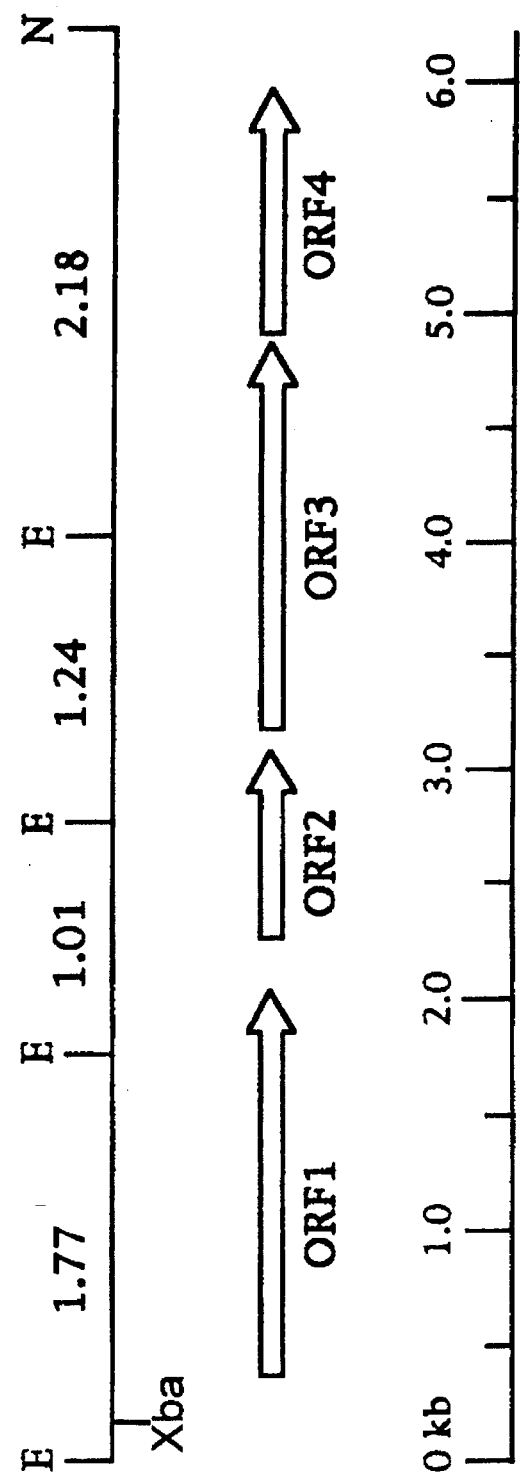
FIG. 5: Localization of the four open reading frames (ORFs 1–4) responsible for pyrrolnitrin biosynthesis in strain MOCG134 on the ~6 kb XbaI/NotI fragment of pCIB169.

DNA sequence analysis was performed on the contiguous 9.7 kb sequence using the GCG software package from Genetics Computer Group, Inc. Madison, Wis. The pattern recognition program "FRAMES" was used to search for open reading frames (ORFs) in all six translation frames of the DNA sequence. Four open reading frames were identified using this program and the codon frequency table from ORF2 of the gafA gene region which was previously published (WO 94/05793; FIG. 5). These ORFs lie entirely within the ~6 kb XbaI/NotI fragment referred to in example 9 (FIG. 4) and are contained within the sequence disclosed as SEQ ID NO:1. By comparing the codon frequency usage table from MOCG134 DNA sequence of the gafA region to these four open reading frames, very few rare codons were used indicating that codon usage was similar in both of these gene regions. This strongly suggested that the four open reading frames were real. At a 3' position to the fourth reading frame numerous ρ-independent stem loop structures were found suggesting a region where transcription could be stopped. It was thus apparent that all four ORFs were translated from a single transcript. Sequence data obtained for the regions beyond the four identified ORFs revealed a fifth open reading frame which was subsequently determined to not be involved in pyrrolnitrin synthesis based on E. coli expression studies.

Example 11

Expression of Pyrrolnitrin Biosynthetic Genes in E. coli

To determine if only four genes were needed for pyrrolnitrin production, these genes were transferred into E. coli which was then assayed for pyrrolnitrin production. The expression vector pKK223-3 was used to over-express the cloned operon in *E. coli.* (Brosius & Holy, Proc. Natl. Acad. Sci. USA 81:6929 (1984)). pKK223-3 contains a strong tac promoter which, in the appropriate host, is regulated by the lac repressor and induced by the addition of isopropyl-β-D-thiogalactoside (IPTG) to the bacterial growth medium. This vector was modified by the addition of further useful restriction sites to the existing multiple cloning site to facilitate the cloning of the ~6 kb XbaI/NotI fragment (see example 7 and FIG. 4) and a 10 kb XbaI/KpnI fragment (see FIG. 4) for expression studies. In each case the cloned fragment was under the control of the *E. coli* tac promoter (with IPTG induction), but was cloned in a transcriptional fusion so that the ribosome binding site used would be that derived from Pseudomonas. Each of these clones was transformed into *E. coli* XL1-blue host cells and induced with 2.5 mM IPTG before being assayed for pyrrolnitrin by thin layer chromatography. Cultures were grown for 24 h after IPTG induction in 10 ml L broth at 37° C. with rapid shaking, then extracted with an equal volume of ethyl acetate. The organic phase was recovered, allowed to evaporated under vacuum and the residue dissolved in 20 µl of methanol. Silica gel thin layer chromatography (TLC) plates were spotted with 10 µl of extract and run with toluene as the mobile phase. The plates were allowed to dry and sprayed with van Urk's reagent to visualize. Urk's reagent comprises 1 g p-Dimethylaminobenzaldehyde in 50 ml 36% HCL and 50 ml 95% ethanol. Under these conditions pyrrolnitrin appears as a purple spot on the TLC plate. This assay confirmed the presence of pyrrolnitrin in both of the expression constructs. HPLC and mass spectrometry analysis further confirmed the presence of pyrrolnitrin in both of the extracts. HPLC analysis can be undertaken directly after redissolving in methanol (in this case the sample is redissolved in 55% methanol) using a Hewlett Packard Hypersil ODS column (5 µM) of dimensions 100×2.1 mm. Pyrrolnitrin elutes after about 14 min.

Example 12

Construction of Pyrrolnitrin Gene Deletion Mutants

Figure 6:
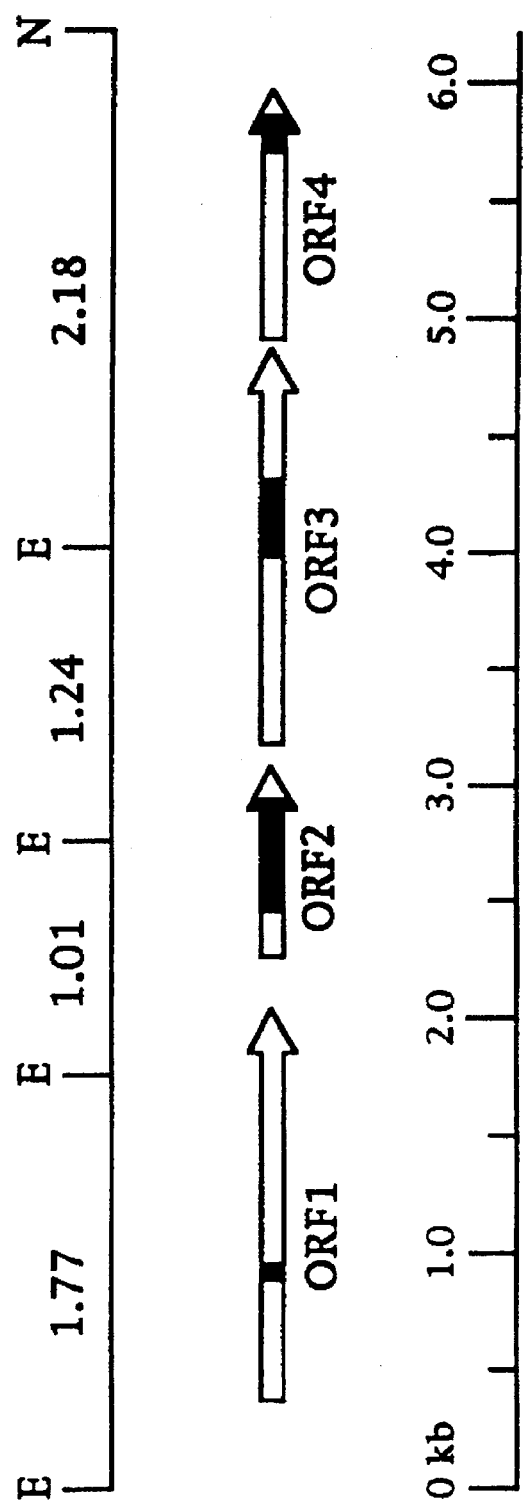
FIG. 6: Location of the sites of disruption of ORFs 1–4 in the pyrrolnitrin gene cluster of MOCG134.

To further demonstrate the involvement of the 4 ORFs in pyrrolnitrin biosynthesis, independent deletions were created in each ORF and transferred back into *Pseudomonas fluorescens* strain MOCG134 by homologous recombination. The plasmids used to generate deletions are depicted in FIG. 4 and the positions of the deletions are shown in FIG. 6. Each ORF is identified within the sequence disclosed as SEQ ID NO:1.

ORF1 (SEQ ID NO:2):

The plasmid pPRN1.77E was digested with Mlu1 to liberate a 78 bp fragment internally from ORF1. The remaining 4.66 kb vector-containing fragment was recovered, religated with T4 DNA ligase, and transformed into the *E. coli* host strain DH5α. This new plasmid was linearized with Mlu1 and the Klenow large fragment of DNA polymerase I was used to create blunt ends (Maniatis et al. Molecular Cloning, Cold Spring Harbor Laboratory (1982)). The neomycin phosphotransferase II (NPTII) gene cassette from pUC4K (Pharmacia) was ligated into the plasmid by blunt end ligation and the new construct, designated pBS (ORF1Δ), was transformed into DH5α. The construct contained a 78 bp deletion of ORF1 at which position the NPTII gene conferring kanamycin resistance had been inserted. The insert of this plasmid (i.e. ORF1 with NPTII insertion) was then excised from the pBluescript 11 KS vector with EcoRI, ligated into the EcoRI site of the vector pBR322 and transformed into the *E. coli* host strain HB101. The new plasmid was verified by restriction enzyme digestion and designated pBR322(ORF1Δ).

ORF2 (SEQ ID NO:3):

The plasmids pPRN1.24E and pPRN1.01E containing contiguous EcoRI fragments spanning ORF2 were double digested with EcoRI and XhoI. The 1.09 kb fragment from pPRN1.24E and the 0.69 Kb fragment from pPRN1.01E were recovered and ligated together into the EcoRI site of pBR322. The resulting plasmid was transformed into the host strain DH5α and the construct was verified by restriction enzyme digestion and electrophoresis. The plasmid was then linearized with XhoI, the NPTII gene cassette from pUC4K was inserted, and the new construct, designated pBR(ORF2Δ), was transformed into HB 101. The construct was verified by restriction digestions and agarose gel electrophoresis and contains NPTII within a 472 bp deletion of the ORF2 gene.

ORF3 (SEQ ID NO:4):

The plasmid pPRN2.56Sph was digested with PstI to liberate a 350 bp fragment. The remaining 2.22 kb vector-containing fragment was recovered and the NPTII gene cassette from pUC4K was ligated into the PstI site. This intermediate plasmid, designated pUC(ORF3Δ), was transformed into DH5α and verified by restriction digestion and agarose gel electrophoresis. The gene deletion construct was excised from pUC with SphI and ligated into the Sph1 site of pBR322. The new plasmid, designated pBR(ORF5Δ), was verified by restriction enzyme digestion and agarose gel electrophoresis. This plasmid contains the NPTII gene within a 350 bp deletion of the ORF3 gene.

ORF4 (SEQ ID NO:5):

The plasmid pPRN2.18E/N was digested with AatII to liberate 156 bp fragment. The remaining 2.0 kb vector-containing fragment was recovered, religated, transformed into DH5α, and verified by restriction enzyme digestion and electrophoresis. The new plasmid was linearized with AatII and T4 DNA polymerase was used to create blunt ends. The NPTII gene cassette was ligated into the plasmid by blunt-end ligation and the new construct, designated pBS (ORF4Δ), was transformed into DH5α. The insert was excised from the pBluescript II KS vector with EcoRI, ligated into the EcoRI site of the vector pBR322 and transformed into the *E. coli* host strain HB101. The identity of the new plasmid, designated pBR(ORF4Δ), was verified by restriction enzyme digestion and agarose gel electrophoresis. This plasmid contains the NPTII gene within a 264 bp deletion of the ORF4 gene.

$Km^R$ Control:

To control for possible effects of the kanamycin resistance marker, the NPTII gene cassette from pUC4K was inserted upstream of the pyrrolnitrin gene region. The plasmid pPRN2.5S (a subclone of pPRN7.2E) was linearized with PstI and the NPTII cassette was ligated into the PstI site. This intermediate plasmid was transformed into DH5α and verified by restriction digestions and agarose gel electrophoresis. The gene insertion construct was excised from pUC with SphI and ligated into the SphI site of pBR322. The new plasmid, designated pBR(2.5SphIKm$^R$), was verified by restriction enzyme digestion and agarose gel electrophoresis. It contains the NPTII region inserted upstream of the pyrrolnitrin gene region.

Each of the gene deletion constructs was mobilized into MOCG134 by triparental mating using the helper plasmid pRK2013 in *E. coli* HB101. Gene replacement mutants were selected by plating on Pseudomonas Minimal Medium (PMM) supplemented with 50 mg/ml kanamycin and counterselected on PMM supplemented with 30 mg/ml tetracycline. Putative perfect replacement mutants were verified by Southern hybridization by probing EcoRI digested DNA with pPRN18Not, pBR322 and an NPTII cassette obtained from pUC4K (Pharmacia 1994 catalog no. 27-4958-01). Verification of perfect hybridization was apparent by lack of hybridization to pBR322, hybridization of pPRN18Not to an appropriately size-shifted EcoRI fragment (reflecting deletion and insertion of NPTII), hybridization of the NPTII probe to the shifted band, and the disappearance of a band corresponding a deleted fragment.

After verification, deletion mutants were tested for production of pyrrolnitrin, 2-hexyl-5-propyl-resorcinol, cyanide, and chitinase production. A deletion in any one of the ORFs abolished pyrrolnitrin production, but did not affect production of the other substances. The presence of the NPTII gene cassette in the $Km^R$ control had no effect on the production of pyrrolnitrin, 2-hexyl-5-propyl-resorcinol, cyanide or chitinase. These experiments demonstrated the requirement of each of the four ORFs for pyrrolnitrin production.

D. Cloning of Resorcinol Biosynthetic Genes from Pseudomonas 2-hexyl-5-propyl-resorcinol is a further APS produced by certain strains of Pseudomonas. It has been shown to have antipathogenic activity against Gram-positive bacteria (in particular Clavibacter spp.), mycobacteria, and fungi.

Example 13

Isolation of Genes Encoding Resorcinol

Two transposon-insertion mutants have been isolated which lack the ability to produce the antipathogenic substance 2-hexyl-5-propyl-resorcinol which is a further substance known to be under the global regulation of the gala gene in *Pseudomonas fluorescens* (WO 94/01561). The insertion transposon TnCIB116 was used to generate libraries of mutants in MOCG134 and a gafA⁻ derivative of MOCG134 (BL1826). The former was screened for changes in fungal inhibition in vitro; the latter was screened for genes regulated by gafA after introduction of gafA on a plasmid (see Section C). Selected mutants were characterized by HPLC to assay for production of known compounds such as pyrrolnitrin and 2-hexyl-5-propyl-resorcinol. The HPLC assay enabled a comparison of the novel mutants to the wild-type parental strain. In each case, the HPLC peak corresponding to 2-hexyl-5-propyl-resorcinol was missing in the mutant. The mutant derived from MOCG134 is designated BL1846. The mutant derived from BL1826 is designated BL1911. HPLC for resorcinol follows the same procedure as for pyrrolnitrin (see example 11) except that 100% methanol is applied to the column at 20 min to elute resorcinol.

The resorcinol biosynthetic genes can be cloned from the above-identified mutants in the following manner. Genomic DNA is prepared from the mutants, and clones containing the transposon insertion and adjacent Pseudomonas sequence are obtained by selecting for kanamycin resistant clones (kanamycin resistance is encoded by the transposon). The cloned Pseudomonas sequence is then used as a probe to identify the native sequences from a genomic library of *P. fluorescens* MOCG134. The cloned native genes are likely to represent resorcinol biosynthetic genes.

E. Cloning Soraphen Biosynthetic Genes from Sorangium

Soraphen is a polyketide antibiotic produced by the myxobacterium *Sorangium cellulosum*. This compound has broad antifungal activities which make it useful for agricultural applications. In particular, soraphen has activity against a broad range of foliar pathogens.

Example 14

Isolation of the Soraphen Gene Cluster

Genomic DNA was isolated from *Sorangium cellulosum* and partially digested with Sau3A. Fragments of between 30 and 40 kb were size selected and cloned into the cosmid vector pHC79 (Hohn & Collins, Gene 11:291–298 (1980)) which had been previously digested with BamHI and treated with alkaline phosphatase to prevent self ligation. The cosmid library thus prepared was probed with a 4.6 kb fragment which contains the graI region of *Streptomyces violaceoruber* strain Tü22 encoding ORFs 1–4 responsible for the biosynthesis of granaticin in *S. violaceoruber*. Cosmid clones which hybridized to the graI probe were identified and DNA was prepared for analysis by restriction digestion and further hybridization. Cosmid p98/1 was identified to contain a 1.8 kb SalI fragment which hybridized strongly to the graI region; this SalI fragment was located within a larger 6.5 kb PvuI fragment within the ~40 kb insert of p98/1. Determination of the sequence of part of the 1.8 kb SalI insert revealed homology to the acetyltransferase proteins required for the synthesis of erythromycin. Restriction mapping of the cosmid p98/1 was undertaken and generated the map depicted in FIG. 7. The DNA sequence of the soraphen gene cluster is disclosed in SEQ ID NO:6. *E. Coli* HB101 containing p98/1 was deposited at the Agricultural Research Culture Collection (NRRL), 1815 N. University Street, Peoria, Ill. 61604 on May 20, 1994, and assigned accession number NRRL B-21255.

Example 15

Functional Analysis of the Soraphen Gene Cluster

The regions within p98/1 that encode proteins with a role in the biosynthesis of soraphen were identified through gene disruption experiments. Initially, DNA fragments were derived from cosmid p98/1 by restriction with PvuI and cloned into the unique PvuI cloning site (which is within the gene for ampicillin resistance) of the wide host-range plasmid pSUP2021 (Simon et al. in: Molecular Genetics of the Bacteria-Plant Interaction (ed: A Puhler), Springer Verlag, Berlin pp 98–106 (1983)). Transformed *E. coli* HB101 was selected for resistance to chloramphenicol, but sensitivity to ampicillin. Selected colonies carrying appropriate inserts were transferred to *Sorangium cellulosum* SJ3 by conjugation using the method described in the published application EP 0 501 921 and EP the later app. (both to Ciba-Geigy). Plasmids were transferred to *E. coli* ED8767 carrying the helper plasmid pUZ8 (Hedges & Mathew, Plasmid 2:269–278 (1979)) and the donor cells were incubated with *Sorangium cellulosum* SJ3 cells from a stationary phase culture for conjugative transfer essentially as described in EP 0 501 921 (example 5) and EP the later app. (example 2). Selection was on kanmycin, phleomycin and streptomycin. It has been determined that no plasmids tested thus far are capable of autonomous replication in *Sorangium cellulosum*, but rather, integration of the entire plasmid into the chromosome by homologous recombination occurs at a site within the cloned fragment at low frequency. These events can be selected for by the presence of antibiotic resistance markers on the plasmid. Integration of the plasmid at a given site results in the insertion of the plasmid into the chromosome and the concomitant disruption of this region from this event. Therefore, a given phenotype of interest, i.e. soraphen production, can be assessed, and disruption of the phenotype will indicate that the DNA region cloned into the plasmid must have a role in the determination of this phenotype.

Figure 7:
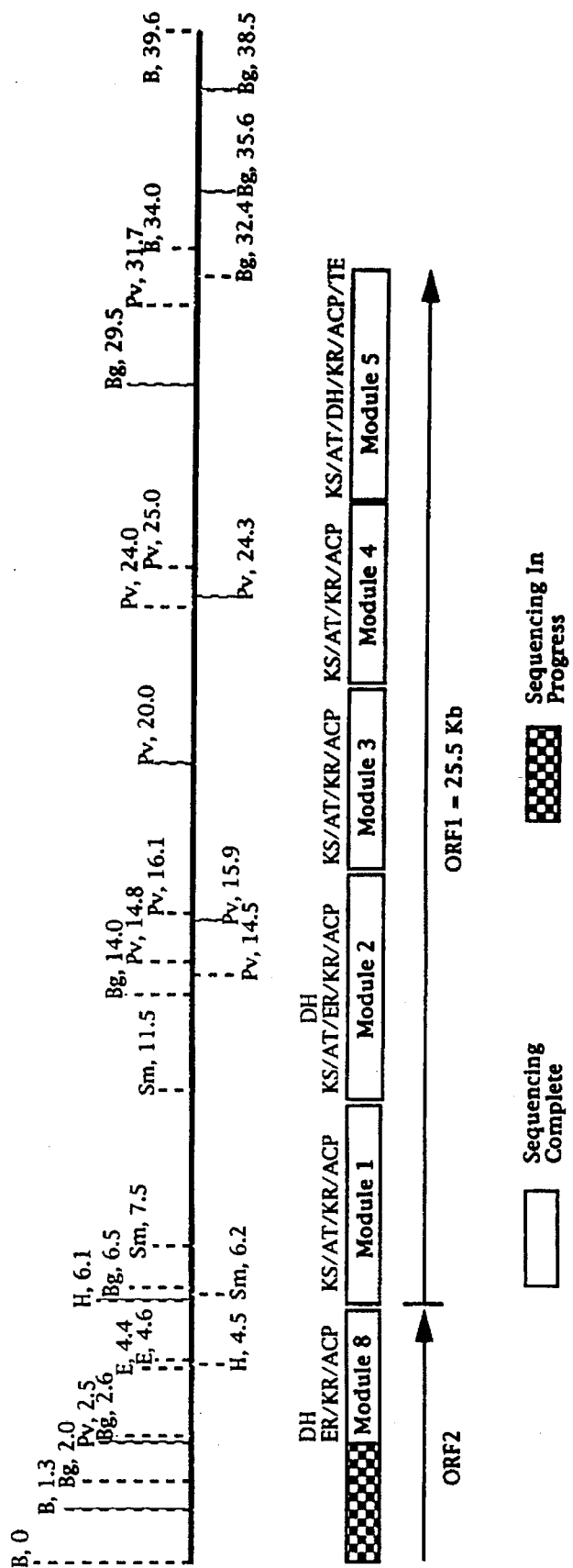
FIG. 7: Restriction map of the cosmid clone p98/1 from *Sorangium cellulosum* carrying the soraphen biosynthetic gene region. The top line depicts the restriction map of p98/1 and shows the position of restriction sites and their distance from the left edge in kilobases. Restriction sites shown include: B, Bam HI; Bg Bgl II; E, Eco RI; H, Hind III; Pv, Pvu I; Sm, Sma I. The boxes below the restriction map depict the location of the biosynthetic modules. The activity domains within each module are designated as follows: β-ketoacylsynthase (KS), Acyltransferase (AT), Ketoreductase (KR), Acyl Carrier Protein (ACP), Dehydratase (DH), Enoyl reductase (ER), and Thioesterase (TE).

Recombinant pSUP2021 clones with PvuI inserts of approximate size 6.5 kb (pSN105/7), 10 kb (pSN120/10), 3.8 kb (pSN120/43-39) and 4.0 kb (pSN120/46) were selected. The map locations (in kb) of these PvuI inserts as shown in FIG. 7 are: pSN105/7-25.0–31.7, pSN120/10-2.5–14.5, pSN120/43–39-16.1–20.0, and pSN120/46-20.0–24.0. pSN105/7 was shown by digestion with PvuI and SalI to contain the 1.8 kb fragment referred to above in example 11. Gene disruptions with the 3.8, 4.0, 6.5, and 10 kb PvuI fragments all resulted in the elimination of soraphen production. These results indicate that all of these fragments contain genes or fragments of genes with a role in the production of this compound.

Figure 8:
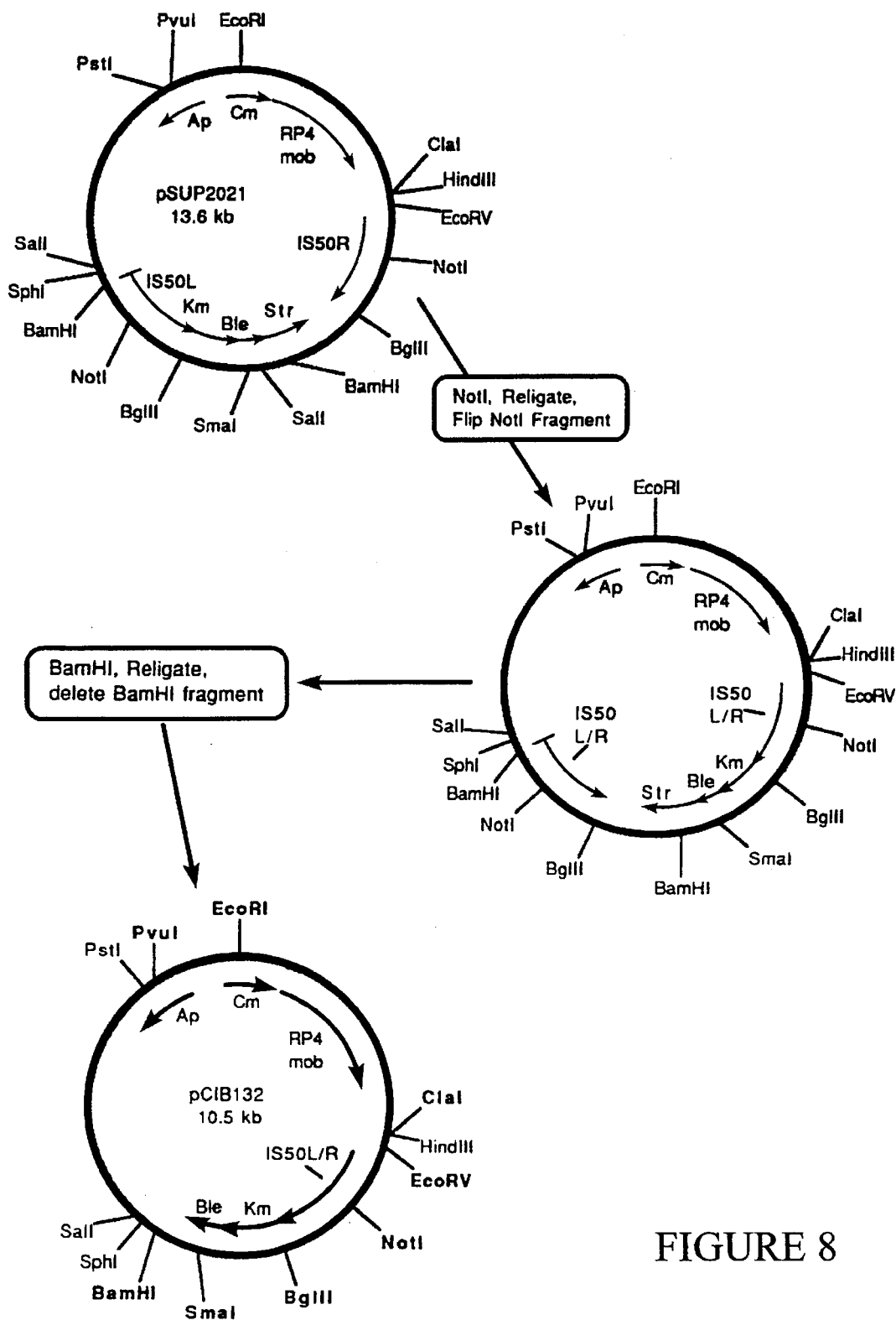
FIG. 8: Construction of pCIB132 from pSUP2021.
Figure 9:
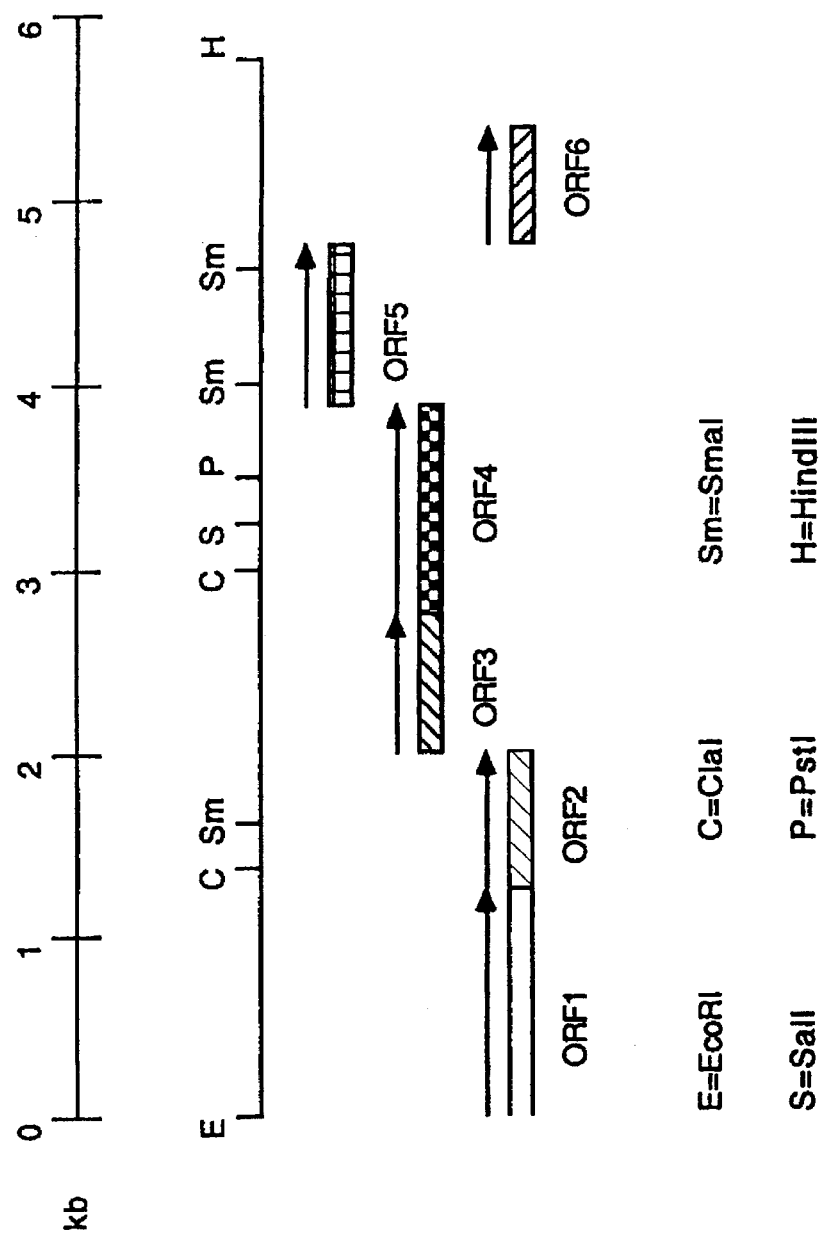
FIG. 9: Restriction map of the clone pLSP18-6H3del3 from *Pseudomonas aureofaciens* carrying the phenazine biosynthetic gene region.

Subsequently gene disruption experiments were performed with two BglII fragments derived from cosmid p98/1. These were of size 3.2 kb (map location 32.4–35.6 on FIG. 7) and 2.9 kb (map location 35.6–38.5 on FIG. 7). These fragments were cloned into the BamHI site of plasmid pCIB132 that was derived from pSUP2021 according to FIG. 8. The ~5 kb NotI fragment of pSUP2021 was excised and inverted, followed by the removal of the ~3 kb BamHI fragment. Neither of these BglII fragments was able to disrupt soraphen biosynthesis when reintroduced into Sorangium using the method described above. This indicates that the DNA of these fragments has no role in soraphen biosynthesis. Examination of the DNA sequence indicates the presence of a thioesterase domain 5' to, but near the BglII site at location 32.4. In addition, there are transcription stop codons immediately after the thioesterase domain which are likely to demarcate the end of the ORF1 coding region. As the 2.9 and 3.2 kb BglII fragments are immediately to the right of these sequences it is likely that there are no other genes downstream from ORF1 that are involved in soraphen biosynthesis.

Delineation of the left end of the biosynthetic region required the isolation of two other cosmid clones, pJL1 and pJL3, that overlap p98/1 on the left end, but include more DNA leftwards of p98/1. These were isolated by hybridization with the 1.3 kb BamHI fragment on the extreme left end of p98/1 (map location 0.0–1.3) to the *Sorangium cellulosum* gene library. It should be noted that the BamHI site at 0.0 does not exist in the *S. cellulosum* chromosome but was formed as an artifact from the ligation of a Sau3A restriction fragment derived from the *Sorangium cellulosum* genome into the BamHI cloning site of pHC79. Southern hybridization with the 1.3 kb BamHI fragment demonstrated that pJL1 and pJL3 each contain an approximately 12.5 kb BamHI fragment that contains sequences common to the 1.3 kb fragment as this fragment is in fact delineated by the BamHI site at position 1.3. Gene disruption experiments using the 12.5 kb BamHI fragment indicated that this fragment contains sequences that are involved in the synthesis of soraphen. Gene disruption using smaller EcoRV fragments derived from this region and also indicated the requirement of this region for soraphen biosynthesis. For example, two EcoRV fragments of 3.4 and 1.1 kb located adjacent to the distal BamHI site at the left end of the 12.5 kb fragment resulted in a reduction in soraphen biosynthesis when used in gene disruption experiments. *E. coli* HB101 containing pJL3 was deposited at the Agricultural Research Culture Collection (NRRL), 1815 N. University Street, Peoria, Ill. 61604 on May 20, 1994, and assigned accession number NRRL B-21254.

Example 16

Sequence Analysis of the Soraphen Gene Cluster

The DNA sequence of the soraphen gene cluster was determined from the PvuI site at position 2.5 to the BglII site at position 32.4 (see FIG. 7) using the Taq DyeDeoxy Terminator Cycle Sequencing Kit supplied by Applied Biosystems, Inc., Foster City, Calif. following the protocol supplied by the manufacturer. Sequencing reactions were run on a Applied Biosystems 373A Automated DNA Sequencer and the raw DNA sequence was assembled and edited using the "INHERIT" software package also from Applied Biosystems, Inc. The pattern recognition program "FRAMES" was used to search for open reading frames (ORFs) in all six translation frames of the DNA sequence. In total approximately 30 kb of contiguous DNA was assembled and this corresponds to the region determined to be critical to soraphen biosynthesis in the disruption experiments described in example 12. This sequence encodes two ORFs which have the structure described below.

ORF1:

ORF1 is approximately 25.5 kb in size and encodes five biosynthetic modules with homology to the modules found in the erythromycin biosynthetic genes of *Saccharopolyspora erythraea* (Donadio et al. Science 252:675–679 (1991)). Each module contains a β-ketoacylsynthase (KS), an acyltransferase (AT), a ketoreductase (KR) and an acyl carrier protein (ACP) domain as well as β-ketone processing domains which may include a dehydratase (DH) and/or enoyl reductase (ER) domain. In the biosynthesis of the polyketide structure each module directs the incorporation of a new two carbon extender unit and the correct processing of the β-ketone carbon.

ORF2:

In addition to ORF1, DNA sequence data from the p98/1 fragment spanning the PvuI site at 2.5 kb and the SmaI site at 6.2 kb, indicated the presence of a further ORF (ORF2) immediately adjacent to ORF1. The DNA sequence demonstrates the presence of a typical biosynthetic module that appears to be encoded on an ORF whose 5' end is not yet sequenced and is some distance to the left. By comparison to other polyketide biosynthetic gene units and the number of carbon atoms in the soraphen ring structure it is likely that there should be a total of eight modules in order to direct the synthesis of 17 carbon molecule soraphen. Since there are five modules in ORF1 described above, it was predicted that ORF2 contains a further three and that these would extend beyond the left end of cosmid p98/1 (position 0 in FIG. 7). This is entirely consistent with the gene description of example 12. The cosmid clones pJL1 and pJL3 extending beyond the left end of p98/1 presumable carry the sequence encoding the remaining modules required for soraphen biosynthesis.

Example 17

Soraphen: Requirement for Methylation

Synthesis of polyketides typically requires, as a first step, the condensation of a starter unit (commonly acetate) and an extender unit (malonate) with the loss of one carbon atom in the form of $CO_2$ to yield a three-carbon chain. All subsequent additions result in the addition of two carbon units to the polyketide ring (Donadio et al. Science 252:675–679 (1991)). Since soraphen has a 17-carbons ring, it is likely that there are 8 biosynthetic modules required for its synthesis. Five modules are encoded in ORF1 and a sixth is present at the 3' end of ORF2. As explained above, it is likely that the remaining two modules are also encoded by ORF2 in the regions that are in the 15 kb BamHI fragment from pJL1 and pJL3 for which the sequence has not yet been determined.

The polyketide modular biosynthetic apparatus present in *Sorangium cellulosum* is required for the production of the compound, soraphen C, which has no antipathogenic activity. The structure of this compound is the same as that of the antipathogenic soraphen A with the exception that the O-methyl groups of soraphen A at positions 6, 7, and 14 of the ring are hydroxyl groups. These are methylated by a specific methyltransferase to form the active compound soraphen A. A similar situation exists in the biosynthesis of erythromycin in *Saccharopolyspora erythraea*. The final step in the biosynthesis of this molecule is the methylation of three hydroxyl groups by a methyltransferase (Haydock et al., Mol. Gen. Genet. 230:120–128 (1991)). It is highly likely, therefore, that a similar methyltransferase (or possibly more than one) operates in the biosynthesis of soraphen A (soraphen C is unmethylated and soraphen B is partially methylated). In all polyketide biosynthesis systems examined thus far, all of the biosynthetic genes and associated methylases are clustered together (Summers et al. J Bacteriol 174:1810–1820 (1992)). It is also probable, therefore, that a similar situation exists in the soraphen operon and that the gene encoding the methyltransferase/s required for the conversion of soraphen B and C to soraphen A is located near the ORF1 and ORF2 that encode the polyketide synthase. The results of the gene disruption experiments described above indicate that this gene is not located immediately downstream from the 3' end of ORF1 and that it is likely located upstream of OKF2 in the DNA contained in pJL1 and pJL3. Thus, using standard techniques in the art, the methyltransferase gene can be cloned and sequenced.

Soraphen Determination

*Sorangium cellulosum* cells were cultured in a liquid growth medium containing an exchange resin, XAD-5 (Rohm and Haas) (5% w/v). The soraphen A produced by the cells bound to the resin which was collected by filtration through a polyester filter (Sartorius B 420-47-N) and the soraphen was released from the resin by extraction with 50 ml isopropanol for 1 hr at 30° C. The isopropanol containing soraphen A was collected and concentrated by drying to a volume of approximately 1 ml. Aliquots of this sample were analyzed by HPLC at 210 nm to detect and quantify the soraphen A. This assay procedure is specific for soraphen A (fully methylated); partially and non-methylated soraphen forms have a different $R_T$ and are not measured by this procedure. This procedure was used to assay soraphen A production after gene disruption.

F. Cloning and Characterization of Phenazine Biosynthetic Genes from *Pseudomonas aureofaciens*

The phenazine antibiotics are produced by a variety of Pseudomonas and Streptomyces species as secondary metabolites branching off the shikimic acid pathway. It has been postulated that two chorismic acid molecules are condensed along with two nitrogens derived from glutamine to form the three-ringed phenazine pathway precursor phenazine-1,6-dicarboxylate. However, there is also genetic evidence that anthranilate is an intermediate between chorismate and phenazine-1,6-dicarboxylate (Essar et al., J. Bacteriol. 172:853–866 (1990)). In *Pseudomonas aureofaciens* 30–84, production of three phenazine antibiotics, phenazine-1-carboxylic acid, 2-hydroxyphenazine-1-carboxylic acid, and 2-hydroxyphenazine, is the major mode of action by which the strain protects wheat from the fungal phytopathogen *Gaeumannomyces graminis* var. tritici (Pierson & Thomashow, MPMI 5:330–339 (1992)). Likewise, in *Pseudomonas fluorescens* 2-79, phenazine production is a major factor in the control of *G. graminis* var. tritici (Thomashow & Weller, J. Bacteriol. 170:3499–3508 (1988)).

Example 18

Isolation of the Phenazine Biosynthetic Genes

Pierson & Thomashow (supra) have previously described the cloning of a cosmid which confers a phenazine biosynthesis phenotype on transposon insertion mutants of *Pseudomonas aureofaciens* strain 30-84 which were disrupted in their ability to synthesize phenazine antibiotics. A mutant library of strain 30-84 was made by conjugation with *E. coli* S17-1(pSUP1021) and mutants unable to produce phenazine antibiotics were selected. Selected mutants were unable to produce phenazine carboxylic acid, 2-hydroxyphenaxine or 2-hydroxy-phenazine carboxylic acid. These mutants were transformed by a cosmid genomic library of strain 30-84 leading to the isolation of cosmid pLSP259 which had the ability to complement phenazine mutants by the synthesis of phenazine carboxylic acid, 2-hydroxyphenazine and 2-hydroxy-phenazine carboxylic acid. pLSP259 was further characterized by transposon mutagenesis using the λ::Tn5 phage described by de Bruijn & Lupski (Gene 27:131–149 (1984)). Thus a segment of approximately 2.8 kb of DNA was identified as being responsible for the phenazine complementing phenotype; this 2.8 kb segment is located within a larger 9.2 kb EcoRI fragment of pLSP259. Transfer of the 9.2 kb EcoRI fragment and various deletion derivatives thereof to *E. coli* under the control of the lacZ promoter was undertaken to assay for the production in *E. coli* of phenazine. The shortest deletion derivative which was found to confer biosynthesis of all three phenazine compounds to *E. coli* contained an insert of approximately 6 kb and was designated pLSP18-6H3del3. This plasmid contained the 2.8 kb segment previously identified as being critical to phenazine biosynthesis in the host 30-84 strain and was provided by Dr. L. S. Pierson (Department of Plant Pathology, U Arizona, Tucson, Ariz.) for sequence characterization. Other deletion derivatives were able to coffer production of phenazine-carboxylic acid on *E. coli*, without the accompanying production of 2-hydroxyphenazine and 2-hydroxyphenazinecarboxylic acid suggesting that at least two genes might be involved in the synthesis of phenazine and its hydroxy derivatives.

The DNA sequence comprising the genes for the biosynthesis of phenazine is disclosed in SEQ ID NO:17. Determination of the DNA sequence of the insert of pLSP18-6H3del3 revealed the presence of four ORFs within and adjacent to the critical 2.8 kb segment. ORF1 (SEQ ID NO:18) was designated phz1, ORF2 (SEQ ID NO:19) was designated phz2, and ORF3 (SEQ ID NO:20) was designated phz3, and ORF4 (SEQ ID NO:22) was designated phz4. ph1B is approximately 1.35 kb in size and has homology at the 5' end to the entB gene or *E. coli*, which encodes isochorismatase phz2 is approximately 1.15 kb in size and has some homology at the 3' end to the trpG gene which encodes the beta subunit of anthranilate synthase. phz3 is approximately 0.85 kb in size. phz4 is approximately 0.65 kb in size and is homologous to the pdxH gene or *E. coli* which encodes pyridoxamine 5'-phosphate oxidase.

Phenazine Determination

Thomashow et al. (Appl Environ Microbiol 56:908–912 (1990)) describe a method for the isolation of phenazine. This involves acidifying cultures to pH 2.0 with HCl and extraction with benzene. Benzene fractions are dehydrated with $Na_2SO_4$ and evaporated to dryness. The residue is redissolved in aqueous 5% $NaHCO_3$, reextracted with an equal volume of benzene, acidified, partitioned into benzene and redried. Phenazine concentrations are determined after fractionation by reverse-phase HPLC as described by Thomashow et al. (supra).

G. Cloning Peptide Antipathogenic Genes

This group of substances is diverse and is classifiable into two groups: (1) those which are synthesized by enzyme systems without the participation of the ribosomal apparatus, and (2) those which require the ribosomally-mediated translation of an mRNA to provide the precursor of the antibiotic.

Non-Ribosomal Peptide Antibiotics.

Non-Ribosomal Peptide Antibiotics are assembled by large, multifunctional enzymes which activate, modify, polymerize and in some cases cyclize the subunit amino acids, forming polypeptide chains. Other acids, such as aminoadipic acid, diaminobutyric acid, diaminopropionic acid, dihydroxyamino acid, isoserine, dihydroxybenzoic acid, hydroxyisovaleric acid, (4R)-4-[(E)-2-butenyl]-4,N-dimethyl-L-threonine, and ornithine are also incorporated (Katz & Demain, Bacteriological Review 41:449–474 (1977); Kleinkauf & von Dohren, Annual Review of Microbiology 41:259–289 (1987)). The products are not encoded by any mRNA, and ribosomes do not directly participate in their synthesis. Peptide antibiotics synthesized non-ribosomally can in turn be grouped according to their general structures into linear, cyclic, lactone, branched cyclopeptide, and depsipeptide categories (Kleinkauf & von Dohren, European Journal of Biochemistry 192:1–15 (1990)). These different groups of antibiotics are produced by the action of modifying and cyclizing enzymes; the basic scheme of polymerization is common to them all. Non-ribosomally synthesized peptide antibiotics are produced by both bacteria and fungi, and include edeine, linear gramicidin, tyrocidine and gramicidin S from *Bacillus brevis*, mycobacillin from *Bacillus subtilis*, polymyxin from *Bacillus polymiyxa*, etamycin from *Streptomyces griseus*, echinomycin from *Streptomyces echinatus*, actinomycin from *Streptomyces clavuligerus*, enterochelin from *Escherichia coli*, gamma-(alpha-L-aminoadipyl)-L-cysteinyl-D-valine (ACV) from *Aspergillus nidulans*, alamethicine from *Trichoderma viride*, destruxin from *Metarhizium anisolpliae*, enniatin from *Fusarium oxysporum*, and beauvericin from *Beauveria bassiana*. Extensive functional and structural similarity exists between the prokaryotic and eukaryotic systems, suggesting a common origin for both. The activities of peptide antibiotics are similarly broad, toxic effects of different peptide antibiotics in animals, plants, bacteria, and fungi are known (Hansen, Annual Review of Microbiology 47:535–564 (1993); Katz & Demain, Bacteriological Reviews 41:449–474 (1977); Kleinkauf & von Dohren, Annual Review of Microbiology 41:259–289 (1987); Kleinkauf & von Dohren, European Journal of Biochemistry 192:1–15 (1990); Kolter & Moreno, Annual Review of Microbiology 46:141–163 (1992)).

Amino acids are activated by the hydrolysis of ATP to form an adenylated amino or hydroxy acid, analogous to the charging reactions carried out by aminoacyl-tRNA synthetases, and then covalent thioester intermediates are formed between the amino acids and the enzyme(s), either at specific cysteine residues or to a thiol donated by pantetheine. The amino acid-dependent hydrolysis of ATP is often used as an assay for peptide antibiotic enzyme complexes (Ishihara, et al., Journal of Bacteriology 171:1705–1711 (1989)). Once bound to the enzyme, activated amino acids may be modified before they are incorporated into the polypeptide. The most common modifications are epimerization of L-amino (hydroxy) acids to the D-form, N-acylations, cyclizations and N-methylations. Polymerization occurs through the participation of a pantetheine cofactor, which allows the activated subunits to be sequentially added to the polypeptide chain. The mechanism by which the peptide is released from the enzyme complex is important in the determination of the structural class in which the product belongs. Hydrolysis or aminolysis by a free amine of the thiolester will yield a linear (unmodified or terminally aminated) peptide such as edeine; aminolysis of the thiolester by amine groups on the peptide itself will give either cyclic (attack by terminal amine), such as gramicidin S, or branched (attack by side chain amine), such as bacitracin, peptides; lactonization with a terminal or side chain hydroxy will give a lactone, such as destruxin, branched lactone, or cyclodepsipeptide, such as beauvericin.

The enzymes which carry out these reactions are large multifunctional proteins, having molecular weights in accord with the variety of functions they perform. For example, gramicidin synthetases 1 and 2 are 120 and 280 kDa, respectively; ACV synthetase is 230 kDa; enniatin synthetase is 250 kDa; bacitracin synthetases 1, 2, 3 are 335, 240, and 380 kDa, respectively (Katz & Demain, Bacteriological Reviews 41:449–474 (1977); Kleinkauf & von Dohren, Annual Review of Microbiology 41:259–289 (1987); Kleinkauf & von Dohren, European Journal of Biochemistry 192:1–15 (1990). The size and complexity of these proteins means that relatively few genes must be cloned in order for the capability for the complete nonribosomal synthesis of peptide antibiotics to be transferred. Further, the functional and structural homology between bacterial and eukaryotic synthetic systems indicates that such genes from any source of a peptide antibiotic can be cloned using the available sequence information, current functional information, and conventional microbiological techniques. The production of a fungicidal, insecticidal, or batericidal peptide antibiotic in a plant is expected to produce an advantage with respect to the resistance to agricultural pests.

Example 19

Cloning of Gramicidin S Biosynthesis Genes

Gramicidin S is a cyclic antibiotic peptide and has been shown to inhibit the germination of fungal spores (Murray, et al., Letters in Applied Microbiology 3:5–7 (1986)), and may therefore be useful in the protection of plants against fungal diseases. The gramicidin S biosynthesis operon (grs) from *Bacillus brevis* ATCC 9999 has been cloned and sequenced, including the entire coding sequences for gramicidin synthetase 1 (GS1, grsA), another gene in the operon of unknown function (grsT), and GS2 (grsB) (Kratzschmar, et al., Journal of Bacteriology 171:5422–5429 (1989); Krause, et al., Journal of Bacteriology 162:1120–1125 (1985)). By methods well known in the art, pairs of PCR primers are designed from the published DNA sequence which are suitable for amplifying segments of approximately 500 base pairs from the grs operon using isolated *Bacillus brevis* ATCC 9999 DNA as a template. The fragments to be amplified are (1) at the 3' end of the coding region of grsB, spanning the termination codon, (2) at the 5' end of the grsB coding sequence, including the initiation codon, (3) at the 3' end of the coding sequence of grsA, including the termination codon, (4) at the 5' end of the coding sequence of grsA, including the initiation codon, (5) at the 3' end of the coding sequence of grsT, including the termination codon, and (6) at the 5' end of the coding sequence of grsT, including the initiation codon. The amplified fragments are radioactively or nonradioactively labeled by methods known in the art and used to screen a genomic library of *Bacillus brevis* ATCC 9999 DNA constructed in a vector such as λEMBL3. The 6 amplified fragments are used in pairs to isolate cloned fragments of genomic DNA which contain intact coding sequences for the three biosynthetic genes. Clones which hybridize to probes 1 and 2 will contain an intact grsB sequence, those which hybridize to probes 3 and 4 will contain an intact grsA gene, those which hybridize to probes 5 and 6 will contain an intact grsT gene. The cloned grsA is introduced into *E. coli* and extracts prepared by lysing transformed bacteria through methods known in the art are tested for activity by the determination of phenylalanine-dependent ATP-PP$_i$ exchange (Krause, et al., Journal of Bacteriology 162:1120–1125 (1985)) after removal of proteins smaller than 120 kDa by gel filtration chromatography. GrsB is tested similarly by assaying gel-filtered extracts from transformed bacteria for proline, valine, ornithine and leucine ATP-PP$_i$ exchange.

Example 20

Cloning of Penicillin Biosynthesis Genes

A 38 kb fragment of genomic DNA from *Penicillium chrysogenum* transfers the ability to synthesize penicillin to fungi, *Aspergillus niger*, and *Neurospora crassa*, which do not normally produce it (Smith, et al., Bio/Technology 8:39–41 (1990)). The genes which are responsible for biosynthesis, delta-(L-alpha-aminoadipyl)-L-cysteinyl-D-valine synthetase, isopenicillin N synthetase, and isopenicillin N acyltranferase have been individually cloned from *P. chrysogenum* and *Aspergillus nidulans*, and their sequences determined (Ramon, et al., Gene 57:171–181 (1987); Smith, et al., EMBO Journal 9:2743–2750 (1990); Tobin, et al., Journal of Bacteriology 172:5908–5914 (1990)). The cloning of these genes is accomplished by following the PCR-based approach described above to obtain probes of approximately 500 base pairs from genomic DNA from either *Penicillium chrysogenum* (for example, strain AS-P-78, from Antibioticos, S. A., Leon, Spain), or from *Aspergillus nidulans* for example, strain G69. Their integrity and function may be checked by transforming the non-producing fungi listed above and assaying for antibiotic production and individual enzyme activities as described (Smith, et al., Bio/Technology 8:39–41 (1990)).

Example 21

Cloning of Bacitracin A Biosynthesis Genes

Bacitracin A is a branched cyclopeptide antibiotic which has potential for the enhancement of disease resistance to bacterial plant pathogens. It is produced by *Bacillus licheniformis* ATCC 10716, and three multifunctional enzymes, bacitracin synthetases (BA) 1, 2, and 3, are required for its synthesis. The molecular weights of BA1, BA2, and BA3 are 335 kDa, 240 kDa, and 380 kDa, respectively. A 32 kb fragment of *Bacillus licheniformis* DNA which encodes the BA2 protein and part of the BA3 protein shows that at least these two genes are linked (Ishihara, et al., Journal of Bacteriology 171:1705–1711 (1989)). Evidence from gramicidin S, penicillin, and surfactin biosynthetic operons suggest that the first protein in the pathway, BA1, will be encoded by a gene which is relatively close to BA2 and BA3. BA3 is purified by published methods, and it is used to raise an antibody in rabbits (Ishihara, et al. supra). A genomic library of *Bacillus licheniformis* DNA is transformed into *E. coli* and clones which express antigenic determinants related to BA3 are detected by methods known in the art. Because BA1, BA2, and BA3 are antigenically related, the detection method will provide clones encoding each of the three enzymes. The identity of each clone is confirmed by testing extracts of transformed *E. coli* for the appropriate amino acid-dependent ATP-PP$_i$ exchange. Clones encoding BA1 will exhibit leucine-, glutamic acid-, and isoleucine-dependent ATP-PP$_i$ exchange, those encoding BA2 will exhibit lysine- and ornithine-dependent exchange, and those encoding BA3 will exhibit isoleucine, phenylalanine-, histidine-, aspartic acid-, and asparagine-dependent exchange. If one or two genes are obtained by this method, the others are isolated by "walking" techniques known in the art.

Example 22

Cloning of Beauvericin and Destruxin Biosynthesis Genes

Beauvericin is an insecticidal hexadepsipeptide produced by the fungus *Beauveria bassiana* (Kleinkauf & von Dohren, European Journal of Biochemistry 192:1–15 (1990)) which will provide protection to plants from insect pests. It is an analog of enniatin, a phytotoxic hexadepsipeptide produced by some phytopathogenic species of Fusarium (Burmeister & Plattner, Phytopathology 77:1483–1487 (1987)). Destruxin is an insecticidal lactone peptide produced by the fungus *Metarhizium anisopliae* (James, et al., Journal of Insect Physiology 39:797–804 (1993)). Monoclonal antibodies directed to the region of the enniatin synthetase complex responsible for N-methylation of activated amino acids cross react with the synthetases for beauvericin and destruxin, demonstrating their structural relatedness (Kleinkauf & von Dohren, European Journal of Biochemistry 192:1–15 (1990)). The gene for enniatin synthetase gene (esyn1) from *Fusarium scirpi* has been cloned and sequenced (Haese, et al., Molecular Microbiology 7:905–914 (1993)), and the sequence information is used to carry out a cloning strategy for the beauvericin synthetase and destruxin synthetase genes as described above. Probes for the beauvericin synthetase (BE) gene and the destruxin synthetase (DXS) gene are produced by amplifying specific regions of *Beauveria bassiana* genomic DNA or *Metarhizium anisopliae* genomic DNA using oligomers whose sequences are taken from the enniatin synthetase sequence as PCR primers. Two pairs of PCR primers are chosen, with one pair capable of causing the amplification of the segment of the BE gene spanning the initiation codon, and the other pair capable of causing the amplification of the segment of the BE gene which spans the termination codon. Each pair will cause the production of a DNA fragment which is approximately 500 base pairs in size. Library of genomic DNA from *Beauveria bassiana* and *Metarhizium anisopliae* are probed with the labeled fragments, and clones which hybridize to both of them are chosen. Complete coding sequences of beauvericin synthetase will cause the appearance of phenylalanine-dependent ATP-$PP_i$ exchange in an appropriate host, and that of destruxin will cause the appearance of valine-, isoleucine-, and alanine-dependent ATP-$PP_i$ exchange. Extracts from these transformed organisms will also carry out the cell-free biosynthesis of beauvericin and destruxin, respectively.

Example 23

Cloning genes for the Biosynthesis of an Unknown Peptide Antibiotic

The genes for any peptide antibiotic are cloned by the use of conserved regions within the coding sequence. The functions common to all peptide antibiotic synthetases, that is, amino acid activation, ATP-, and pantotheine binding, are reflected in a repeated domain structure in which each domain spans approximately 600 amino acids. Within the domains, highly conserved sequences are known, and it is expected that related sequences will exist in any peptide antibiotic synthetase, regardless of its source. The published DNA sequences of peptide synthetase genes, including gramicidin synthetases 1 and 2 (Hori, et al., Journal of Biochemistry 106:639–645 (1989); Krause, et al., Journal of Bacteriology 162:1120–1125 (1985); Turgay, et al., Molecular Microbiology 6:529–546 (1992)), tyrocidine sythethase 1 and 2 (Weckermann, et al., Nucleic Acids Research 16:11841 (1988)), ACV synthetase (MacCabe, et al., Journal of Biological Chemistry 266:12646–12654 (1991)), enniatin synthetase (Haese, et al., Molecular Microbiology 7:905–914 (1993)), and surfactin synthetase (Fuma, et al., Nucleic Acids Research 21:93–97 (1993); Grandi, et al., Eleventh International Spores Conference (1992)) are compared and the individual repeated domains are identified. The domains from all the synthetases are compared as a group, and the most highly conserved sequences are identified. From these conserved sequences, DNA oligomers are designed which are suitable for hybridizing to all of the observed variants of the sequence, and another DNA sequence which lies, for example, from 0.1 to 2 kilobases away from the first DNA sequence, is used to design another DNA oligomer. Such pairs of DNA oligomers are used to amplify by PCR the intervening segment of the unknown gene by combining them with genomic DNA prepared from the organism which produces the antibiotic, and following a PCR amplification procedure. The fragment of DNA which is produced is sequenced to confirm its identity, and used as a probe to identify clones containing larger segments of the peptide synthetase gene in a genomic library. A variation of this approach, in which the oligomers designed to hybridize to the conserved sequences in the genes were used as hybridization probes themselves, rather than as primers of PCR reactions, resulted in the identification of part of the surfactin synthetase gene from *Bacillus subtilis* ATCC 21332 (Borchert, et al., FEMS Microbiological Letters 92:175–180 (1992)). The cloned genomic DNA which hybridizes to the PCR-generated probe is sequenced, and the complete coding sequence is obtained by "walking" procedures. Such "walking" procedures will also yield other genes required for the peptide antibiotic synthesis, because they are known to be clustered.

Another method of obtaining the genes which code for the synthetase(s) of a novel peptide antibiotic is by the detection of antigenic determinants expressed in a heterologous host after transformation with an appropriate genomic library made from DNA from the antibiotic-producing organism. It is expected that the common structural features of the synthetases will be evidenced by cross-reactions with antibodies raised against different synthetase proteins. Such antibodies are raised against peptide synthetases purified from known antibiotic-producing organisms by known methods (Ishihara, et al., Journal of Bacteriology 171:1705–1711 (1989)). Transformed organisms bearing fragments of genomic DNA from the producer of the unknown peptide antibiotic are tested for the presence of antigenic determinants which are recognized by the anti-peptide synthetase antisera by methods known in the art. The cloned genomic DNA carried by cells which are identified by the antisera are recovered and sequenced. "Walking" techniques, as described earlier, are used to obtain both the entire coding sequence and other biosynthetic genes.

Another method of obtaining the genes which code for the synthetase of an unknown peptide antibiotic is by the purification of a protein which has the characteristics of the appropriate peptide synthetase, and determining all or part of its amino acid sequence. The amino acids present in the antibiotic are determined by first purifying it from a chloroform extract of a culture of the antibiotic-producing organism, for example by reverse phase chromatography on a $C_{18}$ column in an ethanol-water mixture. The composition of the purified compound is determined by mass spectrometry, NMR, and analysis of the products of acid hydrolysis. The amino or hydroxy acids present in the peptide antibiotic will produce ATP-$PP_i$ exchange when added to a peptide-synthetase-containing extract from the antibiotic-producing organism. This reaction is used as an assay to detect the presence of the peptide synthetase during the course of a protein purification scheme, such as are known in the art. A substantially pure preparation of the peptide synthetase is used to determine its amino acid sequence, either by the direct sequencing of the intact protein to obtain the N-terminal amino acid sequence, or by the production, purification, and sequencing of peptides derived from the intact peptide synthetase by the action of specific proteolytic enzymes, as are known in the art. A DNA sequence is inferred from the amino acid sequence of the synthetase, and DNA oligomers are designed which are capable of hybridizing to such a coding sequence. The oligomers are used to probe a genomic library made from the DNA of the antibiotic-producing organism. Selected clones are sequenced to identify them, and complete coding sequences and associated genes required for peptide biosynthesis are obtained by using "walking" techniques. Extracts from organisms which have been transformed with the entire complement of peptide biosynthetic genes, for example bacteria or fungi, will produce the peptide antibiotic when provided with the required amino or hydroxy acids, ATP, and pantetheine.

Further methods appropriate for the cloning of genes required for the synthesis of non-ribosomal peptide antibiotics are described in Section B of the examples.

Ribosomally-Synthesized Peptide Antibiotics.

Ribosomally-Synthesized Peptide Antibiotics are characterized by the existence of a structural gene for the antibiotic itself, which encodes a precursor that is modified by specific enzymes to create the mature molecule. The use of the general protein synthesis apparatus for peptide antibiotic synthesis opens up the possibility for much longer polymers to be made, although these peptide antibiotics are not necessarily very large. In addition to a structural gene, further genes are required for extracellular secretion and immunity, and these genes are believed to be located close to the structural gene, in most cases probably on the same operon. Two major groups of peptide antibiotics made on ribosomes exist: those which contain the unusual amino acid lanthionine, and those which do not. Lanthionine-containing antibiotics (lantibiotics) are produced by gram-positive bacteria, including species of Lactococcus, Staphylococcus, Streptococcus, Bacillus, and Streptomyces. Linear lantibiotics (for example, nisin, subtilin, epidermin, and gallidermin), and circular lantibiotics (for example, duramycin and cinnamycin), are known (Hansen, Annual Review of Microbiology 47:535–564 (1993); Kolter & Moreno, Annual Review of Microbiology 46:141–163 (1992)). Lantibiotics often contain other characteristic modified residues such as dehydroalanine (DHA) and dehydrobutyrine (DHB), which are derived from the dehydration of serine and threonine, respectively. The reaction of a thiol from cysteine with DHA yields lanthionine, and with DHB yields β-methyllanthionine. Peptide antibiotics which do not contain lanthionine may contain other modifications, or they may consist only of the ordinary amino acids used in protein synthesis. Non-lanthionine-containing peptide antibiotics are produced by both gram-positive and gram-negative bacteria, including Lactobacillus, Lactococcus, Pediococcus, Enterococcus, and Escherichia. Antibiotics in this category include lactacins, lactocins, sakacin A, pediocins, diplococcin, lactococcins, and microcins (Hansen, supra; Kolter & Moreno, supra). In general, peptide antibiotics whose synthesis is begun on ribosomes are subject to several types of post-translational processing, including proteolytic cleavage and modification of amino acid side chains, and require the presence of a specific transport and/or immunity mechanism. The necessity for protection from the effects of these antibiotics appears to contrast strongly with the lack of such systems for nonribosomal peptide antibiotics. This may be rationalized by considering that the antibiotic activity of many ribosomally-synthesized peptide antibiotics is directed at a narrow range of bacteria which are fairly closely related to the producing organism. In this situation, a particular method of distinguishing the producer from the competitor is required, or else the advantage is lost. As antibiotics, this property has limited the usefulness of this class of molecules for situations in which a broad range of activity if desirable, but enhances their attractiveness in cases when a very limited range of activities is advantageous. In eukaryotic systems, which are not known to be sensitive to any of this type of peptide antibiotic, it is not clear if production of a ribosomally-synthesized peptide antibiotic necessitates one of these transport systems, or if transport out of the cell is merely a matter of placing the antibiotic in a better location to encounter potential pathogens. This question can be addressed experimentally, as shown in the examples which follow.

Example 24

Cloning Genes for the Biosynthesis of a Lantibiotic

Examination of genes linked to the structural genes for the lantibiotics nisin, subtilin, and epidermin show several open reading frames which share sequence homology, and the predicted amino acid sequences suggest functions which are necessary for the maturation and transport of the antibiotic. The spa genes of Bacillus subtilis ATCC 6633, including spaS, the structural gene encoding the precursor to subtilin, have been sequenced (Chung & Hansen, Journal of Bacteriology 174:6699–6702 (1992); Chung, et al., Journal of Bacteriology 174:1417–1422 (1992); Klein, et al., Applied and Environmental Microbiology 58:132–142 (1992)). Open reading frames were found only upstream of spaS, at least within a distance of 1–2 kilobases. Several of the open reading frames appear to part of the same transcriptional unit, spaE, spaD, spaB, and spaC, with a putative promoter upstream of spaE. Both spaB, which encodes a protein of 599 amino acids, and spaD, which encodes a protein of 177 amino acids, share homology to genes required for the transport of hemolysin, coding for the HylB and HlyD proteins, respectively. SpaE, which encodes a protein of 851 amino acids, is homologous to nisB, a gene linked to the structural gene for nisin, for which no function is known. SpaC codes for a protein of 442 amino acids of unknown function, but disruption of it eliminates production of subtilin. These genes are contained on a segment of genomic DNA which is approximately 7 kilobases in size (Chung & Hansen, Journal of Bacteriology 174:6699–6702 (1992); Chung, et al., Journal of Bacteriology 174:1417–1422 (1992); Klein, et al., Applied and Environmental Microbiology 58:132–142 (1992)). It has not been clearly demonstrated if these genes are completely sufficient to confer the ability to produce subtilin. A 13.5 kilobasepair (kb) fragment from plasmid Tü32 of Staphylococcus epidermis Tü3298 containing the structural gene for epidermin (epiA), also contains five open reading frames denoted epiA, epiB, epiC, epiD, epiQ, and epiP. The genes epiBC are homologous to the genes spaBC, while epiQ appears to be involved in the regulation of the expression of the operon, and epiP may encode a protease which acts during the maturation of pre-epidermin to epidermin. EpiD encodes a protein of 181 amino acids which binds the coenzyme flavin mononucleotide, and is suggested to perform post-translational modification of pre-epidermin (Kupke, et al., Journal of Bacteriology 174:(1992); Peschel, et al., Molecular Microbiology 9:31–39 (1993); Schnell, et al., European Journal of Biochemistry 204:57–68 (1992)). It is expected that many, if not all, of the genes required for the biosynthesis of a lantibiotic will be clustered, and physically close together on either genomic DNA or on a plasmid, and an approach which allows one of the necessary genes to be located will be useful in finding and cloning the others. The structural gene for a lantibiotic is cloned by designing oligonucleotide probes based on the amino acid sequence determined from a substantially purified preparation of the lantibiotic itself, as has been done with the lantibiotics lacticin 481 from Lactococcus lactis subsp. lactis CNRZ 481 (Piard, et al., Journal of Biological Chemistry 268:16361–16368 (1993)), streptococcin A-FF22 from Streptococcus pyogenes FF22 (Hynes, et al., Applied and Environmental Microbiology 59:1969–1971 (1993)), and salivaricin A from Streptococcus salivarius 203P (Ross, et al., Applied and Environmental Microbiology 59:2014–2021 (1993)). Fragments of bacterial DNA approximately 10–20 kilobases in size containing the structural gene are cloned and sequenced to determine regions of homology to the characterized genes in the spa, epi, and nis operons. Open reading times which have homology to any of these genes or which lie in the same transcriptional unit as open reading frames having homology to any of these genes are cloned individually using techniques known in the art. A fragment of DNA containing all of the associated reading frames and no others is transformed into a non-producing strain of bacteria, such as Esherichia coli, and the production of the lantibiotic analyzed, in order to demonstrate that all the required genes are present.

Example 25

Cloning Genes for the Biosynthesis of a Non-Lanthionine Containing, Ribosomally Synthesized Peptide Antibiotic The lack of the extensive modifications present in lantibiotics is expected to reduce the number of genes required to account for the complete synthesis of peptide antibiotics exemplified by lactacin F, sakacin A, lactococcin A, and helveticin J. Clustered genes involved in the biosynthesis of antibiotics were found in Lactobacillus johnsonii VPI11088, for lactacin F (Fremaux, et al., Applied and Environmental Microbiology 59:3906–3915 (1993)), in *Lactobacillus sake* Lb706 for sakacin A (Axelsson, et al., Applied and Environmental Microbiology 59:2868–2875 (1993)), in *Lactococcus lactis* for lactococcin A (Stoddard, et al., Applied and Environmental Microbiology 58:1952–1961 (1992)), and in *Pediococcus acidilactici* for pediocin PA-1 (Marugg, et al., Applied and Environmental Microbiology, 58:2360–2367 (1992)). The genes required for the biosynthesis of a novel non-lanthionine-containing peptide antibiotic are cloned by first determining the amino acid sequence of a substantially purified preparation of the antibiotic, designing DNA oligomers based on the amino acid sequence, and probing a DNA library constructed from either genomic or plasmid DNA from the producing bacterium. Fragments of DNA of 5–10 kilobases which contain the structural gene for the antibiotic are cloned and sequenced. Open reading frames which have homology to sakB from *Lactobacillus sake*, or to lafX, ORFY, or ORFZ from *Lactobacillus johnsonii*, or which are part of the same transcriptional unit as the antibiotic structural gene or genes having homology to those genes previously mentioned are individually cloned by methods known in the art. A fragment of DNA containing all of the associated reading frames and no others is transformed into a non-producing strain of bacteria, such as *Esherichia coli*, and the production of the antibiotic analyzed, in order to demonstrate that all the required genes are present.

H. Expression of Antibiotic Biosynthetic Genes in Microbial Hosts

Example 26

Overexpression of APS Biosynthetic Genes for Overproduction of APS using Fermentation-Type Technology The APS biosynthetic genes of this invention can be expressed in heterologous organisms for the purposes of their production at greater quantities than might be possible from their native hosts. A suitable host for heterologous expression is *E. coli* and techniques for gene expression in *E. coli* are well known. For example, the cloned APS genes can be expressed in *E. coli* using the expression vector pKK223 as described in example 11. The cloned genes can be fused in transcriptional fusion, so as to use the available ribosome binding site cognate to the heterologous gene. This approach facilitates the expression of operons which encode more than one open reading frame as translation of the individual ORFs will thus be dependent on their cognate ribosome binding site signals. Alternatively APS genes can be fused to the vector's ATG (e.g. as an NcoI fusion) so as to use the *E. coli* ribosome binding site. For multiple ORF expression in *E. coli* (e.g. in the case of operons with multiple ORFs) this type of construct would require a separate promoter to be fused to each ORF. It is possible, however, to fuse the first ATG of the APS operon to the *E. coli* ribosome binding site while requiring the other ORFs to utilize their cognate ribosome binding sites. These types of construction for the overexpression of genes in *E. coli* are well known in the art. Suitable bacterial promoters include the lac promoter, the tac (trp/lac) promoter, and the Pλ promoter from bacteriophage λ. Suitable commercially available vectors include, for example, pKK223-3, pKK233-2, pDR540, pDR720, pYEJ001 and pPL-Lambda (from Pharmacia, Piscataway, N.J.).

Similarly, gram positive bacteria, notably Bacillus species and particularly *Bacillus licheniformis*, are used in commercial scale production of heterologous proteins and can be adapted to the expression of APS biosynthetic genes (e.g. Quax et al., In: Industrial Microorganisms: Basic and Applied Molecular Genetics, Eds.: Baltz et al., American Society for Microbiology, Washington (1993)). Regulatory signals from a highly expressed Bacillus genes (e.g. amylase promoter, Quax et al., supra) are used to generate transcriptional fusions with the APS biosynthetic genes.

In some instances, high level expression of bacterial genes has been achieved using yeast systems, such as the methylotrophic yeast *Pichia pastoris* (Sreekrishna, In: Industrial microorganisms: basic and applied molecular genetics, Baltz, Hegeman, and Skatrud eds., American Society for Microbiology, Washington (1993)). The APS gene(s) of interest are positioned behind 5' regulatory sequences of the Pichia alcohol oxidase gene in vectors such as pHIL-D1 and pHIL-D2 (Sreekrishna, supra). Such vectors are used to transform Pichia and introduce the heterologous DNA into the yeast genome. Likewise, the yeast *Saccharomyces cerevisiae* has been used to express heterologous bacterial genes (e.g. Dequin & Barre, Biotechnology 12:173–177 (1994)). The yeast *Kluyveromyces lactis* is also a suitable host for heterologous gene expression (e.g. van den Berg et al., Biotechnology 8:135–139 (1990)).

Overexpression of APS genes in organisms such as *E. coli*, Bacillus and yeast, which are known for their rapid growth and multiplication, will enable fermentation-production of larger quantities of APSs. The choice of organism may be restricted by the possible susceptibility of the organism to the APS being overproduced; however, the likely susceptibility can be determined by the procedures outlined in Section J. The APSs can be isolated and purified from such cultures (see "G") for use in the control of microorganisms such as fungi and bacteria.

I. Expression of Antibiotic Biosynthetic Genes in Microbial Hosts for Biocontrol Purposes The cloned APS biosynthetic genes of this invention can be utilized to increase the efficacy of biocontrol strains of various microorganisms. One possibility is the transfer of the genes for a particular APS back into its native host under stronger transcriptional regulation to cause the production of larger quantities of the APS. Another possibility is the transfer of genes to a heterologous host, causing production in the heterologous host of an APS not normally produced by that host.

Microorganisms which are suitable for the heterologous overexpression of APS genes are all microorganisms which are capable of colonizing plants or the rhizosphere. As such they will be brought into contact with phytopathogenic fungi causing an inhibition of their growth. These include gram-negative microorganisms such as Pseudomonas, Enterobacter and Serratia, the gram-positive microorganism Bacillus and the fungi Trichoderma and Gliocladium. Particularly preferred heterologous hosts are *Pseudomonas fluorescens, Pseudomonas putida, Pseudomonas cepacia, Pseudomonas aureofaciens, Pseudomonas aurantiaca, Enterobacter cloacae, Serratia marscesens, Bacillus subtilis, Bacillus cereus, Trichoderma viride, Trichoderma harzianum* and *Gliocladium virens*.

Example 27

Expression of APS Biosynthetic Genes in *E coli* and Other Gram-Negative Bacteria Many genes have been expressed in gram-negative bacteria in a heterologous manner. Example 11 describes the expression of genes for pyrrolnitrin biosynthesis in *E. coli* using the expression vector pKK223-3 (Pharmacia catalogue #27-4935-01). This vector has a strong tac promoter (Brosius, J. et al., Proc. Natl. Acad. Sci. USA 81) regulated by the lac repressor and induced by IPTG. A number of other expression systems have been developed for use in *E coli* and some are detailed in E (above). The thermoinducible expression vector pP$_L$ (Pharmacia #27-4946-01) uses a tightly regulated bacteriophage λ promoter which allows for high level expression of proteins. The lac promoter provides another means of expression but the promoter is not expressed at such high levels as the tac promoter. With the addition of broad host range replicons to some of these expression system vectors, production of antifungal compounds in closely related gram negative-bacteria such as Pseudomonas, Enterobacter, Serratia and Erwinia is possible. For example, pLRKD211 (Kaiser & Kroos, Proc. Natl. Acad. Sci. USA 81:5816–5820 (1984)) contains the broad host range replicon ori T which allows replication in many gram-negative bacteria.

In *E coli*, induction by IPTG is required for expression of the tac (i.e. trp-lac) promoter. When this same promoter (e.g. on wide-host range plasmid pLRKD211) is introduced into Pseudomonas it is constitutively active without induction by IPTG. This trp-lac promoter can be placed in front of any gene or operon of interest for expression in Pseudomonas or any other closely related bacterium for the purposes of the constitutive expression of such a gene. If the operon of interest contains the information for the biosynthesis of an APS, then an otherwise biocontrol-minus strain of a gram-negative bacterium may be able to protect plants against a variety of fungal diseases. Thus, genes for antifungal compounds can therefore be placed behind a strong constitutive promoter, transferred to a bacterium that normally does not produce antifungal products and which has plant or rhizosphere colonizing properties mining these organisms into effective biocontrol strains. Other possible promoters can be used for the constitutive expression of APS genes in gram-negative bacteria. These include, for example, the promoter from the Pseudomonas regulatory genes gafA and lemA (WO 94/01561 ) and the *Pseudomonas savastanoi* IAA operon promoter (Gaffney et al., *J. Bacteriol.* 172:5593–5601 (1990).

Example 28

Expression of APS Biosynthetic Genes in Gram-Positive Bacteria

Heterologous expression of genes encoding APS genes in gram-positive bacteria is another means of producing new biocontrol strains. Expression systems for Bacillus and Streptomyces are the best characterized. The promoter for the erythromycin resistance gene (ermR) from *Streptococcus pneumoniae* has been shown to be active in gram-positive aerobes and anaerobes and also in *E. coli* (Trieu-Cuot et al., Nucl Acids Res 18:3660 (1990)). A further antibiotic resistance promoter from the thiostreptone gene has been used in Streptomyces cloning vectors (Bibb, Mol Gen Genet 199:26–36 (1985)). The shuttle vector pHT3101 is also appropriate for expression in Bacillus (Lereclus, FEMS Microbiol Lett 60:211–218 (1989)). By expressing an operon (such as the pyrrolnitrin operon) or individual APS encoding egens under control of the ermR or other promoters it will be possible to convert soil bacilli into strains able to protect plants against microbial diseases. A significant advantage of this approach is that many gram-positive bacteria produce spores which can be used in formulations that produce biocontrol products with a longer shelf life. Bacillus and Streptomyces species are aggressive colonizers of soils. In fact both produce secondary metabolites including antibiotics active against a broad range of organisms and the addition of heterologous antifungal genes including (including those encoding pyrrolnitrin, soraphen, phenazine or cyclic peptides) to gram-positive bacteria may make these organisms even better biocontrol strains.

Example 29

Expression of APS Biosynthetic Genes in Fungi

*Trichoderma harzianum* and *Gliocladium virens* have been shown to provide varying levels of biocontrol in the field (U.S. Pat. No. 5,165,928 and U.S. Pat. No. 4,996,157, both to Cornell Research Foundation). The successful use of these biocontrol agents will be greatly enhanced by the development of improved strains by the introduction of genes for APSs. This could be accomplished by a number of ways which are well known in the art. One is protoplast mediated transformation of the fungus by PEG or electroporation-mediated techniques. Alternatively, particle bombardment can be used to transform protoplasts or other fungal cells with the ability to develop into regenerated mature structures. The vector pAN7-1, originally developed for Aspergillus transformation and now used widely for fungal transformation (Curragh et al., Mycol. Res. 97(3): 313–317 (1992); Tooley et al., *Curr. Genet.* 21:55–60 (1992); Punt et al., Gene 56:117–124 (1987)) is engineered to contain the pyrrolnitrin operon, or any other genes for APS biosynthesis. This plasmid contains the *E. coli* the hygromycin B resistance gene flanked by the *Aspergillus nidulans* gpd promoter and the trpC terminator (Punt et al., Gene 56:117–124 (1987)).

J. In Vitro Activity of Anti-phytopathogenic Substances Against Plant Pathogens

Example 30

Bioassay Procedures for the Detection of Antifungal Activity

Inhibition of fungal growth by a potential antifungal agent can be determined in a number of assay formats. Macroscopic methods which are commonly used include the agar diffusion assay (Dhingra & Sinclair, Basic Plant Pathology Methods, CRC Press, Boca Raton, Fla. (1985)) and assays in liquid media (Broekaert et al., FEMS Microbiol. Lett. 69:55–60.(1990)). Both types of assay are performed with either fungal spores or mycelia as inocula. The maintenance of fungal stocks is in accordance with standard mycological procedures. Spores for bioassay are harvested from a mature plate of a fungus by flushing the surface of the culture with sterile water or buffer. A suspension of mycelia is prepared by placing fungus from a plate in a blender and homogenizing until the colony is dispersed. The homogenate is filtered through several layers of cheesecloth so that larger particles are excluded. The suspension which passes through the cheesecloth is washed by centrifugation and replacing the supernatant with fresh buffer. The concentration of the mycelial suspension is adjusted empirically, by testing the suspension in the bioassay to be used.

Agar diffusion assays may be performed by suspending spores or mycelial fragments in a solid test medium, and applying the antifungal agent at a point source, from which it diffuses. This may be done by adding spores or mycelia to melted fungal growth medium, then pouring the mixture into a sterile dish and allowing it to gel. Sterile filters are placed on the surface of the medium, and solutions of antifungal agents are spotted onto the filters. After the liquid has been absorbed by the filter, the plates are incubated at the appropriate temperature, usually for 1–2 days. Growth inhibition is indicated by the presence of zones around filters in which spores have not germinated, or in which mycelia have not grown. The antifungal potency of the agent, denoted as the minimal effective dose, may be quantified by spotting serial dilutions of the agent onto filters, and determining the lowest dose which gives an observable inhibition zone. Another agar diffusion assay can be performed by cutting wells into solidified fungal growth medium and placing solutions of antifungal agents into them. The plate is inoculated at a point equidistant from all the wells, usually at the center of the plate, with either a small aliquot of spore or mycelial suspension or a mycelial plug cut directly from a stock culture plate of the fungus. The plate is incubated for several days until the growing mycelia approach the wells, then it is observed for signs of growth inhibition. Inhibition is indicated by the deformation of the roughly circular form which the fungal colony normally assumes as it grows. Specifically, if the mycelial front appears flattened or even concave relative to the uninhibited sections of the plate, growth inhibition has occurred. A minimal effective concentration may be determined by testing diluted solutions of the agent to find the lowest at which an effect can be detected.

Bioassays in liquid media are conducted using suspensions of spores or mycelia which are incubated in liquid fungal growth media instead of solid media. The fungal inocula, medium, and antifungal agent are mixed in wells of a 96-well microtiter plate, and the growth of the fungus is followed by measuring the turbidity of the culture spectrophotometrically. Increases in turbidity correlate with increases in biomass, and are a measure of fungal growth. Growth inhibition is determined by comparing the growth of the fungus in the presence of the antifungal agent with growth in its absence. By testing diluted solutions of antifungal inhibitor, a minimal inhibitory concentration or an $EC_{50}$ may be determined.

Example 31

Bioassay Procedures for the Detection of Antibacterial Activity

A number of bioassays may be employed to determine the antibacterial activity of an unknown compound. The inhibition of bacterial growth in solid media may be assessed by dispersing an inoculum of the bacterial culture in melted medium and spreading the suspension evenly in the bottom of a sterile Petri dish. After the medium has gelled, sterile filter disks are placed on the surface, and aliquots of the test material are spotted onto them. The plate is incubated overnight at an appropriate temperature, and growth inhibition is observed as an area around a filter in which the bacteria have not grown, or in which the growth is reduced compared to the surrounding areas. Pure compounds may be characterized by the determination of a minimal to effective dose, the smallest amount of material which gives a zone of inhibited growth. In liquid media, two other methods may be employed. The growth of a culture may be monitored by measuring the optical density of the culture, in actuality the scattering of incident light. Equal inocula are seeded into equal culture volumes, with one culture containing a known amount of a potential antibacterial agent. After incubation at an appropriate temperature, and with appropriate aeration as required by the bacterium being tested, the optical densities of the cultures are compared. A suitable wavelength for the comparison is 600 nm. The antibacterial agent may be characterized by the determination of a minimal effective dose, the smallest amount of material which produces a reduction in the density of the culture, or by determining an $EC_{50}$, the concentration at which the growth of the test culture is half that of the control. The bioassays described above do not differentiate between bacteriostatic and bacteriocidal effects. Another assay can be performed which will determine the bacteriocidal activity of the agent. This assay is carried out by incubating the bacteria and the active agent together in liquid medium for an amount of time and under conditions which are sufficient for the agent to exert its effect. After this incubation is completed, the bacteria may be either washed by centrifugation and resuspension, or diluted by the addition of fresh medium. In either case, the concentration of the antibacterial agent is reduced to a point at which it is no longer expected to have significant activity. The bacteria are plated and spread on solid medium and the plates are incubated overnight at an appropriate temperature for growth. The number of colonies which arise on the plates are counted, and the number which appeared from the mixture which contained the antibacterial agent is compared with the number which arose from the mixture which contained no antibacterial agent. The reduction in colony-forming units is a measure of the bacteriocidal activity of the agent. The bacteriocidal activity may be quantified as a minimal effective dose, or as an $EC_{50}$, as described above. Bacteria which are used in assays such as these include species of Agrobacterium, Erwinia, Clavibacter, Xanthomonas, and Pseudomonas.

Example 32

Antipathogenic Activity Determination of APSs

APSs are assayed using the procedures of examples 30 and 31 above to identify the range of fungi and bacteria against which they are active. The APS can be isolated from the cells and culture medium of the host organism normally producing it, or can alternatively be isolated from a heterologous host which has been engineered to produce the APS. A further possibility is the chemical synthesis of APS compounds of known chemical structure, or derivatives thereof.

Example 33

Antimicriobial Activity Determination of Pyrrolnitrin

The anti-phytopathogenic activity of a fluorinated 3-cyano-derivative of pyrrolnitrin (designated CGA173506) was observed against the maize fungal phytopathgens *Diplodia maydis*, *Colletotrichum graminicola*, and *Gibberella zeae-maydis*. Spores of the fungi were harvested and suspended in water. Approximately 1000 spores were inoculated into potato dextrose broth and either CGA173506 or water in a total volume of 100 microliters in the wells of 96-well microtiter plates suitable for a plate reader. The compound CGA173506 was obtained as a 50% wettable powder, and a stock suspension was made up at a concentration of 10 mg/ml in sterile water. This stock suspension was diluted with sterile water to provide the 173506 used in the tests. After the spores, medium, and 173506 were mixed, the turbidity in the wells was measured by reading the absorbance at 600 nm in a plate reader. This reading was taken as the background turbidity, and was subtracted from readings taken at later times. After 46 hours of incubation, the presence of 1 microgram/ml of 173506 was determined to reduce the growth of *Diplodia maydis* by 64%, and after 120 hours, the same concentration of 173506 inhibited the growth of *Colletotrichum graminicola* by 50%. After 40 hours of incubation, the presence of 0.5 microgram/ml of 173506 gave 100% inhibition of *Gibberella zeae-maydis*.

K. Expression of Antibiotic Biosynthetic Genes in Transgenic Plants

Example 34

Modification of Coding Sequences and Adjacent Sequences

The cloned APS biosynthetic genes described in this application can be modified for expression in transgenic plant hosts. This is done with the aim of producing extractable quantities of APS from transgenic plants (i.e. for similar reasons to those described in Section E above), or alternatively the aim of such expression can be the accumulation of APS in plant tissue for the provision of pathogen protection on host plants. A host plant expressing genes for the biosynthesis of an APS and which produces the APS in its cells will have enhanced resistance to phytopathogen attack and will be thus better equipped to withstand crop losses associated with such attack.

The transgenic expression in plants of genes derived from microbial sources may require the modification of those genes to achieve and optimize their expression in plants. In particular, bacterial ORFs which encode separate enzymes but which are encoded by the same transcript in the native microbe are best expressed in plants on separate transcripts. To achieve this, each microbial ORF is isolated individually and cloned within a cassette which provides a plant promoter sequence at the 5' end of the ORF and a plant transcriptional terminator at the 3' end of the ORF. The isolated ORF sequence preferably includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. By "plant promoter" and "plant transcriptional terminator" it is intended to mean promoters and transcriptional terminators which operate within plant cells. This includes promoters and transcription terminators which may be derived from non-plant sources such as viruses (an example is the Cauliflower Mosaic Virus).

In some cases, modification to the ORF coding sequences and adjacent sequence will not be required. It is sufficient to isolate a fragment containing the ORF of interest and to insert it downstream of a plant promoter. For example, Gaffney et al. (Science 261:754–756 (1993)) have expressed the Pseudomonas nahG gene in transgenic plants under the control of the CaMV 35S promoter and the CaMV tml terminator successfully without modification of the coding sequence and with 58 bp of the Pseudomonas gene upstream of the ATG still attached, and 165 bp downstream of the STOP codon still attached to the nahG ORF. Preferably as little adjacent microbial sequence should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain sources such as Bacillus. These problems may apply to the APS biosynthetic genes of this invention and the modification of these genes can be undertaken using techniques now well known in the art. The following problems may be encountered:

(1) Codon Usage. The preferred codon usage in plants differs from the preferred codon usage in certain microorganisms. Comparison of the usage of codons within a cloned microbial ORF to usage in plant genes (and in particular genes from the target plant) will enable an identification of the codons within the ORF which should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

(2) GC/AT Content. Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

(3) Sequences Adjacent to the Initiating Methionine. Plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210) have suggested the sequence GTCGACCATGGTC (SEQ ID NO:7) as a consensus translation initiator for the expression of the *E. coli* uidA gene in plants. Further, Joshi (NAR 15:6643–6653 (1987)) has compared many plant sequences adjacent to the ATG and suggests the consensus TAAACAATGGCT (SEQ ID NO:8). In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

| | Position Before the Initiating ATG in 14 Maize Genes: | | | | | | | | | |
|---|---|---|---|---|---|---|---|---|---|---|
| | −10 | −9 | −8 | −7 | −6 | −5 | −4 | −3 | −2 | −1 |
| C | 3 | 8 | 4 | 6 | 2 | 5 | 6 | 0 | 10 | 7 |
| T | 3 | 0 | 3 | 4 | 3 | 2 | 1 | 1 | 1 | 0 |
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which APS genes are being incorporated, and the sequence adjacent to the ATG modified to incorporate the preferred nucleotides.

(4) Removal of Illegitimate Splice Sites. Genes cloned from non-plant sources and not optimized for expression in plants may also contain motifs which may be recognized in plants as 5' or 3' splice sites, and be cleaved, thus generating truncated or deleted messages. These sites can be removed using the techniques described in pending application Ser. No. 07/961,944, hereby incorporated by reference.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy). In most cases it is preferable to assay the expression of gene constructions using transient assay protocols (which are well known in the art) prior to their transfer to transgenic plants.

Example 35

Construction of Plant Transformation Vectors

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformation include the nptII gene which confers resistance to kanamycin and related antibiotics (Messing & Vierra, Gene 19:259–268 (1982); Bevan et al., Nature 304:184–187 (1983)), the bar gene which confers resistance to the herbicide phosphinothricin (White et al., Nucl Acids Res 18:1062 (1990), Spencer et al. Theor Appl Genet 79:625–631(1990)), the hph gene which confers resistance to the antibiotic hygromycin (Blochinger & Diggelmann, Mol Cell Biol 4:2929–2931), and the dhfr gene, which confers resistance to methatrexate (Bourouis et al., EMBO J. 2(7):1099–1104 (1983)).

(1) Construction of Vectors Suitable for Agrobacterium Transformation

Many vectors are available for transformation using *Agrobacterium tumefaciens*. These typically carry at least one T-DNA border sequence and include vectors such as pBIN19 (Bevan, Nucl. Acids Res. (1984)) and pXYZ. Below the construction of two typical vectors is described.

Construction of pCIB200 and pCIB2001

The binary vectors pCIB200 and pCIB2001 are used for the construction of recombinant vectors for use with Agrobacterium and was constructed in the following manner. pTJS75kan was created by NarI digestion of pTJS75 (Schmidhauser & Helinski, J Bacteriol. 164:446–455 (1985)) allowing excision of the tetracycline-resistance gene, followed by insertion of an AccI fragment from pUC4K carrying an NPTII (Messing & Vierra, Gene 19:259–268 (1982); Bevan et al., Nature 304:184–187 (1983); McBride et al., Plant Molecular Biology 14:266–276 (1990)). XhoI linkers were ligated to the EcoRV fragment of pCIB7 which contains the left and right T-DNA borders, a plant selectable nos/nptII chimeric gene and the pUC polylinker (Rothstein et al., Gene 53:153–161 (1987)), and the XhoI-digested fragment was cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 which created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

Construction of pCIB10 and Hygromycin Selection Derivatives thereof

The binary vector pCIB10 contains a gene encoding kanamycin resistance for selection in plants, T-DNA right and left border sequences and incorporates sequences from the wide host-range plasmid pRK252 allowing it to replicate in both *E. coli* and Agrobacterium. Its construction is described by Rothstein et al. (Gene 53:153–161 (1987)). Various derivatives of pCIB10 have been constructed which incorporate the gene for hygromycin B phosphotransferase described by Gritz et al. (Gene 25:179–188 (1983)). These derivatives enable selection of transgenic plant cells on hygromycin only (pCIB743), or hygromycin and kanamycin (pCIB715, pCIB717).

(2) Construction of Vectors Suitable for non-Agrobacterium Transformation.

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques which do not rely on Agrobacterium include transformation via particle bombardment, protoplast uptake (e.g. PEG and electroporation) and microinjection. The choice of vector depends largely on the preferred selection for the species being transformed. Below, the construction of some typical vectors is described.

Construct of pCIB3064 pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites were mutated using standard PCR techniques in such a way as to remove the ATGs and generate the restriction sites SspI and PvuII. The new restriction sites were 96 and 37 bp away from the unique SalI site and 101 and 42 bp away from the actual start site. The resultant derivative of pCIB246 was designated pCIB3025. The GUS gene was then excised from pCIB3025 by digestion with SalI and SacI, the termini rendered blunt and religated to generate plasmid pCIB3060. The plasmid pJIT82 was obtained from the John Innes Centre, Norwich and the a 400 bp SmaI fragment containing the bar gene from *Streptomyces viridochromogenes* was excised and inserted into the HpaI site of pCIB3060 (Thompson et al. EMBO J 6:2519–2523 (1987)). This generated pCIB3064 which comprises the bar gene under the control of the CaMV 35S promoter and terminator for herbicide selection, a gene fro ampicillin resistance (for selection in *E. coli*) and a polylinker with the unique sites SphI, PstI, HindIII, and BamHI. This vector is suitable for the cloning of plant expression cassettes containing their own regulatory signals.

Construction of pSOG19 and pSOG35 pSOG35 is a transformation vector which utilizes the *E. coli* gene dihydrofolate reductase (DHFR) as a selectable marker conferring resistance to methotrexate. PCR was used to amplify the 35S promoter (~800 bp), intron 6 from the maize Adh1 gene (~550 bp) and 18 bp of the GUS untranslated leader sequence from pSOG10. A 250 bp fragment encoding the *E. coli* dihydrofolate reductase type II gene was also amplified by PCR and these two PCR fragments were assembled with a SacI-PstI fragment from pBI221 (Clontech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generated the vector pSOG35. pSOG19 and pSOG35 carry the pUC gene for ampicillin resistance and have HindIII, SphI, PstI and EcoRI sites available for the cloning of foreign sequences.

Example 36

Requirements for Construction of Plant Expression Cassettes

Gene sequences intended for expression in transgenic plants are firstly assembled in expression cassettes behind a suitable promoter and upstream of a suitable transcription terminator. These expression cassettes can then be easily transferred to the plant transformation vectors described above in example B.

Promoter Selection

The selection of promoter used in expression cassettes will determine the spatial and temporal expression pattern of the transgene in the transgenic plant. Selected promoters will express transgenes in specific cell types (such as leaf epidermal cells, meosphyll cells, root cortex cells) or in specific tissues or organs (roots, leaves or flowers, for example) and this selection will reflect the desired location of biosynthesis of the APS. Alternatively, the selected promoter may drive expression of the gene under a light-induced or other temporally regulated promoter. A further alternative is that the selected promoter be chemically regulated. This would provide the possibility of inducing the induction of the APS only when desired and caused by treatment with a chemical inducer.

Transcriptional Terminators

A variety of transcriptional terminators are available for use in expression cassettes. These are responsible for the termination of transcription beyond the transgene and its correct polyadenylation. Appropriate transcriptional terminators and those which are known to function in plants and include the CaMV 35S terminator, the tml terminator, the nopaline synthase terminator, the pea rbcS E9 terminator. These can be used in both monocoylyedons and dicotyledons.

Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develep 1:1183–1200 (1987)). In the same experimental system, the intron from the maize bronze1 gene had a similar effect in enhancing expression (Callis et al., supra). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "Ω-sequence"), Maize Chlorotic Mottle Virus (MCMV), and Alfalfa Mosaic Virus (AMV) have been shown to be effective in enhancing expression (e.g. Gallie et al. Nucl. Acids Res. 15:8693–8711 (1987); Skuzeski et al. Plant Molec. Biol. 15; 65–79 (1990))

Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the aminoterminal end of various proteins and which is cleaved during chloroplast import yielding the mature protein (e.g. Comai et al. J. Biol. Chem. 263:15104–15109 (1988)). These signal sequences can be fused to heterologous gene products to effect the import of heterologous products into the chloroplast (van den Broeck et al. Nature 313:358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized.

Other gene products are localized to other organelles such as the mitochondrion and the peroxisome (e.g. Unger et al. Plant Molec. Biol. 13:411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting to cellular protein bodies has been described by Rogers et al. (Proc. Natl. Acad. Sci. USA 82:6512–6516 (1985)).

In addition sequences have been characterized which cause the targeting of gene products to other cell compartments. Aminoterminal sequences are responsible for targeting to the ER, the apoplast, and extracellular secretion from aleurone cells (Koehler & Ho, Plant Cell 2:769–783 (1990)). Additionally, aminoterminal sequences in conjunction with carboxyterminal sequences are responsible for vacuolar targeting of gene products (Shinshi et al. Plant Molec. Biol. 14:357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the aminoterminal ATG of the transgene. The signal sequence selected should include the known cleavage site and the fusion constructed should take into account any amino acids after the cleavage site which are required for cleavage. In some cases this requirement may be fulfilled by the addition of a small number of amino acids between the cleavage site and the transgene ATG or alternatively replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) Methods in Chloroplast Molecular Biology, Elsevier. pp 1081–1091 (1982); Wasmann et al. Mol. Gen. Genet. 205:446–453 (1986)). These construction techniques are well known in the art and are equally applicable to mitochondria and peroxisomes. The choice of targeting which may be required for APS biosynthetic genes will depend on the cellular localization of the precursor required as the starting point for a given pathway. This will usually be cytosolic or chloroplastic, although it may is some cases be mitochondrial or peroxisomal. The gene products of APS biosynthetic genes will not normally require targeting to the ER, the apoplast or the vacuole.

The above described mechanisms for cellular targeting can be utilized not only in conjunction with their cognate promoters, but also in conjunction with heterologous promoters so as to effect a specific cell targeting goal under the transcriptional regulation of a promoter which has an expression pattern different to that of the promoter from which the targeting signal derives.

Example 37

Examples of Expression Cassette Construction

The present invention encompasses the expression of genes encoding APSs under the regulation of any promoter which is expressible in plants, regardless of the origin of the promoter.

Furthermore, the invention encompasses the use of any plant-expressible promoter in conjunction with any further sequences required or selected for the expression of the APS gene. Such sequences include, but are not restricted to, transcriptional terminators, extraneous sequences to enhance expression (such as introns [e.g. Adh intron 1], viral sequences [e.g. TMV-Ω]), and sequences intended for the targeting of the gene product to specific organelles and cell compartments.

Constitutive Expression: the CaMV 35S Promoter

Construction of the plasmid pCGN1761 is described in the published patent application EP 0 392 225 (example 23). pCGN1761 contains the "double" 35S promoter and the tml transcriptional terminator with a unique EcoRI site between the promoter and the terminator and has a pUC-type backbone. A derivative of pCGN1761 was constructed which has a modified polylinker which includes NotI and XhoI sites in addition to the existing EcoRI site. This derivative was designated pCGN1761ENX. pCGN1761ENX is useful for the cloning of cDNA sequences or gene sequences (including microbial ORF sequences) within its polylinker for the purposes of their expression under the control of the 35S promoter in transgenic plants. The entire 35S promoter-gene sequence-tml terminator cassette of such a construction can be excised by HindIII, SphI, SalI, and XbaI sites 5' to the promoter and XbaI, BamHI and BglI sites 3' to the terminator for transfer to transformation vectors such as those described above in example 35. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter.

Modification of pCGN1761ENX by Optimization of the Translational Initiation Site For any of the constructions described in this section, modifications around the cloning sites can be made by the introduction of sequences which may enhance translation. This is particularly useful when genes derived from microorganisms are to be introduced into plant expression cassettes as these genes may not contain sequences adjacent to their initiating methionine which may be suitable for the initiation of translation in plants. In cases where genes derived from microorganisms are to be cloned into plant expression cassettes at their ATG it may be useful to modify the site of their insertion to optimize their expression. Modification of pCGN1761ENX is described by way of example to incorporate one of several optimized sequences for plant expression (e.g. Joshi, supra).

pCGN1761ENX is cleaved with SphI, treated with T4 DNA polymerase and religated, thus destroying the SphI site located 5' to the double 35S promoter. This generates vector pCGN1761ENX/Sph-. pCGN1761ENX/Sph- is cleaved with EcoRI, and ligated to an annealed molecular adaptor of the sequence 5'-AATTCTAAAGCATGCCGATCGG-3' (SEQ ID NO:9)/5'-AATTCCGATCGGCATGCTTTA-3' (SEQ ID NO:10). This generates the vector pCGNSENX which incorporates the quasi-optimized plant translational initiation sequence TAAA-C adjacent to the ATG which is itself part of an SphI site which is suitable for cloning heterologous genes at their initiating methionine. Downstream of the SphI site, the EcoRI, NotI, and XhoI sites are retained.

An alternative vector is constructed which utilizes an NcoI site at the initiating ATG. This vector, designated pCGN1761NENX is made by inserting an annealed molecular adaptor of the sequence 5'-AATTCTAAACCATGGCGATCGG-3' (SEQ ID NO:11) /5'AATTCCGATCGCCATGGTTTA-3' (SEQ ID NO:12) at the pCGN1761ENX EcoRI site (Sequence ID's 14 & 15). Thus, the vector includes the quasi-optimized sequence TAAACC adjacent to the initiating ATG which is within the NcoI site. Downstream sites are EcoRI, NotI, and XhoI. Prior to this manipulation, however, the two NcoI sites in the pCGN1761ENX vector (at upstream positions of the 5' 35S promoter unit) are destroyed using similar techniques to those described above for SphI or alternatively using "inside-outside" PCR (Innes et al. PCR Protocols: A guide to methods and applications. Academic Press, New York (1990); see Example 41). This manipulation can be assayed for any possible detrimental effect on expression by insertion of any plant cDNA or reporter gene sequence into the cloning site followed by routine expression analysis in plants.

Expression under a Chemically Regulatable Promoter

This section describes the replacement of the double 35S promoter in pCGN1761ENX with any promoter of choice; by way of example the chemically regulated PR-1a promoter is described. The promoter of choice is preferably excised from its source by restriction enzymes, but can alternatively be PCR-amplified using primers which carry appropriate terminal restriction sites. Should PCR-amplification be undertaken, then the promoter should be resequenced to check for amplification errors after the cloning of the amplified promoter in the target vector. The chemically regulatable tobacco PR-1a promoter is cleaved from plasmid pCIB1004 (see EP 0 332 104, example 21 for construction) and transferred to plasmid pCGN1761ENX. pCIB1004 is cleaved with NcoI and the resultant 3' overhang of the linearized fragment is rendered blunt by treatment with T4

DNA polymerase. The fragment is then cleaved with HindIII and the resultant PR-1a promoter containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. Selected APS genes can be inserted into this vector, and the fusion products (i.e. promoter-gene-terminator) can subsequently be transferred to any selected transformation vector, including those described in this application.

Constitutive Expression: the Actin Promoter

Several isoforms of actin are known to be expressed in most cell types and consequently the actin promoter is a good choice for a constitutive promoter. In particular, the promoter from the rice Act1 gene has been cloned and characterized (McElroy et al. Plant Cell 2:163–171 (1990)). A 1.3 kb fragment of the promoter was found to contain all the regulatory elements required for expression in rice protoplasts. Furthermore, numerous expression vectors based on the Act1 promoter have been constructed specifically for use in monocotyledens (McElroy et al. Mol. Gen. Genet. 231:150–160 (1991)). These incorporate the Act1-intron 1, Adh1 5' flanking sequence and Adh1-intron 1 (from the maize alcohol dehydrogenase gene) and sequence from the CaMV 35S promoter. Vectors showing highest expression were fusions of 35S and the Act1 intron or the Act1 5' flanking sequence and the Act1 intron. Optimization of sequences around the initiating ATG (of the GUS reporter gene) also enhanced expression. The promoter expression cassettes described by McElroy et al. (Mol. Gen. Genet. 231:150–160 (1991)) can be easily modified for the expression of APS biosynthetic genes and are particularly suitable for use in monocotyledonous hosts. For example, promoter containing fragments can be removed from the McElroy constructions and used to replace the double 35S promoter in pCGN1761ENX, which is then available for the insertion or specific gene sequences. The fusion genes thus constructed can then be transferred to appropriate transformation vectors. In a separate report the rice Act1 promoter with its first intron has also been found to direct high expression in cultured barley cells (Chibbar et al. Plant Cell Rep. 12:506–509 (1993)).

Constitutive Expression: the Ubiquitin Promoter

Ubiquitin is another gene product known to accumulate in many call types and its promoter has been cloned from several species for use in transgenic plants (e.g. sunflower—Binet et al. Plant Science 79:87–94 (1991), maize—Christensen et al. Plant Molec. Biol. 12:619–632 (1989)). The maize ubiquitin promoter has been developed in transgenic monocot systems and its sequence and vectors constructed for monocot transformation are disclosed in the patent publication EP 0 342 926 (to Lubrizol). Further, Taylor et al. (Plant Cell Rep. 12:491–495 (1993)) describe a vector (pAHC25) which comprises the maize ubiquitin promoter and first intron and its high activity in cell suspensions of numerous monocotyledons when introduced via microprojectile bombardment. The ubiquitin promoter is clearly suitable for the expression of APS biosynthetic genes in transgenic plants, especially monocotyledons. Suitable vectors are derivatives of pAHC25 or any of the transformation vectors described in this application, modified by the introduction of the appropriate ubiquitin promoter and/or intron sequences.

Root Specific Expression

A preferred pattern of expression for the APSs of the instant invention is root expression. Root expression is particularly useful for the control of soil-borne phytopathogens such as Rhizoctonia and Pythium. Expression of APSs only in root tissue would have the advantage of controlling root invading phytopathogens, without a concomitant accumulation of APS in leaf and flower tissue and seeds. A suitable root promoter is that described by de Framond (FEBS 290:103–106 (1991)) and also in the published patent application EP 0 452 269 (to Ciba-Geigy). This promoter is transferred to a suitable vector such as pCGN1761ENX for the insertion of an APS gene of interest and subsequent transfer of the entire promoter-gene-terminator cassette to a transformation vector of interest.

Wound Inducible Promoters

Wound-inducible promoters are particularly suitable for the expression of APS biosynthetic genes because they are typically active not just on wound induction, but also at the sites of phytopathogen infection. Numerous such promoters have been described (e.g. Xu et al. Plant Molec. Biol. 22:573–588 (1993), Logemann et al. Plant Cell 1:151–158 (1989), Rohrmeier & Lehle, Plant Molec. Biol. 22:783–792 (1993), Firek et al. Plant Molec. Biol. 22:129–142 (1993), Warner et al. Plant J. 3:191–201 (1993)) and all are suitable for use with the instant invention. Logemann et al. (supra) describe the 5' upstream sequences of the dicotyledonous potato wun1 gene. Xu et al. (supra) show that a wound inducible promoter from the dicotyledon potato (pin2) is active in the monocotyledon rice. Further, Rohrmeier & Lehle (supra) describe the cloning of the maize Wip1 cDNA which is wound induced and which can be used to isolated the cognate promoter using standard techniques. Similarly, Firek et al. (supra) and Warner et al. (supra) have described a wound induced gene from the monocotyledon *Asparagus officinalis* which is expressed at local wound and pathogen invasion sites. Using cloning techniques well known in the art, these promoters can be transferred to suitable vectors, fused to the APS biosynthetic genes of this invention, and used to express these genes at the sites of phytopathogen infection.

Pith Preferred Expression

Patent Application WO 93/07278 (to Ciba-Geigy) describes the isolation of the maize trpA gene which is preferentially expressed in pith cells. The gene sequence and promoter extend up to −1726 from the start of transcription are presented. Using standard molecular biological techniques, this promoter or parts thereof, can be transferred to a vector such as pCGN1761 where it can replace the 35S promoter and be used to drive the expression of a foreign gene in a pith-preferred manner. In fact fragments containing the pith-preferred promoter or parts thereof can be transferred to any vector and modified for utility in transgenic plants.

Pollen-Specific Expression

Patent Application WO 93/07278 (to Ciba-Geigy) further describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a foreign gene in a pollen-specific manner. In fact fragments containing the pollen-specific promoter or parts thereof can be transferred to any vector and modified for utility in transgenic plants.

Leaf-Specific Expression

A maize gene encoding phosphoenol carboxylase (PEPC) has been described by Hudspeth & Grula (Plant Molec Biol 12:579–589 (1989)). Using standard molecular biological techniques the promoter for this gene can be used to drive the expression of any gene in a leaf-specific manner in transgenic plants.

Expression with Chloroplast Targeting

Chen & Jagendorf (J. Biol. Chem. 268:2363–2367 (1993) have described the successful use of a chloroplast transit peptide for import of a heterologous transgene. This peptide used is the transit

Expression with Chloroplast Targeting

Chen & Jagendorf (J. Biol. Chem. 268:2363–2367 (1993) have described the successful use of a chloroplast transit peptide for import of a heterologous transgene. This peptide used is the transit peptide from the rbcS gene from *Nicotiana plumbaginifolia* (Poulsen et al. Mol. Gen. Genet. 205:193–200 (1986)). Using the restriction enzymes DraI and SphI, or Tsp509I and SphI the DNA sequence encoding this transit peptide can be excised from plasmid prbcS-8B (Poulsen et al. supra) and manipulated for use with any of the constructions described above. The DraI-SphI fragment extends from −58 relative to the initiating rbcS ATG to, and including, the first amino acid (also a methionine) of the mature peptide immediately after the import cleavage site, whereas the Tsp509I-SphI fragment extends from −8 relative to the initiating rbcS ATG to, and including, the first amino acid of the mature peptide. Thus, these fragment can be appropriately inserted into the polylinker of any chosen expression cassette generating a transcriptional fusion to the untranslated leader of the chosen promoter (e.g. 35S, PR-1a, actin, ubiquitin etc.), whilst enabling the insertion of a required APS gene in correct fusion downstream of the transit peptide. Constructions of this kind are routine in the art. For example, whereas the DraI end is already blunt, the 5' Tsp509I site may be rendered blunt by T4 polymerase treatment, or may alternatively be ligated to a linker or adaptor sequence to facilitate its fusion to the chosen promoter. The 3' SphI site may be maintained as such, or may alternatively be ligated to adaptor of linker sequences to facilitate its insertion into the chosen vector in such a way as to make available appropriate restriction sites for the subsequent insertion of a selected APS gene. Ideally the ATG of the SphI site is maintained and comprises the first ATG of the selected APS gene. Chen & Jagendorf (supra) provide consensus sequences for ideal cleavage for chloroplast import, and in each ease a methionine is preferred at the first position of the mature protein. At subsequent positions there is more variation and the amino acid may not be so critical. In any case, fusion constructions can be assessed for efficiency of import in vitro using the methods described by Bartlett et al. (In: Edelmann et al. (Eds.) Methods in Chloroplast Molecular Biology, Elsevier. pp 1081–1091 (1982)) and Wasmann et al. (Mol. Gen. Genet. 205:446–453 (1986)). Typically the best approach may be to generate fusions using the selected APS gene with no modifications at the aminoterminus, and only to incorporate modifications when it is apparent that such fusions are not chloroplast imported at high efficiency, in which case modifications may be made in accordance with the established literature (Chen & Jagendorf, supra; Wasman et al., supra; Ko & Ko, J. Biol. Chem. 267:13910–13916 (1992)).

A preferred vector is constructed by transferring the DraI-SphI transit peptide encoding fragment from prbcS-8B to the cloning vector pCGN1761ENX/Sph-. This plasmid is cleaved with EcoRI and the termini rendered blunt by treatment with T4 DNA polymerase. Plasmid prbcS-8B is cleaved with SphI and ligated to an annealed molecular adaptor of the sequence 5'-CCAGCTGGAATTCCG-3' (SEQ ID NO:13)/5'-CGGAATTCCAGCTGGCATG-3' (SEQ ID NO:14). The resultant product is 5'-terminally phosphorylated by treatment with T4 kinase. Subsequent cleavage with DraI releases the transit peptide encoding fragment which is ligated into the blunt-end ex-EcoRI sites of the modified vector described above. Clones oriented with the 5' end of the insert adjacent to the 3' end of the 35S promoter are identified by sequencing. These clones carry a DNA fusion of the 35S leader sequence to the rbcS-8A promoter-transit peptide sequence extending from −58 relative to the rbcS ATG to the ATG of the mature protein, and including at that position a unique SphI site, and a newly created EcoRI site, as well as the existing NotI and XhoI sites of pCGN1761ENX. This new vector is designated pCGN1761/CT. DNA sequences are transferred to pCGN1761/CT in frame by amplification using PCR techniques and incorporation of an SphI, NsphI, or NlaIII site at the amplified ATG, which following restriction enzyme cleavage with the appropriate enzyme is ligated into SphI-cleaved pCGN1761/CT. To facilitate construction, it may be required to change the second amino acid of cloned gene, however, in almost all cases the use of PCR together with standard site directed mutagenesis will enable the construction of any desired sequence around the cleavage site and first methionine of the mature protein.

A further preferred vector is constructed by replacing the double 35S promoter of pCGN1761ENX with the BamHI-SphI fragment of prbcS-8A which contains the full-length light regulated rbcS-8A promoter from −1038 (relative to the transcriptional start site) up to the first methionine of the mature protein. The modified pCGN1761 with the destroyed SphI site is cleaved with PstI and EcoRI and treated with T4 DNA polymerase to render termini blunt. prbcS-8A is cleaved SphI and ligated to the annealed molecular adaptor of the sequence described above. The resultant product is 5'-terminally phosphorylated by treatment with T4 kinase. Subsequent cleavage with BamHI releases the promoter-transit peptide containing fragment which is treated with T4 DNA polymerase to render the BamHI terminus blunt. The promoter-transit peptide fragment thus generated is cloned into the prepared pCGN1761ENX vector, generating a construction comprising the rbcS-8A promoter and transit peptide with an SphI site located at the cleavage site for insertion of heterologous genes. Further, downstream of the SphI site there are EcoRI (re-created), NotI, and XhoI cloning sites. This construction is designated pCGN1761rbcS/CT.

Similar manipulations can be undertaken to utilize other GS2 chloroplast transit peptide encoding sequences from other sources (monocotyledonous and dicotyledonous) and from other genes. In addition, similar procedures can be followed to achieve targeting to other subcellular compartments such as mitochondria.

Example 38

Techniques for the Isolation of New Promoters Suitable for the Expression of APS Genes New promoters are isolated using standard molecular biological techniques including any of the techniques described below. Once isolated, they are fused to reporter genes such as GUS or LUC and their expression pattern in transgenic plants analyzed (Jefferson et al. EMBO J. 6:3901–3907 (1987); Ow et al. Science 234:856–859 (1986)

). Promoters which show the desired expression pattern are fused to APS genes for expression in planta.

Subtractive cDNA Cloning

Subtractive cDNA cloning techniques are useful for the generation of cDNA libraries enriched for a particular population of mRNAs (e.g. Hara et al. Nucl. Acids Res. 19:1097–7104 (1991)). Recently, techniques have been described which allow the construction of subtractive libraries from small amounts of tissue (Sharma et al. Biotechniques 15:610–612 (1993)). These techniques are suitable for the enrichment of messages specific for tissues which may be available only in small amounts such as the tissue immediately adjacent to wound or pathogen infection sites.

Differential Screening by Standard Plus/Minus Techniques

λ phage carrying cDNAs derived from different RNA populations (viz. root versus whole plant, stem specific versus whole plant, local pathogen infection points versus whole plant, etc.) are plated at low density and transferred to two sets of hybridization filters (for a review of differential screening techniques see Calvet, Pediatr. Nephrol. 5:751–757 (1991). cDNAs derived from the "choice" RNA population are hybridized to the first set and cDNAs from whole plant RNA are hybridized to the second set of filters. Plaques which hybridize to the first probe, but not to the second, are selected for further evaluation. They are picked and their cDNA used to screen Northern blots of "choice" RNA versus RNA from various other tissues and sources. Clones showing the required expression pattern are used to clone gene sequences from a genomic library to enable the isolation of the cognate promoter. Between 500 and 5000 bp of the cloned promoter is then fused to a reporter gene (e.g. GUS, LUC) and reintroduced into transgenic plants for expression analysis.

Differential Screening by Differential Display

RNA is isolated from different sources i.e. the choice source and whole plants as control, and subjected to the differential display technique of Liang and Pardee (Science 257:967–971 (1992)). Amplified fragments which appear in the choice RNA, but not the control are gel purified and used as probes on Northern blots carrying different RNA samples as described above. Fragments which hybridize selectively to the required RNA are cloned and used as probes to isolate the cDNA and also a genomic DNA fragment from which the promoter can be isolated. The isolated promoter is fused to a the GUS or LUC reporter gene as described above to assess its expression pattern in transgenic plants.

Promoter Isolation Using "Promoter Trap" Technology

The insertion of promoterless reporter genes into transgenic plants can be used to identify sequences in a host plant which drive expression in desired cell types or with a desired strength. Variations of this technique is described by Ott & Chua (Mol. Gen. Genet. 223:169–179 (1990)) and Kertbundit et al. (Proc. Natl. Acad. Sci. USA 88:5212–5216 (1991)). In standard transgenic experiments the same principle can be extended to identify enhancer elements in the host genome where a particular transgene may be expressed at particularly high levels.

Example 39

Transformation of Dicotyledons

Transformation techniques for dicotyledons are well known in the art and include Agrobacterium-based techniques and techniques which do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J 3:2717–2722 (1984), Potrykus et al., Mol. Gen. Genet. 199:169–177 (1985), Reich et al., Biotechnology 4:1001–1004 (1986), and Klein et al., Nature 327:70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. The many crop species which are routinely transformable by Agrobacterium include tobacco, tomato, sunflower, cotton, oilseed rape, potato, soybean, alfalfa and poplar (EP 0 317 511 (cotton [1313]), EP 0 249 432 (tomato, to Calgene), WO 87/07299 (Brassica, to Calgene), U.S. Pat. No. 4,795,855 (poplar)). Agrobacterium transformation typically involves the transfer of the binary vector carrying the foreign DNA of interest (e.g. pCIB200 or pCIB2001) to an appropriate Agrobacterium strain which may depend of the complement of vir genes carried by the host Agobacterium strain either on a co-resident Ti plasmid or chromosomally (e.g. strain CIB542 for pCIB200 and pCIB2001 (Uknes et al. Plant Cell 5:159–169 (1993)). The transfer of the recombinant binary vector to Agrobacterium is accomplished by a triparental mating procedure using *E. coli* carrying the recombinant binary vector, a helper *E. coli* strain which carries a plasmid such as pRK2013 and which is able to mobilize the recombinant binary vector to the target Agrobacterium strain. Alternatively, the recombinant binary vector can be transferred to Agobacterium by DNA transformation (Höfgen & Willmitzer, Nucl. Acids Res. 16:9877(1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Example 40

Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4:1093–1096 (1986)).

Patent Applications EP 0 292 435 ([1280/1281] to Ciba-Geigy), EP 0 392 225 (to Ciba-Geigy) and WO 93/07278 (to Ciba-Geigy) describe techniques for the preparation of callus and protoplasts from an élite inbred line of maize, transformation of protoplasts using PEG or electroporation, and the regeneration of maize plants from transformed protoplasts. Gordon-Kamm et al. (Plant Cell 2:603–618 (1990)) and Fromm et al. (Biotechnology 8:833–839 (1990)) have published techniques for transformation of A188-derived maize line using particle bombardment. Furthermore, application WO 93/07278 (to Ciba-Geigy) and Koziel et al. (Biotechnology 11:194–200 (1993)) describe techniques for the transformation of élite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al., Plant Cell Rep 7:379–384 (1988); Shimamoto et al. Nature 338:274–277 (1989); Datta et al. Biotechnology 8:736–740 (1990)). Both types are also routinely transformable using particle bombardment (Christou et al. Biotechnology 9:957–962 (1991)).

Patent Application EP 0 332 581 (to Ciba-Geigy) describes techniques for the generation, transformation and regeneration of Pooideae protoplasts. These techniques allow the transformation of Dactylis and wheat. Furthermore, wheat transformation was been described by Vasil et al. (Biotechnology 10:667–674 (1992)) using particle bombardment into cells of type C long-term regenerable callus, and also by Vasil et al. (Biotechnology 11:1553–1558 (1993)) and Weeks et al. (Plant Physiol. 102:1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashiga & Skoog, Physiologia Plantarum 15:473–497 (1962)) and 3 mg/l 2,4-D for induction of somatic embryos which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contained half-strength MS, 2% sucrose, and the same concentration of selection agent. Patent application 08/147,161 describes methods for wheat transformation and is hereby incorporated by reference.

Example 41

Expression of Pyrrolnitrin in Transgenic Plants

The GC content of all four pyrrolnitrin ORFs is between 62 and 68% and consequently no AT-content related problems are anticipated with their expression in plants. It may, however, be advantageous to modify the genes to include codons preferred in the appropriate target plant species. Fusions of the kind described below can be made to any desired promoter with or without modification (e.g. for optimized translational initiation in plants or for enhanced expression).

Expression behind the 35S Promoter

Each of the four pyrrolnitrin ORFs is transferred to pBluescript KS II for further manipulation. This is done by PCR amplification using primers homologous to each end of each gene and which additionally include a restriction site to facilitate the transfer of the amplified fragments to the pBluescript vector. For ORF1, the aminoterminal primer includes a SalI site and the carboxyterminal primer a NotI site. Similarly for ORF2, the aminoterminal primer includes a SalI site and the carboxyterminal primer a NotI site. For ORF3, the aminoterminal primer includes a NotI site and the carboxyterminal primer an XhoI site. Similarly for ORF4, the aminoterminal primer includes a NotI site and the carboxyterminal palmer an XhoI site. Thus, the amplified fragments are cleaved with the appropriate restriction enzymes (chosen because they do not cleave within the ORF) and are then ligated into pBluescript, also correspondingly cleaved. The cloning of the individual ORFs in pBluescript facilitates their subsequent manipulation.

Destruction of internal restriction sites which are required for further construction is undertaken using the procedure of "inside-outside PCR" (Innes et al. PCR Protocols: A guide to methods and applications. Academic Press, New York (1990)). Unique restriction sites sought at either side of the site to be destroyed (ideally between 100 and 500 bp from the site to be destroyed) and two separate amplifications are set up. One extends from the unique site left of the site to be destroyed and amplifies DNA up to the site to be destroyed with an amplifying oligonucleotide which spans this site and incorporates an appropriate base change. The second amplification extends from the site to be destroyed up to the unique site rightwards of the site to be destroyed. The oligonucleotide spanning the site to be destroyed in this second reaction incorporates the same base change as in the first amplification and ideally shares an overlap of between 10 and 25 nucleotides with the oligonucleotide from the first reaction. Thus the products of both reactions share an overlap which incorporates the same base change in the restriction site corresponding to that made in each amplification. Following the two amplifications, the amplified products are gel purified (to remove the four oligonucleotide primers used), mixed together and reamplified in a PCR reaction using the two primers spanning the unique restriction sites. In this final PCR reaction the overlap between the two amplified fragments provides the priming necessary for the first round of synthesis. The product of this reactions extends from the leftwards unique restriction site to the rightwards unique restriction site and includes the modified restriction site located internally. This product can be cleaved with the unique sites and inserted into the unmodified gene at the appropriate location by replacing the wild-type fragment.

To render ORF1 free of the first of its two internal SphI sites oligonucleotides spanning and homologous to the unique XmaI and EspI are designed. The XmaI oligonucleotide is used in a PCR reaction together with an oligonucleotide spanning the first SphI site and which includes the sequence . . . CCCCCTCATGC . . . (lower strand, SEQ ID NO:15), thus introducing a base change into to SphI site. A second PCR reaction utilizes an oligonucleotide spanning the SphI site (upper strand) incorporating the sequence . . . GCATGAGGGGG . . . (SEQ ID NO:16) and is used in combination with the EspI site-spanning oligonucleotide. The two products are gel purified and themselves amplified with the XmaI and EspI-spanning oligonucleotides and the resultant fragment is cleaved with XmaI and EspI and used to replace the native fragment in the ORF1 clone. According to the above description, the modified SphI site is GCATGA and does not cause a codon change. Other changes in this site are possible (i.e. changing the second nucleotide to a G, T, or A) without corrupting amino acid integrity.

A similar strategy is used to destroy the second SphI site in ORF1. In this case, EspI is a suitable leftwards-located restriction site, and the rightwards-located restriction site is PstI, located close to the 3' end of the gene or alternatively SstI which is not found in the ORF sequence, but immediately adjacent in the pBluescript polylinker. In this case an appropriate oligonucleotide is one which spans this site, or alternatively one of the available and pBluescript sequencing primers. This SphI site is modified to GAATGC or GCATGT or GAATGT. Each of these changes destroys the site without causing a codon change.

To render ORF2 free of its single SphI site a similar procedure is used. Leftward restriction sites are provided by PstI or MluI, and a suitable rightwards restriction site is provided by SstI in the pBluescript polylinker. In this case the site is changed to GCTTGC, GCATGC or GCTTGT; these changes maintain amino acid integrity.

ORF3 has no internal SphI sites.

In the case of ORF4, PstI provides a suitable rightwards unique site, but there is no suitable site located leftwards of the single SphI site to be changed. In this case a restriction site in the pBluescript polylinker can be used to the same effect as already described above. The SphI site is modified to GGATGC, GTATGC, GAATGC, or GCATGT etc.

The removal of SphI sites from the pyrrolnitrin biosynthetic genes as described above facilitates their transfer to the pCGN1761SENX vector by amplification using an aminoterminal oligonucleotide primer which incorporates an SphI site at the ATG and a carboxyterminal primer which incorporates a restriction site not found in the gene being amplified. The resultant amplified fragment is cleaved with SphI and the carboxyterminal enzyme and cloned into pCGN1761SENX. Suitable restriction enzyme sites for incorporation into the carboxyterminal primer are NotI (for all four ORFs), XhoI (for ORF3 and ORF4), and EcoRI (for ORF4). Given the requirement for the nucleotide C at position 6 within the SphI recognition site, in some cases the second codon of the ORF may require changing so as to start with the nucleotide C. This construction fuses each ORF at its ATG to the SphI sites of the translation-optimized vector pCGN1761SENX in operable linkage to the double 35S promoter. After construction is complete the final gene insertions and fusion points are resequenced to ensure that no undesired base changes have occurred.

By utilizing an aminoterminal oligonucleotide primer which incorporates an NcoI site at its ATG instead of an SphI site, ORFs 1–4 can also be easily cloned into to the translation-optimized vector pCGN1761NENX. None of the four pyrrolnitrin biosynthetic gene ORFs carry an NcoI site and consequently there is no requirement in this case to destroy internal restriction sites. Primers for the carboxyterminus of the gene are designed as described above and the cloning is undertaken in a similar fashion. Given the requirement for the nucleotide G at position 6 within the NcoI recognition site, in some cases the second codon of the ORF may require changing so as to start with the nucleotide G. This construction fuses each ORF at its ATG to the NcoI site of pCGN1761NENX in operable linkage to the double 35S promoter.

The expression cassettes of the appropriate pCGN1761-derivative vectors are transferred to transformation vectors. Where possible multiple expression cassettes are transferred to a single transformation vector so as to reduce the number of plant transformations and crosses between transformants which may be required to produce plants expressing all four ORFs and thus producing pyrrolnitrin.

Expression behind 35S with Chloroplast Targeting

The pyrrolnitrin ORFs 1–4 amplified using oligonucleotides carrying an SphI site at their aminoterminus are cloned into the 35S-chloroplast targeted vector pCGN1761/CT. The fusions are made to the SphI site located at the cleavage site of the rbcS transit peptide. The expression cassettes thus created are transferred to appropriate transformation vectors (see above) and used to generate transgenic plants. As tryptophan, the precursor for pyrrolnitrin biosynthesis, is synthesized in the chloroplast, it may be advantageous to express the biosynthetic genes for pyrrolnitrin in the chloroplast to ensure a ready supply of substrate. Transgenic plants expressing all four ORFs will target all four gene products to the chloroplast and will thus synthesize pyrrolnitrin in the chloroplast.

Expression behind rbcS with Chloroplast Targeting

The pyrrolnitrin ORFs 1–4 amplified using oligonucleotides carrying an SphI site at their aminoterminus are cloned into the rbcS-chloroplast targeted vector pCGN1761rbcS/CT. The fusions are made to the SphI site located at the cleavage site of the rbcS transit peptide. The expression cassettes thus created are transferred to appropriate transformation vectors (see above) and used to generate transgenic plants. As tryptophan, the precursor for pyrrolnitrin biosynthesis, is synthesized in the chloroplast, it may be advantageous to express the biosynthetic genes for pyrrolnitrin in the chloroplast to ensure a ready supply of substrate. Transgenic plants expressing all four ORFs will target all four gene products to the chloroplast and will thus synthesize pyrrolnitrin in the chloroplast. The expression of the four ORFs will, however, be light induced.

Example 42

Expression of Soraphen in Transgenic Plants

Clone p98/1 contains the entirety of the soraphen biosynthetic gene ORF1 which encodes five biosynthetic modules for soraphen biosynthesis. The partially sequenced ORF2 contains the remaining three modules, and further required for soraphen biosynthesis is the soraphen methylase located on the same operon.

Soraphen ORF1 is manipulated for expression in transgenic plants in the following manner. A DNA fragment is amplified from the aminoterminus of ORF1 using PCR and p98/1 as template. The 5' oligonucleotide primer includes either an SphI site or an NcoI site at the ATG for cloning into the vectors pCGN1761SENX or pCGNNENX respectively. Further, the 5' oligonucleotide includes either the base C (for SphI cloning) or the base G (for NcoI cloning) immediately after the ATG, and thus the second amino acid of the protein is changed either to a histidine or an aspartate (other amino acids can be selected for position 2 by additionally changing other bases of the second codon). The 3' oligonucleotide for the amplification is located at the first BglII site of the ORF and incorporates a distal EcoRI site enabling the amplified fragment to be cleaved with SphI (or NcoI) and EcoRI, and then cloned into pCGN1761SENX (or pCGN1761NENX). To facilitate cleavage of the amplified fragments, each oligonucleotide includes several additional bases at its 5' end. The oligonucleotides preferably have 12–30 bp homology to the ORF1 template, in addition to the required restriction sites and additional sequences. This manipulation fuses the aminoterminal ~112 amino acids of ORF1 at its ATG to the SphI or NcoI sites of the translation optimized vectors pCGN1761SENX or pCGN1761NENX in linkage to the double 35S promoter. The remainder of ORF1 is carried on three BglII fragments which can be sequentially cloned into the unique BglII site of the above-detailed constructions. The introduction of the first of these fragments is no problem, and requires only the cleavage of the aminoterminal construction with BglII followed by introduction of the first of these fragments. For the introduction of the two remaining fragments, partial digestion of the aminoterminal construction is required (since this construction now has an additional BglII site), followed by introduction of the next BglII fragment. Thus, it is possible to construct a vector containing the entire ~25 kb of soraphen ORF1 in operable fusion to the 35S promoter.

An alternative approach to constructing the soraphen ORF1 by the fusion of sequential restriction fragments is to amplify the entire ORF using PCR. Barnes (Proc. Natl. Acad. Sci USA 91:2216–2220 (1994)) has recently described techniques for the high-fidelity amplification of fragments by PCR of up to 35 kb, and these techniques can be applied to ORF1. Oligonucleotides specific for each end of ORF1, with appropriate restriction sites added are used to amplify the entire coding region, which is then cloned into appropriate sites in a suitable vector such as pCGN1761 or its derivatives. Typically after PCR amplification, resequencing is advised to ensure that no base changes have arisen in the amplified sequence. Alternatively, a functional assay can be done directly in transgenic plants.

Yet another approach to the expression of the genes for polyketide biosynthesis (such as soraphen) in transgenic plants is the construction, for expression in plants, of transcriptional units which comprise less than the usual complement of modules, and to provide the remaining modules on other transcriptional units. As it is believed that the biosynthesis of polyketide antibiotics such as soraphen is a process which requires the sequential activity of specific modules and that for the synthesis of a specific molecule these activities should be provided in a specific sequence, it is likely that the expression of different transgenes in a plant carrying different modules may lead to the biosynthesis of novel polyketide molecules because the sequential enzymatic nature of the wild-type genes is determined by their configuration on a single molecule. It is assumed that the localization of five specific modules for soraphen biosynthesis on ORF1 is determinatory in the biosynthesis of soraphen, and that the expression of, say three modules on one transgene and the other two on another, together with ORF2, may result in biosynthesis of a polyketide with a different molecular structure and possibly with a different antipathogenic activity. This invention encompasses all such deviations of module expression which may result in the synthesis in transgenic organisms of novel polyketides.

Although specific construction details are only provided for ORF1 above, similar techniques are used to express ORF2 and the soraphen methylase in transgenic plants. For the expression of functional soraphen in plants it is anticipated that all three genes must be expressed and this is done as detailed in this specification.

Fusions of the kind described above can be made to any desired promoter with or without modification (e.g. for optimized translational initiation in plants or for enhanced expression). As the ORFs identified for soraphen biosynthesis are around 70% GC rich it is not anticipated that the coding sequences should require modification to increase GC content for optimal expression in plants. It may, however, be advantageous to modify the genes to include codons preferred in the appropriate target plant species.

Example 43

Expression of Phenazine in Transgenic Plants

The GC content of all the cloned genes encoding biosynthetic enzymes for phenazine synthesis is between 58 and 65% and consequently no AT-content related problems are anticipated with their expression in plants (although it may be advantageous to modify the genes to include codons preferred in the appropriate target plant species.). Fusions of the kind described below can be made to any desired promoter with or without modification (e.g. for optimized translational initiation in plants or for enhanced expression).

Expression behind the 35S Promoter

Each of the three phenazine ORFs is transferred to pBluescript SK II for further manipulation. The phzB ORF is transferred as an EcoRI-BglII fragment cloned from plasmid pLSP18-6H3del3 containing the entire phenazine operon. This fragment is transferred to the EcoRI-BamHI sites of pBluescdpt SK II. The phzC ORF is transferred from pLSP18-6H3del3 as an XhoI-ScaI fragment cloned into the XhoI-SmaI sites of pBluescfipt II SK. The phzD ORF is transferred from pLSP18-6H3del3 as a BglII-HindIII fragment into the BamHI-HindIII sites of pBluescript II SK.

Destruction of internal restriction sites which are required for further construction is undertaken using the procedure of "inside-outside PCR" described above (Innes et al. supra). In the case of the phzB ORF two SphI sites are destroyed (one site located upstream of the ORF is left intact). The first of these is destroyed using the unique restriction sites EcoRI (left of the SphI site to be destroyed) and BclI (right of the SphI site). For this manipulation to be successful, the DNA to be BclI cleaved for the final assembly of the inside-outside PCR product must be produced in a dam-minus *E. coli* host such as SCS110 (Stratagene). For the second phzB SphI sites, the selected unique restriction sites are PstI and SpeI, the latter being beyond the phzB ORF in the pBluescript polylinker. The phzC ORF has no internal SphI sites, and so this procedure is not required for phzC. The phzD ORF, however, has a single SphI site which can be removed using the unique restriction sites XmaI and HindIII (the XmaI/SmaI site of the pBluescript polylinker is no longer present due to the insertion of the ORF between the BamHI and HindIII sites).

The removal of SphI sites from the phenazine biosynthetic genes as described above facilitates their transfer to the pCGN1761SENX vector by amplification using an aminoterminal oligonucleotide primer which incorporates an SphI site at the ATG and a carboxyterminal primer which incorporates a restriction site not found in the gene being amplified. The resultant amplified fragment is reaved with SphI and the carboxyterminal enzyme and cloned into pCGN1761SENX. Suitable restriction enzyme sites for incorporation into the carboxyterminal primer are EcoRI and NotI (for all three ORFs; NotI will need checking when sequence complete), and XhoI (for phzB and phzD). Given the requirement for the nucleotide C at position 6 within the SphI recognition site, in some cases the second codon of the ORF may require changing so as to start with the nucleotide C. This construction fuses each ORF at its ATG to the SphI sites of the translation-optimized vector pCGN1761SENX in operable linkage to the double 35S promoter. After construction is complete the final gene insertions and fusion points are resequenced to ensure that no undesired base changes have occurred.

By utilizing an aminoterminal oligonucleotide primer which incorporates an NcoI site at its ATG instead of an SphI site, the three phz ORFs can also be easily cloned into to the translation-optimized vector pCGN1761NENX. None of the three phenazine biosynthetic gene ORFs carry an NcoI site and consequently there is no requirement in this case to destroy internal restriction sites. Primers for the carboxyterminus of the gene are designed as described above and the cloning is undertaken in a similar fashion. Given the requirement for the nucleotide G at position 6 within the NcoI recognition site, in some cases the second codon of the ORF may require changing so as to start with the nucleotide G. This construction fuses each ORF at its ATG to the NcoI site of pCGN1761NENX in operable linkage to the double 35S promoter.

The expression cassettes of the appropriate pCGN1761-derivative vectors are transferred to transformation vectors. Where possible multiple expression cassettes are transferred to a single transformation vector so as to reduce the number of plant transformations and crosses between transformants which may be required to produce plants expressing all four ORFs and thus producing phenazine.

Expression behind 35S with Chloroplast Targeting

The three phenazine ORFs amplified using oligonucleotides carrying an SphI site at the aminoterminus are cloned into the 35S-chloroplast targeted vector pCGN1761/CT. The fusions are made to the SphI site located at the cleavage site of the rbcS transit peptide. The expression cassettes thus created are transferred to appropriate transformation vectors (see above) and used to generate transgenic plants. As chorismate, the likely precursor for phenazine biosynthesis, is synthesized in the chloroplast, it may be advantageous to express the biosynthetic genes for phenazine in the chloroplast to ensure a ready supply of substrate. Transgenic plants expressing all three ORFs will target all three gene products to the chloroplast and will thus synthesize phenazine in the chloroplast.

Expression behind rbcS with Chloroplast Targeting

The three phenazine ORFs amplified using oligonucleotides carrying an SphI site at their aminoterminus are cloned into the rbcS-chloroplast targeted vector pCGN1761rbcS/CT. The fusions are made to the SphI site located at the cleavage site of the rbcS transit peptide. The expression cassettes thus created are transferred to appropriate transformation vectors (see above) and used to generate transgenic plants. Aschorismate, the likely precursor for phenazine biosynthesis, is synthesized in the chloroplast, it may be advantageous to express the biosynthetic genes for phenazine in the chloroplast to ensure a ready supply of substrate. Transgenic plants expressing all three ORFs will target all four gene products to the chloroplast and will thus synthesize phenazine in the chloroplast. The expression of the three ORFs will, however, be light induced.

Example 44

Expression of the Non-Ribosomally Synthesized Peptide Antibiotic Gramicidin in Transgenic Plants The three *Bacillus brevis* gramicidin biosynthetic genes grsA, grsB and grsT have been previously cloned and sequenced (Turgay et al. Mol. Microbiol. 6:529–546 (1992); Kraetzschmar et al. J. Bacteriol. 171:5422–5429 (1989)). They are 3296, 13358, and 770 bp in length, respectively. These sequences are also published as GenBank accession numbers X61658 and M29703. The manipulations described here can be undertaken using the publicly available clones published by Turgay et al. (supra) and Kraetzschmar et al. (supra), or alternatively from newly isolated clones from *Bacillus brevis* isolated as described herein.

Each of the three ORFs grsA, grsB, and grsT is PCR amplified using oligonucleotides which span the entire coding sequence. The leftward (upstream) oligonucleotide includes an SstI site and the rightward (downstream) oligonucleotide includes an XhoI site. These restriction sites are not found within any of the three coding sequences and enable the amplified products to be cleaved with SstI and XhoI for insertion into the corresponding sites of pBluescript II SK. This generates the clones pBL-GRSa, pBLGRSb and pBLGRSt. The CG content of these genes lies between 35 and 38%. Ideally, the coding sequences encoding the three genes may be remade using the techniques referred to in Section K, however it is possible that the unmodified genes may be expressed at high levels in transgenic plants without encountering problems due to their AT content. In any case it may be advantageous to modify the genes to include codons preferred in the appropriate target plant species.

The ORF grsA contains no SphI site and no NcoI site. This gene can be thus amplified from pBLGSRa using an aminoterminal oligonucleotide which incorporates either an SphI site or an NcoI site at the ATG, and a second carboxyterminal oligonucleotide which incorporates an XhoI site, thus enabling the amplification product to be cloned directly into pCGN1761SENX or pCGN1761NENX behind the double 35S promoter.

The ORF grsB contains no NcoI site and therefore this gene can be amplified using an aminoterminal oligonucleotide containing an NcoI site in the same was as described above for the grsA ORF; the amplified fragment is cleaved with NcoI and XhoI and ligated into pCGN1761NENX. However, the grsB ORF contains three SphI sites and these are destroyed to facilitate the subsequent cloning steps. The sites are destroyed using the "inside-outside" PCR technique described above. Unique cloning sites found within the grsB gene but not within pBluescript II SK are EcoN1, PflM1, and RsrII. Either EcoN1 or PflM1 can be used together with RsrII to remove the first two sites and RsrII can be used together with the ApaI site of the pBluescript polylinker to remove the third site. Once these sites have been destroyed (without causing a change in amino acid), the entirety of the grsB ORF can be amplified using an aminoterminal oligonucleotide including an SphI site at the ATG and a carboxyterminal oligonucleotide incorporating an XhoI site. The resultant fragment is cloned into pCGN1761SENX. In order to successfully PCR-amplify fragments of such size, amplification protocols are modified in view of Barnes (1994, supra) who describes the high fidelity amplification of large DNA fragments. An alternative approach to the transfer of the grsB ORF to pCGN1761SENX without necessitating the destruction of the three SphI restriction sites involves the transfer to the SphI and XhoI cloning sites of pCGN1761SENX of an aminoterminal fragment of grsB by amplification from the ATG of the gene using an aminoterminal oligonucleotide which incorporates a SphI site at the ATG, and a second oligonucleotide which is adjacent and 3' to the PflM1 site in the ORF and which includes an XhoI site. Thus the aminoterminal amplified fragment is cleaved with SphI and XhoI and cloned into pCGN1761SENX. Subsequently the remaining portion of the grsB gene is excised from pBLGRSb using PflMI and XhoI (which cute in the pBluescript polylinker) and cloned into the aminoterminal carrying construction cleaved with PflMI and XhoI to reconstitute the gene.

The ORF grsT contains no SphI site and no NcoI site. This gene can be thus amplified from pBLGSRt using an aminoterminal oligonucleotide which incorporates either an SphI site or an NcoI site at the initiating codon which is changed to ATG (from GTG) for expression in plants, and a second carboxyterminal oligonucleotide which incorporates an XhoI site, thus enabling the amplification product to be cloned directly into pCGN1761SENX or pCGN1761NENX behind the double 35S promoter.

Given the requirement for the nucleotide C at position 6 within the SphI recognition site, and the requirement for the nucleotide G at position 6 within the NcoI recognition site, in some cases the second codon of the ORF may require changing so as to start with the appropriate nucleotide.

Transgenic plants are created which express all three gramicidin biosynthetic genes as described elsewhere in the specification. Transgenic plants expressing all three genes synthesize gramicidin.

Example 45

Expression of the Ribosomally Synthesized Peptide Lantibiotic Epidermin in Transgenic Plants The epiA ORF encodes the structural unit for epidermin biosynthesis and is approximately 420 bp in length (GenBank Accession No. X07840; Schnell et al. Nature 333:276–278 (1988)). This gene can be subcloned using PCR techniques from the plasmid pTü32 into pBluescript SK II using oligonucleotides carrying the terminal restriction sites BamHI (5') and PstI (3'). The epiA gene sequence has a GC content of 27% and this can be increased using techniques of gene synthesis referred to elsewhere in this specification; this sequence modification may not be essential, however, to ensure high-level expression in plants. Subsequently the epiA ORF is transferred to the cloning vector pCGN1761SENX or pCGN1761NENX by PCR amplification of the gene using an aminoterminal oligonucleotide spanning the initiating methionine and carrying an SphI site (for cloning into pCGN1761SENX) or an NcoI site (for cloning into pCGN1761NENX), together with a carboxyterminal oligonucleotide carrying an EcoRI, a NotI, or an XhoI site for cloning into either pCGN1761SENX or pCGN1761NENX. Given the requirement for the nucleotide C at position 6 within the SphI recognition site, and the requirement for the nucleotide G at position 6 within the NcoI recognition site, in some cases the second codon of the ORF may require changing so as to start with the appropriate nucleotide.

Using cloning techniques described in this specification or well known in the art, the remaining genes of the epi operon (viz. epiB, epiC, epiD, epiQ, and epiP) are subcloned from plasmid pTü32 into pBluescript SK II. These genes are responsible for the modification and polymerization of the epiA-encoded structural unit and are described in Kupke et al. (J. Bacteriol. 174:5354–5361 (1992)) and Schnell et al. (Eur. J. Biochem. 204:57–68 (1992)). The subcloned ORFs are manipulated for transfer to pCGN1761-derivative vectors as described above. The expression cassettes of the appropriate pCGN1761-derivative vectors are transferred to transformation vectors. Where possible multiple expression cassettes are transferred to a single transformation vector so as to reduce the number of plant transformations and crosses between transformants which may be required to produce plants expressing all required ORFs and thus producing epidermin.

L. Analysis of Transgenic Plants for APS Accumulation

Example 46

Analysis of APS Gene Expression

Expression of APS genes in transgenic plants can be analyzed using standard Northern blot techniques to assess the amount of APS mRNA accumulating in tissues. Alternatively, the quantity of APS gene product can be assessed by Western analysis using antisera raised to APS biosynthetic gene products. Antisera can be raised using conventional techniques and proteins derived from the expression of APS genes in a host such as E. coli. To avoid the raising of antisera to multiple gene products from E. coli expressing multiple APS genes from multiple ORF operons, the APS biosynthetic genes can be expressed individually in E. coli. Alternatively, antisera can be raised to synthetic peptides designed to be homologous or identical to known APS biosynthetic predicted amino acid sequence. These techniques are well known in the art.

Example 47

Analysis of APS Production in Transgenic Plants

For each APS, known protocols are used to detect production of the APS in transgenic plant tissue. These protocols are available in the appropriate APS literature. For pyrrolnitrin, the procedure described in example 11 is used, and for soraphen the procedure described in example 17. For phenazine determination, the procedure described in example 18 can be used. For non-ribosomal peptide antibiotics such as gramicidin S, an appropriate general technique is the assaying of ATP-PP$_i$ exchange. In the case of gramicidin, the grsA gene can be assayed by phenylalanine-dependent ATP-PP$_i$ exchange and the grsB gene can be assayed by proline, valine, ornithine, or leucine-dependent ATP-PP$_i$ exchange. Alternative techniques are described by Gause & Brazhnmikova (Lancet 247:715 (1944)). For ribosomally synthesized peptide antibiotics isolation can be achieved by butanol extraction, dissolving in methanol and diethyl ether, followed by chromatography as described by Allgaier et al. for epidermin (Eur. Ju. Biochem. 160:9–22 (1986)). For many APSs (e.g. pyrrolnitrin, gramicidin, phenazine) appropriate techniques are provided in the Merck Index (Merck & Co., Rahway, N.J. (1989)).

M. Assay of Disease Resistance in Transgenic Plants

Transgenic plants expressing APS biosynthetic genes are assayed for resistance to phytopathogens using techniques well known in phytopathology. For foliar pathogens, plants are grown in the greenhouse and at an appropriate stage of development inoculum of a phytopathogen of interest is introduced at in an appropriate manner. For soil-borne phytopathogens, the pathogen is normally introduced into the soil before or at the time the seeds are planted. The choice of plant cultivar selected for introduction of the genes will have taken into account relative phytopathogen sensitivity. Thus, it is preferred that the cultivar chosen will be susceptible to most phytopathogens of interest to allow a determination of enhanced resistance.

Assay of Resistance to Foliar Phytopathogens

Example 48

Disease Resistance to Tobacco Foliar Phytopathogens

Transgenic tobacco plants expressing APS genes and shown to produce APS compound are subjected to the following disease tests.

Phytophthora parasitica/Black shank

Assays for resistance to *Phytophthora parasitica*, the causative organism of black shank are performed on six-week-old plants grown as described in Alexander et al., Pro. Natl. Acad. Sci. USA 90:7327–7331. Plants are watered, allowed to drain well, and then inoculated by applying 10 mL of a sporangium suspension (300 sporangia/mL) to the soil. Inoculated plants are kept in a greenhouse maintained at 23°–25° C. day temperature, and 20°–22° C. night temperature. The wilt index used for the assay is as follows: 0=no symptoms; 1=some sign of wilting, with reduced turgidity; 2=clear wilting symptoms, but no rotting or stunting; 3=clear wilting symptoms with stunting, but no apparent stem rot; 4=severe wilting, with visible stem rot and some damage to root system; 5=as for 4, but plants near death or dead, and with severe reduction of root system. All assays are scored blind on plants arrayed in a random design.

Pseudomonas syringae

*Pseudomonas syringae* pv. tabaci (strain #551) is injected into the two lower leaves of several 6–7 week old plants at a concentration of $10^6$ or 333 $10^6$ per ml in $H_2O$. Six individual plants are evaluated at each time point. *Pseudomonas tabaci* infected plants are rated on a 5 point disease severity scale, 5=100% dead tissue, 0=no symptoms. A T-test (LSD) is conducted on the evaluations for each day and the groupings are indicated after the Mean disease rating value. Values followed by the same letter on that day of evaluation are not statistically significantly different.

Cercospora nicotianae

A spore suspension of *Cercospora nicotianae* (ATCC #18366) (100,000–150,000 spores per ml) is sprayed to imminent run-off on to the surface of the leaves. The plants were maintained in 100% humidity for five days. Thereafter the plants are misted with $H_2O$ 5–10 times per day. Six individual plants were evaluated at each time point. *Cercospora nicotianae* was rated on a % leaf area showing disease symptoms basis. A T-test (LSD) is conducted on the evaluations for each day and the groupings are indicated after the Mean disease rating value. Values followed by the same letter on that day of evaluation are not statistically significantly different.

Statistical Analyses

All tests include non-transgenic tobacco (six plants per assay, or the same cultivar as the transgenic lines) (Alexander et al., Pro. Natl. Acad. Sci. USA 90:7327–7331). Pairwise T-tests were performed to compare different genotype and treatment groups for each rating date.

Assay of Resistance to Soil-Borne Phytopathogens

Example 49

Resistance to *Rhizoctonia solani*

Plant assays to determine resistance to *Rhizoctonia solani* are conducted by planting or transplanting seeds or seedlings into naturally or artificially infested soil. To create artificially infested soil, millet, rice, oat, or other similar seeds are first moistened with water, then autoclaved and inoculated with plugs of the fungal phytopathogen taken from an agar plate. When the seeds are fully overgrown with the phytopathogen, they are air-dried and ground into a powder. The powder is mixed into soil at a rate experimentally determined to cause disease. Disease may be assessed by comparing stand counts, root lesions ratings, and shoot and root weights of transgenic and non-transgenic plants grown in the infested soil. The disease ratings may also be compared to the ratings of plants grown under the same conditions but without phytopathogen added to the soil.

Example 50

Resistance to *Pseudomonas solanacearum*

Plant assays to determine resistance to *Pseudomonas solanacearum* are conducted by planting or transplanting seeds or seedlings into naturally or artificially infested soil. To create artificially infested soil, bacteria are grown in shake flask cultures, then mixed into the soil at a rate experimentally determined to cause disease. The roots of the plants may need to be slightly wounded to ensure disease development. Disease may be assessed by comparing stand counts, degree of wilting and shoot and root weights of transgenic and non-transgenic plants grown in the infested soil. The disease ratings may also be compared to the ratings of plants grown under the same conditions but without phytopathogen added to the soil.

Example 51

Resistance to Soil-Borne Fungi which are Vectors for Virus Transmission

Many soil-borne Polymyxa, Olpidium and Spongospora species are vectors for the transmission of viruses. These include (1) *Polymyxa betae* which transmits Beet Necrotic Yellow Vein Virus (the causative agent of rhizomania disease) to sugar beet, (2) *Polymyxa graminis* which transmits Wheat Soil-Borne Mosaic Virus to wheat, and Barley Yellow Mosaic Virus and Barley Mild Mosaic Virus to barley, (3) *Olpidium brassicae* which transmits Tobacco Necrosis Virus to tobacco, and (4) *Spongospora subterranea* which transmits Potato Mop Top Virus to potato. Seeds or plants expressing APSs in their roots (e.g. constitutively or under root specific expression) are sown or transplanted in sterile soil and fungal inocula carrying the virus of interest are introduced to the soil. After a suitable time period the transgenic plants are assayed for vital symptoms and accumulation of virus by ELISA and Northern blot. Control experiments involve no inoculation, and inoculation with fungus which does not carry the virus under investigation. The transgenic plant lines under analysis should ideally be susceptible to the virus in order to test the efficacy of the APS-based protection. In the case of viruses such as Barley Mild Mosaic Virus which are both Polymyxa-transmitted and mechanically transmissible, a further control is provided by the successful mechanical introduction of the virus into plants which are protected against soil-infection by APS expression in roots.

Resistance to virus-transmitting fungi offered by expression of APSs will thus prevent virus infections of target crops thus improving plant health and yield.

Example 52

Resistance to Nematodes

Transgenic plants expressing APSs are analyzed for resistance to nematodes. Seeds or plants expressing APSs in their roots (e.g. constitutively or under root specific expression) are sown or transplanted in sterile soil and nematode inocula carrying are introduced to the soil. Nematode damage is assessed at an appropriate time point. Root knot nematodes such as Meloidogyne spp. are introduced to transgenic tobacco or tomato expressing APSs. Cyst nematodes such as Heterodera spp. are introduced to transgenic cereals, potato and sugar beet. Lesion nematodes such as Pratylenchus spp. are introduced to transgenic soybean, alfalfa or corn. Reniform nematodes such as Rotylenchulus spp. are introduced to transgenic soybean, cotton, or tomato. Ditylenchus spp. are introduced to transgenic alfalfa. Detailed techniques for screening for resistance to nematodes are provided in Starr (Ed.; Methods for Evaluating Plant Species for resistance to Plant Parasitic Nematodes, Society of Nematologists, Hyattsville, Md. (1990))
Examples of Important Phytopathogens in Agricultural Crop Species

Example 53

Disease Resistance in Maize

Transgenic maize plants expressing APS genes and shown to produce APS compound are subjected to the following disease tests. Tests for each phytopathogen are conducted according to standard phytopathological procedures.
Leaf Diseases and Stalk Rots (1) Northern Corn Leaf Blight (*Helminthosporium turcicum†* syn. Exserohilum turcicum).
(2) Anthracnose (*Colletotrichum graminicola†*-same as for Stalk Rot)
(3) Southern Corn Leaf Blight (*Helminthosporium maydis†* syn. Bipolaris maydis).
(3) Eye Spot (*Kabatiella zeae*)
(4) Common Rust (*Puccinia sorghi*).
(4) Southern Rust (*Puccinia polysora*).
(5) Gray Leaf Spot (*Cercospora zeae-maydis†* and *C. sorghi*)
(6) Stalk Rots (a complex of two or more of the following pathogens-*Pythium aphanidermatum†*-early, *Erwinia chrysanthemi-zeae*-early, *Colletotrichum graminicola†*, *Diplodia maydis†*, *D. macrospora*, *Gibberella zeae†*, *Fusarium moniliforme†*, *Macrophomina phaseolina*, *Cephalosporium acremonium*)
(7) Goss' Disease (*Clavibacter nebraskanense*)

Important-Ear Molds (1) Gibberella Ear Rot (*Gibberella zeae†*-same as for Stalk Rot) *Aspergillus flavus*, A. parasiticus. Aflatoxin
(2) Diplodia Ear Rot (*Diplodia maydis†* and *D. macrospora*-same organisms as for Stalk Rot)
(3) Head Smut (*Sphacelotheca reiliana*—syn. Ustilago reiliana)

Example 54

Disease Resistance in Wheat

Transgenic wheat plants expressing APS genes and shown to produce APS compound are subjected to the following disease tests. Tests for each pathogen are conducted according to standard phytopathological procedures.

(1) Septoria Diseases (*Septoria tritici, S. nodorum*)
(2) Powdery Mildew (*Erysiphe graminis*)
(3) Yellow Rust (*Puccinia striiformis*)
(4) Brown Rust (*Puccinia recondita, P. hordei*)
(5) Others-Brown Foot Rot/Seedling Blight (*Fusarium culmorum* and *Fusarium roseum*), Eyespot (*Pseudocercosporella herpotrichoides*), Take-All (*Gaeumannomyces graminis*)
(6) Viruses (barley yellow mosaic virus, barley yellow dwarf virus, wheat yellow mosaic virus).

N. Assay of Biocontrol Efficacy in Microbial Strains Expressing APS Genes

Example 55

Protection of Cotton against *Rhizoctonia solani*

Assays to determine protection of cotton from infection caused by *Rhizoctonia solani* are conducted by planting seeds treated with the biocontrol strain in naturally or artificially infested soil. To create artificially infested soil, millet, rice, oat, or other similar seeds are first moistened with water, then autoclaved and inoculated with plugs of the fungal pathogen taken from an agar plate. When the seeds are fully overgrown with the pathogen, they are air-dried and ground into a powder. The powder is mixed into soil at a rate experimentally determined to cause disease. This infested soil is put into pots, and seeds are placed in furrows 1.5 cm deep. The biocontrol strains are grown in shake flasks in the laboratory. The cells are harvested by centrifugation, resuspended in water, and then drenched over the seeds. Control plants are drenched with water only. Disease may be assessed 14 days later by comparing stand counts and root lesions ratings of treated and nontreated seedlings. The disease ratings may also be compared to the ratings of seedlings grown under the same conditions but without pathogen added to the soil.

Example 56

Protection of Potato against *Claviceps michiganese* subsp. speedonicum

*Claviceps michiganese* subsp. speedonicum is the causal agent of potato ring rot disease and is typically spread before planting when "seed" potato tubers are knife cut to generate more planting material. Transmission of the pathogen on the surface of the knife results in the inoculation of entire "seed" batches. Assays to determine protection of potato from the causal agent of ring rot disease are conducted by inoculating potato seed pieces with both the pathogen and the biocontrol strain. The pathogen is introduced by first cutting a naturally infected tuber, then using the knife to cut other tubers into seed pieces. Next, the seed pieces are treated with a suspension of biocontrol bacteria or water as a control. Disease is assessed at the end of the growing season by evaluating plant vigor, yield, and number of tubers infected with Clavibacter.

O. Isolation of APSs from Organisms Expressing the Cloned Genes

Example 57

Extraction Procedures for APS Isolation

Active APSs can be isolated from the cells or growth medium of wild-type of transformed strains that produces the APS. This can be undertaken using known protocols for the isolation of molecules of known characteristics.

For example, for APSs which contain multiple benzene rings (pyrrolnitrin and soraphen) cultures are grown for 24 h in 10 ml L broth at an appropriate temperature and then extracted with an equal volume of ethyl acetate. The organic phase is recovered, allowed to evaporated under vacuum and the residue dissolved in 20 μl of methanol.

In the case of pyrrolnitrin a further procedure has been used successfully for the extraction of the active antipathogenic compound from the growth medium of the transformed strain producing this antibiotic. This is accomplished by extraction of the medium with 80% acetone followed by removal of the acetone by evaporation and a second extraction with diethyl ether. The diethyl ether is removed by evaporation and the dried extract is resuspended in a small volume of water. Small aliquots of the antibiotic extract applied to small sterile filter paper discs placed on an agar plate will inhibit the growth of *Rhizoctonia solani*, indicating the presence of the active antibiotic compound.

A preferred method for phenazine isolation is described by Thomashow et al. (Appl Environ Microbiol 56:908–912 (1990)). This involves acidifying cultures to pH 2.0 with HCl and extraction with benzene. Benzene fractions are dehydrated with $Na_2SO_4$ and evaporated to dryness. The residue is redissolved in aqueous 5% $NaHCO_3$, reextracted with an equal volume of benzene, acidified, partitioned into benzene and redried.

For peptide antibiotics (which are typically hydrophobic) extraction techniques using butanol, methanol, chloroform or hexane are suitable. In the case of gramicidin, isolation can be carried out according to the procedure described by Gause & Brazhnikova (Lancet 247:715 (1944)). For epidermin, the procedure described by Allgaier et al. for epidermin (Eur. Ju. Biochem. 160:9–22 (1986)) is suitable and involves butanol extraction, and dissolving in methanol and diethyl ether. For many APSs (e.g. pyrrolnitrin, gramicidin, phenazine) appropriate techniques are provided in the Merck Index (Merck & Co., Rahway, N.J. (1989)).

P. Formulation and Use of Isolated Antibiotics

Antifungal formulations can be made using active ingredients which comprise either the isolated APSs or alternatively suspensions or concentrates of cells which produce them. Formulations can be made in liquid or solid form.

Example 58

Liquid Formulation of Antifungal Compositions

In the following examples, percentages of composition are given by weight:

| 1. Emulsifiable concentrates: | a | b | c |
|---|---|---|---|
| Active ingredient | 20% | 40% | 50% |
| Calcium dodecylbenzenesulfonate | 5% | 8% | 6% |
| Castor oil polyethlene glycol ether (36 moles of ethylene oxide) | 5% | — | — |
| Tributylphenol polyethylene glyco ether (30 moles of ethylene oxide) | — | 12% | 4% |
| Cyclohexanone | — | 15% | 20% |
| Xylene mixture | 70% | 25% | 20% |

Emulsions of any required concentration can be produced from such concentrates by dilution with water.

| 2. Solutions: | a | b | c | d |
|---|---|---|---|---|
| Active ingredient | 80% | 10% | 5% | 95% |
| Ethylene glycol monomethyl ether | 20% | — | — | — |
| Polyethylene glycol 400 | — | 70% | — | — |
| N-methyl-2-pyrrolidone | — | 20% | — | — |
| Epoxidised coconut oil | — | — | 1% | 5% |
| Petroleum distillate (boiling range 160–190°) | — | — | 94% | — |

These solutions are suitable for application in the form of microdrops.

| 3. Granulates: | a | b |
|---|---|---|
| Active ingredient | 5% | 10% |
| Kaolin | 94% | — |
| Highly dispersed silicic acid | 1% | — |
| Attapulgit | — | 90% |

The active ingredient is dissolved in methylene chloride, the solution is sprayed onto the carrier, and the solvent is subsequently evaporated off in vacuo.

| 4. Dusts: | a | b |
|---|---|---|
| Active ingredient | 2% | 5% |
| Highly dispersed silicic acid | 1% | 5% |
| Talcum | 97% | — |
| Kaolin | — | 90% |

Ready-to-use dusts are obtained by intimately mixing the carriers with the active ingredient.

Example 59

Solid Formulation of Antifungal Compositions

In the following examples, percentages of compositions are by weight.

| 1. Wettable powders: | a | b | c |
|---|---|---|---|
| Active ingredient | 20% | 60% | 75% |
| Sodium lignosulfonate | 5% | 5% | — |
| Sodium lauryl sulfate | 3% | — | 5% |
| Sodium diisobutylnaphthalene sulfonate | — | 6% | 10% |
| Octylphenol polyethylene glycol ether (7–8 moles of ethylene oxide) | — | 2% | — |
| Highly dispersed silicic acid | 5% | 27% | 10% |
| Kaolin | 67% | — | — |

The active ingredient is thoroughly mixed with the adjuvants and the mixture is thoroughly ground in a suitable mill, affording wettable powders which can be diluted with water to give suspensions of the desired concentrations.

| 2. Emulsifiable concentrate | |
|---|---|
| Active ingredient | 10% |
| Octylphenol polyethylene glycol ether (4–5 moles of ethylene oxide) | 3% |
| Calcium dodecylbenzenesulfonate | 3% |
| Castor oil polyglycol ether (36 moles of ethylene oxide) | 4% |
| Cyclohexanone | 30% |
| Xylene mixture | 50% |

Emulsions of any required concentration can be obtained from this concentrate by dilution with water.

| 3. Dusts: | a | b |
|---|---|---|
| Active ingredient | 5% | 8% |
| Talcum | 95% | — |
| Kaolin | — | 92% |

Ready-to-use dusts are obtained by mixing the active ingredient with the carriers, and grinding the mixture in a suitable mill.

| 4. Extruder granulate: | |
|---|---|
| Active ingredient | 10% |
| Sodium lignosulfonate | 2% |
| Carboxymethylcellulose | 1% |
| Kaolin | 87% |

The active ingredient is mixed and ground with the adjuvants, and the mixture is subsequently moistened with water. The mixture is extruded and then dried in a stream of air.

| 5. Coated granulate: | |
|---|---|
| Active ingredient | 3% |
| Polyethylene glycol 200 | 3% |
| Kaolin | 94% |

The finely ground active ingredient is uniformly applied, in a mixer, to the kaolin moistened with polyethylene glycol. Non-dusty coated granulates are obtained in this manner.

| 6. Suspension concentrate: | |
|---|---|
| Active ingredient | 40% |
| Ethylene glycol | 10% |
| Nonylphenol polyethylene glycol (15 moles of ethylene oxide) | 6% |
| Sodium lignosulfonate | 10% |
| Carboxymethylcellulose | 1% |
| 37% aqueous formaldehyde solution | 0.2% |
| Silicone oil in 75% aqueous emulsion | 0.8% |
| Water | 32% |

The finely ground active ingredient is intimately mixed with the adjuvants, giving a suspension concentrate from which suspensions of any desire concentration can be obtained by dilution with water.

While the present invention has been described with reference to specific embodiments thereof, it will be appreciated that numerous variations, modifications, and embodiments are possible, and accordingly, all such variations, modifications and embodiments are to be regarded as being within the spirit and scope of the present invention.

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 7001 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 423..2036
        ( D ) OTHER INFORMATION: /label=ORF1
            / note= "Open Reading Frame #1 of DNA sequence"

( i x ) FEATURE:
        ( A ) NAME/KEY: CDS
        ( B ) LOCATION: 2039..3121
        ( D ) OTHER INFORMATION: /label=ORF2
            / note= "Open Reading Frame #2 of DNA sequence"

( i x ) FEATURE:
        ( A ) NAME/KEY: CDS
        ( B ) LOCATION: 3167..4867
        ( D ) OTHER INFORMATION: /label=ORF3
            / note= "Open Reading Frame #3 of DNA sequence"

( i x ) FEATURE:
        ( A ) NAME/KEY: CDS
        ( B ) LOCATION: 4895..5983
        ( D ) OTHER INFORMATION: /label=ORF4
            / note= "Open Reading Frame #4 of DNA sequence"

( i x ) FEATURE:

( A ) NAME/KEY: misc_feature
( B ) LOCATION: 1..7001
( D ) OTHER INFORMATION: /note= "Four open reading frames
 ( O R F s ) were identified within this DNA sequence and are
 transcribed as a single message, as described in Examples
 10 and 12 of the specification."

( x i ) SEQUENCE DESCRIPTION: SEQ ID NO:1:

| | | | | | |
|---|---|---|---|---|---|
| GAATTCCGAC | AACGCCGAAG | AAGCGCGGAA | CCGCTGAAAG | AGGAGCAGGA | ACTGGAGCAA | 60 |
| ACGCTGTCCC | AGGTGATCGA | CAGCCTGCCA | CTGCGCATCG | AGGGCCGATG | AACAGCATTG | 120 |
| GCAAAAGCTG | GCGGTGCGCA | GTGCGCGAGT | GATCCGATCA | TTTTGATCG | GCTCGCCTCT | 180 |
| TCAAAATCGG | CGGTGGATGA | AGTCGACGGC | GGACTGATCA | GGCGCAAAAG | AACATGCGCC | 240 |
| AAAACCTTCT | TTTATAGCGA | ATACCTTTGC | ACTTCAGAAT | GTTAATTCGG | AAACGGAATT | 300 |
| TGCATCGCTT | TTCCGGCAGT | CTAGAGTCTC | TAACAGCACA | TTGATGTGCC | TCTTGCATGG | 360 |
| ATGCACGAAG | ACTGGCGGCC | TCCCCTCGTC | ACAGGCGGCC | CGCCTTTGAA | ACAAGGAGTG | 420 |

```
TT ATG AAC AAG CCG ATC AAG AAT ATC GTC ATC GTG GGC GGC GGT ACT      467
   Met Asn Lys Pro Ile Lys Asn Ile Val Ile Val Gly Gly Gly Thr
    1               5                  10                  15

GCG GGC TGG ATG GCC GCC TCG TAC CTC GTC CGG GCC CTC CAA CAG CAG      515
Ala Gly Trp Met Ala Ala Ser Tyr Leu Val Arg Ala Leu Gln Gln Gln
                 20                  25                  30

GCG AAC ATT ACG CTC ATC GAA TCT GCG GCG ATC CCT CGG ATC GGC GTG      563
Ala Asn Ile Thr Leu Ile Glu Ser Ala Ala Ile Pro Arg Ile Gly Val
             35                  40                  45

GGC GAA GCG ACC ATC CCA AGT TTG CAG AAG GTG TTC TTC GAT TTC CTC      611
Gly Glu Ala Thr Ile Pro Ser Leu Gln Lys Val Phe Phe Asp Phe Leu
         50                  55                  60

GGG ATA CCG GAG CGG GAA TGG ATG CCC CAA GTG AAC GGC GCG TTC AAG      659
Gly Ile Pro Glu Arg Glu Trp Met Pro Gln Val Asn Gly Ala Phe Lys
     65                  70                  75

GCC GCG ATC AAG TTC GTG AAT TGG AGA AAG TCT CCC GAC CCC TCG CGC      707
Ala Ala Ile Lys Phe Val Asn Trp Arg Lys Ser Pro Asp Pro Ser Arg
 80                  85                  90                  95

GAC GAT CAC TTC TAC CAT TTG TTC GGC AAC GTG CCG AAC TGC GAC GGC      755
Asp Asp His Phe Tyr His Leu Phe Gly Asn Val Pro Asn Cys Asp Gly
                100                 105                 110

GTG CCG CTT ACC CAC TAC TGG CTG CGC AAG CGC GAA CAG GGC TTC CAG      803
Val Pro Leu Thr His Tyr Trp Leu Arg Lys Arg Glu Gln Gly Phe Gln
            115                 120                 125

CAG CCG ATG GAG TAC GCG TGC TAC CCG CAG CCC GGG GCA CTC GAC GGC      851
Gln Pro Met Glu Tyr Ala Cys Tyr Pro Gln Pro Gly Ala Leu Asp Gly
        130                 135                 140

AAG CTG GCA CCG TGC CTG TCC GAC GGC ACC CGC CAG ATG TCC CAC GCG      899
Lys Leu Ala Pro Cys Leu Ser Asp Gly Thr Arg Gln Met Ser His Ala
145                 150                 155

TGG CAC TTC GAC GCG CAC CTG GTG GCC GAC TTC TTG AAG CGC TGG GCC      947
Trp His Phe Asp Ala His Leu Val Ala Asp Phe Leu Lys Arg Trp Ala
160                 165                 170                 175

GTC GAG CGC GGG GTG AAC CGC GTG GTC GAT GAG GTG GTG GAC GTT CGC      995
Val Glu Arg Gly Val Asn Arg Val Val Asp Glu Val Val Asp Val Arg
                180                 185                 190

CTG AAC AAC CGC GGC TAC ATC TCC AAC CTG CTC ACC AAG GAG GGG CGG     1043
Leu Asn Asn Arg Gly Tyr Ile Ser Asn Leu Leu Thr Lys Glu Gly Arg
            195                 200                 205

ACG CTG GAG GCG GAC CTG TTC ATC GAC TGC TCC GGC ATG CGG GGG CTC     1091
Thr Leu Glu Ala Asp Leu Phe Ile Asp Cys Ser Gly Met Arg Gly Leu
        210                 215                 220

CTG ATC AAT CAG GCG CTG AAG GAA CCC TTC ATC GAC ATG TCC GAC TAC     1139
```

```
Leu Ile Asn Gln Ala Leu Lys Glu Pro Phe Ile Asp Met Ser Asp Tyr
    225             230                 235

CTG CTG TGC GAC AGC GCG GTC GCC AGC GCC GTG CCC AAC GAC GAC GCG    1187
Leu Leu Cys Asp Ser Ala Val Ala Ser Ala Val Pro Asn Asp Asp Ala
240             245                 250                 255

CGC GAT GGG GTC GAG CCG TAC ACC TCC TCG ATC GCC ATG AAC TCG GGA    1235
Arg Asp Gly Val Glu Pro Tyr Thr Ser Ser Ile Ala Met Asn Ser Gly
                260                 265                 270

TGG ACC TGG AAG ATT CCG ATG CTG GGC CGG TTC GGC AGC GGC TAC GTC    1283
Trp Thr Trp Lys Ile Pro Met Leu Gly Arg Phe Gly Ser Gly Tyr Val
            275                 280                 285

TTC TCG AGC CAT TTC ACC TCG CGC GAC CAG GCC ACC GCC GAC TTC CTC    1331
Phe Ser Ser His Phe Thr Ser Arg Asp Gln Ala Thr Ala Asp Phe Leu
        290                 295                 300

AAA CTC TGG GGC CTC TCG GAC AAT CAG CCG CTC AAC CAG ATC AAG TTC    1379
Lys Leu Trp Gly Leu Ser Asp Asn Gln Pro Leu Asn Gln Ile Lys Phe
    305                 310                 315

CGG GTC GGG CGC AAC AAG CGG GCG TGG GTC AAC AAC TGC GTC TCG ATC    1427
Arg Val Gly Arg Asn Lys Arg Ala Trp Val Asn Asn Cys Val Ser Ile
320             325                 330                 335

GGG CTG TCG TCG TGC TTT CTG GAG CCC CTG GAA TCG ACG GGA ATC TAC    1475
Gly Leu Ser Ser Cys Phe Leu Glu Pro Leu Glu Ser Thr Gly Ile Tyr
                340                 345                 350

TTC ATC TAC GCG GCG CTT TAC CAG CTC GTG AAG CAC TTC CCC GAC ACC    1523
Phe Ile Tyr Ala Ala Leu Tyr Gln Leu Val Lys His Phe Pro Asp Thr
            355                 360                 365

TCG TTC GAC CCG CGG CTG AGC GAC GCT TTC AAC GCC GAG ATC GTC CAC    1571
Ser Phe Asp Pro Arg Leu Ser Asp Ala Phe Asn Ala Glu Ile Val His
        370                 375                 380

ATG TTC GAC GAC TGC CGG GAT TTC GTC CAA GCG CAC TAT TTC ACC ACG    1619
Met Phe Asp Asp Cys Arg Asp Phe Val Gln Ala His Tyr Phe Thr Thr
    385                 390                 395

TCG CGC GAT GAC ACG CCG TTC TGG CTC GCG AAC CGG CAC GAC CTG CGG    1667
Ser Arg Asp Asp Thr Pro Phe Trp Leu Ala Asn Arg His Asp Leu Arg
400             405                 410                 415

CTC TCG GAC GCC ATC AAA GAG AAG GTT CAG CGC TAC AAG GCG GGG CTG    1715
Leu Ser Asp Ala Ile Lys Glu Lys Val Gln Arg Tyr Lys Ala Gly Leu
                420                 425                 430

CCG CTG ACC ACC ACG TCG TTC GAC GAT TCC ACG TAC TAC GAG ACC TTC    1763
Pro Leu Thr Thr Thr Ser Phe Asp Asp Ser Thr Tyr Tyr Glu Thr Phe
            435                 440                 445

GAC TAC GAA TTC AAG AAT TTC TGG TTG AAC GGC AAC TAC TAC TGC ATC    1811
Asp Tyr Glu Phe Lys Asn Phe Trp Leu Asn Gly Asn Tyr Tyr Cys Ile
        450                 455                 460

TTT GCC GGC TTG GGC ATG CTG CCC GAC CGG TCG CTG CCG CTG TTG CAG    1859
Phe Ala Gly Leu Gly Met Leu Pro Asp Arg Ser Leu Pro Leu Leu Gln
    465                 470                 475

CAC CGA CCG GAG TCG ATC GAG AAA GCC GAG GCG ATG TTC GCC AGC ATC    1907
His Arg Pro Glu Ser Ile Glu Lys Ala Glu Ala Met Phe Ala Ser Ile
480             485                 490                 495

CGG CGC GAG GCC GAG CGT CTG CGC ACC AGC CTG CCG ACA AAC TAC GAC    1955
Arg Arg Glu Ala Glu Arg Leu Arg Thr Ser Leu Pro Thr Asn Tyr Asp
                500                 505                 510

TAC CTG CGG TCG CTG CGT GAC GGC GAC GCG GGC CTG TCG CGC GGC CAG    2003
Tyr Leu Arg Ser Leu Arg Asp Gly Asp Ala Gly Leu Ser Arg Gly Gln
            515                 520                 525

CGT GGG CCG AAG CTC GCA GCG CAG GAA AGC CTG TA GTG AAC GCC ACC     2050
Arg Gly Pro Lys Leu Ala Ala Gln Glu Ser Leu    Met Glu Arg Thr
        530                 535                      1

TTG GAC CGG GTA GGC GTA TTC GCG GCC ACC CAC GCT GCC GTG GCG GCC    2098
```

|     |     |     |     |     |     |     |     |     |     |     |     |     |     |     |      |
|-----|-----|-----|-----|-----|-----|-----|-----|-----|-----|-----|-----|-----|-----|-----|------|
| Leu | Asp | Arg | Val | Gly | Val | Phe | Ala | Ala | Thr | His | Ala | Ala | Val | Ala | Ala  |
| 5   |     |     |     | 10  |     |     |     |     | 15  |     |     |     |     | 20  |      |

| TGC | GAT | CCG | CTG | CAG | GCG | CGC | GCG | CTC | GTT | CTG | CAA | CTG | CCG | GGC | CTG | 2146 |
|-----|-----|-----|-----|-----|-----|-----|-----|-----|-----|-----|-----|-----|-----|-----|-----|------|
| Cys | Asp | Pro | Leu | Gln | Ala | Arg | Ala | Leu | Val | Leu | Gln | Leu | Pro | Gly | Leu |      |
|     |     |     |     | 25  |     |     |     |     | 30  |     |     |     |     | 35  |     |      |

| AAC | CGT | AAC | AAG | GAC | GTG | CCC | GGT | ATC | GTC | GGC | CTG | CTG | CGC | GAG | TTC | 2194 |
| Asn | Arg | Asn | Lys | Asp | Val | Pro | Gly | Ile | Val | Gly | Leu | Leu | Arg | Glu | Phe |      |
|     |     |     | 40  |     |     |     |     | 45  |     |     |     |     | 50  |     |     |      |

| CTT | CCG | GTG | CGC | GGC | CTG | CCC | TGC | GGC | TGG | GGT | TTC | GTC | GAA | GCC | GCC | 2242 |
| Leu | Pro | Val | Arg | Gly | Leu | Pro | Cys | Gly | Trp | Gly | Phe | Val | Glu | Ala | Ala |      |
|     |     | 55  |     |     |     |     | 60  |     |     |     |     | 65  |     |     |     |      |

| GCC | GCG | ATG | CGG | GAC | ATC | GGG | TTC | TTC | CTG | GGG | TCG | CTC | AAG | CGC | CAC | 2290 |
| Ala | Ala | Met | Arg | Asp | Ile | Gly | Phe | Phe | Leu | Gly | Ser | Leu | Lys | Arg | His |      |
|     | 70  |     |     |     |     | 75  |     |     |     |     | 80  |     |     |     |     |      |

| GGA | CAT | GAG | CCC | GCG | GAG | GTG | GTG | CCC | GGG | CTT | GAG | CCG | GTG | CTG | CTC | 2338 |
| Gly | His | Glu | Pro | Ala | Glu | Val | Val | Pro | Gly | Leu | Glu | Pro | Val | Leu | Leu |      |
| 85  |     |     |     |     | 90  |     |     |     |     | 95  |     |     |     |     | 100 |      |

| GAC | CTG | GCA | CGC | GCG | ACC | AAC | CTG | CCG | CCG | CGC | GAG | ACG | CTC | CTG | CAT | 2386 |
| Asp | Leu | Ala | Arg | Ala | Thr | Asn | Leu | Pro | Pro | Arg | Glu | Thr | Leu | Leu | His |      |
|     |     |     |     | 105 |     |     |     |     | 110 |     |     |     |     | 115 |     |      |

| GTG | ACG | GTC | TGG | AAC | CCC | ACG | GCG | GCC | GAC | GCG | CAG | CGC | AGC | TAC | ACC | 2434 |
| Val | Thr | Val | Trp | Asn | Pro | Thr | Ala | Ala | Asp | Ala | Gln | Arg | Ser | Tyr | Thr |      |
|     |     |     | 120 |     |     |     |     | 125 |     |     |     |     | 130 |     |     |      |

| GGG | CTG | CCC | GAC | GAA | GCG | CAC | CTG | CTC | GAG | AGC | GTG | CGC | ATC | TCG | ATG | 2482 |
| Gly | Leu | Pro | Asp | Glu | Ala | His | Leu | Leu | Glu | Ser | Val | Arg | Ile | Ser | Met |      |
|     |     | 135 |     |     |     |     | 140 |     |     |     |     | 145 |     |     |     |      |

| GCG | GCC | CTC | GAG | GCG | GCC | ATC | GCG | TTG | ACC | GTC | GAG | CTG | TTC | GAT | GTG | 2530 |
| Ala | Ala | Leu | Glu | Ala | Ala | Ile | Ala | Leu | Thr | Val | Glu | Leu | Phe | Asp | Val |      |
| 150 |     |     |     |     | 155 |     |     |     |     | 160 |     |     |     |     |     |      |

| TCC | CTG | CGG | TCG | CCC | GAG | TTC | GCG | CAA | AGG | TGC | GAC | GAG | CTG | GAA | GCC | 2578 |
| Ser | Leu | Arg | Ser | Pro | Glu | Phe | Ala | Gln | Arg | Cys | Asp | Glu | Leu | Glu | Ala |      |
| 165 |     |     |     |     | 170 |     |     |     |     | 175 |     |     |     |     | 180 |      |

| TAT | CTG | CAG | AAA | ATG | GTC | GAA | TCG | ATC | GTC | TAC | GCG | TAC | CGC | TTC | ATC | 2626 |
| Tyr | Leu | Gln | Lys | Met | Val | Glu | Ser | Ile | Val | Tyr | Ala | Tyr | Arg | Phe | Ile |      |
|     |     |     |     | 185 |     |     |     |     | 190 |     |     |     |     | 195 |     |      |

| TCG | CCG | CAG | GTC | TTC | TAC | GAT | GAG | CTG | CGC | CCC | TTC | TAC | GAA | CCG | ATT | 2674 |
| Ser | Pro | Gln | Val | Phe | Tyr | Asp | Glu | Leu | Arg | Pro | Phe | Tyr | Glu | Pro | Ile |      |
|     |     |     | 200 |     |     |     |     | 205 |     |     |     |     | 210 |     |     |      |

| CGA | GTC | GGG | GGC | CAG | AGC | TAC | CTC | GGC | CCC | GGT | GCC | GTA | GAG | ATG | CCC | 2722 |
| Arg | Val | Gly | Gly | Gln | Ser | Tyr | Leu | Gly | Pro | Gly | Ala | Val | Glu | Met | Pro |      |
|     |     | 215 |     |     |     |     | 220 |     |     |     |     | 225 |     |     |     |      |

| CTC | TTC | GTG | CTG | GAG | CAC | GTC | CTC | TGG | GGC | TCG | CAA | TCG | GAC | GAC | CAA | 2770 |
| Leu | Phe | Val | Leu | Glu | His | Val | Leu | Trp | Gly | Ser | Gln | Ser | Asp | Asp | Gln |      |
|     |     | 230 |     |     |     |     | 235 |     |     |     |     | 240 |     |     |     |      |

| ACT | TAT | CGA | GAA | TTC | AAA | GAG | ACG | TAC | CTG | CCC | TAT | GTG | CTT | CCC | GCG | 2818 |
| Thr | Tyr | Arg | Glu | Phe | Lys | Glu | Thr | Tyr | Leu | Pro | Tyr | Val | Leu | Pro | Ala |      |
| 245 |     |     |     |     | 250 |     |     |     |     | 255 |     |     |     |     | 260 |      |

| TAC | AGG | GCG | GTC | TAC | GCT | CGG | TTC | TCC | GGG | GAG | CCG | GCG | CTC | ATC | GAC | 2866 |
| Tyr | Arg | Ala | Val | Tyr | Ala | Arg | Phe | Ser | Gly | Glu | Pro | Ala | Leu | Ile | Asp |      |
|     |     |     |     | 265 |     |     |     |     | 270 |     |     |     |     | 275 |     |      |

| CGC | GCG | CTC | GAC | GAG | GCG | CGA | GCG | GTC | GGT | ACG | CGG | GAC | GAG | CAC | GTC | 2914 |
| Arg | Ala | Leu | Asp | Glu | Ala | Arg | Ala | Val | Gly | Thr | Arg | Asp | Glu | His | Val |      |
|     |     |     | 280 |     |     |     |     | 285 |     |     |     |     | 290 |     |     |      |

| CGG | GCT | GGG | CTG | ACA | GCC | CTC | GAG | CGG | GTC | TTC | AAG | GTC | CTG | CTG | CGC | 2962 |
| Arg | Ala | Gly | Leu | Thr | Ala | Leu | Glu | Arg | Val | Phe | Lys | Val | Leu | Leu | Arg |      |
|     |     | 295 |     |     |     |     | 300 |     |     |     |     | 305 |     |     |     |      |

| TTC | CGG | GCG | CCT | CAC | CTC | AAA | TTG | GCG | GAG | CGG | GCG | TAC | GAA | GTC | GGG | 3010 |
| Phe | Arg | Ala | Pro | His | Leu | Lys | Leu | Ala | Glu | Arg | Ala | Tyr | Glu | Val | Gly |      |
|     | 310 |     |     |     |     | 315 |     |     |     |     | 320 |     |     |     |     |      |

| CAA | AGC | GGC | CCC | GAA | ATC | GGC | AGC | GGG | GGG | TAC | GCG | CCC | AGC | ATG | CTC | 3058 |

```
Gln Ser Gly Pro Glu Ile Gly Ser Gly Gly Tyr Ala Pro Ser Met Leu
325                 330                 335                 340

GGT GAG CTG CTC ACG CTG ACG TAT GCC GCG CGG TCC CGC GTC CGC GCC    3106
Gly Glu Leu Leu Thr Leu Thr Tyr Ala Ala Arg Ser Arg Val Arg Ala
                    345                 350                 355

GCG CTC GAC GAA TCC TGATGCGCGC GACCCAGTGT TATCTCACAA GGAGAGTTTG    3161
Ala Leu Asp Glu Ser
                360

CCCCC ATG ACT CAG AAG AGC CCC GCG AAC GAA CAC GAT AGC AAT CAC      3208
      Met Thr Gln Lys Ser Pro Ala Asn Glu His Asp Ser Asn His
       1           5                   10

TTC GAC GTA ATC ATC CTC GGC TCG GGC ATG TCC GGC ACC CAG ATG GGG    3256
Phe Asp Val Ile Ile Leu Gly Ser Gly Met Ser Gly Thr Gln Met Gly
 15              20                  25                  30

GCC ATC TTG GCC AAA CAA CAG TTT CGC GTG CTG ATC ATC GAG GAG TCG    3304
Ala Ile Leu Ala Lys Gln Gln Phe Arg Val Leu Ile Ile Glu Glu Ser
                 35                  40                  45

TCG CAC CCG CGG TTC ACG ATC GGC GAA TCG TCG ATC CCC GAG ACG TCT    3352
Ser His Pro Arg Phe Thr Ile Gly Glu Ser Ser Ile Pro Glu Thr Ser
             50                  55                  60

CTT ATG AAC CGC ATC ATC GCT GAT CGC TAC GGC ATT CCG GAG CTC GAC    3400
Leu Met Asn Arg Ile Ile Ala Asp Arg Tyr Gly Ile Pro Glu Leu Asp
         65                  70                  75

CAC ATC ACG TCG TTT TAT TCG ACG CAA CGT TAC GTC GCG TCG AGC ACG    3448
His Ile Thr Ser Phe Tyr Ser Thr Gln Arg Tyr Val Ala Ser Ser Thr
     80                  85                  90

GGC ATT AAG CGC AAC TTC GGC TTC GTG TTC CAC AAG CCC GGC CAG GAG    3496
Gly Ile Lys Arg Asn Phe Gly Phe Val Phe His Lys Pro Gly Gln Glu
 95              100                 105                 110

CAC GAC CCG AAG GAG TTC ACC CAG TGC GTC ATT CCC GAG CTG CCG TGG    3544
His Asp Pro Lys Glu Phe Thr Gln Cys Val Ile Pro Glu Leu Pro Trp
                 115                 120                 125

GGG CCG GAG AGC CAT TAT TAC CGG CAA GAC GTC GAC GCC TAC TTG TTG    3592
Gly Pro Glu Ser His Tyr Tyr Arg Gln Asp Val Asp Ala Tyr Leu Leu
             130                 135                 140

CAA GCC GCC ATT AAA TAC GGC TGC AAG GTC CAC CAG AAA ACT ACC GTG    3640
Gln Ala Ala Ile Lys Tyr Gly Cys Lys Val His Gln Lys Thr Thr Val
         145                 150                 155

ACC GAA TAC CAC GCC GAT AAA GAC GGC GTC GCG GTG ACC ACC GCC CAG    3688
Thr Glu Tyr His Ala Asp Lys Asp Gly Val Ala Val Thr Thr Ala Gln
160                 165                 170

GGC GAA CGG TTC ACC GGC CGG TAC ATG ATC GAC TGC GGA GGA CCT CGC    3736
Gly Glu Arg Phe Thr Gly Arg Tyr Met Ile Asp Cys Gly Gly Pro Arg
175                 180                 185                 190

GCG CCG CTC GCG ACC AAG TTC AAG CTC CGC GAA GAA CCG TGT CGC TTC    3784
Ala Pro Leu Ala Thr Lys Phe Lys Leu Arg Glu Glu Pro Cys Arg Phe
                195                 200                 205

AAG ACG CAC TCG CGC AGC CTC TAC ACG CAC ATG CTC GGG GTC AAG CCG    3832
Lys Thr His Ser Arg Ser Leu Tyr Thr His Met Leu Gly Val Lys Pro
            210                 215                 220

TTC GAC GAC ATC TTC AAG GTC AAG GGG CAG CGC TGG CGC TGG CAC GAG    3880
Phe Asp Asp Ile Phe Lys Val Lys Gly Gln Arg Trp Arg Trp His Glu
        225                 230                 235

GGG ACC TTG CAC CAC ATG TTC GAG GGC GGC TGG CTC TGG GTG ATT CCG    3928
Gly Thr Leu His His Met Phe Glu Gly Gly Trp Leu Trp Val Ile Pro
240                 245                 250

TTC AAC AAC CAC CCG CGG TCG ACC AAC AAC CTG GTG AGC GTC GGC CTG    3976
Phe Asn Asn His Pro Arg Ser Thr Asn Asn Leu Val Ser Val Gly Leu
255                 260                 265                 270

CAG CTC GAC CCG CGT GTC TAC CCG AAA ACC GAC ATC TCC GCA CAG CAG    4024
```

```
Gln Leu Asp Pro Arg Val Tyr Pro Lys Thr Asp Ile Ser Ala Gln Gln
            275                 280                 285

GAA TTC GAT GAG TTC CTC GCG CGG TTC CCG AGC ATC GGG GCT CAG TTC         4072
Glu Phe Asp Glu Phe Leu Ala Arg Phe Pro Ser Ile Gly Ala Gln Phe
            290                 295                 300

CGG GAC GCC GTG CCG GTG CGC GAC TGG GTC AAG ACC GAC CGC CTG CAA         4120
Arg Asp Ala Val Pro Val Arg Asp Trp Val Lys Thr Asp Arg Leu Gln
            305                 310                 315

TTC TCG TCG AAC GCC TGC GTC GGC GAC CGC TAC TGC CTG ATG CTG CAC         4168
Phe Ser Ser Asn Ala Cys Val Gly Asp Arg Tyr Cys Leu Met Leu His
            320                 325                 330

GCG AAC GGC TTC ATC GAC CCG CTC TTC TCC CGG GGG CTG GAA AAC ACC         4216
Ala Asn Gly Phe Ile Asp Pro Leu Phe Ser Arg Gly Leu Glu Asn Thr
335                 340                 345                 350

GCG GTG ACC ATC CAC GCG CTC GCG GCG CGC CTC ATC AAG GCG CTG CGC         4264
Ala Val Thr Ile His Ala Leu Ala Ala Arg Leu Ile Lys Ala Leu Arg
                355                 360                 365

GAC GAC GAC TTC TCC CCC GAG CGC TTC GAG TAC ATC GAG CGC CTG CAG         4312
Asp Asp Asp Phe Ser Pro Glu Arg Phe Glu Tyr Ile Glu Arg Leu Gln
            370                 375                 380

CAA AAG CTT TTG GAC CAC AAC GAC GAC TTC GTC AGC TGC TGC TAC ACG         4360
Gln Lys Leu Leu Asp His Asn Asp Asp Phe Val Ser Cys Cys Tyr Thr
385                 390                 395

GCG TTC TCG GAC TTC CGC CTA TGG GAC GCG TTC CAC AGG CTG TGG GCG         4408
Ala Phe Ser Asp Phe Arg Leu Trp Asp Ala Phe His Arg Leu Trp Ala
400                 405                 410

GTC GGC ACC ATC CTC GGG CAG TTC CGG CTC GTG CAG GCC CAC GCG AGG         4456
Val Gly Thr Ile Leu Gly Gln Phe Arg Leu Val Gln Ala His Ala Arg
415                 420                 425                 430

TTC CGC GCG TCG CGC AAC GAG GGC GAC CTC GAT CAC CTC GAC AAC GAC         4504
Phe Arg Ala Ser Arg Asn Glu Gly Asp Leu Asp His Leu Asp Asn Asp
                435                 440                 445

CCT CCG TAT CTC GGA TAC CTG TGC GCG GAC ATG GAG GAG TAC TAC CAG         4552
Pro Pro Tyr Leu Gly Tyr Leu Cys Ala Asp Met Glu Glu Tyr Tyr Gln
            450                 455                 460

TTG TTC AAC GAC GCC AAA GCC GAG GTC GAG GCC GTG AGT GCC GGG CGC         4600
Leu Phe Asn Asp Ala Lys Ala Glu Val Glu Ala Val Ser Ala Gly Arg
            465                 470                 475

AAG CCG GCC GAT GAG GCC GCG GCG CGG ATT CAC GCC CTC ATT GAC GAA         4648
Lys Pro Ala Asp Glu Ala Ala Ala Arg Ile His Ala Leu Ile Asp Glu
        480                 485                 490

CGA GAC TTC GCC AAG CCG ATG TTC GGC TTC GGG TAC TGC ATC ACC GGG         4696
Arg Asp Phe Ala Lys Pro Met Phe Gly Phe Gly Tyr Cys Ile Thr Gly
495                 500                 505                 510

GAC AAG CCG CAG CTC AAC AAC TCG AAG TAC AGC CTG CTG CCG GCG ATG         4744
Asp Lys Pro Gln Leu Asn Asn Ser Lys Tyr Ser Leu Leu Pro Ala Met
                515                 520                 525

CGG CTG ATG TAC TGG ACG CAA ACC CGC GCG CCG GCA GAG GTG AAA AAG         4792
Arg Leu Met Tyr Trp Thr Gln Thr Arg Ala Pro Ala Glu Val Lys Lys
            530                 535                 540

TAC TTC GAC TAC AAC CCG ATG TTC GCG CTG CTC AAG GCG TAC ATC ACG         4840
Tyr Phe Asp Tyr Asn Pro Met Phe Ala Leu Leu Lys Ala Tyr Ile Thr
            545                 550                 555

ACC CGC ATC GGC CTG GCG CTG AAG AAG TAGCCGCTCG ACGACGACAT              4887
Thr Arg Ile Gly Leu Ala Leu Lys Lys
560                 565

AAAAACG ATG AAC GAC ATT CAA TTG GAT CAA GCG AGC GTC AAG AAG CGT        4936
        Met Asn Asp Ile Gln Leu Asp Gln Ala Ser Val Lys Lys Arg
        1                 5                   10

CCC TCG GGC GCG TAC GAC GCA ACC ACG CGC CTG GCC GCG AGC TGG TAC        4984
```

|  |  |  |  |  |  |  |  |  |  |  |  |  |  |  |  |
|---|---|---|---|---|---|---|---|---|---|---|---|---|---|---|---|
| Pro | Ser | Gly | Ala | Tyr | Asp | Ala | Thr | Thr | Arg | Leu | Ala | Ala | Ser | Trp | Tyr |
| 15 |  |  |  | 20 |  |  |  |  | 25 |  |  |  |  |  | 30 |

| GTC | GCG | ATG | CGC | TCC | AAC | GAG | CTC | AAG | GAC | AAG | CCG | ACC | GAG | TTG | ACG | 5032 |
|---|---|---|---|---|---|---|---|---|---|---|---|---|---|---|---|---|
| Val | Ala | Met | Arg | Ser | Asn | Glu | Leu | Lys | Asp | Lys | Pro | Thr | Glu | Leu | Thr |  |
|  |  |  |  | 35 |  |  |  |  | 40 |  |  |  |  | 45 |  |  |

| CTC | TTC | GGC | CGT | CCG | TGC | GTG | GCG | TGG | CGC | GGA | GCC | ACG | GGG | CGG | GCC | 5080 |
|---|---|---|---|---|---|---|---|---|---|---|---|---|---|---|---|---|
| Leu | Phe | Gly | Arg | Pro | Cys | Val | Ala | Trp | Arg | Gly | Ala | Thr | Gly | Arg | Ala |  |
|  |  |  | 50 |  |  |  |  | 55 |  |  |  |  | 60 |  |  |  |

| GTG | GTG | ATG | GAC | CGC | CAC | TGC | TCG | CAC | CTG | GGC | GCG | AAC | CTG | GCT | GAC | 5128 |
|---|---|---|---|---|---|---|---|---|---|---|---|---|---|---|---|---|
| Val | Val | Met | Asp | Arg | His | Cys | Ser | His | Leu | Gly | Ala | Asn | Leu | Ala | Asp |  |
|  |  | 65 |  |  |  |  | 70 |  |  |  |  | 75 |  |  |  |  |

| GGG | CGG | ATC | AAG | GAC | GGG | TGC | ATC | CAG | TGC | CCG | TTT | CAC | CAC | TGG | CGG | 5176 |
|---|---|---|---|---|---|---|---|---|---|---|---|---|---|---|---|---|
| Gly | Arg | Ile | Lys | Asp | Gly | Cys | Ile | Gln | Cys | Pro | Phe | His | His | Trp | Arg |  |
|  | 80 |  |  |  |  | 85 |  |  |  |  |  | 90 |  |  |  |  |

| TAC | GAC | GAA | CAG | GGC | CAG | TGC | GTT | CAC | ATC | CCC | GGC | CAT | AAC | CAG | GCG | 5224 |
|---|---|---|---|---|---|---|---|---|---|---|---|---|---|---|---|---|
| Tyr | Asp | Glu | Gln | Gly | Gln | Cys | Val | His | Ile | Pro | Gly | His | Asn | Gln | Ala |  |
| 95 |  |  |  |  | 100 |  |  |  |  | 105 |  |  |  |  | 110 |  |

| GTG | CGC | CAG | CTG | GAG | CCG | GTG | CCG | CGC | GGG | GCG | CGT | CAG | CCG | ACG | TTG | 5272 |
|---|---|---|---|---|---|---|---|---|---|---|---|---|---|---|---|---|
| Val | Arg | Gln | Leu | Glu | Pro | Val | Pro | Arg | Gly | Ala | Arg | Gln | Pro | Thr | Leu |  |
|  |  |  |  | 115 |  |  |  |  | 120 |  |  |  |  | 125 |  |  |

| GTC | ACC | GCC | GAG | CGA | TAC | GGC | TAC | GTG | TGG | GTC | TGG | TAC | GGC | TCC | CCG | 5320 |
|---|---|---|---|---|---|---|---|---|---|---|---|---|---|---|---|---|
| Val | Thr | Ala | Glu | Arg | Tyr | Gly | Tyr | Val | Trp | Val | Trp | Tyr | Gly | Ser | Pro |  |
|  |  |  | 130 |  |  |  |  | 135 |  |  |  |  | 140 |  |  |  |

| CTG | CCG | CTG | CAC | CCG | CTG | CCC | GAA | ATC | TCC | GCG | GCC | GAT | GTC | GAC | AAC | 5368 |
|---|---|---|---|---|---|---|---|---|---|---|---|---|---|---|---|---|
| Leu | Pro | Leu | His | Pro | Leu | Pro | Glu | Ile | Ser | Ala | Ala | Asp | Val | Asp | Asn |  |
|  |  | 145 |  |  |  |  | 150 |  |  |  |  | 155 |  |  |  |  |

| GGC | GAC | TTT | ATG | CAC | CTG | CAC | TTC | GCG | TTC | GAG | ACG | ACC | ACG | GCG | GTC | 5416 |
|---|---|---|---|---|---|---|---|---|---|---|---|---|---|---|---|---|
| Gly | Asp | Phe | Met | His | Leu | His | Phe | Ala | Phe | Glu | Thr | Thr | Thr | Ala | Val |  |
|  | 160 |  |  |  |  | 165 |  |  |  |  | 170 |  |  |  |  |  |

| TTG | CGG | ATC | GTC | GAG | AAC | TTC | TAC | GAC | GCG | CAG | CAC | GCA | ACC | CCG | GTG | 5464 |
|---|---|---|---|---|---|---|---|---|---|---|---|---|---|---|---|---|
| Leu | Arg | Ile | Val | Glu | Asn | Phe | Tyr | Asp | Ala | Gln | His | Ala | Thr | Pro | Val |  |
| 175 |  |  |  |  | 180 |  |  |  |  | 185 |  |  |  |  | 190 |  |

| CAC | GCA | CTC | CCG | ATC | TCG | GCC | TTC | GAA | CTC | AAG | CTC | TTC | GAC | GAT | TGG | 5512 |
|---|---|---|---|---|---|---|---|---|---|---|---|---|---|---|---|---|
| His | Ala | Leu | Pro | Ile | Ser | Ala | Phe | Glu | Leu | Lys | Leu | Phe | Asp | Asp | Trp |  |
|  |  |  |  | 195 |  |  |  |  | 200 |  |  |  |  | 205 |  |  |

| CGC | CAG | TGG | CCG | GAG | GTT | GAG | TCG | CTG | GCC | CTG | GCG | GGC | GCG | TGG | TTC | 5560 |
|---|---|---|---|---|---|---|---|---|---|---|---|---|---|---|---|---|
| Arg | Gln | Trp | Pro | Glu | Val | Glu | Ser | Leu | Ala | Leu | Ala | Gly | Ala | Trp | Phe |  |
|  |  |  | 210 |  |  |  |  | 215 |  |  |  |  | 220 |  |  |  |

| GGT | GCC | GGG | ATC | GAC | TTC | ACC | GTG | GAC | CGG | TAC | TTC | GGC | CCC | CTC | GGC | 5608 |
|---|---|---|---|---|---|---|---|---|---|---|---|---|---|---|---|---|
| Gly | Ala | Gly | Ile | Asp | Phe | Thr | Val | Asp | Arg | Tyr | Phe | Gly | Pro | Leu | Gly |  |
|  |  | 225 |  |  |  |  | 230 |  |  |  |  | 235 |  |  |  |  |

| ATG | CTG | TCA | CGC | GCG | CTC | GGC | CTG | AAC | ATG | TCG | CAG | ATG | AAC | CTG | CAC | 5656 |
|---|---|---|---|---|---|---|---|---|---|---|---|---|---|---|---|---|
| Met | Leu | Ser | Arg | Ala | Leu | Gly | Leu | Asn | Met | Ser | Gln | Met | Asn | Leu | His |  |
|  | 240 |  |  |  |  | 245 |  |  |  |  | 250 |  |  |  |  |  |

| TTC | GAT | GGC | TAC | CCC | GGC | GGG | TGC | GTC | ATG | ACC | GTC | GCC | CTG | GAC | GGA | 5704 |
|---|---|---|---|---|---|---|---|---|---|---|---|---|---|---|---|---|
| Phe | Asp | Gly | Tyr | Pro | Gly | Gly | Cys | Val | Met | Thr | Val | Ala | Leu | Asp | Gly |  |
| 255 |  |  |  |  | 260 |  |  |  |  | 265 |  |  |  |  | 270 |  |

| GAC | GTC | AAA | TAC | AAG | CTG | CTC | CAG | TGT | GTG | ACG | CCG | GTG | AGC | GAA | GGC | 5752 |
|---|---|---|---|---|---|---|---|---|---|---|---|---|---|---|---|---|
| Asp | Val | Lys | Tyr | Lys | Leu | Leu | Gln | Cys | Val | Thr | Pro | Val | Ser | Glu | Gly |  |
|  |  |  | 275 |  |  |  |  | 280 |  |  |  |  | 285 |  |  |  |

| AAG | AAC | GTC | ATG | CAC | ATG | CTC | ATC | TCG | ATC | AAG | AAG | GTG | GGC | GGC | ATC | 5800 |
|---|---|---|---|---|---|---|---|---|---|---|---|---|---|---|---|---|
| Lys | Asn | Val | Met | His | Met | Leu | Ile | Ser | Ile | Lys | Lys | Val | Gly | Gly | Ile |  |
|  |  |  | 290 |  |  |  |  | 295 |  |  |  |  | 300 |  |  |  |

| CTG | CGC | CGC | GCG | ACC | GAC | TTC | GTG | CTG | TTC | GGG | CTG | CAG | ACC | AGG | CAG | 5848 |
|---|---|---|---|---|---|---|---|---|---|---|---|---|---|---|---|---|
| Leu | Arg | Arg | Ala | Thr | Asp | Phe | Val | Leu | Phe | Gly | Leu | Gln | Thr | Arg | Gln |  |
|  |  |  | 305 |  |  |  |  | 310 |  |  |  |  | 315 |  |  |  |

| GCC | GCG | GGG | TAC | GAC | GTC | AAA | ATC | TGG | AAC | GGA | ATG | AAG | CCG | GAC | GGC | 5896 |
|---|---|---|---|---|---|---|---|---|---|---|---|---|---|---|---|---|
| Ala | Ala | Gly | Tyr | Asp | Val | Lys | Ile | Trp | Asn | Gly | Met | Lys | Pro | Asp | Gly |  |
| 320 |  |  |  |  | 325 |  |  |  |  | 330 |  |  |  |  |  |  |

| GGC | GGC | GCG | TAC | AGC | AAG | TAC | GAC | AAG | CTC | GTG | CTC | AAG | TAC | CGG | GCG | 5944 |
|---|---|---|---|---|---|---|---|---|---|---|---|---|---|---|---|---|

| Gly | Gly | Ala | Tyr | Ser | Lys | Tyr | Asp | Lys | Leu | Val | Leu | Lys | Tyr | Arg | Ala | |
|---|---|---|---|---|---|---|---|---|---|---|---|---|---|---|---|---|
| 335 | | | | | 340 | | | | 345 | | | | | | 350 | |

| TTC | TAT | CGA | GGC | TGG | GTC | GAC | CGC | GTC | GCA | AGT | GAG | CGG | TGATGCGTGA | 5993 |
|---|---|---|---|---|---|---|---|---|---|---|---|---|---|---|
| Phe | Tyr | Arg | Gly | Trp | Val | Asp | Arg | Val | Ala | Ser | Glu | Arg | | |
| | | | | 355 | | | | | 360 | | | | | |

| AGCCGAGCCG | CTCTCGACCG | CGTCGCTGCG | CCAGGCGCTC | GCGAACCTGG | CGAGCGGCGT | 6053 |
| GACGATCACG | GCCTACGGCG | CGCCGGGCCC | GCTTGGGCTC | GCGGCCACCA | GCTTCGTGTC | 6113 |
| GGAGTCGCTC | TTTGCGAGGT | ATTCATGACT | ATCTGGCTGT | TGCAACTCGT | GCTGGTGATC | 6173 |
| GCGCTCTGCA | ACGTCTGCGG | CCGCATTGCC | GAACGGCTCG | CCAGTGCGC | GGTCATCGGC | 6233 |
| GAGATCGCGG | CCGGTTTGCT | GTTGGGGCCG | TCGCTGTTCG | GCGTGATCGC | ACCGAGTTTC | 6293 |
| TACGACCTGT | TGTTCGGCCC | CCAGGTGCTG | TCAGCGATGG | CGCAAGTCAG | CGAAGTCGGC | 6353 |
| CTGGTACTGC | TGATGTTCCA | GGTCGGCCTG | CATATGGAGT | TGGGCGAGAC | GCTGCGCGAC | 6413 |
| AAGCGCTGGC | GCATGCCCGT | CGCGATCGCA | GCGGGCGGGC | TCGTCGCACC | GGCCGCGATC | 6473 |
| GGCATGATCG | TCGCCATCGT | TTCGAAAGGC | ACGCTCGCCA | GCGACGCGCC | GGCGCTGCCC | 6533 |
| TATGTGCTCT | TCTGCGGTGT | CGCACTTGCG | GTATCGGCGG | TGCCGGTGAT | GGCGCGCATC | 6593 |
| ATCGACGACC | TGGAGCTCAG | CGCCATGGTG | GGCGCGCGGC | ACGCAATGTC | TGCCGCGATG | 6653 |
| CTGACGGATG | CGCTCGGATG | GATGCTGCTT | GCAACGATTG | CCTCGCTATC | GAGCGGGCCC | 6713 |
| GGCTGGGCAT | TTGCGCGCAT | GCTCGTCAGC | CTGCTCGCGT | ATCTGGTGCT | GTGCGCGCTG | 6773 |
| CTGGTGCGCT | TCGTGGTTCG | ACCGACCCTT | GCGCGGCTCG | CGTCGACCGC | GCATGCGACG | 6833 |
| CGCGACCGCT | TGGCCGTGTT | GTTCTGCTTC | GTAATGTTGT | CGGCACTCGC | GACGTCGCTG | 6893 |
| ATCGGATTCC | ATAGCGCTTT | TGGCGCACTT | GCCGCGGCGC | TGTTCGTGCG | CCGGGTGCCC | 6953 |
| GGCGTCGCGA | AGGAGTGGCG | CGACAACGTC | GAAGGTTTCG | TCAAGCTT | | 7001 |

( 2 ) INFORMATION FOR SEQ ID NO:2:

( i ) SEQUENCE CHARACTERISTICS:
    ( A ) LENGTH: 538 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

| Met | Asn | Lys | Pro | Ile | Lys | Asn | Ile | Val | Ile | Val | Gly | Gly | Gly | Thr | Ala |
|---|---|---|---|---|---|---|---|---|---|---|---|---|---|---|---|
| 1 | | | | 5 | | | | | 10 | | | | | 15 | |

| Gly | Trp | Met | Ala | Ala | Ser | Tyr | Leu | Val | Arg | Ala | Leu | Gln | Gln | Gln | Ala |
|---|---|---|---|---|---|---|---|---|---|---|---|---|---|---|---|
| | | | 20 | | | | 25 | | | | | 30 | | | |

| Asn | Ile | Thr | Leu | Ile | Glu | Ser | Ala | Ala | Ile | Pro | Arg | Ile | Gly | Val | Gly |
|---|---|---|---|---|---|---|---|---|---|---|---|---|---|---|---|
| | | 35 | | | | | 40 | | | | | 45 | | | |

| Glu | Ala | Thr | Ile | Pro | Ser | Leu | Gln | Lys | Val | Phe | Phe | Asp | Phe | Leu | Gly |
|---|---|---|---|---|---|---|---|---|---|---|---|---|---|---|---|
| | 50 | | | | | 55 | | | | | 60 | | | | |

| Ile | Pro | Glu | Arg | Glu | Trp | Met | Pro | Gln | Val | Asn | Gly | Ala | Phe | Lys | Ala |
|---|---|---|---|---|---|---|---|---|---|---|---|---|---|---|---|
| 65 | | | | | 70 | | | | | 75 | | | | | 80 |

| Ala | Ile | Lys | Phe | Val | Asn | Trp | Arg | Lys | Ser | Pro | Asp | Pro | Ser | Arg | Asp |
|---|---|---|---|---|---|---|---|---|---|---|---|---|---|---|---|
| | | | | 85 | | | | | 90 | | | | | 95 | |

| Asp | His | Phe | Tyr | His | Leu | Phe | Gly | Asn | Val | Pro | Asn | Cys | Asp | Gly | Val |
|---|---|---|---|---|---|---|---|---|---|---|---|---|---|---|---|
| | | | | 100 | | | | | 105 | | | | | 110 | |

| Pro | Leu | Thr | His | Tyr | Trp | Leu | Arg | Lys | Arg | Glu | Gln | Gly | Phe | Gln | Gln |
|---|---|---|---|---|---|---|---|---|---|---|---|---|---|---|---|
| | | | 115 | | | | | 120 | | | | | 125 | | |

| Pro | Met | Glu | Tyr | Ala | Cys | Tyr | Pro | Gln | Pro | Gly | Ala | Leu | Asp | Gly | Lys |
|---|---|---|---|---|---|---|---|---|---|---|---|---|---|---|---|
| | 130 | | | | | 135 | | | | | 140 | | | | |

```
Leu Ala Pro Cys Leu Ser Asp Gly Thr Arg Gln Met Ser His Ala Trp
145                 150                 155                 160

His Phe Asp Ala His Leu Val Ala Asp Phe Leu Lys Arg Trp Ala Val
                165                 170                 175

Glu Arg Gly Val Asn Arg Val Val Asp Val Val Asp Val Arg Leu
            180             185                 190

Asn Asn Arg Gly Tyr Ile Ser Asn Leu Leu Thr Lys Glu Gly Arg Thr
        195                 200             205

Leu Glu Ala Asp Leu Phe Ile Asp Cys Ser Gly Met Arg Gly Leu Leu
    210             215                 220

Ile Asn Gln Ala Leu Lys Glu Pro Phe Ile Asp Met Ser Asp Tyr Leu
225             230             235                 240

Leu Cys Asp Ser Ala Val Ala Ser Ala Val Pro Asn Asp Asp Ala Arg
                245             250                 255

Asp Gly Val Glu Pro Tyr Thr Ser Ser Ile Ala Met Asn Ser Gly Trp
            260             265                 270

Thr Trp Lys Ile Pro Met Leu Gly Arg Phe Gly Ser Gly Tyr Val Phe
        275             280             285

Ser Ser His Phe Thr Ser Arg Asp Gln Ala Thr Ala Asp Phe Leu Lys
    290             295             300

Leu Trp Gly Leu Ser Asp Asn Gln Pro Leu Asn Gln Ile Lys Phe Arg
305             310             315                 320

Val Gly Arg Asn Lys Arg Ala Trp Val Asn Asn Cys Val Ser Ile Gly
            325             330                 335

Leu Ser Ser Cys Phe Leu Glu Pro Leu Glu Ser Thr Gly Ile Tyr Phe
            340             345             350

Ile Tyr Ala Ala Leu Tyr Gln Leu Val Lys His Phe Pro Asp Thr Ser
        355             360             365

Phe Asp Pro Arg Leu Ser Asp Ala Phe Asn Ala Glu Ile Val His Met
    370             375             380

Phe Asp Asp Cys Arg Asp Phe Val Gln Ala His Tyr Phe Thr Thr Ser
385             390             395             400

Arg Asp Asp Thr Pro Phe Trp Leu Ala Asn Arg His Asp Leu Arg Leu
            405             410             415

Ser Asp Ala Ile Lys Glu Lys Val Gln Arg Tyr Lys Ala Gly Leu Pro
            420             425             430

Leu Thr Thr Thr Ser Phe Asp Asp Ser Thr Tyr Tyr Glu Thr Phe Asp
        435             440             445

Tyr Glu Phe Lys Asn Phe Trp Leu Asn Gly Asn Tyr Tyr Cys Ile Phe
    450             455             460

Ala Gly Leu Gly Met Leu Pro Asp Arg Ser Leu Pro Leu Leu Gln His
465             470             475             480

Arg Pro Glu Ser Ile Glu Lys Ala Glu Ala Met Phe Ala Ser Ile Arg
            485             490             495

Arg Glu Ala Glu Arg Leu Arg Thr Ser Leu Pro Thr Asn Tyr Asp Tyr
            500             505             510

Leu Arg Ser Leu Arg Asp Gly Asp Ala Gly Leu Ser Arg Gly Gln Arg
        515             520             525

Gly Pro Lys Leu Ala Ala Gln Glu Ser Leu
        530             535
```

( 2 ) INFORMATION FOR SEQ ID NO:3:

( i ) SEQUENCE CHARACTERISTICS:
( A ) LENGTH: 361 amino acids (B) TYPE: amino acid
(D) TOPOLOGY: linear (ii) MOLECULE TYPE: protein (xi) SEQUENCE DESCRIPTION: SEQ ID NO:3:

```
Val Glu Arg Thr Leu Asp Arg Val Gly Val Phe Ala Ala Thr His Ala
  1               5                  10                  15
Ala Val Ala Ala Cys Asp Pro Leu Gln Ala Arg Ala Leu Val Leu Gln
             20                  25                  30
Leu Pro Gly Leu Asn Arg Asn Lys Asp Val Pro Gly Ile Val Gly Leu
             35                  40                  45
Leu Arg Glu Phe Leu Pro Val Arg Gly Leu Pro Cys Gly Trp Gly Phe
         50                  55                  60
Val Glu Ala Ala Ala Ala Met Arg Asp Ile Gly Phe Phe Leu Gly Ser
 65                  70                  75                  80
Leu Lys Arg His Gly His Glu Pro Ala Glu Val Val Pro Gly Leu Glu
                 85                  90                  95
Pro Val Leu Leu Asp Leu Ala Arg Ala Thr Asn Leu Pro Pro Arg Glu
            100                 105                 110
Thr Leu Leu His Val Thr Val Trp Asn Pro Thr Ala Ala Asp Ala Gln
            115                 120                 125
Arg Ser Tyr Thr Gly Leu Pro Asp Glu Ala His Leu Leu Glu Ser Val
        130                 135                 140
Arg Ile Ser Met Ala Ala Leu Glu Ala Ala Ile Ala Leu Thr Val Glu
145                 150                 155                 160
Leu Phe Asp Val Ser Leu Arg Ser Pro Glu Phe Ala Gln Arg Cys Asp
                165                 170                 175
Glu Leu Glu Ala Tyr Leu Gln Lys Met Val Glu Ser Ile Val Tyr Ala
            180                 185                 190
Tyr Arg Phe Ile Ser Pro Gln Val Phe Tyr Asp Glu Leu Arg Pro Phe
        195                 200                 205
Tyr Glu Pro Ile Arg Val Gly Gly Gln Ser Tyr Leu Gly Pro Gly Ala
    210                 215                 220
Val Glu Met Pro Leu Phe Val Leu Glu His Val Leu Trp Gly Ser Gln
225                 230                 235                 240
Ser Asp Asp Gln Thr Tyr Arg Glu Phe Lys Glu Thr Tyr Leu Pro Tyr
                245                 250                 255
Val Leu Pro Ala Tyr Arg Ala Val Tyr Ala Arg Phe Ser Gly Glu Pro
            260                 265                 270
Ala Leu Ile Asp Arg Ala Leu Asp Glu Ala Arg Ala Val Gly Thr Arg
        275                 280                 285
Asp Glu His Val Arg Ala Gly Leu Thr Ala Leu Glu Arg Val Phe Lys
    290                 295                 300
Val Leu Leu Arg Phe Arg Ala Pro His Leu Lys Leu Ala Glu Arg Ala
305                 310                 315                 320
Tyr Glu Val Gly Gln Ser Gly Pro Glu Ile Gly Ser Gly Gly Tyr Ala
                325                 330                 335
Pro Ser Met Leu Gly Glu Leu Leu Thr Leu Thr Tyr Ala Ala Arg Ser
            340                 345                 350
Arg Val Arg Ala Ala Leu Asp Glu Ser
        355                 360
```

(2) INFORMATION FOR SEQ ID NO:4:

(i) SEQUENCE CHARACTERISTICS:

(A) LENGTH: 567 amino acids
(B) TYPE: amino acid
(D) TOPOLOGY: linear (ii) MOLECULE TYPE: protein (xi) SEQUENCE DESCRIPTION: SEQ ID NO:4:

| Met | Thr | Gln | Lys | Ser | Pro | Ala | Asn | Glu | His | Asp | Ser | Asn | His | Phe | Asp |
|---|---|---|---|---|---|---|---|---|---|---|---|---|---|---|---|
| 1 | | | | 5 | | | | | 10 | | | | | 15 | |
| Val | Ile | Ile | Leu | Gly | Ser | Gly | Met | Ser | Gly | Thr | Gln | Met | Gly | Ala | Ile |
| | | | 20 | | | | 25 | | | | | 30 | | | |
| Leu | Ala | Lys | Gln | Gln | Phe | Arg | Val | Leu | Ile | Ile | Glu | Glu | Ser | Ser | His |
| | | 35 | | | | | 40 | | | | | 45 | | | |
| Pro | Arg | Phe | Thr | Ile | Gly | Glu | Ser | Ser | Ile | Pro | Glu | Thr | Ser | Leu | Met |
| | 50 | | | | | 55 | | | | | | 60 | | | |
| Asn | Arg | Ile | Ile | Ala | Asp | Arg | Tyr | Gly | Ile | Pro | Glu | Leu | Asp | His | Ile |
| 65 | | | | | 70 | | | | | 75 | | | | | 80 |
| Thr | Ser | Phe | Tyr | Ser | Thr | Gln | Arg | Tyr | Val | Ala | Ser | Ser | Thr | Gly | Ile |
| | | | | 85 | | | | | 90 | | | | | 95 | |
| Lys | Arg | Asn | Phe | Gly | Phe | Val | Phe | His | Lys | Pro | Gly | Gln | Glu | His | Asp |
| | | | 100 | | | | | 105 | | | | | 110 | | |
| Pro | Lys | Glu | Phe | Thr | Gln | Cys | Val | Ile | Pro | Glu | Leu | Pro | Trp | Gly | Pro |
| | | 115 | | | | | 120 | | | | | 125 | | | |
| Glu | Ser | His | Tyr | Tyr | Arg | Gln | Asp | Val | Asp | Ala | Tyr | Leu | Leu | Gln | Ala |
| | 130 | | | | | 135 | | | | | 140 | | | | |
| Ala | Ile | Lys | Tyr | Gly | Cys | Lys | Val | His | Gln | Lys | Thr | Thr | Val | Thr | Glu |
| 145 | | | | | 150 | | | | | 155 | | | | | 160 |
| Tyr | His | Ala | Asp | Lys | Asp | Gly | Val | Ala | Val | Thr | Thr | Ala | Gln | Gly | Glu |
| | | | | 165 | | | | | 170 | | | | | 175 | |
| Arg | Phe | Thr | Gly | Arg | Tyr | Met | Ile | Asp | Cys | Gly | Gly | Pro | Arg | Ala | Pro |
| | | | 180 | | | | | 185 | | | | | 190 | | |
| Leu | Ala | Thr | Lys | Phe | Lys | Leu | Arg | Glu | Glu | Pro | Cys | Arg | Phe | Lys | Thr |
| | | | 195 | | | | | 200 | | | | | 205 | | |
| His | Ser | Arg | Ser | Leu | Tyr | Thr | His | Met | Leu | Gly | Val | Lys | Pro | Phe | Asp |
| | 210 | | | | | 215 | | | | | 220 | | | | |
| Asp | Ile | Phe | Lys | Val | Lys | Gly | Gln | Arg | Trp | Arg | Trp | His | Glu | Gly | Thr |
| 225 | | | | | 230 | | | | | 235 | | | | | 240 |
| Leu | His | His | Met | Phe | Glu | Gly | Gly | Trp | Leu | Trp | Val | Ile | Pro | Phe | Asn |
| | | | | 245 | | | | | 250 | | | | | 255 | |
| Asn | His | Pro | Arg | Ser | Thr | Asn | Asn | Leu | Val | Ser | Val | Gly | Leu | Gln | Leu |
| | | | 260 | | | | | 265 | | | | | 270 | | |
| Asp | Pro | Arg | Val | Tyr | Pro | Lys | Thr | Asp | Ile | Ser | Ala | Gln | Gln | Glu | Phe |
| | | 275 | | | | | 280 | | | | | 285 | | | |
| Asp | Glu | Phe | Leu | Ala | Arg | Phe | Pro | Ser | Ile | Gly | Ala | Gln | Phe | Arg | Asp |
| | 290 | | | | | 295 | | | | | 300 | | | | |
| Ala | Val | Pro | Val | Arg | Asp | Trp | Val | Lys | Thr | Asp | Arg | Leu | Gln | Phe | Ser |
| 305 | | | | | 310 | | | | | 315 | | | | | 320 |
| Ser | Asn | Ala | Cys | Val | Gly | Asp | Arg | Tyr | Cys | Leu | Met | Leu | His | Ala | Asn |
| | | | | 325 | | | | | 330 | | | | | 335 | |
| Gly | Phe | Ile | Asp | Pro | Leu | Phe | Ser | Arg | Gly | Leu | Glu | Asn | Thr | Ala | Val |
| | | | 340 | | | | | 345 | | | | | 350 | | |
| Thr | Ile | His | Ala | Leu | Ala | Ala | Arg | Leu | Ile | Lys | Ala | Leu | Arg | Asp | Asp |
| | | 355 | | | | | 360 | | | | | 365 | | | |
| Asp | Phe | Ser | Pro | Glu | Arg | Phe | Glu | Tyr | Ile | Glu | Arg | Leu | Gln | Gln | Lys |
| | 370 | | | | | 375 | | | | | 380 | | | | |

```
Leu  Leu  Asp  His  Asn  Asp  Asp  Phe  Val  Ser  Cys  Cys  Tyr  Thr  Ala  Phe
385                 390                 395                 400

Ser  Asp  Phe  Arg  Leu  Trp  Asp  Ala  Phe  His  Arg  Leu  Trp  Ala  Val  Gly
                405                 410                 415

Thr  Ile  Leu  Gly  Gln  Phe  Arg  Leu  Val  Gln  Ala  His  Ala  Arg  Phe  Arg
                420                 425                 430

Ala  Ser  Arg  Asn  Glu  Gly  Asp  Leu  Asp  His  Leu  Asp  Asn  Asp  Pro  Pro
           435                 440                 445

Tyr  Leu  Gly  Tyr  Leu  Cys  Ala  Asp  Met  Glu  Glu  Tyr  Tyr  Gln  Leu  Phe
          450                 455                 460

Asn  Asp  Ala  Lys  Ala  Glu  Val  Glu  Ala  Val  Ser  Ala  Gly  Arg  Lys  Pro
465                 470                 475                 480

Ala  Asp  Glu  Ala  Ala  Ala  Arg  Ile  His  Ala  Leu  Ile  Asp  Glu  Arg  Asp
                485                 490                 495

Phe  Ala  Lys  Pro  Met  Phe  Gly  Phe  Gly  Tyr  Cys  Ile  Thr  Gly  Asp  Lys
               500                 505                 510

Pro  Gln  Leu  Asn  Asn  Ser  Lys  Tyr  Ser  Leu  Leu  Pro  Ala  Met  Arg  Leu
               515                 520                 525

Met  Tyr  Trp  Thr  Gln  Thr  Arg  Ala  Pro  Ala  Glu  Val  Lys  Lys  Tyr  Phe
     530                 535                 540

Asp  Tyr  Asn  Pro  Met  Phe  Ala  Leu  Leu  Lys  Ala  Tyr  Ile  Thr  Thr  Arg
545                 550                 555                 560

Ile  Gly  Leu  Ala  Leu  Lys  Lys
                565
```

( 2 ) INFORMATION FOR SEQ ID NO:5:

( i ) SEQUENCE CHARACTERISTICS:
        ( A ) LENGTH: 363 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met  Asn  Asp  Ile  Gln  Leu  Asp  Gln  Ala  Ser  Val  Lys  Lys  Arg  Pro  Ser
 1                  5                  10                  15

Gly  Ala  Tyr  Asp  Ala  Thr  Thr  Arg  Leu  Ala  Ala  Ser  Trp  Tyr  Val  Ala
                20                  25                  30

Met  Arg  Ser  Asn  Glu  Leu  Lys  Asp  Lys  Pro  Thr  Glu  Leu  Thr  Leu  Phe
          35                  40                  45

Gly  Arg  Pro  Cys  Val  Ala  Trp  Arg  Gly  Ala  Thr  Gly  Arg  Ala  Val  Val
     50                  55                  60

Met  Asp  Arg  His  Cys  Ser  His  Leu  Gly  Ala  Asn  Leu  Ala  Asp  Gly  Arg
65                  70                  75                  80

Ile  Lys  Asp  Gly  Cys  Ile  Gln  Cys  Pro  Phe  His  His  Trp  Arg  Tyr  Asp
                85                  90                  95

Glu  Gln  Gly  Gln  Cys  Val  His  Ile  Pro  Gly  His  Asn  Gln  Ala  Val  Arg
               100                 105                 110

Gln  Leu  Glu  Pro  Val  Pro  Arg  Gly  Ala  Arg  Gln  Pro  Thr  Leu  Val  Thr
          115                 120                 125

Ala  Glu  Arg  Tyr  Gly  Tyr  Val  Trp  Val  Trp  Tyr  Gly  Ser  Pro  Leu  Pro
     130                 135                 140

Leu  His  Pro  Leu  Pro  Glu  Ile  Ser  Ala  Ala  Asp  Val  Asp  Asn  Gly  Asp
145                 150                 155                 160

Phe  Met  His  Leu  His  Phe  Ala  Phe  Glu  Thr  Thr  Thr  Ala  Val  Leu  Arg
               165                 170                 175
```

```
Ile  Val  Glu  Asn  Phe  Tyr  Asp  Ala  Gln  His  Ala  Thr  Pro  Val  His  Ala
               180                      185                 190

Leu  Pro  Ile  Ser  Ala  Phe  Glu  Leu  Lys  Leu  Phe  Asp  Asp  Trp  Arg  Gln
          195                      200                 205

Trp  Pro  Glu  Val  Glu  Ser  Leu  Ala  Leu  Ala  Gly  Ala  Trp  Phe  Gly  Ala
     210                      215                 220

Gly  Ile  Asp  Phe  Thr  Val  Asp  Arg  Tyr  Phe  Gly  Pro  Leu  Gly  Met  Leu
225                      230                 235                           240

Ser  Arg  Ala  Leu  Gly  Leu  Asn  Met  Ser  Gln  Met  Asn  Leu  His  Phe  Asp
               245                      250                      255

Gly  Tyr  Pro  Gly  Gly  Cys  Val  Met  Thr  Val  Ala  Leu  Asp  Gly  Asp  Val
               260                      265                 270

Lys  Tyr  Lys  Leu  Leu  Gln  Cys  Val  Thr  Pro  Val  Ser  Glu  Gly  Lys  Asn
          275                      280                 285

Val  Met  His  Met  Leu  Ile  Ser  Ile  Lys  Lys  Val  Gly  Gly  Ile  Leu  Arg
     290                      295                 300

Arg  Ala  Thr  Asp  Phe  Val  Leu  Phe  Gly  Leu  Gln  Thr  Arg  Gln  Ala  Ala
305                      310                 315                           320

Gly  Tyr  Asp  Val  Lys  Ile  Trp  Asn  Gly  Met  Lys  Pro  Asp  Gly  Gly  Gly
                    325                 330                      335

Ala  Tyr  Ser  Lys  Tyr  Asp  Lys  Leu  Val  Leu  Lys  Tyr  Arg  Ala  Phe  Tyr
               340                      345                 350

Arg  Gly  Trp  Val  Asp  Arg  Val  Ala  Ser  Glu  Arg
          355                      360
```

( 2 ) INFORMATION FOR SEQ ID NO:6:

( i ) SEQUENCE CHARACTERISTICS:
        ( A ) LENGTH: 28958 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

```
CGATCGCGTC  GGCCTCGACA  CCGTCGAAGA  GGTCACGCTC  GAAGCTCCCC  TCGCTCTCCC      60
CTCTCAAGGC  ACCATTCTCA  TCCAGATCTC  CGTCGGACCC  ATGGACGAGG  CGGGACGAAG     120
GTCGCTCTCC  CTCCATGGCC  GGACCGAGGA  CGCTCCTCAG  GACGCCCTT   GGACGCGCCA     180
CGCGAGCGGG  TCGCTCGCTA  AAGCTGCCCC  CTCCCTCTCC  TTCGATCTTC  ACGAATGGGC     240
TCCTCGGGGG  GGCACGCCGG  TGGACACCCA  AGGCTCTTAC  GCAGGCCTCG  AAAGCGGGGG     300
GCTCGCCTAT  GGGCCTCAGT  TCCAGGGACT  TCGCTCCGTC  TGGAAGCGCG  GCGACGAGCT     360
CTTCGCCGAG  GCCAAGCTCC  CGGACGCAGG  CGCCAAGGAT  GCCGCTCGGT  TCGCCCTCCA     420
CCCCGCCCTG  TTCGACAGCG  CCCTGCACGC  GCTTGTCCTT  GAAGACGAGC  GGACGCCGGG     480
CGTCGCTCTG  CCCTTCTCGT  GGAGAGGAGT  CTCGCTGCGC  TCCGTCGGCG  CCACCACCCT     540
GCGCGTGCGC  TTCCATCGTC  CGAATGGCAA  GTCCTCCGTG  TCGCTCCTCC  TCGGCGACGC     600
CGCAGGCGAG  CCCCTCGCCT  CGGTCCAAGC  GCTCGCCACG  CGCATACGT   CCCAGGAGCA     660
GCTCCGCACC  CAGGGAGCTT  CCCTCCACGA  TGCTCTCTTC  CGGGTTGTCT  GGAGAGATCT     720
GCCCAGCCCT  ACGTCGCTCT  CTGAGGCCCC  GAAGGGTGTC  CTCCTAGAGA  CAGGGGGTCT     780
```

| | | | | | |
|---|---|---|---|---|---|
|CGACCTCGCG|CTGCAGGCGT|CTCTCGCCCG|CTACGACGGT|CTCGCTGCCC|TCCGGAGCGC|840|
|GCTCGACCAA|GGCGCTTCGC|CTCCGGGCCT|CGTCGTCGTC|CCCTTCATCG|ATTCGCCCTC|900|
|TGGCGACCTC|ATAGAGAGCG|CTCACAACTC|CACCGCGCGC|GCCCTCGCCT|TGCTGCAAGC|960|
|GTGGCTTGAC|GACGAACGCC|TCGCCTCCTC|GCGCCTCGTC|CTGCTCACCC|GACAGGCCAT|1020|
|CGCAACCCAC|CCCGACGAGG|ACGTCCTCGA|CCTCCCTCAC|GCTCCTCTCT|GGGGCCTTGT|1080|
|GCGCACCGCG|CAAAGCGAAC|ACCCGGAGCT|CCCTCTCTTC|CTCGTCGACC|TGGACCTCGG|1140|
|TCAGGCCTCG|GAGCGCGCCC|TGCTCGGCGC|GCTCGACACA|GGAGAGCGTC|AGCTCGCTCT|1200|
|CCGCCATGGA|AAATGCCTCG|TCCCGAGGTT|GGTGAATGCA|CGCTCGACAG|AGGCGCTCAT|1260|
|CGCGCCGAAC|GTATCCACGT|GGAGCCTTCA|TATCCCGACC|AAAGGCACCT|TCGACTCGCT|1320|
|CGCCCTCGTC|GACGCTCCTC|TAGCCCGTGC|GCCCCTCGCA|CAAGGCCAAG|TCCGCGTCGC|1380|
|CGTGCACGCG|GCAGGTCTCA|ACTTCCGCGA|TGTCCTCAAC|ACCCTTGGCA|TGCTTCCGGA|1440|
|CAACGCGGGG|CCGCTCGGCG|GCGAAGGCGC|GGGCATTGTC|ACCGAAGTCG|GCCCAGGTGT|1500|
|TTCCCGATAC|ACTGTAGGCG|ACCGGGTGAT|GGGCATCTTC|CGCGGAGGCT|TTGGCCCCAC|1560|
|GGTCGTCGCC|GACGCCCGCA|TGATCTGCCC|CATCCCGAT|GCCTGGTCCT|TCGTCCAAGC|1620|
|CGCCAGCGTC|CCCGTCGTCT|TTCTCACCGC|CTACTATGGA|CTCGTCGATG|TCGGGCATCT|1680|
|CAAGCCCAAT|CAACGTGTCC|TCATCCATGC|GGCCGCAGGC|GGCGTCGGTA|CTGCCGCCGT|1740|
|CCAGCTCGCG|CGCCACCTCG|GCGCCGAAGT|CTTCGCCACC|GCCAGTCCAG|GGAAGTGGGA|1800|
|CGCTCTGCGC|GCGCTCGGCT|TCGACGATGC|GCACCTCGCG|TCCTCACGTG|ACCTGGAATT|1860|
|CGAGCAGCAT|TTCCTGCGCT|CCACACGAGG|GCGCGGCATG|GATGTCGTCC|TCAACGCCTT|1920|
|GGCGCGCGAG|TTCGTCGACG|CTTCGCTGCG|TCTCCTGCCG|AGCGGTGGAA|GCTTTGTCGA|1980|
|GATGGGCAAG|ACGGATATCC|GCGAGCCCGA|CGCCGTAGGC|CTCGCCTACC|CCGGCGTCGT|2040|
|TTACCGCGCC|TTCGATCTCT|TGGAGGCTGG|ACCGGATCGA|ATTCAAGAGA|TGCTCGCAGA|2100|
|GCTGCTCGAC|CTGTTCGAGC|GCGGCGTGCT|TCGTCCGCCG|CCCATCACGT|CCTGGGACAT|2160|
|CCGGCATGCC|CCCCAGGCGT|TCCGCGCGCT|CGCTCAGGCG|CGGCATATTG|GAAAGTTCGT|2220|
|CCTCACCGTT|CCCGTCCCAT|CGATCCCCGA|AGGCACCATC|CTCGTCACGG|GAGGCACCGG|2280|
|CACGCTCGGC|GCGCTCATCG|CGCGCCACCT|CGTCGCCAAT|CGCGGCGACA|AGCACCTGCT|2340|
|CCTCACCTCG|CGAAAGGGTG|CGAGCGCTCC|GGGGGCCGAG|GCATTGCGGA|GCGAGCTCGA|2400|
|AGCTCTGGGG|GCTGCGGTCA|CGCTCGCCCG|GTGCGACGCG|GCCGATCCAC|GCGCGCTCCA|2460|
|AGCCCTCTTG|GACAGCATCC|CGAGCGCTCA|CCCGCTCACG|GCCGTCGTGC|ACGCCGCGG|2520|
|CGCCCTTGAC|GATGGGCTGA|TCAGCGACAT|GAGCCCCGAG|CGCATCGACC|GCGTCTTTGC|2580|
|TCCCAAGCTC|GACGCCGCTT|GGCACTTGCA|TCAGCTCACC|CAGGACAAGG|CCGCTCGGGG|2640|
|CTTCGTCCTC|TTCTCGTCCG|CCTCCGGCGT|CCTCGGCGGT|ATGGGTCAAT|CCAACTACGC|2700|
|GGGGGGCAAT|GCGTTCCTTG|ACGCGCTCGC|GCATCACCGA|CGCGTCCATG|GGCTCCCAGG|2760|
|CTCCTCGCTC|GCATGGGCC|ATTGGGCCGA|GCGCAGCGGA|ATGACCCGAC|AACCTCAGCG|2820|
|GCGTCGATAC|CGCTCGCATG|AGGCGCGCGG|TCTCCGATCC|ATCGCCTCGG|ACGAGGGTCT|2880|
|CGCCCTCTTC|GATATGGCGC|TCGGGCGCCC|GGAGCCCGCG|CTGGTCCCCG|CCCGCTTCGA|2940|
|CATGAACGCG|CTCGGCGCGA|AGGCCGACGG|GCTACCCTCG|ATGTTCCAGG|GTCTCGTCCG|3000|
|CGCTCGCGTC|GCGCGCAAGG|TCGCCAGCAA|TAATGCCCTG|GCCGCGTCGC|TCACCCAGCG|3060|
|CCTCGCCTCC|CTCCCGCCCA|CCGACCGCGA|GCGCATGCTG|CTCGATCTCG|TCCGCGCCGA|3120|
|AGCCGCCATC|GTCCTCGGCC|TCGCCTCGTT|CGAATCGCTC|GATCCCCGTC|GCCCTCTTCA|3180|

-continued

| | | | | | | |
|---|---|---|---|---|---|---|
| AGAGCTCGGT | CTCGATTCCC | TCATGGCCAT | CGAGCTCCGA | AATCGACTCG | CCGCCGCCAC | 3240 |
| AGGCTTGCGA | CTCCAAGCCA | CCCTCCTCTT | CGACCACCCG | ACGCCCGCCG | CGCTCGCGAC | 3300 |
| CCTGCTGCTC | GGGAAGCTCC | TCCAGCATGA | AGCTGCCGAT | CCTCGCCCCT | TGGCCGCAGA | 3360 |
| GCTCGACAGG | CTAGAGGCCA | CTCTCTCCGC | GATAGCCGTG | GACGCTCAAG | CACGCCCGAA | 3420 |
| GATCATATTA | CGCCTGCAAT | CCTGGTTGTC | GAAGTGGAGC | GACGCTCAGG | CTGCCGACGC | 3480 |
| TGGACCGATT | CTCGGCAAGG | ATTTCAAGTC | TGCTACGAAG | GAAGAGCTCT | TCGCTGCTTG | 3540 |
| TGACGAAGCG | TTCGGAGGCC | TGGGTAAATG | AATAACGACG | AGAAGCTTGT | CTCCTACCTA | 3600 |
| CAGCAGGCGA | TGAATGAGCT | TCAGCGTGCT | CATCAGCCCC | TCCGCGCGGT | CGAAGAGAAG | 3660 |
| GAGCACGAGC | CCATCGCCAT | CGTGGCGATG | AGCTGCCGCT | TCCCGGGCGA | CGTGCGCACG | 3720 |
| CCCGAGGATC | TCTGGAAGCT | CTTGCTCGAT | GGGAAGATG | CTATCTCCGA | CCTTCCCCCA | 3780 |
| AACCGTGGTT | GGAAGCTCGA | CGCGCTCGAC | GTCCACGGTC | GCTCCCAGT | CCGAGAGGGA | 3840 |
| GGCTTCTTCT | ACGACGCAGA | CGCCTTCGAT | CCGGCCTTCT | TCGGGATCAG | CCCACGCGAG | 3900 |
| GCGCTCGCCA | TCGATCCCCA | GCAGCGGCTC | CTCCTCGAGA | TCTCATGGGA | AGCCTTCGAG | 3960 |
| CGTGCGGGCA | TCGACCCTGC | CTCGCTCCAA | GGGAGCCAAA | GCGGCGTCTT | CGTCGGCGTG | 4020 |
| ATACACAACG | ACTACGACGC | ATTGCTGGAG | AACGCAGCTG | GCGAACACAA | AGGATTCGTT | 4080 |
| TCCACCGGCA | GCACAGCGAG | CGTCGCCTCC | GGCCGGATCG | CGTATACATT | CGGCTTTCAA | 4140 |
| GGGCCCGCCA | TCAGCGTGGA | CACGGCGTGC | AGCTCCTCGC | TCGTCGCGGT | TCACCTCGCC | 4200 |
| TGCCAGGCCC | TGCGCCGTGG | CGAATGCTCC | CTGGCGCTCG | CCGGCGGCGT | GACCGTCATG | 4260 |
| GCCACGCCAG | CAGTCTTCGT | CGCGTTCGAT | TCCGAGAGCG | CGGGCGCCCC | CGATGGTCGC | 4320 |
| TGCAAGTCGT | TCTCGGTGGA | GGCCAACGGT | TCGGGCTGGG | CCGAGGGCGC | CGGGATGCTC | 4380 |
| CTGCTCGAGC | GCCTCTCCGA | TGCCGTCCAA | AACGGTCATC | CCGTCCTCGC | CGTCCTTCGA | 4440 |
| GGCTCCGCCG | TCAACCAGGA | CGGCCGGAGC | CAAGGCCTCA | CCGCGCCCAA | TGGCCCTGCC | 4500 |
| CAAGAGCGCG | TCATCCGGCA | AGCGCTCGAC | AGCGCGCGGC | TCACTCCAAA | GGACGTCGAC | 4560 |
| GTCGTCGAGG | CTCACGGCAC | GGGAACCACC | CTCGGAGACC | CCATCGAGGC | ACAGGCCATT | 4620 |
| CTTGCCACCT | ATGGCGAGGC | CCATTCCCAA | GACAGACCCC | TCTGGCTTGG | AAGTCTCAAG | 4680 |
| TCCAACCTGG | GACATGCTCA | GGCCGCGGCC | GGCGTGGGAA | GCGTCATCAA | GATGGTGCTC | 4740 |
| GCGTTGCAGC | AAGGCCTCTT | GCCCAAGACC | CTCCATGCCC | AGAATCCCTC | CCCCCACATC | 4800 |
| GACTGGTCTC | CGGGCACGGT | AAAGCTCCTG | AACGAGCCCG | TCGTCTGGAC | GACCAACGGG | 4860 |
| CATCCTCGCC | ACGCCGGCGT | CTCCGCCTTC | GGCATCTCCG | GCACCAACGC | CCACGTCATC | 4920 |
| CTCGAAGAGG | CCCCCGCCAT | CGCCCGGGTC | GAGCCCGCAG | CGTCACAGCC | CGCGTCCGAG | 4980 |
| CCGCTTCCCG | CAGCGTGGCC | CGTGCTCCTG | TCGGCCAAGA | GCGAGGCGGC | CGTGCGCGCC | 5040 |
| CAGGCAAAGC | GGCTCCGCGA | CCACCTCCTC | GCCAAAAGCG | AGCTCGCCCT | CGCCGATGTG | 5100 |
| GCCTATTCGC | TCGCGACCAC | GCGCGCCCAC | TTCGAGCAGC | GCGCCGCTCT | CCTCGTCAAA | 5160 |
| GGCCGCGACG | AGCTCCTCTC | CGCCCTCGAT | GCGCTGGCCC | AAGGACATTC | CGCCGCCGTG | 5220 |
| CTCGGACGAA | GCGGGGCCCC | AGGAAAGCTC | GCCGTCCTCT | TCACGGGGCA | AGGAAGCCAG | 5280 |
| CGGCCCACCA | TGGGCCGCGG | CCTCTACGAC | GTTTTCCCCG | TCTTCCGGGA | CGCCCTCGAC | 5340 |
| ACCGTCGGCG | CCCACCTCGA | CCGCGAGCTC | GACCGCCCCC | TGCGCGACGT | CCTCTTCGCT | 5400 |
| CCCGACGGCT | CCGAGCAGGC | CGCGCGCCCT | GAGCAAACCG | CCTTCACCCA | GCCGGCCCTG | 5460 |
| TTTGCCCTCG | AAGTCGCCCT | CTTTCAGCTT | CTACAATCCT | TCGGTCTGAA | GCCCGCTCTC | 5520 |
| CTCCTCGGAC | ACTCCATTGG | CGAGCTCGTC | GCCGCCCACG | TCGCCGGCGT | CCTTTCTCTC | 5580 |

| | | | | | | |
|---|---|---|---|---|---|---|
| CAGGACGGCT | GCACCCTCGT | CGCCGCCCGC | GCAAAGCTCA | TGCAAGCGCT | CCCACAAGGC | 5640 |
| GGCGCCATGG | TCACCCTCCG | AGCCTCCGAG | GAGGAAGTCC | GCGACCTTCT | CCAGCCCTAC | 5700 |
| GAAGGCCGAG | CTAGCCTCGC | CGCCCTCAAT | GGGCCTCTCT | CCACCGTCGT | CGCTGGCGAT | 5760 |
| GAAGACGCGG | TGGTGGAGAT | CGCCCGCCAG | GCCGAAGCCC | TCGGACGAAA | GACCACACGC | 5820 |
| CTGCGCGTCA | GCCACGCCTT | CCATTCCCCG | CACATGGACG | GAATGCTCGA | CGACTTCCGC | 5880 |
| CGCGTCGCCC | AGAGCCTCAC | CTACCATCCC | GCACGCATCC | CCATCATCTC | CAACGTCACC | 5940 |
| GGCGCGCGCG | CCACGGACCA | CGAGCTCGCC | TCGCCCGACT | ACTGGGTCCG | CCACGTTCGC | 6000 |
| CACACCGTCC | GCTTCCTCGA | CGGCGTACGT | GCCCTTCACG | CCGAAGGGGC | ACGTGTCTTT | 6060 |
| CTCGAGCTCG | GGCCTCACGC | TGTCCTCTCC | GCCCTTGCGC | AAGACGCCCT | CGGACAGGAC | 6120 |
| GAAGGCACGT | CGCCATGCGC | CTTCCTTCCC | ACCTCCGCA | AGGGACGCGA | CGACGCCGAG | 6180 |
| GCGTTCACCG | CCGCGCTCGG | CGCTCTCCAC | TCCGCAGGCA | TCACACCCGA | CTGGAGCGCT | 6240 |
| TTCTTCGCCC | CCTTCGCTCC | ACGCAAGGTC | TCCCTCCCCA | CCTATGCCTT | CCAGCGCGAG | 6300 |
| CGCTTCTGGC | CCGACGCCTC | CAAGGCACCC | GGCGCCGACG | TCAGCCACCT | TGCTCCGCTC | 6360 |
| GAGGGGGGGC | TCTGGCAAGC | CATCGAGCGC | GGGGACCTCG | ATGCGCTCAG | CGGTCAGCTC | 6420 |
| CACGTGGACG | GCGACGAGCG | GCGCGCCGCG | CTCGCCCTGC | TCCTTCCCAC | CCTCTCGAGC | 6480 |
| TTTCGCCACG | AGCGGCAAGA | GCAGAGCACG | GTCGACGCCT | GGCGCTACCG | TATCACCTGG | 6540 |
| AAGCCTCTGA | CCACCGCCGA | AACACCCGCC | GACCTCGCCG | GCACCTGGCT | CGTCGTCGTG | 6600 |
| CCGGCCGCTC | TGGACGACGA | CGCGCTCCCC | TCCGCGCTCA | CCGAGGCGCT | CACCCGGCGC | 6660 |
| GGCGCGCGCG | TCCTCGCCTT | GCGCCTGAGC | CAGGCCCACC | TGGACCGCGA | GGCTCTCGCC | 6720 |
| GAGCATCTGC | GCCAGGCTTG | CGCCGAGACC | GCCCGATTC | GCGGCGTGCT | CTCGCTCCTC | 6780 |
| GCCCTCGACG | AGCGCCCCCT | CGCAGACCGT | CCTGCCCTGC | CCGCCGGACT | CGCCCTCTCG | 6840 |
| CTTTCTCTCG | CTCAAGCCCT | CGGCGACCTC | GACCTCGAGG | CGCCCTTGTG | GTTCTTCACG | 6900 |
| CGCGGCGCCG | TCTCCATTGG | ACACTCTGAC | CCCCTCGCCC | ATCCGCCCA | GGCCATGACC | 6960 |
| TGGGGCTTGG | GCCGCGTCAT | CGGCCTCGAG | CACCCCGACC | GGTGGGGAGG | TCTCGTCGAC | 7020 |
| GTCTGCGCTG | GGGTCGACGA | GAGCGCCGTG | GGCCGCTTGC | TGCCGGCCCT | CGCCGAGCGC | 7080 |
| CACGACGAAG | ACCAGCTCGC | TCTCCGCCCG | GCCGGACTCT | ACGCTCGCCG | CATCGTCCGC | 7140 |
| GCCCCGCTCG | GCGATGCGCC | TCCCGCGCGC | GACTTCACGC | CCGGAGGCAC | CATTCTCATC | 7200 |
| ACCGGCGGCA | CCGGCGCCAT | GGCGCTCAC | GTCGCCCGAT | GGCTCGCTCG | AAGAGGCGCT | 7260 |
| CAGCACCTCG | TCCTCATCAG | CCGCCGAGGC | GCCGAGGCCC | CTGGCGCCTC | GGAGCTCCAC | 7320 |
| GACGAGCTCT | CGGCCCTCGG | CGCGCGCACC | ACCCTCGCCG | CGTGCGATGT | CGCCGACCGG | 7380 |
| AATGCTGTCG | CCACGCTTCT | TGAGCAGCTC | GACGCCGAAG | GGTCGCAGGT | CCGCGCCGTG | 7440 |
| TTCCACGCGA | GCGGCATCGA | ACACCACGCT | CCGCTCGACG | CCACCTCTTT | CAGGGATCTC | 7500 |
| GCCGAGGTTG | TCTCCGGCAA | GGTCGAAGGT | GCAAAGCACC | TCCACGACCT | GCTCGGCTCT | 7560 |
| CGACCCCTCG | ACGCCTTTGT | TCTCTTTTCG | TCCGGCGCGG | CCGTCTGGGG | CGGCGGACAG | 7620 |
| CAAGGCGGCT | ACGCGGCCGC | AAACGCCTTC | CTCGACGCCC | TTGCCGAGCA | TCGGCGCAGC | 7680 |
| GCTGGATTGA | CAGCGACGTC | GGTGGCCTGG | GGCGCGTGGG | GCGGCGGCGG | CATGGCCACC | 7740 |
| GATCAGGCGG | CAGCCCACCT | CCAACAGCGC | GGTCTGTCGC | GGATGGCCCC | CTCGCTTGCC | 7800 |
| CTGGCGGCGC | TCGCGCTGGC | TCTGGAGCAC | GACGAGACCA | CCGTCACCGT | CGCCGACATC | 7860 |
| GACTGGGCGC | GCTTTGCGCC | TTCGTTCAGC | GCCGCTCGCC | CCGCCCGCT | CCTGCGCGAT | 7920 |
| TTGCCCGAGG | CGCAGCGCGC | TCTCGAGACC | AGCGAAGGCG | CGTCCTCCGA | GCATGGCCCG | 7980 |

| | | | | | | |
|---|---|---|---|---|---|---|
| GCCCCCGACC | TCCTCGACAA | GCTCCGGAGC | CGCTCGGAGA | GCGAGCAGCT | TCGTCTGCTC | 8040 |
| GTCTCGCTGG | TGCGCCACGA | GACGGCCCTC | GTCCTCGGCC | ACGAAGGCGC | CTCCCATGTC | 8100 |
| GACCCCGACA | AGGGCTTCCT | CGATCTCGGT | CTCGATTCGC | TCATGGCCGT | CGAGCTTCGC | 8160 |
| CGGCGCTTGC | AACAGGCCAC | CGGCATCAAG | CTCCCGGCCA | CCCTCGCCTT | CGACCATCCC | 8220 |
| TCTCCTCATC | GAGTCGCGCT | CTTCTTGCGC | GACTCGCTCG | CCCACGCCCT | CGGCACGAGG | 8280 |
| CTCTCCGTCG | AGCCCGACGC | CGCCGCGCTC | CCGGCGCTTC | GCGCCGCGAG | CGACGAGCCC | 8340 |
| ATCGCCATCG | TCGGCATGGC | CCTCCGCCTG | CCGGGCGGCG | TCGGCGATGT | CGACGCTCTT | 8400 |
| TGGGAGTTCC | TGGCCCAGGG | ACGCGACGGC | GTCGAGCCCA | TTCCAAAGGC | CCGATGGGAT | 8460 |
| GCCGCTGCGC | TCTACGACCC | CGACCCCGAC | GCCAAGACCA | AGAGCTACGT | CCGGCATGCC | 8520 |
| GCCATGCTCG | ACCAGGTCGA | CCTCTTCGAC | CCTGCCTTCT | TTGGCATCAG | CCCCCGGGAG | 8580 |
| GCCAAACACC | TCGACCCCCA | GCACCGCCTG | CTCCTCGAAT | CTGCCTGGCA | GGCCCTCGAA | 8640 |
| GACGCCGGCA | TCGTCCCCCC | CACCCTCAAG | GATTCCCCCA | CCGGCGTCTT | CGTCGGCATC | 8700 |
| GGCGCCAGCG | AATACGCATT | GCGAGAGGCG | AGCACCGAAG | ATTCCGACGC | TTATGCCCTC | 8760 |
| CAAGGCACCG | CCGGGTCCTT | TGCCGCGGGG | CGCTTGGCCT | ACACGCTCGG | CCTGCAAGGG | 8820 |
| CCCGCGCTCT | CGGTCGACAC | CGCCTGCTCC | TCCTCGCTCG | TCGCCCTCCA | CCTCGCCTGC | 8880 |
| CAAGCCCTCC | GACAGGGCGA | GTGCAACCTC | GCCCTCGCCG | CGGGCGTCTC | CGTCATGGCC | 8940 |
| TCCCCCGAGG | GCTTCGTCCT | CCTTTCCCGC | CTGCGCGCCT | TGGCGCCCGA | CGGCCGCTCC | 9000 |
| AAGACCTTCT | CGGCCAACGC | CGACGGCTAC | GGACGCGGAG | AAGGCGTCAT | CGTCCTTGCC | 9060 |
| CTCGAGCGGC | TCGGTGACGC | CCTCGCCCGA | GGACACCGCG | TCCTCGCCCT | CGTCCGCGGC | 9120 |
| ACCGCCATCA | ACCACGACGG | CGCGTCGAGC | GGTATCACCG | CCCCAACGG | CACCTCCCAG | 9180 |
| CAGAAGGTCC | TCCGCGCCGC | GCTCCACGAC | GCCCGCATCA | CCCCCGCCGA | CGTCGACGTC | 9240 |
| GTCGAGTGCC | ATGGCACCGG | CACCTCCTTG | GGAGACCCCA | TCGAGGTGCA | AGCCCTGGCC | 9300 |
| GCCGTCTACG | CCGACGGCAG | ACCCGCTGAA | AAGCCTCTCC | TTCTCGGCGC | GCTCAAGACC | 9360 |
| AACATCGGCC | ATCTCGAGGC | CGCCTCCGGC | CTCGCGGGCG | TCGCCAAGAT | CGTCGCCTCC | 9420 |
| CTCCGCCATG | ACGCCCTGCC | CCCCACCCTC | CACACGGGCC | CGCGCAATCC | CTTGATTGAT | 9480 |
| TGGGATACAC | TCGCCATCGA | CGTCGTTGAT | ACCCCGAGGT | CTTGGGCCCG | CCACGAAGAT | 9540 |
| AGCAGTCCCC | GCCGCGCCGG | CGTCTCCGCC | TTCGGACTCT | CCGGCACCAA | CGCCCACGTC | 9600 |
| ATCCTCGAGG | AGGCTCCCGC | CGCCCTGTCG | GGCGAGCCCG | CCACCTCACA | GACGGCGTCG | 9660 |
| CGACCGCTCC | CCGCGGCGTG | TGCCGTGCTC | CTGTCGGCCA | GGAGCGAGGC | CGCCGTCCGC | 9720 |
| GCCCAGGCGA | AGCGGCTCCG | CGACCACCTC | CTCGCCCACG | ACGACCTCGC | CCTTATCGAT | 9780 |
| GTGGCCTATT | CGCAGGCCAC | CACCCGCGCC | CACTTCGAGC | ACCGCCGCGC | TCTCCTGGCC | 9840 |
| CGCGACCGCG | ACGAGCTCCT | CTCCGCGCTC | GACTCGCTCG | CCCAGGACAA | GCCCGCCCCG | 9900 |
| AGCACCGTTC | TCGGCCGGAG | CGGAAGCCAC | GGCAAGGTCG | TCTTCGTCTT | TCCTGGGCAA | 9960 |
| GGCTCGCAGT | GGGAAGGGAT | GGCCCTCTCC | CTGCTCGACT | CCTCGCCGGT | CTTCCGCGCT | 10020 |
| CAGCTCGAAG | CATGCGAGCG | CGCGCTCGCT | CCTCACGTCG | AGTGGAGCCT | GCTCGCCGTC | 10080 |
| CTGCGCCGCG | ACGAGGGCGC | CCCCTCCCTC | GACCGCGTCG | ACGTCGTACA | GCCCGCCCTC | 10140 |
| TTTGCCGTCA | TGGTCTCCCT | GGCCGCCCTC | TGGCGCTCGC | TCGGCGTCGA | GCCCGCCGCC | 10200 |
| GTCGTCGGCC | ACAGCCAGGG | CGAGATCGCC | GCCGCCTTCG | TCGCAGGCGC | TCTCTCCCTC | 10260 |
| GAGGACGCGG | CGCGCATCGC | CGCCCTGCGC | AGGAAAGCGC | TCACCACCGT | CGGCGGCAAC | 10320 |
| GGCGGCATGG | CCGCCGTCGA | GCTCGGCGCC | TCCGACCTCC | AGACCTACCT | CGCTCCCTGG | 10380 |

| | | | | | |
|---|---|---|---|---|---|
| GGCGACAGGC | TCTCCACCGC | CGCCGTCAAC | AGCCCCAGGG | CTACCCTCGT | ATCCGGCGAG | 10440 |
| CCCGCCGCCG | TCGACGCGCT | GCTCGACGTC | CTCACCGCCA | CCAAGGTGTT | CGCCCGCAAG | 10500 |
| ATCCGCGTCG | ACTACGCCTC | CCACTCCGCC | CAGATGGACG | CCGTCCAAGA | CGAGCTCGCC | 10560 |
| GCAGGTCTAG | CCAACATCGC | TCCTCGGACG | TGCGAGCTCC | CTCTTTATTC | GACCGTCACC | 10620 |
| GGCACCAGGC | TCGACGGCTC | CGAGCTCGAC | GGCGCGTACT | GGTATCGAAA | CCTCCGGCAA | 10680 |
| ACCGTCCTGT | TCTCGAGCGC | GACCGAGCGG | CTCCTCGACG | ATGGGCATCG | CTTCTCCGTC | 10740 |
| GAGGTCAGCC | CCCATCCCGT | GCTCACGCTC | GCCCTCCGCG | AGACCTGCGA | GCGCTCACCG | 10800 |
| CTCGATCCCG | TCGTCGTCGG | CTCCATTCGA | CGAGAAGAAG | GCCACCTCGC | CCGCCTGCTC | 10860 |
| CTCTCCTGGG | CGGAGCTCTC | TACCCGAGGC | CTCGCGCTCG | ACTGGAAGGA | CTTCTTCGCG | 10920 |
| CCCTACGCTC | CCCGCAAGGT | CTCCCTCCCC | ACCTACCCCT | TCCAGCGAGA | GCGGTTCTGG | 10980 |
| CTCGACGTCT | CCACGGACGA | ACGCTTCCGA | CGTCGCCTCC | GCAGGCCTGA | CCTCGGCCGA | 11040 |
| CCAATCCCGC | TGCTCGGCGC | CGCCGTCGCC | TTCGCCGACC | GCGGTGGCTT | TCTCTTTACA | 11100 |
| GGGCGGCTCT | CCCTCGCAGA | GCACCCGTGG | CTCGAAGGCC | ATGCCGTCTT | CGGCACACCC | 11160 |
| ATCCTACCGG | GCACCGGCTT | TCTCGAGCTC | GCCCTGCACG | TCGCCCACCG | CGTCGGCCTC | 11220 |
| GACACCGTCG | AAGAGCTCAC | GCTCGAGGCC | CCTCTCGCTC | TCCCATCGCA | GGACACCGTC | 11280 |
| CTCCTCCAGA | TCTCCGTCGG | GCCCGTGGAC | GACGCAGGAC | GAAGGGCGCT | CTCTTTCCAT | 11340 |
| AGCCGACAAG | AGGACGCGCT | TCAGGATGGC | CCCTGGACTC | GCCACGCCAG | CGGCTCTCTC | 11400 |
| TCGCCGGCGA | CCCCATCCCT | CTCCGCCGAT | CTCCACGAGT | GGCCTCCCTC | GAGTGCCATC | 11460 |
| CCGGTGGACC | TCGAAGGCCT | CTACGCAACC | CTCGCCAACC | TCGGGCTTGC | CTACGGCCCC | 11520 |
| GAGTTCCAGG | GCCTCCGCTC | CGTCTACAAG | CGCGGCGACG | AGCTCTTTGC | CGAAGCCAAG | 11580 |
| CTCCCGGAAG | CGGCCGAAAA | GGATGCCGCC | CGGTTTGCCC | TCCACCCTGC | GCTGCTCGAC | 11640 |
| AGCGCCCTGC | ATGCACTGGC | CTTTGAGGAC | GAGCAGAGAG | GGACGGTCGC | TCTGCCCTTC | 11700 |
| TCGTGGAGCG | GAGTCTCGCT | GCGCTCCGTC | GGTGCCACCA | CCTTGCGCGT | GCGCTTCCAC | 11760 |
| CGTCCCAAGG | GTGAATCCTC | CGTCTCGATC | GTCCTGGCCG | ACGCCGCAGG | TGACCCTCTT | 11820 |
| GCCTCGGTGC | AAGCGCTCGC | CATGCGGACG | ACGTCGCCG | CGCAGCTCCG | CACCCCGGCA | 11880 |
| GCTTCCCACC | ATGATGCGCT | CTTCGCCGTC | GACTGGAGCG | AGCTCCAAAG | CCCCACTTCA | 11940 |
| CCGCCTGCCG | CCCCGAGCGG | CGTCCTTCTC | GGCACAGGCG | GCCACGATCT | CGCGCTCGAC | 12000 |
| GCCCGCTCG | CCCGCTACGC | CGACCTCGCT | GCCCTCCGAA | GCGCCCTCGA | CCAGGGCGCT | 12060 |
| TCGCCTCCCG | GCCTCGTCGT | CGCCCCCTTC | ATCGATCGAC | CGGCAGGCGA | CCTCGTCCCG | 12120 |
| AGCGCCCACG | AGGCCACCGC | GCTCGCACTC | GCCCTCTTGC | AAGCCTGGCT | CGCCGACGAA | 12180 |
| CGCCTCGCCT | CGTCGCGCCT | CGTCCTCGTC | ACCCGACGCG | CCGTCGCCAC | CCACACCGAA | 12240 |
| GACGACGTCA | AGGACCTCGC | TCACGCGCCG | CTCTGGGGGC | TCGCGCGCTC | CGCGCAAAGT | 12300 |
| GAGCACCCAG | ACCTCCCGCT | CTTCCTCGTC | GACATCGACC | TCAGCGAGGC | CTCCCAGCAG | 12360 |
| GCCCTGCTAG | GCGCGCTCGA | CACAGGAGAA | CGCCAGCTCG | CCCTCCGCAA | CGGGAAACCC | 12420 |
| CTCATCCCGA | GGTTGGCGCA | ACCACGCTCG | ACGGACGCGC | TCATCCCGCC | GCAAGCACCC | 12480 |
| ACGTGGCGCC | TCCATATTCC | GACCAAAGGC | ACCTTCGACG | CGCTCGCCCT | CGTCGACGCC | 12540 |
| CCCGAGGCCC | AGGCGCCCCT | CGCACACGGC | CAAGTCCGCA | TCGCCGTGCA | CGCGGCAGGG | 12600 |
| CTCAACTTCC | GCGATGTCGT | CGACACCCTT | GGCATGTATC | CGGGCGACGC | GCCGCCGCTC | 12660 |
| GGAGGCGAAG | GCGCGGGCAT | CGTTACTGAA | GTCGGTCCAG | GTGTCTCCCG | ATACACCGTA | 12720 |
| GGCGACCGGG | TGATGGGGGT | CTTCGGCGCA | GCCTTTGGTC | CCACGGCCAT | CGCCGACGCC | 12780 |

```
CGCATGATCT GCCCCATCCC CCACGCCTGG TCCTTCGCCC AAGCCGCCAG CGTCCCCATC   12840
ATCTATCTCA CCGCCTACTA TGGACTCGTC GATCTCGGGC ATCTGAAACC CAATCAACGT   12900
GTCCTCATCC ATGCGGCCGC CGGCGGCGTC GGGACGGCCG CCGTTCAGCT CGCACGCCAC   12960
CTCGGCGCCG AGGTCTTTGC CACCGCCAGT CCAGGGAAGT GGAGCGCTCT CCGCGCGCTC   13020
GGCTTCGACG ATGCGCACCT CGCGTCCTCA CGTGACCTGG GCTTCGAGCA GCACTTCCTG   13080
CGCTCCACGC ATGGGCGCGG CATGGATGTC GTCCTCGACT GTCTGGCACG CGAGTTCGTC   13140
GACGCCTCGC TGCGCCTCAT GCCGAGCGGT GGACGCTTCA TCGAGATGGG AAAGACGGAC   13200
ATCCGTGAGC CCGACGCGAT CGGCCTCGCC TACCCTGGCG TCGTTTACCG CGCCTTCGAC   13260
GTCACAGAGG CCGGACCGGA TCGAATTGGG CAGATGCTCG CAGAGCTGCT CAGCCTCTTC   13320
GAGCGCGGTG TGCTTCGTCT GCCACCCATC ACATCCTGGG ACATCCGTCA TGCCCCCCAG   13380
GCCTTCCGCG CGCTCGCCCA GGCGCGGCAT GTTGGGAAGT TCGTCCTCAC CATTCCCCGT   13440
CCGATCGATC CCGAGGGGAC CGTCCTCATC ACGGGAGGCA CCGGGACGCT AGGAGTCCTG   13500
GTCGCACGCC ACCTCGTCGC GAAACACAGC GCCAAACACC TGCTCCTCAC CTCGAGGAAG   13560
GGCGCGCGTG CTCCGGGCGC GGAGGCTCTG CGAAGCGAGC TCGAAGCGCT GGGGGCCTCG   13620
GTCACCCTCG TCGCGTGCGA CGTGGCCGAC CCACGCGCCC TCCGGACCCT CCTGGACAGC   13680
ATCCCGAGGG ATCATCCGAT CACGGCCGTC GTGCACGCCG CCGGCGCCCT CGACGACGGG   13740
CCGCTCGGTA GCATGAGCGC CGAGCGCATC GCTCGCGTCT TTGACCCCAA GCTCGATGCC   13800
GCTTGGTACT TGCATGAGCT CACCCAGGAC GAGCCGGTCG CGGCCTTCGT CCTCTTCTCG   13860
GCCGCCTCCG GCGTCCTTGG TGGTCCAGGT CAGTCGAACT ACGCCGCTGC CAATGCCTTC   13920
CTCGATGCGC TCGCACATCA CCGGCGCGCC CAAGGACTCC CAGCCGCTTC GCTCGCCTGG   13980
GGCTACTGGG CCGAGCGCAG TGGGATGACC CGGCACCTCA GCGCCGCCGA CGCCGCTCGC   14040
ATGAGGCGCG CCGGCGTCCG GCCCCTCGAC ACTGACGAGG CGCTCTCCCT CTTCGATGTG   14100
GCTCTCTTGC GACCCGAGCC CGCTCTGGTC CCCGCCCCCT TCGACTACAA CGTGCTCAGC   14160
ACGAGTGCCG ACGGCGTGCC CCCGCTGTTC CAGCGTCTCG TCCGCGCTCG CATCGCGCGC   14220
AAGGCCGCCA GCAATACTGC CCTCGCCTCG TCGCTTGCAG AGCACCTCTC CTCCCTCCCG   14280
CCCGCCGAAC GCGAGCGCGT CCTCCTCGAT CTCGTCCGCA CCGAAGCCGC CTCCGTCCTC   14340
GGCCTCGCCT CGTTCGAATC GCTCGATCCC CATCGCCCTC TACAAGAGCT CGGCCTCGAT   14400
TCCCTCATGG CCCTCGAGCT CCGAAATCGA CTCGCCGCCG CCGCCGGGCT GCGGCTCCAG   14460
GCTACTCTCC TCTTCGACTA TCCAACCCCG ACTGCGCTCT CACGCTTTTT CACGACGCAT   14520
CTCTTCGGGG GAACCACCCA CCGCCCCGGC GTACCGCTCA CCCCGGGGGG GAGCGAAGAC   14580
CCTATCGCCA TCGTGGCGAT GAGCTGCCGC TTCCCGGGCG ACGTGCGCAC GCCCGAGGAT   14640
CTCTGGAAGC TCTTGCTCGA CGGACAAGAT GCCATCTCCG GCTTTCCCCA AAATCGCGGC   14700
TGGAGTCTCG ATGCGCTCGA CGCCCCCGGT CGCTTCCCAG TCCGGGAGGG GGGCTTCGTC   14760
TACGACGCAG ACGCCTTCGA TCCGGCCTTC TTCGGGATCA GTCCACGTGA AGCGCTCGCC   14820
GTTGATCCCC AACAGCGCAT TTTGCTCGAG ATCACATGGG AAGCCTTCGA GCGTGCAGGC   14880
ATCGACCCGG CCTCCCTCCA AGGAAGCCAA AGCGGGGTCT TCGTTGGCGT ATGGCAGAGC   14940
GACTACCAAT GCATCGCTGG TGAACGCGAC TGGCGAATAC AAGGACTCGT TGCCACCGGT   15000
AGCGCAGCGC GTCCGTCCGG CCGAATCGCA TACACGTTCG GACTTCAAGG GCCCGCCATC   15060
AGCGTGGAGA CGGCGTGCAG CTTCCTCGTC GCGGTTCACC TCGCCTGCCA GGCCCCCCCC   15120
CACGGCGAAT ACTCCCTGGC GCTCGCTGGC GGCGTGACCA TCATGGCCAC GCCAGCCATA   15180
```

| | | | | | |
|---|---|---|---|---|---|
| TTCATCGCGT | TCGACTCCGA | GAGCGCGGGT | GCCCCCGACG | GTCGCTGCAA | GGCCTTCTCG | 15240 |
| CCGGAAGCCG | ACGGTTCGGG | CTGGGCCGAA | GGCGCCGGGA | TGCTCCTGCT | CGAGCGCCTC | 15300 |
| TCCGATGCCG | TCCAAAACGG | TCATCCCGTC | CTCGCCGTCC | TTCGAGGCTC | CGCCGTCAAC | 15360 |
| CAGGACGGCC | GGAGCCAAGG | CCTCACCGCG | CCCAATGGCC | CTGCCCAGGA | GCGCGTCATC | 15420 |
| CGGCAAGCGC | TCGACAGCGC | GCGGCTCACT | CCAAAGGACG | TCGACGTCGT | CGAGGCTCAC | 15480 |
| GGCACGGGAA | CCACCCTCGG | AGACCCATC | GAGGCACAGG | CCGTTTTGC | CACCTATGGC | 15540 |
| GAGGCCCATT | CCCAAGACAG | ACCCCTCTGG | CTTGGAAGCC | TCAAGTCCAA | CCTGGGACAT | 15600 |
| ACTCAGGCCG | CGGCCGGCGT | CGGCGGCATC | ATCAAGATGG | TGCTCGCGTT | GCAGCACGGT | 15660 |
| CTCTTGCCCA | AGACCCTCCA | TGCCCAGAAT | CCCTCCCCCC | ACATCGACTG | GTCTCCAGGC | 15720 |
| ATCGTAAAGC | TCCTGAACGA | GGCCGTCGCC | TGGACGACCA | GCGGACATCC | TCGCCGCGCC | 15780 |
| GGTGTTTCCT | CGTTCGGCGT | CTCCGGCACC | AACGCCCATG | TCATCCTCGA | AGAGGCTCCC | 15840 |
| GCCGCCACGC | GGGCCGAGTC | AGGCGCTTCA | CAGCCTGCAT | CGCAGCCGCT | CCCCGCGGCG | 15900 |
| TGGCCCGTCG | TCCTGTCGGC | CAGGAGCGAG | GCCGCCGTCC | GCGCCCAGGC | TCAAAGGCTC | 15960 |
| CGCGAGCACC | TGCTCGCCCA | AGGCGACCTC | ACCCTCGCCG | ATGTGGCCTA | TTCGCTGGCC | 16020 |
| ACCACCCGCG | CCCACTTCGA | GCACCGCGCC | GCTCTCGTAG | CCCACGACCG | CGACGAGCTC | 16080 |
| CTCTCCGCGC | TCGACTCGCT | CGCCCAGGAC | AAGCCCGCAC | CGAGCACCGT | CCTCGGACGG | 16140 |
| AGCGGAAGCC | ACGGCAAGGT | CGTCTTCGTC | TTTCCTGGGC | AAGGCTCGCA | GTGGGAAGGG | 16200 |
| ATGGCCCTCT | CCCTGCTCGA | CTCCTCGCCC | GTCTTCCGCA | CACAGCTCGA | AGCATGCGAG | 16260 |
| CGCGCGCTCC | GTCCTCACGT | CGAGTGGAGC | CTGCTCGCCG | TCCTGCGCCG | CGACGAGGGC | 16320 |
| GCCCCCTCCC | TCGACCGCGT | CGACGTCGTG | CAGCCCGCCC | TCTTTGCCGT | CATGGTCTCC | 16380 |
| CTGGCCGCCC | TCTGGCGCTC | GCTCGGCGTC | GAGCCCGCCG | CCGTCGTCGG | CCACAGCCAG | 16440 |
| GGCGAGATAG | CCGCCGCCTT | CGTCGCAGGC | GCTCTCTCCC | TCGAGGACGC | GGCCCGCATC | 16500 |
| GCCGCCCTGC | GCAGCAAAGC | GTCACCACCG | TCGCCGGCAA | CGGGCATGGC | CGCCGTCGAG | 16560 |
| CTCGGCGCCT | CCGACCTCCA | GACCTACCTC | GCTCCCTGGG | GCGACAGGCT | CTCCATCGCC | 16620 |
| GCCGTCAACA | GCCCCAGGGC | CACGCTCGTA | TCCGGCGAGC | CCGCCGCCGT | CGACGCGCTG | 16680 |
| ATCGACTCGC | TCACCGCAGC | GCAGGTCTTC | GCCCGAAGAG | TCCGCGTCGA | CTACGCCTCC | 16740 |
| CACTCAGCCC | AGATGGACGC | CGTCCAAGAC | GAGCTCGCCG | CAGGTCTAGC | CAACATCGCT | 16800 |
| CCTCGGACGT | GCGAGCTCCC | TCTTTATTCG | ACCGTCACCG | GCACCAGGCT | CGACGGCTCC | 16860 |
| GAGCTCGACG | GCGCGTACTG | GTATCGAAAC | CTCCGGCAAA | CCGTCCTGTT | CTCGAGCGCG | 16920 |
| ACCGAGCGGC | TCCTCGACGA | TGGGCATCGC | TTCTTCGTCG | AGGTCAGCCC | TCATCCCGTG | 16980 |
| CTCACGCTCG | CCCTCCGCGA | GACCTGCGAG | CGCTCACCGC | TCGATCCCGT | CGTCGTCGGC | 17040 |
| TCCATTCGAC | GCGACGAAGG | CCACCTCCCC | CGTCTCCTTG | CTCTCTTGGG | CCGAGCTCTA | 17100 |
| TGGCCGGGCC | TCACGCCCGA | GTGGAAGGCC | TTCTTCGCGC | CCTTCGCTCC | CCGCAAGGTC | 17160 |
| TCACTCCCCA | CCTACGCCTT | CCAGCGCGAG | CGTTTCTGGC | TCGACGCCCC | CAACGCACAC | 17220 |
| CCCGAAGGCG | TCGCTCCCGC | TGCGCCGATC | GATGGGCGGT | TTTGGCAAGC | CATCGAACGC | 17280 |
| GGGGACCTCG | ACGCGCTCAG | CGGCCAGCTC | CACGCGGACG | GCGACGAGCA | GCGCGCCGCC | 17340 |
| CTCGCCCTGC | TCCTTCCCAC | CCTCTCGAGC | TTTCACCACC | AGCGCCAAGA | GCAGAGCACG | 17400 |
| GTCGACACCT | GGCGCTACCG | CATCACGTGG | AGGCCTCTGA | CCACCGCCGC | CACGCCCGCC | 17460 |
| GACCTCGCCG | GCACCTGGCT | CCTCGTCGTG | CCGTCCGCGC | TCGGCGACGA | CGCGCTCCCT | 17520 |
| GCCACGCTCA | CCGATGCGCT | TACCCGGCGC | GGCGCGCGTG | TCCTCGCGCT | GCGCCTGAGC | 17580 |

-continued

```
CAGGTTCACA TAGGCCGCGC GGCTCTCACC GAGCACCTGC GCGAGGCTGT TGCCGAGACT    17640
GCCCCGATTC GCGGCGTGCT CTCCCTCCTC GCCCTCGACG AGCGCCCCT  CGCGGACCAT    17700
GCCGCCCTGC CCGCGGGCCT TGCCCTCTCG CTCGCCCTCG TCCAAGCCCT CGGCGACCTC    17760
GCCCTCGAGG CTCCCTTGTG GCTCTTCACG CGCGGCGCCG TCTCGATTGG ACACTCCGAC    17820
CCACTCGCCC ATCCCACCCA GGCCATGATC TGGGGCTTGG GCCGCGTCGT CGGCCTCGAG    17880
CACCCCGAGC GGTGGGGCGG GCTCGTCGAC CTCGGCGCAG CGCTCGACGC GAGCGCCGCA    17940
GGCCGCTTGC TCCCGGCCCT CGCCCAGCGC CACGACGAAG ACCAGCTCGC GCTGCGCCCG    18000
GCCGGCCTCT ACGCACGCCG CTTCGTCCGC GCCCCGCTCG GCGATGCGCC TGCCGCTCGC    18060
GGCTTCATGC CCCGAGGCAC CATCCTCATC ACCGGTGGTA CCGGCGCCAT TGGCGCTCAC    18120
GTCGCCCGAT GGCTCGCTCG AAAAGGCGCT GAGCACCTCG TCCTCATCAG CCGACGAGGG    18180
GCCCAGGCCG AAGGCGCCGT GGAGCTCCAC GCCGAGCTCA CCGCCCTCGG CGCGCGCGTC    18240
ACCTTCGCCG CGTGCGATGT CGCCGACAGG AGCGCTGTCG CCACGCTTCT CGAGCAGCTC    18300
GACGCCGGAG GGCCACAGGT GAGCGCCGTG TTCCACGCGG GCGGCATCGA GCCCCACGCT    18360
CCGCTCGCCG CCACCTCCAT GGAGGATCTC GCCGAGGTTG TCTCCGGCAA GGTACAAGGT    18420
GCAAGACACC TCCACGACCT GCTCGGCTCT CGACCCCTCG ACGCCTTTGT TCTCTTCTCG    18480
TCCGGCGCGG TCGTCTGGGG CGGCGGACAA CAAGGCGGCT ATGCCGCTGC GAACGCCTTC    18540
CTCGATGCCC TGGCCGAGCA GCGGCGCAGC CTTGGGCTGA CGGCGACATC GGTGGCCTGG    18600
GGCGTGTGGG GCGGCGGCGG CATGGCTACC GGGCTCCTGG CAGCCCAGCT AGAGCAACGC    18660
GGTCTGTCGC CGATGGCCCC CTCGCTGGCC GTGGCGACGC TCGCGCTGGC GCTGGAGCAC    18720
GACGAGACCA CCCTCACCGT CGCCGACATC GACTGGGCGC GCTTTGCGCC TTCGTTCAGC    18780
GCCGCTCGCT CCCGCCCGCT CCTGCGCGAT TTGCCCGAGG CGCAGCGCGC TCTCGAAGCC    18840
AGCGCCGATG CGTCCTCCGA GCAAGACGGG GCCACAGGCC TCCTCGACAA GCTCCGAAAC    18900
CGCTCGGAGA GCGAGCAGAT CCACCTGCTC TCCTCGCTGG TGCGCCACGA AGCGGCCCTC    18960
GTCCTGGGCC ATACCGACGC CTCCCAGGTC GACCCCCACA AGGGCTTCAT GGACCTCGGC    19020
CTCGATTCGC TCATGACCGT CGAGCTTCGT CGGCGCTTGC AGCAGGCCAC CGGCATCAAG    19080
CTCCCGGCCA CCCTCGCCTT CGACCATCCC TCTCCTCATC GCGTCGCGCT CTTCTTGCGC    19140
GACTCGCTCG CCCACGCCCT CGGCGCGAGG CTCTCCGTCG AGCGCGACGC CGCCGCGCTC    19200
CCGGCGCTTC GCTCGGCGAG CGACGAGCCC ATCGCCATCG TCGGCATGGC CCTCCGCTTG    19260
CCGGGCGGCA TCGGCGATGT CGACGCTCTT TGGGAGTTCC TCGCCCAAGG ACGCGACGCC    19320
GTCGAGCCCA TTCCCCATGC CCGATGGGAT GCCGGTGCCC TCTACGACCC CGACCCCGAC    19380
GCCAAGGCCA AGAGCTACGT CCGGCATGCC GCCATGCTCG ACCAGGTCGA CCTCTTCGAT    19440
CCTGCCTTCT TTGGCATCAG CCCTCGCGAG GCCAAATACC TCGACCCCCA GCACCGCCTG    19500
CTCCTCGAAT CTGCCTGGCT GGCCCTCGAG GACGCCGGCA TCGTCCCCTC CACCCTCAAG    19560
GATTCTCCCA CCGGCGTCTT CGTCGGCATC GGCGCCAGCG AATACGCACT GCGAAACACG    19620
AGCTCCGAAG AGGTCGAAGC GTATGCCCTC CAAGGCACCG CCGGGTCCTT TGCCGCGGGG    19680
CGCTTGGCCT ACACGCTCGG CCTGCAAGGG CCCGCGCTCT CGGTCGACAC CGCCTGCTCC    19740
TCCTCGCTCG TCGCCCTCCA CCTCGCCTGC CAAGCCCTCC GACAGGGCGA GTGCAACCTC    19800
GCCCTCGCCG CGGGCGTCTC CGTCATGGCC TCCCCGGGC  TCTTCGTCGT CCTTTCCCGC    19860
ATGCGTGCTT TGGCGCCCGA TGGCCGCTCC AAGACCTTCT CGACCAACGC CGACGGCTAC    19920
GGACGCGGAG AGGGCGTCGT CGTCCTTGCC CTCGAGCGGC TCGGCGACGC CCTCGCCCGA    19980
```

```
GGACACCGCG TCCTCGCCCT CGTCCGCGGC ACCGCCATGA ACCATGACGG CGCGTCGAGC    20040
GGCATCACCG CCCCCAATGG CACCTCCCAC CAGAAGGTCC TCCGCGCCGC GCTCCACGAC    20100
GCCCATATCG GCCCTGCCGA CGTCGACGTC GTCGAATGCC ATGGCACCGG CACCTCCTTG    20160
GGAGACCCCA TCGAGGTGCA AGCCCTGGCC GCCGTCTACG CCGATGGCAG ACCCGCTGAA    20220
AAGCCTCTCC TTCTCGGCGC ACTCAAGACC AACATTGGCC ATCTCGAGGC CGCCTCCGGC    20280
CTCGCGGGCG TCGCCAAGAT CGTCGCCTCC CTCCGCCATG ACGCCCTGCC CCCCACCCTC    20340
CACACGACCC CGCGCAATCC CCTGATCGAG TGGGATGCGC TCGCCATCGA CGTCGTCGAT    20400
GCCACGAGGG CGTGGGCCCG CCACGAAGAT GGCAGTCCCC GCCGCGCCGG CGTCTCCGCC    20460
TTCGGACTCT CCGGCACCAA CGCCCACGTT ATCCTCGAAG AGGCTCCCGC GATCCCGCAG    20520
GCCGAGCCCA CCGCGGCACA GCTCGCGTCG CAGCCGCTTC CCGCAGCCTG GCCCGTGCTC    20580
CTGTCGGCCA GGAGCGAGCC GGCCGTGCGC GCCCAGGCCC AGAGGCTCCG CGACCACCTC    20640
CTCGCCCACG ACGACCTCGC CCTGGCCGAT GTAGCCTACT CGCTCGCCAC CACCCGGGCT    20700
ACCTTCGAGC ACCGTGCCGC TCTCGTGGTC CACGACCGCG AAGAGCTCCT CTCCGCGCTC    20760
GATTCGCTCG CCCAGGGAAG GCCCGCCCCG AGCACCGTCG TCGAACGAAG CGGAAGCCAC    20820
GGCAAGGTCG TCTTCGTCTT TCCTGGGCAA GGCTCGCAGT GGGAAGGGAT GGCCCTCTCC    20880
CTGCTCGATA CCTCGCCGGT CTTCCGGGCA CAGCTCGAAG CGTGCGAGCG CGCCCTCGCG    20940
CCCCACGTGG ACTGGTCGCT GCTCGCGGTG CTCCGCGGCG AGGAGGGCGC GCCCCCGCTC    21000
GACCGGGTCG ACGTGGTCCA GCCCGCGCTG TTCTCGATGA TGGTCTCGCT GGCCGCCCTG    21060
TGGCGCTCCA TGGGCGTCGA GCCCGACGCG GTGGTCGGCC ATAGCCAGGG CGAGATCGCC    21120
GCGGCCTGTG TGGCGGGCGC GCTGTCGCTC GAGGACGCTG CCAAGCTGGT GGCGCTGCGC    21180
AGCCGTGCGC TCGTGGAGCT CGCCGGCCAG GGGGCCATGG CCGCGGTGGA GCTGCCGGAG    21240
GCCGAGGTCG CACGGCGCCT CCAGCGCTAT GGCGATCGGC TCTCCATCGG GGCGATCAAC    21300
AGCCCTCGTT TCACGACGAT CTCCGGCGAG CCCCCTGCCG TCGCCGCCCT GCTCCGCGAT    21360
CTGGAGTCCG AGGGCGTCTT CGCCCTCAAG CTGAGTTACG ACTTCGCCTC CCACTCCGCG    21420
CAGGTCGAGT CGATTCGCGA CGAGCTCCTC GATCTCCTGT CGTGGCTCGA GCCGCGCTCG    21480
ACGGCGGTCC CGTTCTACTC CACGGTGAGC GGCGCCGCGA TCGACGGGAG CGAGCTCGAC    21540
GCCGCCTACT GGTACCGGAA CCTCCGGCAG CCGGTCCGCT CGCAGACGCG TGTGCAAGGC    21600
CTCCTTGCCG GAGAACATCG CTTCTTCGTG GAGGTGAGCC CCAGTCCTGT GCTGACCTTG    21660
GCCTTGCACG AGCTCCTCGA AGCGTCGGAG CGCTCGGCGG CGGTGGTCGG CTCTCTGTGG    21720
AGCGACGAAG GGGATCTACG GCGCTTCCTC GTCTCGCTCT CCGAGCTCTA CGTCAACGGC    21780
TTCGCCCTGG ATTGGACGAC GATCCTGCCC CCGGGAAGC GGGTGCCGCT GCCCACCTAC    21840
CCCTTCCAGC GCGAGCGCTT CTGGCTCGAC GCCTCCACGG CACCCGCCGC CGGCGTCAAC    21900
CACCTTGCTC CGCTCGAGGG GCGGTTCTGG CAGGCCATCG AGAGCGGGAA TATCGACGCG    21960
CTCAGCGGCC AGCTCCACGT GGACGGCGAC GAGCAGCGCG CCGCCCTTGC CCTGCTCCTT    22020
CCCACCCTCG CGAGCTTTCG CCACGAGCGG CAAGAGCAGG GCACGGTCGA CGCCTGGCGC    22080
TACCGCATCA CGTGGAAGCC TCTGACCACC GCCACCACGC CGCCGACCT GGCCGGCACC    22140
TGGCTCCTCG TCGTGCCGGC CGCTCTGGAC GACGACGCGC TCCCCTCCGC GCTCACCGAG    22200
GCGCTCGCCC GGCGCGGCGC GCGCGTCCTC GCCGTGCGCC TGAGCCAGGC CACCTGGAC    22260
CGCGAGGCTC TCGCCGAGCA CCTGCGCCAG GCTTGCGCCG AGACCGCGCC GCCTCGCGGC    22320
GTGCTCTCGC TCCTCGCCCT CGACGAAAGT CCCCTCGCCG ACCATGCCGC CGTGCCCGCG    22380
```

```
GGACTCGCCT TCTCGCTCAC CCTCGTCCAA GCCCTCGGCG ACATCGCCCT CGACGCGCCC    22440
TTGTGGCTCT TCACCCGCGG CGCCGTCTCC GTCGGACACT CCGACCCCAT CGCCCATCCG    22500
ACGCAGGCGA TGACCTGGGG CCTGGGCCGC GTCGTCGGCC TCGAGCACCC CGAGCGCTGG    22560
GGAGGGCTCG TCGACGTCGG CGCAGCGATC GACGCGAGCG CCGTGGGCCG CTTGCTCCCG    22620
GTCCTCGCCC TGCGCAACGA TGAGGACCAG CTCGCTCTCC GCCCGGCCGG GTTCTACGCT    22680
CGCCGCCTCG TCCGCGCTCC GCTCGGCGAC GCGCCGCCCG CACGTACCTT CAAGCCCCGA    22740
GGCACCCTCC TCATCACCGG AGGCACCGGC GCCGCTGGCG CTCACGTCGC CCGATGGCTC    22800
GCTCGAGAAG CGCAGAGCA CCTCGTCCTC ATCAGCCGCC GAGGGCCCA GGCCGAGGGC      22860
GCCTCGGAGC TCCACGCCGA GCTCACGGCC CTGGGCGCGC GCGTCACCTT CGCCGCGTGT    22920
GATGTCGCCG ACAGGAGCGC TGTCGCCACG CTTCTCGAGC AGCTCGACGC CGAAGGGTCG    22980
CAGGTCCGCG CCGTGTTCCA CGCGGGCGGC ATCGGGCGCC ACGCTCCGCT CGCCGCCACC    23040
TCTCTCATGG AGCTCGCCGA CGTTGTCTCT GCCAAGGTCC TAGGCGCAGG GAACCTCCAC    23100
GACCTGCTCG GTCCTCGACC CCTCGACGCC TTCGTCCTTT TCTCGTCCAT CGCAGGCGTC    23160
TGGGGCGGCG GACAACAAGC CGGATACGCC GCCGGAAACG CCTTCCTCGA CGCCCTGGCC    23220
GACCAGCGGC GCAGTCTTGG ACAGCCGGAC ACGTCCGTGG TGTGGGGCGC GTGGGGCGGC    23280
GGCGGTGGTA TATTCACGGG GCCCCTGGCA GCCCAGCTGG AGCAACGTCG TCTGTCGCCG    23340
ATGGCCCCTT CGCTGGCCGT GGCGGCGCTC GCGCAAGCCC TGGAGCACGA CGAGACCACC    23400
GTCACCGTCG CCGACATCGA CTGGGCGCGC TTTGCGCCTT CGATCAGCGT CGCTCGCTCC    23460
CGCCGCTCCT GCGCGACTTG CCCGAGCAGC GCGCCCTCGA AGACAGAGAA GGCGCGTCCT    23520
CCTCCGAGCA CGGCCCGGCC CCCCGACCTC CTCGACAAGC TCCGGAGCCG CTCGGAGAGC    23580
GAGCAGCTCC GTCTGCTCGC CGCGCTGGTG TGCGACGAGA CGGCCCTCGT CCTCGGCCAC    23640
GAAGGCCGCT TCCCAGCTCG ACCCCGACAA GGCTTCTTCG ACCTCGGTCT CGATTCGATC    23700
ATGACCGTCG AGCTTCGTCG GCGCTTGCAA CAGGCCACCG GCATCAAGCT CCCGGCCACC    23760
CTCGCCTTCG ACCATCCCTC TCCTCATCGC GTCGCGCTCT TCATGCGCGA CTCGCTCGCC    23820
CACGCCCTCG GCACGAGGCT CTCCGCCGAG GCGACGCCGC CGCGCTCCGG CCGCGCCTCG    23880
AGCGACGAGC CCATCGCCAT CGTCGGCATG GCCCTGCGCC TGCCGGGCGG CGTCGGCGAT    23940
GTCGACGCTC TTTGGGAGTT CCTCCACCAA GGGCGCGACG CGGTCGAGCC CATTCCACAG    24000
AGCCGCTGGG ACGCCGGTGC CCTCTACGAC CCCGACCCCG ACGCCGACGC CAAGAGCTAC    24060
GTCCGGCATG CCGCGATGCT CGACCAGATC GACCTCTTCG ACCCTGCCTT CTTCGGCATC    24120
AGCCCCCGGG AGGCCAAACA CCTCGACCCC CAGCACCGCC TGCTCCTCGA ATCTGCCTGG    24180
CTGGCCCTCG AGGACGCCGG CATCGTCCCC ACCTCCCTCA GGACTCCCT CACCGGCGTC     24240
TTCGTCGGCA TCTGCGCCGG CGAATACGCG ATGCAAGAGG CGAGCTCGGA AGGTTCCGAG    24300
GTTTACTTCA TCCAAGGCAC TTCCGCGTCC TTTGGCGCGG GGGCTTGGC CTATACGCTC     24360
GGGCTCCAGG GGCCGCGATC TTCGGTCGAC ACCGCCTGCT CCTCCTCGCT CGTCTCCCTC    24420
CACCTCGCCT GCCAAGCCCT CCGACAGGGC GAGTGCAACC TCGCCCTCGC CGCGGGCGTG    24480
TCGCTCATGG TCTCCCCCCA GACCTTCGTC ATCCTTTCCC GTCTGCGCGC CTTGGCGCCC    24540
GACGGCCGCT CCAAGACCTT CTCGGACAAC GCCGACGGCT ACGGACGCGG AGAAGGCGTC    24600
GTCGTCCTTG CCCTCGAGCG GATCGGCGAC GCCCTCGCCC GGAGACACCG CGTCCTCGTC    24660
CTCGTCCGCG GCACCGCCAT CAACCACGAC GGCGCGTCGA GCGGTATCAC CGCCCCCAAC    24720
GGCACCTCCC AGCAGAAGGT CCTCCGGGCC GCGCTCCACG ACGCCCGCAT CACCCCCGCC    24780
```

```
GACGTCGACG TCGTCGAGTG CCATGGCACC GGCACCTCGC TGGGAGACCC CATCGAGGTG   24840
CAAGCCCTGG CCGCCGTCTA CGCCGACGGC AGACCCGCTG AAAAGCCTCT CCTTCTCGGC   24900
GCGCTCAAGA CCAACATCGG CCATCTCGAG GCCGCCTCCG GCCTCGCGGG CGTCGCCAAG   24960
ATGGTCGCCT CGCTCCGCCA CGACGCCCTG CCCCCCACCC TCCACGCGAC CCCACGCAAT   25020
CCCCTCATCG AGTGGGAGGC GCTCGCCATC GACGTCGTCG ATACCCCGAG GCCTTGGCCC   25080
CGCCACGAAG ATGGCAGTCC CCGCCGCGCC GGCATCTCCG CCTTCGGATT CTCGGGCACC   25140
AACGCCCACG TCATCCTCGA AGAGGCTCCC GCCGCCCTGC CGGCCGAGCC CGCCACCTCA   25200
CAGCCGGCGT CGCAAGCCGC TCCCGCGGCG TGGCCCGTGC TCCTGTCGGC CAGGAGCGAG   25260
GCCGCCGTCC GCGCCCAGGC GAAGCGGCTC CGCGACCACC TCGTCGCCCA CGACGACCTC   25320
ACCCTCGCGG ATGTGGCCTA TTCGCTGGCC ACCACCCGCG CCCACTTCGA GCACCGCGCC   25380
GCTCTCGTAG CCCACAACCG CGACGAGCTC CTCTCCGCGC TCGACTCGCT CGCCCAGGAC   25440
AAGCCCGCCC CGAGCACCGT CCTCGGACGG AGCGGAAGCC ACGGCAAGCT CGTCTTCGTC   25500
TTTCCTGGGC AAGGCTCGCA GTGGGAAGGG ATGGCCCTCT CGCTGCTCGA CTCCTCGCCC   25560
GTCTTCCGCG CTCAGCTCGA AGCATGCGAG CGCGCGCTCG CTCCTCACGT CGAGTGGAGC   25620
CTGCTCGCCG TCCTGCGCCG CGACGAGGGC GCCCCCTCCC TCGACCGCGT CGACGTCGTA   25680
CAGCCCGCCC TCTTTGCCGT CATGGTCTCC CTGGCGGCCC TCTGGCGCTC GCTCGGCGTA   25740
GAGCCCGCCG CCGTCGTCGG CCACAGTCAG GGCGAGATCG CCGCCGCCTT CGTCGCAGGC   25800
GCTCTCTCCC TCGAGGACGC GGCCCGCATC GCCGCCCTGC GCAGCAAAGC GCTCACCACC   25860
GTCGCCGGCA ACGGGGCCAT GGCCGCCGTC GAGCTCGGCG CCTCCGACCT CCAGACCTAC   25920
CTCGCTCCCT GGGGCGACAG GCTCTCCATC GCCGCCGTCA ACAGCCCAG GGCCACGCTC   25980
GTGTCCGGCG AGCCCGCCGC CATCGACGCG CTGATCGACT CGCTCACCGC AGCGCAGGTC   26040
TTCGCCCGAA AAGTCCGCGT CGACTACGCC TCCCACTCCG CCCAGATGGA CGCCGTCCAA   26100
GACGAGCTCG CCGCAGGTCT AGCCAACATC GCTCCTCGGA CGTGCGAGCT CCCTCTTTAT   26160
TCGACCGTCA CCGGCACCAG GCTCGACGGC TCCGAGCTCG ACGGCGCGTA CTGGTATCGA   26220
AACCTCCGGC AAACCGTCCT GTTCTCGAGC GCGACCGAGC GGCTCCTCGA CGATGGGCAT   26280
CGCTTCTTCG TCGAGGTCAG CCCCCATCCC GTGCTCACGC TCGCCCTCCG CGAGACCTGC   26340
GAGCGCTCAC CGCTCGATCC CGTCGTCGTC GGCTCCATTC GACGCGACGA AGGCCACCTC   26400
GCCCGCCTGC TCCTCTCCTG GGCGGAGCTC TCTACCCGAG GCCTCGCGCT CGACTGGAAC   26460
GCCTTCTTCG CGCCCTTCGC TCCCCGCAAG GTCTCCCTCC CCACCTACCC CTTCCAACGC   26520
GAGCGCTTCT GGCTCGACGC CTCCACGGCG CACGCTGCCG ACGTCGCCTC CGCAGGCCTG   26580
ACCTCGGCCG ACCACCCGCT GCTCGGCGCC GCCGTCGCCC TCGCCGACCG CGATGGCTTT   26640
GTCTTCACAG GACGGCTCTC CCTCGCAGAG CACCCGTGGC TCGAAGACCA CGTCGTCTTC   26700
GGCATACCCT GTCCTGCCAG GCGCCGCCTC CTCGAGCTCG CCCTGCATGT CGCCCATCTC   26760
GTCGGCCTCG ACACCGTCGA AGACGTCACG CTCGACCCCC CCTCGCTCT CCCATCGCAG   26820
GGCGCCGTCC TCCTCCAGAT CTCCGTCGGG CCCGCGGACG GTGCTGGACG AAGGGCGCTC   26880
TCCGTTCATA GCCGGCGCCA CGACGCGCTT CAGGATGGCC CCTGGACTCG CCACGCCAGC   26940
GGCTCTCTCG CGCAAGCTAG CCCGTCCCAT TGCCTTCGAT GCTCCGCGAA TGGCCCCCCC   27000
TCGGGCGCCA CCCAGGTGGA CACCCAAGGT TTCTACGCAG CCCTCGAGAG CGCTGGGCTT   27060
GCTTATGGCC CCGAGTTCCA GGGCCTCCGC CGCCGTCTAC AAGCGCGGCG ACGAGCTCTT   27120
CGCCGAAGCC AAGCTCCCGG ACGCCGCCGA AGAGGACGCC GCTCGTTTTG CCCTCCACCC   27180
```

-continued

| | | | | | |
|---|---|---|---|---|---|
| CGCCCTGCTC | GACAGCGCCT | TGCAGGCGCT | CGCCTTTGTA | GACGACCAGG | CAAAGGCCTT | 27240 |
| CAGGATGCCC | TTCTCGTGGA | GCGGAGTATC | GCTGCGCTCC | GGTCGGAGCC | ACCACCCTGC | 27300 |
| GCGTGCGTTT | CCACCGTCCT | GAGGGCGAAT | CCTCGCGCTC | GCTCCTCCTC | GCCGACGCCA | 27360 |
| GAGGCGAACC | CATCGCCTCG | GTGCAAGCGC | TCGCCATGCG | CGCCGCGTCC | GCCGAGCAGC | 27420 |
| TCCGCAGACC | CGGGAGCGTC | CCACCTCGAT | GCCCTCTTCC | GCATCGACTG | GAGCGAGCTG | 27480 |
| CAAAGCCCCA | CCTCACCGCC | CATCGCCCCG | AGCGGTGCCC | TCCTCGGCAC | AGAAGGTCTC | 27540 |
| GACCTCGGGA | CCAGGGTGCC | TCTCGACCGC | TATACCGACC | TTGCTGCTCT | ACGCAGCGCC | 27600 |
| CTCGACCAGG | GCGCTTCGCC | TCCAAGCCTC | GTCATCGCCC | CCTTCATCGC | TCTGCCCGAA | 27660 |
| GGCGACCTCA | TCGCGAGCGC | CCGCGAGACC | ACCGCGCACG | CGCTCGCCCT | CTTGCAAGCC | 27720 |
| TGGCTCGCCG | ACGAGCGCCT | CGCCTCCTCG | CGCCTCGCCC | TCGTCACCCG | ACGCGCCGTC | 27780 |
| GCCACCCACG | CTGAAGAAGA | CGTCAAGGGC | CTCGCTCACG | CGCCTCTCTG | GGGTCTCGCT | 27840 |
| CGCTCCGCGC | AGAGCGAGCA | CCCAGAGCGC | CCTCTCGTCC | TCGTCGACCT | CGACGACAGC | 27900 |
| GAGGCCTCCC | AGCACGCCCT | GCTCGGCGCG | CTCGACGCAA | GAGAGCCAGA | GATCGCCCTC | 27960 |
| CGCAACGGCA | AACCCCTCGT | TCCAAGGCTC | TCACGCCTGC | CCCAGGCGCC | CACGGACACA | 28020 |
| GCGTCCCCCG | CAGGCCTCGG | AGGCACCGTC | CTCATCACGG | GAGGCACCGG | CACGCTCGGC | 28080 |
| GCCCTGGTCG | CGCGCCGCCT | CGTCGTAAAC | CACGACGCCA | AGCACCTGCT | CCTCACCTCG | 28140 |
| CGCCAGGGCG | CGAGCGCTCC | GGGTGCTGAT | GTCTTGCGAA | GCGAGCTCGA | AGCTCTGGGG | 28200 |
| GCTTCGGTCA | CCCTCGCCGC | GTGCGACGTG | GCCGATCCAC | GCGCTCTAAA | GGACCTTCTG | 28260 |
| GATAACATTC | CGAGCGCTCA | CCCGGTCGCC | GCCGTCGTGC | ATGCCGCCAG | CGTCCTCGAC | 28320 |
| GGCGATCTGC | TCGGCGCCAT | GAGCCTCGAG | CGGATCGACC | GCGTCTTCGC | CCCCAAGATC | 28380 |
| GATGCCGCCT | GGCACTTGCA | TCAGCTCACC | CAAGATAAGC | CCCTTGCCGC | CTTCATCCTC | 28440 |
| TTCTCGTCCG | TCGCCGGCGT | CCTCGGCAGC | TCAGGTCACT | CCAACTACGC | CGCTGCGAGC | 28500 |
| GCCTTCCTCG | ATGCGCTTGC | GCACCACCGG | CGCGCGCAAG | GGCTCCCTGC | CTCATCGCTC | 28560 |
| GCGTGGAGCC | ACTGGGCCGA | GCGCAGCGCA | ATGACAGAGC | ACGTCAGCGC | CGCCGGCGCC | 28620 |
| CCTCGCATGG | AGCGCGCCGG | CCTTCCCTCG | ACCTCTGAGG | AGAGGCTCGC | CCTCTTCGAT | 28680 |
| GCGGCGCTCT | TCCGAACCGA | GACCGCCCTG | GTCCCCGCGC | GCTTCGACTT | GAGCGCGCTC | 28740 |
| AGGGCGAACG | CCGGCAGCGT | CCCCCCGTTG | TTCCAACGTC | TCGTCCGCGC | TCGCACCGTA | 28800 |
| CGCAAGGCCG | CCAGCAACAC | CGCCCAGGCC | TCGTCGCTTA | CAGAGCGCCT | CTCAGCCCTC | 28860 |
| CCGCCCGCCG | AACGCGAGCG | TGCCCTGCTC | GATCTCATCC | GCACCGAAGC | CGCCGCCGTC | 28920 |
| CTCGGCCTCG | CCTCCTTCGA | ATCGCTCGAT | CCCGATCG | | | 28958 |

( 2 ) INFORMATION FOR SEQ ID NO:7:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( i x ) FEATURE:
        ( A ) NAME/KEY: misc_feature
        ( B ) LOCATION: 1..13
        ( D ) OTHER INFORMATION: /note= "sequence of a plant
            consensus translation initiator (Clontech)"

(x i) SEQUENCE DESCRIPTION: SEQ ID NO:7:

GTCGACCATG GTC                                                                                      13

(2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: other nucleic acid (i i i) HYPOTHETICAL: NO (i v) ANTI-SENSE: NO (i x) FEATURE:
        (A) NAME/KEY: misc_feature
        (B) LOCATION: 1..12
        (D) OTHER INFORMATION: /note= "sequence of a plant
            consensus translation initiator (Joshi)"

(x i) SEQUENCE DESCRIPTION: SEQ ID NO:8:

TAAACAATGG CT                                                                                       12

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: other nucleic acid (i i i) HYPOTHETICAL: NO (i v) ANTI-SENSE: NO (i x) FEATURE:
        (A) NAME/KEY: misc_feature
        (B) LOCATION: 1..22
        (D) OTHER INFORMATION: /note= "sequence of an
            oligonucleotide for use in a molecular adaptor"

(x i) SEQUENCE DESCRIPTION: SEQ ID NO:9:

AATTCTAAAG CATGCCGATC GG                                                                            22

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid (i i i) HYPOTHETICAL: NO (i v) ANTI-SENSE: NO (i x) FEATURE:
        (A) NAME/KEY: misc_feature
        (B) LOCATION: 1..21
        (D) OTHER INFORMATION: /note= "sequence of an
            oligonucleotide for use in a molecular adaptor"

(x i) SEQUENCE DESCRIPTION: SEQ ID NO:10:

AATTCCGATC GGCATGCTTT A                                                                             21

( 2 ) INFORMATION FOR SEQ ID NO:11:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( i x ) FEATURE:
        ( A ) NAME/KEY: misc_feature
        ( B ) LOCATION: 1..22
        ( D ) OTHER INFORMATION: /note= "sequence of an
            oligonucleotide for use in a molecular adaptor"

( x i ) SEQUENCE DESCRIPTION: SEQ ID NO:11:

AATTCTAAAC CATGGCGATC GG                       22

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( i x ) FEATURE:
        ( A ) NAME/KEY: misc_feature
        ( B ) LOCATION: 1..21
        ( D ) OTHER INFORMATION: /note= "sequence of an
            oligonucleotide for use in a molecular adaptor"

( x i ) SEQUENCE DESCRIPTION: SEQ ID NO:12:

AATTCCGATC GCCATGGTTT A                       21

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( i x ) FEATURE:
        ( A ) NAME/KEY: misc_feature
        ( B ) LOCATION: 1..15
        ( D ) OTHER INFORMATION: /note= "sequence of an
            oligonucleotide for use in a molecular adaptor"

( x i ) SEQUENCE DESCRIPTION: SEQ ID NO:13:

CCAGCTGGAA TTCCG                               15

( 2 ) INFORMATION FOR SEQ ID NO:14:

( i ) SEQUENCE CHARACTERISTICS:
        ( A ) LENGTH: 19 base pairs (B) TYPE: nucleic acid
(C) STRANDEDNESS: single
(D) TOPOLOGY: linear (ii) MOLECULE TYPE: other nucleic acid (iii) HYPOTHETICAL: NO (iv) ANTI-SENSE: NO (ix) FEATURE:
(A) NAME/KEY: misc_feature
(B) LOCATION: 1..19
(D) OTHER INFORMATION: /note= "sequence of an oligonucleotide for use in a molecular adaptor"

(xi) SEQUENCE DESCRIPTION: SEQ ID NO:14:

CGGAATTCCA GCTGGCATG 19

(2) INFORMATION FOR SEQ ID NO:15:

(i) SEQUENCE CHARACTERISTICS:
(A) LENGTH: 11 base pairs
(B) TYPE: nucleic acid
(C) STRANDEDNESS: single
(D) TOPOLOGY: linear (ii) MOLECULE TYPE: other nucleic acid (iii) HYPOTHETICAL: NO (iv) ANTI-SENSE: NO (ix) FEATURE:
(A) NAME/KEY: misc_feature
(B) LOCATION: 1..11
(D) OTHER INFORMATION: /note= "oligonucleotide used to introduce base change into SphI site of ORF1 of pyrrolnitrin gene cluster"

(xi) SEQUENCE DESCRIPTION: SEQ ID NO:15:

CCCCCTCATG C 11

(2) INFORMATION FOR SEQ ID NO:16:

(i) SEQUENCE CHARACTERISTICS:
(A) LENGTH: 11 base pairs
(B) TYPE: nucleic acid
(C) STRANDEDNESS: single
(D) TOPOLOGY: linear (ii) MOLECULE TYPE: other nucleic acid (iii) HYPOTHETICAL: NO (iv) ANTI-SENSE: NO (ix) FEATURE:
(A) NAME/KEY: misc_feature
(B) LOCATION: 1..11
(D) OTHER INFORMATION: /note= "oligonucleotide used to introduce base change into SphI site of ORF1 of pyrrolnitrin gene cluster"

(xi) SEQUENCE DESCRIPTION: SEQ ID NO:16:

GCATGAGGGG G 11

(2) INFORMATION FOR SEQ ID NO:17:

(i) SEQUENCE CHARACTERISTICS:
(A) LENGTH: 4603 base pairs
(B) TYPE: nucleic acid
(C) STRANDEDNESS: single
(D) TOPOLOGY: linear ( i i ) MOLECULE TYPE: DNA (genomic)

( i x ) FEATURE:
    ( A ) NAME/KEY: CDS
    ( B ) LOCATION: 230..1594
    ( D ) OTHER INFORMATION: /gene= "phz1"
        / label= ORF1
        / note= "Open Reading Frame #1 for DNA sequence"

( i x ) FEATURE:
    ( A ) NAME/KEY: CDS
    ( B ) LOCATION: 1598..2758
    ( D ) OTHER INFORMATION: /gene= "phz2"
        / label= ORF2
        / note= "Open Reading Frame #2 for DNA sequence"

( i x ) FEATURE:
    ( A ) NAME/KEY: CDS
    ( B ) LOCATION: 2764..3597
    ( D ) OTHER INFORMATION: /gene= "phz3"
        / label= ORF3
        / note= "Open Reading Frame #3 for DNA sequence"

( i x ) FEATURE:
    ( A ) NAME/KEY: misc_feature
    ( B ) LOCATION: 3597..4262
    ( D ) OTHER INFORMATION: /label=ORF4
        / note= "Open Reading Frame #4 of DNA sequence. This information is repeated in SEQ ID NO:21 due to overlapping ORFs."

( i x ) FEATURE:
    ( A ) NAME/KEY: misc_feature
    ( B ) LOCATION: 1..4603
    ( D ) OTHER INFORMATION: /note= "Four open reading frames ( O R F s ) were identified within this DNA sequence as described in Example 18 of the specification."

( x i ) SEQUENCE DESCRIPTION: SEQ ID NO:17:

```
GCATGCCGTG ACCTCCGCCG GTGGCGTGGC CGCCGGCCTG CACCTGGAAA CCACCCCTGA    60

CGACGTCAGC GAGTGCGCTT CCGATGCCGC CGGCCTGCAT CAGGTCGCCA GCCGCTACAA   120

AAGCCTGTGC GACCCGCGCC TGAACCCCTG GCAAGCCATT ACTGCGGTGA TGGCCTGGAA   180

AAACCAGCCC TCTTCAACCC TTGCCTCCTT TTGACTGGAG TTTGTCGTC ATG ACC       235
                                                    Met Thr
                                                     1

GGC ATT CCA TCG ATC GTC CCT TAC GCC TTG CCT ACC AAC CGC GAC CTG     283
Gly Ile Pro Ser Ile Val Pro Tyr Ala Leu Pro Thr Asn Arg Asp Leu
         5              10                  15

CCC GTC AAC CTC GCG CAA TGG AGC ATC GAC CCC GAG CGT GCC GTG CTG     331
Pro Val Asn Leu Ala Gln Trp Ser Ile Asp Pro Glu Arg Ala Val Leu
        20                  25                  30

CTG GTG CAT GAC ATG CAG CGC TAC TTC CTG CGG CCC TTG CCC GAC GCC     379
Leu Val His Asp Met Gln Arg Tyr Phe Leu Arg Pro Leu Pro Asp Ala
 35.                 40                  45                  50

CTG CGT GAC GAA GTC GTG AGC AAT GCC GCG CGC ATT CGC CAG TGG GCT     427
Leu Arg Asp Glu Val Val Ser Asn Ala Ala Arg Ile Arg Gln Trp Ala
                 55                  60                  65

GCC GAC AAC GGC GTT CCG GTG GCC TAC ACC GCC CAG CCC GGC AGC ATG     475
Ala Asp Asn Gly Val Pro Val Ala Tyr Thr Ala Gln Pro Gly Ser Met
             70                  75                  80

AGC GAG GAG CAA CGC GGG CTG CTC AAG GAC TTC TGG GGC CCG GGC ATG     523
Ser Glu Glu Gln Arg Gly Leu Leu Lys Asp Phe Trp Gly Pro Gly Met
         85                  90                  95

AAG GCC AGC CCC GCC GAC CGC GAG GTG GTC GGC GCC CTG ACG CCC AAG     571
Lys Ala Ser Pro Ala Asp Arg Glu Val Val Gly Ala Leu Thr Pro Lys
    100                 105                 110

CCC GGC GAC TGG CTG CTG ACC AAG TGG CGC TAC AGC GCG TTC TTC AAC     619
```

| | | | | | | | | | | | | | | | | |
|---|---|---|---|---|---|---|---|---|---|---|---|---|---|---|---|---|
| Pro | Gly | Asp | Trp | Leu | Leu | Thr | Lys | Trp | Arg | Tyr | Ser | Ala | Phe | Phe | Asn | |
| 115 | | | | 120 | | | | | 125 | | | | | | 130 | |

| TCC | GAC | CTG | CTG | GAA | CGC | ATG | CGC | GCC | AAC | GGG | CGC | GAT | CAG | TTG | ATC | 667 |
|---|---|---|---|---|---|---|---|---|---|---|---|---|---|---|---|---|
| Ser | Asp | Leu | Leu | Glu | Arg | Met | Arg | Ala | Asn | Gly | Arg | Asp | Gln | Leu | Ile | |
| | | | | 135 | | | | | 140 | | | | | 145 | | |

| CTG | TGC | GGG | GTG | TAC | GCC | CAT | GTC | GGG | GTA | CTG | ATT | TCC | ACC | GTG | GAT | 715 |
|---|---|---|---|---|---|---|---|---|---|---|---|---|---|---|---|---|
| Leu | Cys | Gly | Val | Tyr | Ala | His | Val | Gly | Val | Leu | Ile | Ser | Thr | Val | Asp | |
| | | | 150 | | | | | 155 | | | | | 160 | | | |

| GCC | TAC | TCC | AAC | GAT | ATC | CAG | CCG | TTC | CTC | GTT | GCC | GAC | GCG | ATC | GCC | 763 |
|---|---|---|---|---|---|---|---|---|---|---|---|---|---|---|---|---|
| Ala | Tyr | Ser | Asn | Asp | Ile | Gln | Pro | Phe | Leu | Val | Ala | Asp | Ala | Ile | Ala | |
| | | 165 | | | | | 170 | | | | | 175 | | | | |

| GAC | TTC | AGC | AAA | GAG | CAC | CAC | TGG | ATG | CCA | TCG | AAT | ACG | CCG | CCA | GCC | 811 |
|---|---|---|---|---|---|---|---|---|---|---|---|---|---|---|---|---|
| Asp | Phe | Ser | Lys | Glu | His | His | Trp | Met | Pro | Ser | Asn | Thr | Pro | Pro | Ala | |
| | | 180 | | | | 185 | | | | | 190 | | | | | |

| GTT | GCG | CCA | TGT | CAT | CAC | CAC | CGA | CGA | GGT | GGT | GCT | ATG | AGC | CAG | ACC | 859 |
|---|---|---|---|---|---|---|---|---|---|---|---|---|---|---|---|---|
| Val | Ala | Pro | Cys | His | His | His | Arg | Arg | Gly | Gly | Ala | Met | Ser | Gln | Thr | |
| 195 | | | | | 200 | | | | | 205 | | | | | 210 | |

| GCA | GCC | CAC | CTC | ATG | GAA | CGC | ATC | CTC | CAA | CCG | GCT | CCC | GAG | CCG | TTT | 907 |
|---|---|---|---|---|---|---|---|---|---|---|---|---|---|---|---|---|
| Ala | Ala | His | Leu | Met | Glu | Arg | Ile | Leu | Gln | Pro | Ala | Pro | Glu | Pro | Phe | |
| | | | | 215 | | | | | 220 | | | | | 225 | | |

| GCC | CTG | TTG | TAC | CGC | CCG | GAA | TCC | AGT | GGC | CCC | GGC | CTG | CTG | GAC | GTG | 955 |
|---|---|---|---|---|---|---|---|---|---|---|---|---|---|---|---|---|
| Ala | Leu | Leu | Tyr | Arg | Pro | Glu | Ser | Ser | Gly | Pro | Gly | Leu | Leu | Asp | Val | |
| | | | 230 | | | | | 235 | | | | | 240 | | | |

| CTG | ATC | GGC | GAA | ATG | TCG | GAA | CCG | CAG | GTC | CTG | GCC | GAT | ATC | GAC | TTG | 1003 |
|---|---|---|---|---|---|---|---|---|---|---|---|---|---|---|---|---|
| Leu | Ile | Gly | Glu | Met | Ser | Glu | Pro | Gln | Val | Leu | Ala | Asp | Ile | Asp | Leu | |
| | | 245 | | | | | 250 | | | | | 255 | | | | |

| CCT | GCC | ACC | TCG | ATC | GGC | GCG | CCT | CGC | CTG | GAT | GTA | CTG | GCG | CTG | ATC | 1051 |
|---|---|---|---|---|---|---|---|---|---|---|---|---|---|---|---|---|
| Pro | Ala | Thr | Ser | Ile | Gly | Ala | Pro | Arg | Leu | Asp | Val | Leu | Ala | Leu | Ile | |
| | 260 | | | | | 265 | | | | | 270 | | | | | |

| CCC | TAC | CGC | CAG | ATC | GCC | GAA | CGC | GGT | TTC | GAG | GCG | GTG | GAC | GAT | GAG | 1099 |
|---|---|---|---|---|---|---|---|---|---|---|---|---|---|---|---|---|
| Pro | Tyr | Arg | Gln | Ile | Ala | Glu | Arg | Gly | Phe | Glu | Ala | Val | Asp | Asp | Glu | |
| 275 | | | | | 280 | | | | | 285 | | | | | 290 | |

| TCG | CCG | CTG | CTG | GCG | ATG | AAC | ATC | ACC | GAG | CAG | CAA | TCC | ATC | AGC | ATC | 1147 |
|---|---|---|---|---|---|---|---|---|---|---|---|---|---|---|---|---|
| Ser | Pro | Leu | Leu | Ala | Met | Asn | Ile | Thr | Glu | Gln | Gln | Ser | Ile | Ser | Ile | |
| | | | | 295 | | | | | 300 | | | | | 305 | | |

| GAG | CGC | TTG | CTG | GGA | ATG | CTG | CCC | AAC | GTG | CCG | ATC | CAG | TTG | AAC | AGC | 1195 |
|---|---|---|---|---|---|---|---|---|---|---|---|---|---|---|---|---|
| Glu | Arg | Leu | Leu | Gly | Met | Leu | Pro | Asn | Val | Pro | Ile | Gln | Leu | Asn | Ser | |
| | | | 310 | | | | | 315 | | | | | 320 | | | |

| GAA | CGC | TTC | GAC | CTC | AGC | GAC | GCG | AGC | TAC | GCC | GAG | ATC | GTC | AGC | CAG | 1243 |
|---|---|---|---|---|---|---|---|---|---|---|---|---|---|---|---|---|
| Glu | Arg | Phe | Asp | Leu | Ser | Asp | Ala | Ser | Tyr | Ala | Glu | Ile | Val | Ser | Gln | |
| | | 325 | | | | | 330 | | | | | 335 | | | | |

| GTG | ATC | GCC | AAT | GAA | ATC | GGC | TCC | GGG | GAA | GGC | GCC | AAC | TTC | GTC | ATC | 1291 |
|---|---|---|---|---|---|---|---|---|---|---|---|---|---|---|---|---|
| Val | Ile | Ala | Asn | Glu | Ile | Gly | Ser | Gly | Glu | Gly | Ala | Asn | Phe | Val | Ile | |
| | 340 | | | | | 345 | | | | | 350 | | | | | |

| AAA | CGC | ACC | TTC | CTG | GCC | GAG | ATC | AGC | GAA | TAC | GGC | CCG | GCC | AGT | GCG | 1339 |
|---|---|---|---|---|---|---|---|---|---|---|---|---|---|---|---|---|
| Lys | Arg | Thr | Phe | Leu | Ala | Glu | Ile | Ser | Glu | Tyr | Gly | Pro | Ala | Ser | Ala | |
| 355 | | | | | 360 | | | | | 365 | | | | | 370 | |

| CTG | TCG | TTC | TTT | CGC | CAT | CTG | CTG | GAA | CGG | GAG | AAA | GGC | GCC | TAC | TGG | 1387 |
|---|---|---|---|---|---|---|---|---|---|---|---|---|---|---|---|---|
| Leu | Ser | Phe | Phe | Arg | His | Leu | Leu | Glu | Arg | Glu | Lys | Gly | Ala | Tyr | Trp | |
| | | | | 375 | | | | | 380 | | | | | 385 | | |

| ACG | TTC | ATC | ATC | CAC | ACC | GGC | AGC | CGT | ACC | TTC | GTG | GGT | GCG | TCC | CCC | 1435 |
|---|---|---|---|---|---|---|---|---|---|---|---|---|---|---|---|---|
| Thr | Phe | Ile | Ile | His | Thr | Gly | Ser | Arg | Thr | Phe | Val | Gly | Ala | Ser | Pro | |
| | | | 390 | | | | | 395 | | | | | 400 | | | |

| GAG | CGC | CAC | ATC | AGC | ATC | AAG | GAT | GGG | CTC | TCG | GTG | ATG | AAC | CCC | ATC | 1483 |
|---|---|---|---|---|---|---|---|---|---|---|---|---|---|---|---|---|
| Glu | Arg | His | Ile | Ser | Ile | Lys | Asp | Gly | Leu | Ser | Val | Met | Asn | Pro | Ile | |
| | | 405 | | | | | 410 | | | | | 415 | | | | |

| AGC | GGC | ACT | TAC | CGC | TAT | CCG | CCC | GCC | GGC | CCC | AAC | CTG | TCG | GAA | GTC | 1531 |
|---|---|---|---|---|---|---|---|---|---|---|---|---|---|---|---|---|
| Ser | Gly | Thr | Tyr | Arg | Tyr | Pro | Pro | Ala | Gly | Pro | Asn | Leu | Ser | Glu | Val | |
| | 420 | | | | | 425 | | | | | 430 | | | | | |

| ATG | GAC | TTC | CTG | GCG | GAT | CGC | AAG | GAA | GCC | GAC | GAG | CTC | TAC | ATG | GTG | 1579 |

| | | | | | | | | | | | | | | | | |
|---|---|---|---|---|---|---|---|---|---|---|---|---|---|---|---|---|
| Met | Asp | Phe | Leu | Ala | Asp | Arg | Lys | Glu | Ala | Asp | Glu | Leu | Tyr | Met | Val | |
| 435 | | | | 440 | | | | 445 | | | | | | 450 | | |

| GTG | GAT | GAA | GAG | CTG | TAA | ATG | ATG | GCG | CGC | ATT | TGT | GAG | GAC | GGC | GGC | 1627 |
|---|---|---|---|---|---|---|---|---|---|---|---|---|---|---|---|---|
| Val | Asp | Glu | Glu | Leu | | Met | Met | Ala | Arg | Ile | Cys | Glu | Asp | Gly | Gly | |
| | | | | 455 | | 1 | | | 5 | | | | | | 10 | |

| CAC | GTC | CTC | GGC | CCT | TAC | CTC | AAG | GAA | ATG | GCG | CAC | CTG | GCC | CAC | ACC | 1675 |
|---|---|---|---|---|---|---|---|---|---|---|---|---|---|---|---|---|
| His | Val | Leu | Gly | Pro | Tyr | Leu | Lys | Glu | Met | Ala | His | Leu | Ala | His | Thr | |
| | | | | 15 | | | | 20 | | | | | | 25 | | |

| GAG | TAC | TTC | ATC | GAA | GGC | AAG | ACC | CAT | CGC | GAT | GTA | CGG | GAA | ATC | CTG | 1723 |
|---|---|---|---|---|---|---|---|---|---|---|---|---|---|---|---|---|
| Glu | Tyr | Phe | Ile | Glu | Gly | Lys | Thr | His | Arg | Asp | Val | Arg | Glu | Ile | Leu | |
| | | | 30 | | | | | 35 | | | | | 40 | | | |

| CGC | GAA | ACC | CTG | TTT | GCG | CCC | ACC | GTC | ACC | GGC | AGC | CCA | CTG | GAA | AGC | 1771 |
|---|---|---|---|---|---|---|---|---|---|---|---|---|---|---|---|---|
| Arg | Glu | Thr | Leu | Phe | Ala | Pro | Thr | Val | Thr | Gly | Ser | Pro | Leu | Glu | Ser | |
| | | 45 | | | | | 50 | | | | | 55 | | | | |

| GCC | TGC | CGG | GTC | ATC | CAG | CGC | TAT | GAN | CCG | CAA | GGC | CGC | GCG | TAC | TAC | 1819 |
|---|---|---|---|---|---|---|---|---|---|---|---|---|---|---|---|---|
| Ala | Cys | Arg | Val | Ile | Gln | Arg | Tyr | Xaa | Pro | Gln | Gly | Arg | Ala | Tyr | Tyr | |
| | 60 | | | | | 65 | | | | | 70 | | | | | |

| AGC | GGC | ATG | GCT | GCG | CTG | ATC | GGC | AGC | GAT | GGC | AAG | GGC | GGG | CGT | TCC | 1867 |
|---|---|---|---|---|---|---|---|---|---|---|---|---|---|---|---|---|
| Ser | Gly | Met | Ala | Ala | Leu | Ile | Gly | Ser | Asp | Gly | Lys | Gly | Gly | Arg | Ser | |
| 75 | | | | | 80 | | | | | 85 | | | | | 90 | |

| CTG | GAC | TCC | GCG | ATC | CTG | ATT | CGT | ACC | GCC | GAC | ATC | GAT | AAC | AGC | GGC | 1915 |
|---|---|---|---|---|---|---|---|---|---|---|---|---|---|---|---|---|
| Leu | Asp | Ser | Ala | Ile | Leu | Ile | Arg | Thr | Ala | Asp | Ile | Asp | Asn | Ser | Gly | |
| | | | | 95 | | | | | 100 | | | | | 105 | | |

| GAG | GTG | CGG | ATC | AGC | GTG | GGC | TCG | ACC | ATC | GTG | CGC | CAT | TCC | GAC | CCG | 1963 |
|---|---|---|---|---|---|---|---|---|---|---|---|---|---|---|---|---|
| Glu | Val | Arg | Ile | Ser | Val | Gly | Ser | Thr | Ile | Val | Arg | His | Ser | Asp | Pro | |
| | | | 110 | | | | | 115 | | | | | 120 | | | |

| ATG | ACC | GAG | GCT | GCC | GAA | AGC | CGG | GCC | AAG | GCC | ACT | GGC | CTG | ATC | AGC | 2011 |
|---|---|---|---|---|---|---|---|---|---|---|---|---|---|---|---|---|
| Met | Thr | Glu | Ala | Ala | Glu | Ser | Arg | Ala | Lys | Ala | Thr | Gly | Leu | Ile | Ser | |
| | | 125 | | | | | 130 | | | | | 135 | | | | |

| GCA | CTG | AAA | AAC | CAG | GCG | CCC | TCG | CGC | TTC | GGC | AAT | CAC | CTG | CAA | GTG | 2059 |
|---|---|---|---|---|---|---|---|---|---|---|---|---|---|---|---|---|
| Ala | Leu | Lys | Asn | Gln | Ala | Pro | Ser | Arg | Phe | Gly | Asn | His | Leu | Gln | Val | |
| | 140 | | | | | 145 | | | | | 150 | | | | | |

| CGC | GCC | GCA | TTG | GCC | AGC | CGC | AAT | GCC | TAC | GTC | TCG | GAC | TTC | TGG | CTG | 2107 |
|---|---|---|---|---|---|---|---|---|---|---|---|---|---|---|---|---|
| Arg | Ala | Ala | Leu | Ala | Ser | Arg | Asn | Ala | Tyr | Val | Ser | Asp | Phe | Trp | Leu | |
| 155 | | | | | 160 | | | | | 165 | | | | | 170 | |

| ATG | GAC | AGC | CAG | CAG | CGG | GAG | CAG | ATC | CAG | GCC | GAC | TTC | AGT | GGG | CGC | 2155 |
|---|---|---|---|---|---|---|---|---|---|---|---|---|---|---|---|---|
| Met | Asp | Ser | Gln | Gln | Arg | Glu | Gln | Ile | Gln | Ala | Asp | Phe | Ser | Gly | Arg | |
| | | | | 175 | | | | | 180 | | | | | 185 | | |

| CAG | GTG | CTG | ATC | GTC | GAC | GCC | GAA | GAC | ACC | TTC | ACC | TCG | ATG | ATC | GCC | 2203 |
|---|---|---|---|---|---|---|---|---|---|---|---|---|---|---|---|---|
| Gln | Val | Leu | Ile | Val | Asp | Ala | Glu | Asp | Thr | Phe | Thr | Ser | Met | Ile | Ala | |
| | | | 190 | | | | | 195 | | | | | 200 | | | |

| AAG | CAA | CTG | CGG | GCC | CTG | GGC | CTG | GTA | GTG | ACG | GTG | TGC | AGC | TTC | AGC | 2251 |
|---|---|---|---|---|---|---|---|---|---|---|---|---|---|---|---|---|
| Lys | Gln | Leu | Arg | Ala | Leu | Gly | Leu | Val | Val | Thr | Val | Cys | Ser | Phe | Ser | |
| | | 205 | | | | | 210 | | | | | 215 | | | | |

| GAC | GAA | TAC | AGC | TTT | GAA | GGC | TAC | GAC | CTG | GTC | ATC | ATG | GGC | CCC | GGC | 2299 |
|---|---|---|---|---|---|---|---|---|---|---|---|---|---|---|---|---|
| Asp | Glu | Tyr | Ser | Phe | Glu | Gly | Tyr | Asp | Leu | Val | Ile | Met | Gly | Pro | Gly | |
| 220 | | | | | | 225 | | | | | 230 | | | | | |

| CCC | GGC | AAC | CCG | AGC | GAA | GTC | CAA | CAG | CCG | AAA | ATC | AAC | CAC | CTG | CAC | 2347 |
|---|---|---|---|---|---|---|---|---|---|---|---|---|---|---|---|---|
| Pro | Gly | Asn | Pro | Ser | Glu | Val | Gln | Gln | Pro | Lys | Ile | Asn | His | Leu | His | |
| 235 | | | | | 240 | | | | | 245 | | | | | 250 | |

| GTG | GCC | ATC | CGC | TCC | TTG | CTC | AGC | CAG | CAG | CGG | CCA | TTC | CTC | GCG | GTG | 2395 |
|---|---|---|---|---|---|---|---|---|---|---|---|---|---|---|---|---|
| Val | Ala | Ile | Arg | Ser | Leu | Leu | Ser | Gln | Gln | Arg | Pro | Phe | Leu | Ala | Val | |
| | | | | 255 | | | | | 260 | | | | | 265 | | |

| TGC | CTG | AGC | CAT | CAG | GTG | CTG | AGC | CTG | TGC | CTG | GGC | CTG | GAA | CTG | CAG | 2443 |
|---|---|---|---|---|---|---|---|---|---|---|---|---|---|---|---|---|
| Cys | Leu | Ser | His | Gln | Val | Leu | Ser | Leu | Cys | Leu | Gly | Leu | Glu | Leu | Gln | |
| | | | 270 | | | | | 275 | | | | | 280 | | | |

| CGC | AAA | GCC | ATT | CCC | AAC | CAG | GGC | GTG | CAA | AAA | CAG | ATC | GAC | CTG | TTT | 2491 |
|---|---|---|---|---|---|---|---|---|---|---|---|---|---|---|---|---|
| Arg | Lys | Ala | Ile | Pro | Asn | Gln | Gly | Val | Gln | Lys | Gln | Ile | Asp | Leu | Phe | |
| | | 285 | | | | | 290 | | | | | 295 | | | | |

| GGC | AAT | GTC | GAA | CGG | GTG | GGT | TTC | TAC | AAC | ACC | TTC | GCC | GCC | CAG | AGC | 2539 |
|---|---|---|---|---|---|---|---|---|---|---|---|---|---|---|---|---|

-continued

| | | | | | | | | | | | | | | |
|---|---|---|---|---|---|---|---|---|---|---|---|---|---|---|
| Gly | Asn | Val | Glu | Arg | Val | Gly | Phe | Tyr | Asn | Thr | Phe | Ala | Ala | Gln | Ser |
| | 300 | | | | | 305 | | | | | 310 | | | | |

| TCG | AGT | GAC | CGC | CTG | GAC | ATC | GAC | GGC | ATC | GGC | ACC | GTC | GAA | ATC | AGC | 2587 |
|---|---|---|---|---|---|---|---|---|---|---|---|---|---|---|---|---|
| Ser | Ser | Asp | Arg | Leu | Asp | Ile | Asp | Gly | Ile | Gly | Thr | Val | Glu | Ile | Ser | |
| 315 | | | | | 320 | | | | | 325 | | | | | 330 | |

| CGC | GAC | AGC | GAG | ACC | GGC | GAG | GTG | CAT | GCC | CTG | CGT | GGC | CCC | TCG | TTC | 2635 |
|---|---|---|---|---|---|---|---|---|---|---|---|---|---|---|---|---|
| Arg | Asp | Ser | Glu | Thr | Gly | Glu | Val | His | Ala | Leu | Arg | Gly | Pro | Ser | Phe | |
| | | | | 335 | | | | | 340 | | | | | 345 | | |

| GCC | TCC | ATG | CAG | TTT | CAT | GCC | GAG | TCG | CTG | CTG | ACC | CAG | GAA | GGT | CCG | 2683 |
|---|---|---|---|---|---|---|---|---|---|---|---|---|---|---|---|---|
| Ala | Ser | Met | Gln | Phe | His | Ala | Glu | Ser | Leu | Leu | Thr | Gln | Glu | Gly | Pro | |
| | | | 350 | | | | | 355 | | | | | 360 | | | |

| CGC | ATC | ATC | GCC | GAC | CTG | CTG | CGG | CAC | GCC | CTG | ATC | CAC | ACA | CCT | GTC | 2731 |
|---|---|---|---|---|---|---|---|---|---|---|---|---|---|---|---|---|
| Arg | Ile | Ile | Ala | Asp | Leu | Leu | Arg | His | Ala | Leu | Ile | His | Thr | Pro | Val | |
| | | 365 | | | | | 370 | | | | | 375 | | | | |

| GAG | AAC | AAC | GCT | TCG | GCC | GCC | GGG | AGA | TAACC | ATG | CAC | CAT | TAC | GTC | | 2778 |
|---|---|---|---|---|---|---|---|---|---|---|---|---|---|---|---|---|
| Glu | Asn | Asn | Ala | Ser | Ala | Ala | Gly | Arg | | Met | His | His | Tyr | Val | | |
| 380 | | | | | 385 | | | | | 1 | | | | 5 | | |

| ATC | ATC | GAC | GCC | TTT | GCC | AGC | GTC | CCG | CTG | GAA | GGC | AAT | CCG | GTC | GCG | 2826 |
|---|---|---|---|---|---|---|---|---|---|---|---|---|---|---|---|---|
| Ile | Ile | Asp | Ala | Phe | Ala | Ser | Val | Pro | Leu | Glu | Gly | Asn | Pro | Val | Ala | |
| | | | | 10 | | | | | 15 | | | | | 20 | | |

| GTG | TTC | TTT | GAC | GCC | GAT | GAC | TTG | TCG | GCC | GAG | CAA | ATG | CAA | CGC | ATT | 2874 |
|---|---|---|---|---|---|---|---|---|---|---|---|---|---|---|---|---|
| Val | Phe | Phe | Asp | Ala | Asp | Asp | Leu | Ser | Ala | Glu | Gln | Met | Gln | Arg | Ile | |
| | | | 25 | | | | | 30 | | | | | 35 | | | |

| GCC | CGG | GAG | ATG | AAC | CTG | TCG | GAA | ACC | ACT | TTC | GTG | CTC | AAG | CCA | CGT | 2922 |
|---|---|---|---|---|---|---|---|---|---|---|---|---|---|---|---|---|
| Ala | Arg | Glu | Met | Asn | Leu | Ser | Glu | Thr | Thr | Phe | Val | Leu | Lys | Pro | Arg | |
| | | 40 | | | | | 45 | | | | | 50 | | | | |

| AAC | TGC | GGC | GAT | GCG | CTG | ATC | CGG | ATC | TTC | ACC | CCG | GTC | AAC | GAA | CTG | 2970 |
|---|---|---|---|---|---|---|---|---|---|---|---|---|---|---|---|---|
| Asn | Cys | Gly | Asp | Ala | Leu | Ile | Arg | Ile | Phe | Thr | Pro | Val | Asn | Glu | Leu | |
| | 55 | | | | | 60 | | | | | 65 | | | | | |

| CCC | TTC | GCC | GGG | CAC | CCG | TTG | CTG | GGC | ACG | GAC | ATT | GCC | CTG | GGT | GCG | 3018 |
|---|---|---|---|---|---|---|---|---|---|---|---|---|---|---|---|---|
| Pro | Phe | Ala | Gly | His | Pro | Leu | Leu | Gly | Thr | Asp | Ile | Ala | Leu | Gly | Ala | |
| 70 | | | | | 75 | | | | | 80 | | | | | 85 | |

| CGC | ACC | GAC | AAT | CAC | CGG | CTG | TTC | CTG | GAA | ACC | CAG | ATG | GGC | ACC | ATC | 3066 |
|---|---|---|---|---|---|---|---|---|---|---|---|---|---|---|---|---|
| Arg | Thr | Asp | Asn | His | Arg | Leu | Phe | Leu | Glu | Thr | Gln | Met | Gly | Thr | Ile | |
| | | | | 90 | | | | | 95 | | | | | 100 | | |

| GCC | TTT | GAG | CTG | GAG | CGC | CAG | AAC | GGC | AGC | GTC | ATC | GCC | GCC | AGC | ATG | 3114 |
|---|---|---|---|---|---|---|---|---|---|---|---|---|---|---|---|---|
| Ala | Phe | Glu | Leu | Glu | Arg | Gln | Asn | Gly | Ser | Val | Ile | Ala | Ala | Ser | Met | |
| | | | | 105 | | | | | 110 | | | | | 115 | | |

| GAC | CAG | CCG | ATA | CCG | ACC | TGG | ACG | GCC | CTG | GGG | CGC | GAC | GCC | GAG | TTG | 3162 |
|---|---|---|---|---|---|---|---|---|---|---|---|---|---|---|---|---|
| Asp | Gln | Pro | Ile | Pro | Thr | Trp | Thr | Ala | Leu | Gly | Arg | Asp | Ala | Glu | Leu | |
| | | 120 | | | | | 125 | | | | | 130 | | | | |

| CTC | AAG | GCC | CTG | GGC | ATC | AGC | GAC | TCG | ACC | TTT | CCC | ATC | GAG | ATC | TAT | 3210 |
|---|---|---|---|---|---|---|---|---|---|---|---|---|---|---|---|---|
| Leu | Lys | Ala | Leu | Gly | Ile | Ser | Asp | Ser | Thr | Phe | Pro | Ile | Glu | Ile | Tyr | |
| | 135 | | | | | 140 | | | | | 145 | | | | | |

| CAC | AAC | GGC | CCG | CGT | CAT | GTG | TTT | GTC | GGC | CTG | CCA | AGC | ATC | GCC | GCG | 3258 |
|---|---|---|---|---|---|---|---|---|---|---|---|---|---|---|---|---|
| His | Asn | Gly | Pro | Arg | His | Val | Phe | Val | Gly | Leu | Pro | Ser | Ile | Ala | Ala | |
| 150 | | | | | 155 | | | | | 160 | | | | | 165 | |

| CTG | TCG | GCC | CTG | CAC | CCC | GAC | CAC | CGT | GCC | CTG | TAC | AGC | TTC | CAC | GAC | 3306 |
|---|---|---|---|---|---|---|---|---|---|---|---|---|---|---|---|---|
| Leu | Ser | Ala | Leu | His | Pro | Asp | His | Arg | Ala | Leu | Tyr | Ser | Phe | His | Asp | |
| | | | | 170 | | | | | 175 | | | | | 180 | | |

| ATG | GCC | ATC | AAC | TGT | TTT | GCC | GGT | GCG | GGA | CGG | CGC | TGG | CGC | AGC | CGG | 3354 |
|---|---|---|---|---|---|---|---|---|---|---|---|---|---|---|---|---|
| Met | Ala | Ile | Asn | Cys | Phe | Ala | Gly | Ala | Gly | Arg | Arg | Trp | Arg | Ser | Arg | |
| | | | 185 | | | | | 190 | | | | | 195 | | | |

| ATG | TTC | TCG | CCG | GCC | TAT | GGG | GTG | GTC | GAG | GAT | GCG | NCC | ACG | GGC | TCC | 3402 |
|---|---|---|---|---|---|---|---|---|---|---|---|---|---|---|---|---|
| Met | Phe | Ser | Pro | Ala | Tyr | Gly | Val | Val | Glu | Asp | Ala | Xaa | Thr | Gly | Ser | |
| | | 200 | | | | | 205 | | | | | 210 | | | | |

| GCT | GCC | GGG | CCC | TTG | GCG | ATC | CAT | CTG | GCG | CGG | CAT | GGC | CAG | ATC | GAG | 3450 |
|---|---|---|---|---|---|---|---|---|---|---|---|---|---|---|---|---|
| Ala | Ala | Gly | Pro | Leu | Ala | Ile | His | Leu | Ala | Arg | His | Gly | Gln | Ile | Glu | |
| | 215 | | | | | 220 | | | | | 225 | | | | | |

| TTC | GGC | CAG | CAG | ATC | GAA | ATT | CTT | CAG | GGC | GTG | GAA | ATC | GGC | CGC | CCC | 3498 |

|  |  |  |  |  |  |  |  |  |  |  |  |  |  |  |
|---|---|---|---|---|---|---|---|---|---|---|---|---|---|---|
| Phe | Gly | Gln | Gln | Ile | Glu | Ile | Leu | Gln | Gly | Val | Glu | Ile | Gly | Arg | Pro |
| 230 |  |  |  | 235 |  |  |  |  | 240 |  |  |  |  | 245 |

| TCA | CTC | ATG | TTC | GCC | CGG | GCC | GAG | GGC | CGC | GCC | GAT | CAA | CTG | ACG | CGG | 3546 |
|---|---|---|---|---|---|---|---|---|---|---|---|---|---|---|---|---|
| Ser | Leu | Met | Phe | Ala | Arg | Ala | Glu | Gly | Arg | Ala | Asp | Gln | Leu | Thr | Arg |  |
|  |  |  | 250 |  |  |  | 255 |  |  |  |  |  | 260 |  |  |  |

| GTC | GAA | GTA | TCA | GGC | AAT | GGC | ATC | ACC | TTC | GGA | CGG | GGG | ACC | ATC | GTT | 3594 |
|---|---|---|---|---|---|---|---|---|---|---|---|---|---|---|---|---|
| Val | Glu | Val | Ser | Gly | Asn | Gly | Ile | Thr | Phe | Gly | Arg | Gly | Thr | Ile | Val |  |
|  |  |  | 265 |  |  |  | 270 |  |  |  |  |  | 275 |  |  |  |

```
CTA TGAACAGTTC AGTACTAGGC AAGCCGCTGT TGGGTAAAGG CATGTCGGAA        3647
Leu

TCGCTGACCG GCACACTGGA TGCGCCGTTC CCCGAGTACC AGAAGCCGCC TGCCGATCCC   3707
ATGAGCGTGC TGCACAACTG GCTCGAACGC GCACGCCGCG TGGGCATCCG CGAACCCCGT   3767
GCGCTGGCGC TGGCCACGGC TGACAGCCAG GGCCGGCCTT CGACACGCAT CGTGGTGATC   3827
AGTGAGATCA GTGACACCGG GGTGCTGTTC AGCACCCATG CCGGAAGCCA GAAAGGCCGC   3887
GAACTGACAG AGAACCCCTG GCCTCGGGG ACGCTGTATT GGCGCGAAAC CAGCCAGCAG    3947
ATCATCCTCA ATGGCCAGGC CGTGCGCATG CCGGATGCCA AGGCTGACGA GGCCTGGTTG   4007
AAGCGCCCTT ATGCCACGCA TCCGATGTCA TCGGTGTCTC GCCAGAGTGA AGAACTCAAG   4067
GATGTTCAAG CCATGCGCAA CGCCGCCAGG GAACTGGCCG AGGTTCAAGG TCCGCTGCCG   4127
CGTCCCGAGG GTTATTGCGT GTTTGAGTTA CGGCTTGAAT CGCTGGAGTT CTGGGGTAAC   4187
GGCGAGGAGC GCCTGCATGA ACGCTTGCGC TATGACCGCA GCGCTGAAGG CTGGAAACAT   4247
CGCCGGTTAC AGCCATAGGG TCCCGCGATA ACATGCTTT GAAGTGCCTG GCTGCTCCAG    4307
CTTCGAACTC ATTGCGCAAA CTTCAACACT TATGACACCC GGTCAACATG AGAAAAGTCC   4367
AGATGCGAAA GAACGCGTAT TCGAAATACC AAACAGAGAG TCCGGATCAC CAAAGTGTGT   4427
AACGACATTA ACTCCTATCT GAATTTTATA GTTGCTCTAG AACGTTGTCC TTGACCCAGC   4487
GATAGACATC GGGCCAGAAC CTACATAAAC AAAGTCAGAC ATTACTGAGG CTGCTACCAT   4547
GCTAGATTTT CAAAACAAGC GTAAATATCT GAAAAGTGCA GAATCCTTCA AAGCTT        4603
```

(2) INFORMATION FOR SEQ ID NO:18:

(i) SEQUENCE CHARACTERISTICS:
        (A) LENGTH: 455 amino acids
        (B) TYPE: amino acid
        (D) TOPOLOGY: linear (ii) MOLECULE TYPE: protein (xi) SEQUENCE DESCRIPTION: SEQ ID NO:18:

|  |  |  |  |  |  |  |  |  |  |  |  |  |  |  |
|---|---|---|---|---|---|---|---|---|---|---|---|---|---|---|
| Met | Thr | Gly | Ile | Pro | Ser | Ile | Val | Pro | Tyr | Ala | Leu | Pro | Thr | Asn | Arg |
| 1 |  |  |  | 5 |  |  |  |  | 10 |  |  |  |  | 15 |  |

| Asp | Leu | Pro | Val | Asn | Leu | Ala | Gln | Trp | Ser | Ile | Asp | Pro | Glu | Arg | Ala |
|---|---|---|---|---|---|---|---|---|---|---|---|---|---|---|---|
|  |  |  | 20 |  |  |  |  | 25 |  |  |  |  | 30 |  |  |

| Val | Leu | Leu | Val | His | Asp | Met | Gln | Arg | Tyr | Phe | Leu | Arg | Pro | Leu | Pro |
|---|---|---|---|---|---|---|---|---|---|---|---|---|---|---|---|
|  |  |  | 35 |  |  |  |  | 40 |  |  |  |  | 45 |  |  |

| Asp | Ala | Leu | Arg | Asp | Glu | Val | Val | Ser | Asn | Ala | Ala | Arg | Ile | Arg | Gln |
|---|---|---|---|---|---|---|---|---|---|---|---|---|---|---|---|
|  |  |  | 50 |  |  |  |  | 55 |  |  |  |  | 60 |  |  |

| Trp | Ala | Ala | Asp | Asn | Gly | Val | Pro | Val | Ala | Tyr | Thr | Ala | Gln | Pro | Gly |
|---|---|---|---|---|---|---|---|---|---|---|---|---|---|---|---|
| 65 |  |  |  |  | 70 |  |  |  |  | 75 |  |  |  |  | 80 |

| Ser | Met | Ser | Glu | Glu | Gln | Arg | Gly | Leu | Leu | Lys | Asp | Phe | Trp | Gly | Pro |
|---|---|---|---|---|---|---|---|---|---|---|---|---|---|---|---|
|  |  |  |  | 85 |  |  |  |  | 90 |  |  |  |  | 95 |  |

| Gly | Met | Lys | Ala | Ser | Pro | Ala | Asp | Arg | Glu | Val | Val | Gly | Ala | Leu | Thr |
|---|---|---|---|---|---|---|---|---|---|---|---|---|---|---|---|
|  |  |  | 100 |  |  |  |  | 105 |  |  |  |  | 110 |  |  |

| Pro | Lys | Pro | Gly | Asp | Trp | Leu | Leu | Thr | Lys | Trp | Arg | Tyr | Ser | Ala | Phe |
|---|---|---|---|---|---|---|---|---|---|---|---|---|---|---|---|

```
             115                      120                       125
Phe  Asn  Ser  Asp  Leu  Leu  Glu  Arg  Met  Arg  Ala  Asn  Gly  Arg  Asp  Gln
     130                      135                 140

Leu  Ile  Leu  Cys  Gly  Val  Tyr  Ala  His  Val  Gly  Val  Leu  Ile  Ser  Thr
145                      150                      155                      160

Val  Asp  Ala  Tyr  Ser  Asn  Asp  Ile  Gln  Pro  Phe  Leu  Val  Ala  Asp  Ala
                    165                      170                      175

Ile  Ala  Asp  Phe  Ser  Lys  Glu  His  His  Trp  Met  Pro  Ser  Asn  Thr  Pro
               180                      185                      190

Pro  Ala  Val  Ala  Pro  Cys  His  His  His  Arg  Arg  Gly  Gly  Ala  Met  Ser
          195                      200                      205

Gln  Thr  Ala  Ala  His  Leu  Met  Glu  Arg  Ile  Leu  Gln  Pro  Ala  Pro  Glu
     210                      215                      220

Pro  Phe  Ala  Leu  Leu  Tyr  Arg  Pro  Glu  Ser  Ser  Gly  Pro  Gly  Leu  Leu
225                      230                      235                      240

Asp  Val  Leu  Ile  Gly  Glu  Met  Ser  Glu  Pro  Gln  Val  Leu  Ala  Asp  Ile
                    245                      250                      255

Asp  Leu  Pro  Ala  Thr  Ser  Ile  Gly  Ala  Pro  Arg  Leu  Asp  Val  Leu  Ala
               260                      265                      270

Leu  Ile  Pro  Tyr  Arg  Gln  Ile  Ala  Glu  Arg  Gly  Phe  Glu  Ala  Val  Asp
          275                      280                      285

Asp  Glu  Ser  Pro  Leu  Leu  Ala  Met  Asn  Ile  Thr  Glu  Gln  Gln  Ser  Ile
     290                      295                      300

Ser  Ile  Glu  Arg  Leu  Leu  Gly  Met  Leu  Pro  Asn  Val  Pro  Ile  Gln  Leu
305                      310                      315                      320

Asn  Ser  Glu  Arg  Phe  Asp  Leu  Ser  Asp  Ala  Ser  Tyr  Ala  Glu  Ile  Val
                    325                      330                      335

Ser  Gln  Val  Ile  Ala  Asn  Glu  Ile  Gly  Ser  Gly  Glu  Gly  Ala  Asn  Phe
               340                      345                      350

Val  Ile  Lys  Arg  Thr  Phe  Leu  Ala  Glu  Ile  Ser  Glu  Tyr  Gly  Pro  Ala
          355                      360                      365

Ser  Ala  Leu  Ser  Phe  Phe  Arg  His  Leu  Leu  Glu  Arg  Glu  Lys  Gly  Ala
     370                      375                      380

Tyr  Trp  Thr  Phe  Ile  Ile  His  Thr  Gly  Ser  Arg  Thr  Phe  Val  Gly  Ala
385                      390                      395                      400

Ser  Pro  Glu  Arg  His  Ile  Ser  Ile  Lys  Asp  Gly  Leu  Ser  Val  Met  Asn
                    405                      410                      415

Pro  Ile  Ser  Gly  Thr  Tyr  Arg  Tyr  Pro  Pro  Ala  Gly  Pro  Asn  Leu  Ser
               420                      425                      430

Glu  Val  Met  Asp  Phe  Leu  Ala  Asp  Arg  Lys  Glu  Ala  Asp  Glu  Leu  Tyr
          435                      440                      445

Met  Val  Val  Asp  Glu  Glu  Leu
     450                      455
```

( 2 ) INFORMATION FOR SEQ ID NO:19:

( i ) SEQUENCE CHARACTERISTICS:
        ( A ) LENGTH: 387 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Met  Met  Ala  Arg  Ile  Cys  Glu  Asp  Gly  Gly  His  Val  Leu  Gly  Pro  Tyr
1                   5                        10                       15
```

| | | | | | | | | | | | | | |
|---|---|---|---|---|---|---|---|---|---|---|---|---|---|
| Leu | Lys | Glu | Met | Ala | His | Leu | Ala | His | Thr | Glu | Tyr | Phe | Ile | Glu | Gly |
| | | | 20 | | | | | 25 | | | | | 30 | | |
| Lys | Thr | His | Arg | Asp | Val | Arg | Glu | Ile | Leu | Arg | Glu | Thr | Leu | Phe | Ala |
| | | 35 | | | | | 40 | | | | | 45 | | | |
| Pro | Thr | Val | Thr | Gly | Ser | Pro | Leu | Glu | Ser | Ala | Cys | Arg | Val | Ile | Gln |
| | 50 | | | | | 55 | | | | | 60 | | | | |
| Arg | Tyr | Xaa | Pro | Gln | Gly | Arg | Ala | Tyr | Tyr | Ser | Gly | Met | Ala | Ala | Leu |
| 65 | | | | | 70 | | | | | 75 | | | | | 80 |
| Ile | Gly | Ser | Asp | Gly | Lys | Gly | Gly | Arg | Ser | Leu | Asp | Ser | Ala | Ile | Leu |
| | | | | 85 | | | | | 90 | | | | | 95 | |
| Ile | Arg | Thr | Ala | Asp | Ile | Asp | Asn | Ser | Gly | Glu | Val | Arg | Ile | Ser | Val |
| | | | 100 | | | | | 105 | | | | | 110 | | |
| Gly | Ser | Thr | Ile | Val | Arg | His | Ser | Asp | Pro | Met | Thr | Glu | Ala | Ala | Glu |
| | | 115 | | | | | 120 | | | | | 125 | | | |
| Ser | Arg | Ala | Lys | Ala | Thr | Gly | Leu | Ile | Ser | Ala | Leu | Lys | Asn | Gln | Ala |
| | 130 | | | | | 135 | | | | | 140 | | | | |
| Pro | Ser | Arg | Phe | Gly | Asn | His | Leu | Gln | Val | Arg | Ala | Ala | Leu | Ala | Ser |
| 145 | | | | | 150 | | | | | 155 | | | | | 160 |
| Arg | Asn | Ala | Tyr | Val | Ser | Asp | Phe | Trp | Leu | Met | Asp | Ser | Gln | Gln | Arg |
| | | | | 165 | | | | | 170 | | | | | 175 | |
| Glu | Gln | Ile | Gln | Ala | Asp | Phe | Ser | Gly | Arg | Gln | Val | Leu | Ile | Val | Asp |
| | | | 180 | | | | | 185 | | | | | 190 | | |
| Ala | Glu | Asp | Thr | Phe | Thr | Ser | Met | Ile | Ala | Lys | Gln | Leu | Arg | Ala | Leu |
| | | 195 | | | | | 200 | | | | | 205 | | | |
| Gly | Leu | Val | Val | Thr | Val | Cys | Ser | Phe | Ser | Asp | Glu | Tyr | Ser | Phe | Glu |
| | 210 | | | | | 215 | | | | | 220 | | | | |
| Gly | Tyr | Asp | Leu | Val | Ile | Met | Gly | Pro | Gly | Pro | Gly | Asn | Pro | Ser | Glu |
| 225 | | | | | 230 | | | | | 235 | | | | | 240 |
| Val | Gln | Gln | Pro | Lys | Ile | Asn | His | Leu | His | Val | Ala | Ile | Arg | Ser | Leu |
| | | | | 245 | | | | | 250 | | | | | 255 | |
| Leu | Ser | Gln | Gln | Arg | Pro | Phe | Leu | Ala | Val | Cys | Leu | Ser | His | Gln | Val |
| | | | 260 | | | | | 265 | | | | | 270 | | |
| Leu | Ser | Leu | Cys | Leu | Gly | Leu | Glu | Leu | Gln | Arg | Lys | Ala | Ile | Pro | Asn |
| | | 275 | | | | | 280 | | | | | 285 | | | |
| Gln | Gly | Val | Gln | Lys | Gln | Ile | Asp | Leu | Phe | Gly | Asn | Val | Glu | Arg | Val |
| | 290 | | | | | 295 | | | | | 300 | | | | |
| Gly | Phe | Tyr | Asn | Thr | Phe | Ala | Ala | Gln | Ser | Ser | Ser | Asp | Arg | Leu | Asp |
| 305 | | | | | 310 | | | | | 315 | | | | | 320 |
| Ile | Asp | Gly | Ile | Gly | Thr | Val | Glu | Ile | Ser | Arg | Asp | Ser | Glu | Thr | Gly |
| | | | | 325 | | | | | 330 | | | | | 335 | |
| Glu | Val | His | Ala | Leu | Arg | Gly | Pro | Ser | Phe | Ala | Ser | Met | Gln | Phe | His |
| | | | 340 | | | | | 345 | | | | | 350 | | |
| Ala | Glu | Ser | Leu | Leu | Thr | Gln | Glu | Gly | Pro | Arg | Ile | Ile | Ala | Asp | Leu |
| | | 355 | | | | | 360 | | | | | 365 | | | |
| Leu | Arg | His | Ala | Leu | Ile | His | Thr | Pro | Val | Glu | Asn | Asn | Ala | Ser | Ala |
| | 370 | | | | | 375 | | | | | 380 | | | | |
| Ala | Gly | Arg | | | | | | | | | | | | | |
| 385 | | | | | | | | | | | | | | | |

( 2 ) INFORMATION FOR SEQ ID NO:20:

( i ) SEQUENCE CHARACTERISTICS:
        ( A ) LENGTH: 278 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

| Met | His | His | Tyr | Val | Ile | Ile | Asp | Ala | Phe | Ala | Ser | Val | Pro | Leu | Glu |
|---|---|---|---|---|---|---|---|---|---|---|---|---|---|---|---|
| 1 | | | | 5 | | | | | 10 | | | | | 15 | |

| Gly | Asn | Pro | Val | Ala | Val | Phe | Phe | Asp | Ala | Asp | Asp | Leu | Ser | Ala | Glu |
|---|---|---|---|---|---|---|---|---|---|---|---|---|---|---|---|
| | | | 20 | | | | | 25 | | | | | 30 | | |

| Gln | Met | Gln | Arg | Ile | Ala | Arg | Glu | Met | Asn | Leu | Ser | Glu | Thr | Thr | Phe |
|---|---|---|---|---|---|---|---|---|---|---|---|---|---|---|---|
| | | 35 | | | | | 40 | | | | | 45 | | | |

| Val | Leu | Lys | Pro | Arg | Asn | Cys | Gly | Asp | Ala | Leu | Ile | Arg | Ile | Phe | Thr |
|---|---|---|---|---|---|---|---|---|---|---|---|---|---|---|---|
| | 50 | | | | | 55 | | | | | 60 | | | | |

| Pro | Val | Asn | Glu | Leu | Pro | Phe | Ala | Gly | His | Pro | Leu | Leu | Gly | Thr | Asp |
|---|---|---|---|---|---|---|---|---|---|---|---|---|---|---|---|
| 65 | | | | | 70 | | | | | 75 | | | | | 80 |

| Ile | Ala | Leu | Gly | Ala | Arg | Thr | Asp | Asn | His | Arg | Leu | Phe | Leu | Glu | Thr |
|---|---|---|---|---|---|---|---|---|---|---|---|---|---|---|---|
| | | | | 85 | | | | | 90 | | | | | 95 | |

| Gln | Met | Gly | Thr | Ile | Ala | Phe | Glu | Leu | Glu | Arg | Gln | Asn | Gly | Ser | Val |
|---|---|---|---|---|---|---|---|---|---|---|---|---|---|---|---|
| | | | 100 | | | | | 105 | | | | | 110 | | |

| Ile | Ala | Ala | Ser | Met | Asp | Gln | Pro | Ile | Pro | Thr | Trp | Thr | Ala | Leu | Gly |
|---|---|---|---|---|---|---|---|---|---|---|---|---|---|---|---|
| | | 115 | | | | | 120 | | | | | 125 | | | |

| Arg | Asp | Ala | Glu | Leu | Leu | Lys | Ala | Leu | Gly | Ile | Ser | Asp | Ser | Thr | Phe |
|---|---|---|---|---|---|---|---|---|---|---|---|---|---|---|---|
| | 130 | | | | | 135 | | | | | 140 | | | | |

| Pro | Ile | Glu | Ile | Tyr | His | Asn | Gly | Pro | Arg | His | Val | Phe | Val | Gly | Leu |
|---|---|---|---|---|---|---|---|---|---|---|---|---|---|---|---|
| 145 | | | | | 150 | | | | | 155 | | | | | 160 |

| Pro | Ser | Ile | Ala | Ala | Leu | Ser | Ala | Leu | His | Pro | Asp | His | Arg | Ala | Leu |
|---|---|---|---|---|---|---|---|---|---|---|---|---|---|---|---|
| | | | | 165 | | | | | 170 | | | | | 175 | |

| Tyr | Ser | Phe | His | Asp | Met | Ala | Ile | Asn | Cys | Phe | Ala | Gly | Ala | Gly | Arg |
|---|---|---|---|---|---|---|---|---|---|---|---|---|---|---|---|
| | | | 180 | | | | | 185 | | | | | 190 | | |

| Arg | Trp | Arg | Ser | Arg | Met | Phe | Ser | Pro | Ala | Tyr | Gly | Val | Val | Glu | Asp |
|---|---|---|---|---|---|---|---|---|---|---|---|---|---|---|---|
| | | 195 | | | | | 200 | | | | | 205 | | | |

| Ala | Xaa | Thr | Gly | Ser | Ala | Ala | Gly | Pro | Leu | Ala | Ile | His | Leu | Ala | Arg |
|---|---|---|---|---|---|---|---|---|---|---|---|---|---|---|---|
| | 210 | | | | | 215 | | | | | 220 | | | | |

| His | Gly | Gln | Ile | Glu | Phe | Gly | Gln | Gln | Ile | Glu | Ile | Leu | Gln | Gly | Val |
|---|---|---|---|---|---|---|---|---|---|---|---|---|---|---|---|
| 225 | | | | | 230 | | | | | 235 | | | | | 240 |

| Glu | Ile | Gly | Arg | Pro | Ser | Leu | Met | Phe | Ala | Arg | Ala | Glu | Gly | Arg | Ala |
|---|---|---|---|---|---|---|---|---|---|---|---|---|---|---|---|
| | | | | 245 | | | | | 250 | | | | | 255 | |

| Asp | Gln | Leu | Thr | Arg | Val | Glu | Val | Ser | Gly | Asn | Gly | Ile | Thr | Phe | Gly |
|---|---|---|---|---|---|---|---|---|---|---|---|---|---|---|---|
| | | | 260 | | | | | 265 | | | | | 270 | | |

| Arg | Gly | Thr | Ile | Val | Leu |
|---|---|---|---|---|---|
| | | 275 | | | |

( 2 ) INFORMATION FOR SEQ ID NO:21:

( i ) SEQUENCE CHARACTERISTICS:
        ( A ) LENGTH: 1007 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..669
        ( D ) OTHER INFORMATION: /gene= "phz4"
            / label= ORF4
            / note= "This DNA sequence is repeated from SEQ ID
            NO:17 so that the overlapping ORF4 may be separately translated"

(xi) SEQUENCE DESCRIPTION: SEQ ID NO:21:

```
ATG AAC AGT TCA GTA CTA GGC AAG CCG CTG TTG GGT AAA GGC ATG TCG        48
Met Asn Ser Ser Val Leu Gly Lys Pro Leu Leu Gly Lys Gly Met Ser
 1               5                  10                  15

GAA TCG CTG ACC GGC ACA CTG GAT GCG CCG TTC CCC GAG TAC CAG AAG        96
Glu Ser Leu Thr Gly Thr Leu Asp Ala Pro Phe Pro Glu Tyr Gln Lys
             20                  25                  30

CCG CCT GCC GAT CCC ATG AGC GTG CTG CAC AAC TGG CTC GAA CGC GCA       144
Pro Pro Ala Asp Pro Met Ser Val Leu His Asn Trp Leu Glu Arg Ala
         35                  40                  45

CGC CGC GTG GGC ATC CGC GAA CCC CGT GCG CTG GCG CTG GCC ACG GCT       192
Arg Arg Val Gly Ile Arg Glu Pro Arg Ala Leu Ala Leu Ala Thr Ala
     50                  55                  60

GAC AGC CAG GGC CGG CCT TCG ACA CGC ATC GTG GTG ATC AGT GAG ATC       240
Asp Ser Gln Gly Arg Pro Ser Thr Arg Ile Val Val Ile Ser Glu Ile
 65                  70                  75                  80

AGT GAC ACC GGG GTG CTG TTC AGC ACC CAT GCC GGA AGC CAG AAA GGC       288
Ser Asp Thr Gly Val Leu Phe Ser Thr His Ala Gly Ser Gln Lys Gly
                 85                  90                  95

CGC GAA CTG ACA GAG AAC CCC TGG GCC TCG GGG ACG CTG TAT TGG CGC       336
Arg Glu Leu Thr Glu Asn Pro Trp Ala Ser Gly Thr Leu Tyr Trp Arg
             100                 105                 110

GAA ACC AGC CAG CAG ATC ATC CTC AAT GGC CAG GCC GTG CGC ATG CCG       384
Glu Thr Ser Gln Gln Ile Ile Leu Asn Gly Gln Ala Val Arg Met Pro
         115                 120                 125

GAT GCC AAG GCT GAC GAG GCC TGG TTG AAG CGC CCT TAT GCC ACG CAT       432
Asp Ala Lys Ala Asp Glu Ala Trp Leu Lys Arg Pro Tyr Ala Thr His
     130                 135                 140

CCG ATG TCA TCG GTG TCT CGC CAG AGT GAA GAA CTC AAG GAT GTT CAA       480
Pro Met Ser Ser Val Ser Arg Gln Ser Glu Glu Leu Lys Asp Val Gln
145                 150                 155                 160

GCC ATG CGC AAC GCC GCC AGG GAA CTG GCC GAG GTT CAA GGT CCG CTG       528
Ala Met Arg Asn Ala Ala Arg Glu Leu Ala Glu Val Gln Gly Pro Leu
                 165                 170                 175

CCG CGT CCC GAG GGT TAT TGC GTG TTT GAG TTA CGG CTT GAA TCG CTG       576
Pro Arg Pro Glu Gly Tyr Cys Val Phe Glu Leu Arg Leu Glu Ser Leu
             180                 185                 190

GAG TTC TGG GGT AAC GGC GAG GAG CGC CTG CAT GAA CGC TTG CGC TAT       624
Glu Phe Trp Gly Asn Gly Glu Glu Arg Leu His Glu Arg Leu Arg Tyr
         195                 200                 205

GAC CGC AGC GCT GAA GGC TGG AAA CAT CGC CGG TTA CAG CCA TAGGGTCCCG   676
Asp Arg Ser Ala Glu Gly Trp Lys His Arg Arg Leu Gln Pro
     210                 215                 220

CGATAAACAT GCTTTGAAGT GCCTGGCTGC TCCAGCTTCG AACTCATTGC GCAAACTTCA    736

ACACTTATGA CACCCGGTCA ACATGAGAAA AGTCCAGATG CGAAAGAACG CGTATTCGAA    796

ATACCAAACA GAGAGTCCGG ATCACCAAAG TGTGTAACGA CATTAACTCC TATCTGAATT    856

TTATAGTTGC TCTAGAACGT TGTCCTTGAC CCAGCGATAG ACATCGGGCC AGAACCTACA    916

TAAACAAAGT CAGACATTAC TGAGGCTGCT ACCATGCTAG ATTTTCAAAA CAAGCGTAAA    976

TATCTGAAAA GTGCAGAATC CTTCAAAGCT T                                  1007
```

(2) INFORMATION FOR SEQ ID NO:22:

(i) SEQUENCE CHARACTERISTICS:
(A) LENGTH: 222 amino acids
(B) TYPE: amino acid
(D) TOPOLOGY: linear (ii) MOLECULE TYPE: protein (xi) SEQUENCE DESCRIPTION: SEQ ID NO:22:

| Met<br>1 | Asn | Ser | Ser | Val<br>5 | Leu | Gly | Lys | Pro | Leu<br>10 | Leu | Gly | Lys | Gly | Met<br>15 | Ser |
|---|---|---|---|---|---|---|---|---|---|---|---|---|---|---|---|
| Glu | Ser | Leu | Thr<br>20 | Gly | Thr | Leu | Asp | Ala<br>25 | Pro | Phe | Pro | Glu | Tyr<br>30 | Gln | Lys |
| Pro | Pro | Ala<br>35 | Asp | Pro | Met | Ser | Val<br>40 | Leu | His | Asn | Trp | Leu<br>45 | Glu | Arg | Ala |
| Arg | Arg<br>50 | Val | Gly | Ile | Arg | Glu<br>55 | Pro | Arg | Ala | Leu | Ala<br>60 | Leu | Ala | Thr | Ala |
| Asp<br>65 | Ser | Gln | Gly | Arg | Pro<br>70 | Ser | Thr | Arg | Ile | Val<br>75 | Val | Ile | Ser | Glu | Ile<br>80 |
| Ser | Asp | Thr | Gly | Val<br>85 | Leu | Phe | Ser | Thr | His<br>90 | Ala | Gly | Ser | Gln | Lys<br>95 | Gly |
| Arg | Glu | Leu | Thr<br>100 | Glu | Asn | Pro | Trp | Ala<br>105 | Ser | Gly | Thr | Leu | Tyr<br>110 | Trp | Arg |
| Glu | Thr | Ser<br>115 | Gln | Gln | Ile | Ile | Leu<br>120 | Asn | Gly | Gln | Ala | Val<br>125 | Arg | Met | Pro |
| Asp | Ala<br>130 | Lys | Ala | Asp | Glu | Ala<br>135 | Trp | Leu | Lys | Arg | Pro<br>140 | Tyr | Ala | Thr | His |
| Pro<br>145 | Met | Ser | Ser | Val | Ser<br>150 | Arg | Gln | Ser | Glu | Glu<br>155 | Leu | Lys | Asp | Val | Gln<br>160 |
| Ala | Met | Arg | Asn | Ala<br>165 | Ala | Arg | Glu | Leu | Ala<br>170 | Glu | Val | Gln | Gly | Pro<br>175 | Leu |
| Pro | Arg | Pro | Glu<br>180 | Gly | Tyr | Cys | Val | Phe<br>185 | Glu | Leu | Arg | Leu | Glu<br>190 | Ser | Leu |
| Glu | Phe | Trp<br>195 | Gly | Asn | Gly | Glu | Glu<br>200 | Arg | Leu | His | Glu | Arg<br>205 | Leu | Arg | Tyr |
| Asp | Arg<br>210 | Ser | Ala | Glu | Gly | Trp<br>215 | Lys | His | Arg | Arg | Leu<br>220 | Gln | Pro | | |

What is claimed is:

1. A method for protecting a plant against a phytopathogen, comprising treating said plant with a biocontrol agent transformed with one or more vectors collectively capable of expressing all of the polypeptides in the biosynthetic pathway of pyrrolnitrin, whereby pyrrolnitrin is produced in amounts which inhibit said phytopathogen.

2. The method of claim 1, wherein said polypeptides have the amino acid sequences set forth in SEQ ID NO:2, SEQ ID NO:3, SEQ ID NO:4, and SEQ ID NO:5.

3. The method of claim 1, wherein said vector comprises a DNA molecule having a nucleic acid sequence selected from the following group: ORF1 of SEQ ID NO:1, ORF2 of SEQ ID NO:1, ORF3 of SEQ ID NO:1, and ORF4 of SEQ ID NO:1.

4. The method of claim 1, wherein said vector comprises a DNA molecule isolated from a strain of Pseudomonas.

5. The method of claim 4, wherein said DNA molecule is isolated from *Pseudomonas fluorescens*.

* * * * *

UNITED STATES PATENT AND TRADEMARK OFFICE
CERTIFICATE OF CORRECTION

PATENT NO  : 5,662,898
DATED      : September 2, 1997
INVENTOR(S): Ligon et al.

It is certified that error appears in the above-identified patent and that said Letters Patent is hereby corrected as shown below:

On the title page, item [75] Inventors should read: -- James M. Ligon; Dwight Steven Hill; Stephen Ting Lam; Philip E. Hammer --.

Signed and Sealed this

Thirty-first Day of March, 1998

*Attest:*

BRUCE LEHMAN

*Attesting Officer*   Commissioner of Patents and Trademarks